(12) United States Patent
Sun et al.

(10) Patent No.: US 7,223,562 B2
(45) Date of Patent: May 29, 2007

(54) COMPOSITIONS FOR CONTROLLING HAIR GROWTH

(75) Inventors: Tung-Tien Sun, Dobbs Ferry, NY (US); Qiong Cao, Boston, MA (US)

(73) Assignee: New York University, New York, NY (US)

(*) Notice: Subject to any disclaimer, the term of this patent is extended or adjusted under 35 U.S.C. 154(b) by 75 days.

(21) Appl. No.: 11/096,070

(22) Filed: Mar. 31, 2005

(65) Prior Publication Data

US 2005/0287098 A1  Dec. 29, 2005

Related U.S. Application Data

(60) Provisional application No. 60/558,341, filed on Mar. 31, 2004.

(51) Int. Cl.
| | |
|---|---|
| C12P 21/02 | (2006.01) |
| C12N 1/21 | (2006.01) |
| C12N 1/19 | (2006.01) |
| C12N 15/63 | (2006.01) |
| C12N 5/10 | (2006.01) |
| C07H 21/04 | (2006.01) |

(52) U.S. Cl. ............. 435/69.1; 435/252.3; 435/254.11; 435/320.1; 435/325; 536/23.5

(58) Field of Classification Search ...................... None
See application file for complete search history.

(56) References Cited

U.S. PATENT DOCUMENTS

| | | |
|---|---|---|
| 4,139,619 A | 2/1979 | Chidsey, III |
| 5,643,898 A | 7/1997 | Grollier et al. |
| 5,656,300 A | 8/1997 | Levin |
| 5,663,160 A | 9/1997 | Meybeck et al. |
| 5,674,497 A | 10/1997 | Kuwana et al. |
| 5,679,378 A | 10/1997 | Fischer |
| 5,723,149 A | 3/1998 | Bonte et al. |
| 5,739,111 A | 4/1998 | Mahe |
| 5,741,816 A | 4/1998 | Tsujihara et al. |
| 5,750,107 A | 5/1998 | Nomura |
| 5,753,713 A | 5/1998 | Bass |
| 5,767,152 A | 6/1998 | Nielsen et al. |
| 5,798,341 A | 8/1998 | Klingelholler |
| 5,800,477 A | 9/1998 | Groux |
| 6,093,748 A | 7/2000 | Ahluwalia et al. |
| 6,291,740 B1 | 9/2001 | Bremel et al. |

FOREIGN PATENT DOCUMENTS

| | | |
|---|---|---|
| WO | WO-9513796 | 5/1995 |

OTHER PUBLICATIONS

Yuan et al., "siRNA Selection Server: an automated siRNA oligonucleotide prediction server," Nucleic Acids Research, 2004, vol. 32, Web Server issue.*

Green et al., "Multidomain TIGR/Olfactomedin Protein Family with Conserved Strustural Similarity in the N-terminal Region and Conserved Motifs in the C-terminal Region," Molecular & Cellular Proteomics 1:394-403 (2002).*
Bal et al., *Biochemistry*, 32(4):1047-53, 1993.
Bertolino et al., "Differentiation of the hair shaft" in *Differentiation of the Hair Shaft*, pp. 21-37, Olsen EA (ed.), McGraw Hill, Inc. New York, 1994.
Bertolino et al. Disorders of epidermal appendages and related disorders. *Dermatology in General Medicine*, 1993, 4th ed., pp. 671-695, Fitzpatrick et al. eds., McGraw-Hill.
Botchkarev et al., *J. Exp. Zool. Mol. Dev. Evol.*, 298(1):164-180, 2003.
Cao et al. Expression of an Olfactomedin-related Gene in Rat Hair Follicular Papilla Cells, *J. Invest. Dermatol.*, 2005, pp. 24-33, vol. 125, No. 1.
Cotsarelis et al., Existence of Slow-Cycling Limbal Epithelial Basal Cells That Can be Preferentially Stimulated to Proliferate: Implications on Epithelial Stem Cells, *Cell*, 1989, pp. 201-209, vol. 57.
Cotsarelis et al., Trends Mol. Med., 7(7):293-301, 2001.
Elliott et al., *J. Invest Dermatol.*, 113:873-877, 1999.
Fields et al., *Trends Genet.*, 10(8):286-92, 1994.
Garces et al., *Methods Mol. Biol.*, 161:3-8, 2001.
Green et al., *Mol. Cell. Prot.*, 1.5:394-403, 2002.
Hardy, *Trends Genet.*, 8:55-61, 1992.
Hutchinson et al., *J. Biol. Chem.*, 253:6551, 1978.
Jahoda, C. A., *Development*, 115:1103-1109, 1992.
Jahoda et al., *Nature*, 311:560-562, 1984.
Jahoda et al., *Exp. Dermatol.*, 10(4):229-37, 2001.
Kamimura et al., *J. Invest. Dermatol.*, 109(4):534-40, 1997.
Kim et al., *Dermatol. Surg.*, 21(4):312-313, 1995.
Lachgar et al., *Br. J. Dermatol.*, 138:407-411, 1998.
Lehrer et al. Strategies of epithelial repair: modulation of stem cell and transit amplifying cell proliferation, *Journal of Cell Science*, 1998, pp. 2867-2975, vol. 111.
Muller-Rover et al., *J. Invest. Dermatol.*, 117:3-15, 2001.
Oshima et al., *Cell*, 104:233-245, 2001.
Oliver, *J. Embryol. Exp. Morphol.*, 15:331-347, 1966.
Philpott et al., *J. Dermatol. Sci. 7 Suppl*, S55-72.
Philpott et al. Whole Hair Follicle Culture, *Dermatologic Clinics*, 1996, pp. 595-607, vol. 14, No. 4.
Porter, *J. Anat.*, 202:125-131, 2003.
Reynolds, A. J. et al., *Nature*, 402:33-34, 1999.
Snyder et al., *Biochem.*, 30(38):9143-153, 1991.
Stenn et al., *Physiol. Rev.*, 81:449-494, 2001.
Trimble and Maley, *Anal. Biochem.*, 141(2):515-22, 1984.
Yokoe et al., *Proc. Natl. Acad. Sci. USA* 90:4655-4659, 1993.

* cited by examiner

*Primary Examiner*—Robert A. Wax
(74) *Attorney, Agent, or Firm*—Wilmer Cutler Pickering Hale and Dorr LLP

(57) ABSTRACT

FP-1 is a protein that is specifically expressed in the follicular papilla of the hair follicle. The nucleic acid and amino acid sequences of FP-1, as well as antibodies that specifically bind FP-1 are provided. In addition, methods of isolating follicular papilla cells and methods of modulating hair growth are also disclosed.

22 Claims, 49 Drawing Sheets

FIG. 2A

```
  1                                                               M  T  R  A  A  E  R  G  Q  G  A  T  G  W  G
  1   ACGCGGGGAGTGCTGCCCTGAGTCGTTCGGCCTGAGCACAGAGACATGACCCGAGCCGCAGAGCCGAGGCCAAGGGCTACAGGCTGGGA

16    L  R  G  A  L  M  A  V  A  L  L  S  V  L  N  A  V  G  T  V  F  V  L  Y  Q  W  R  E  L  S
 91   CTGCGAGGGCGCCCTGATGGCCGTGGCGCTGCTGTCAGTGCTGAACGCCGTGGGCACCGTGTTCGTGCTGTACCAGTGGCGCGAGCTGAGC

46    A  A  L  R  A  L  E  A  Q  H  G  Q  E  Q  R  E  D  S  A  L  R  A  F  L  A  E  L  S  R  A
181   GCGGCGCTGCGGGCACTGGAGGCGCAACACGGCCAGGAGCAGCGCGAGGACAGCGCCCTACGCGCCTTTCTAGCTGAATTAAGTCGTGCG

76    P  A  R  V  P  E  P  P  Q  D  P  P  M  S  A  A  R  N  K  R  S  H  G  G  E  P  A  S  H  I  R
271   CCAGCCCGAGTCCCCGAACCACCCCCAGGACCCCCCATGAGTGCAGCGCGCAATAAGCGCAGCCACGGCGGCGAGCCTGCCTCACACATCCGC

106    A  E  S  Q  D  M  M  M  M  T  Y  S  M  V  P  I  R  V  M  I  D  L  C  N  S  T  Q  G  I
361   GCGGAGAGCCAGGACATGATGATGATGACCTACAGCATGGTGCCGATCCGGGTGATGATAGACCTGTGCAACAGCACCCAGGGCATC

136    C  L  T  G  P  P  P  G  P  P  P  P  G  A  G  G  L  P  G  H  N  G  S  D  G  Q  P  G  L  Q
451   TGCCTTACAGGACCACCACCGGGCCCACCACCTCCAGGAGCTGGTGGGTTACCAGGCCACACAATGGATCAGATGGACAGCCTGGTCTCCAG

166    G  P  K  G  E  K  G  A  V  G  K  R  G  K  M  G  L  P  G  A  T  G  N  P  G  E  K  G  E  K
541   GGCCCAAAAGGAGAAAAGGAGCAGTTGGGAAGAGAGGAGAAAATGGGGTTACCCGGAGCCACAGGAAATCCAGGGGAAAAGGGAGAGAAG

196    G  D  A  G  E  L  G  L  P  G  N  E  G  P  P  G  Q  K  G  D  K  G  D  V  S  N  D
631   GGAGATGCTGGTGAACTGGGCCTACCTGGAAATGAGGGACCACCAGGACAGAAAAGGAGACAAAGGAGATGTGTCCAATGAC
```

```
226  V  L  L  T  G  A  K  G  D  Q  G  P  P  P  G  P  P  P  G  P  P  S  G  S  R  R  A
721  GTGCTTTTGACAGGTGCCAAAGGTGACCAAGGGCCCCCCAGGCCCTCCAGGCCCTTCTGGAAGCAGAAGAGCC

256  K  G  P  R  Q  P  N  S  F  T  N  Q  C  P  G  E  T  C  V  I  P  N  D  D  T  L  V  G  R  A
811  AAAGGCCCTCGGCAGCCAAATTCGTTCACCAACCAGTGTCCAGGGGAGACGTGTCATACCCAATGATGATACCTTGGTGGGAGAGCT

286  D  E  K  V  N  E  R  H  S  P  Q  T  E  P  M  I  T  S  I  G  N  P  A  Q  V  L  K  V  K  E
901  GATGAGAAAGTCAATGAGCGGCATTCTCCACAAACAGAACCCATGATCACGTTCCATTGGTAACCCGCCAAGTCCTCAAAGTGAAAGAG

316  T  F  G  T  W  L  R  E  S  A  N  R  S  D  D  R  I  W  T  E  H  F  S  G  I  M  V  K  E
991  ACTTTTGGGACCTGGCTGCTAAGAGAGTCTGCTAACAGAGAGTGATGACCGCATTTGGGTGACTGAACATTTTCAGGCATCATGGTGAAGGAG

346  F  E  D  L  P  A  L  L  N  S  S  F  T  L  L  H  P  H  Y  F  H  G  C  G  H  A  V  Y  N
1081 TTTGAAGACCTGCCCGCCCTCCTGAATAGCAGCTTCACCCTCCTCCACCTTCCACATTACTTCCATGGCTGCGGGCACGCTGTTTACAAC

376  N  S  L  Y  Y  H  K  G  G  S  N  T  I  V  R  F  E  F  G  K  E  T  P  Q  T  L  K  L  E  D
1171 AACTCTCTCTACTACCACAAAGGAGGCTCCAACACCATAGTGAGATTTGAGATTTGGGAAAGAGACACCTCAAACTCTGAAGCTTGAAGAT

406  A  L  Y  F  D  R  K  Y  L  F  A  N  S  K  T  Y  F  N  I  A  V  D  E  K  G  L  W  I  I  Y
1261 GCTTTGTATTTGATCGAAAATACCTCTTTGCGAATTCAACATAGCAGTGGATGAGAAGGGCCTCTGGATTATCTAC

436  A  S  S  V  D  G  S  S  I  L  V  A  Q  L  D  E  R  T  F  S  V  L  Q  H  I  N  T  T  Y  P
1351 GCCTCGAGTGTGGATGGCTCCAAGCATCCTTGTGGCACAGCTGGACGAGAGACATTCTCTGTGCTGCAGCACATCAATACCACATACCCC
```

FIG. 2B

```
466        K  S  K  A  G  N  A  F  I  A  Q  G  I  L  Y  V  T  D  T  K  D  T  R  V  T  F  A  F  D  L
1441  AAGTCCAAGGCTGGCAATGCCTTCATAGCTCAAGGGATCCTCTATGTCACGGACACAAAGATACAAGGTCACGTTGCCTTTGATTTG

496        L  R  G  K  Q  I  N  A  N  F  G  L  R  M  S  Q  S  V  L  A  M  L  S  Y  N  M  R  D  Q  H
1531  TTACGAGGGAAGCAGATCAATGCAAACTTCGGTCTCAGAATGTCACAGTCTGTTCTTGCCATGTTGTCGTACAATATGAGAGACCAGCAT

526        L  Y  S  W  E  D  G  H  L  M  L  Y  P  V  H  F  S  S  T  A  P  S  Q  R  (SEQ ID NO:2)
1621  TTGTACTCGTGGGAAGACGGCCACCTGATGCTCTATCCTGTGCACTTTTCGTCAACAGCACCCAGCCAGCGATAGGCCTGCAGTCGGCTC

1711  CCTCATTATGCACCACACATTTCTGGGGTTGACCAAGCCCAACGGAAAGAAGGCCTGTAAAGGATATCCAGATACTCAGAGCATACGC

1801  CCGTGTTACGGGCTTTTGTGCATGTGGCAAGTCCCCCTGTAAGCCAGGTTAACTAAAGGCTGGAAGTTGAAATGGATAACATTTGGTGA

1891  CCCTTGGTCCCCTTCAAACTTAGCAAGTTAGTGCTCCCCCCTGACCTTAGTGTCCCCATCAGTATATGAAACATCTGTGTGATTGCAG

1981  CATTTCCTATACCTATATGAAGTTCTGTGATTCTTGCCTGGTTATATATTAGATTGCTTTCAGGTTTCTTTTTTTTCTCCACATGTAA

2071  ATGAGTTTACCTGCAGCTTGAGGGGTGTGCCTATCAGTGATGACGGACATTTGTTGGTGTGTTAGGGAAAAAGCATTGTTTCTTATGGCT

2161  TTTAAAGTATTATATTATTCCATAATTTGATATTTTTTTTGAATACGCCCCTGCCACTACAGAATGATTATTGTTTCAGCTCCTAAGTA

2251  CAAATCCAAGATTAATAAAAAAAAAAAAAAAAAAAAACATGAATAGAAAAAAAAAAAAAACTCGAGAGTATTAGTCGATGAGGAAAAAC(SEQ ID NO:1)
```

FIG. 2C

```
                  M  T  R  A  A  E  R  G  Q  G  A  T  G  W  G
  1   ACGCGGGGAGTGCTGCCCTGAGTCGTTCGGCCTGAGCACAGAGACATGACCCGAGCCGCAGAGCGAGGCCAAGGGCTACAGGCTGGGA

16   L  R  G  A  L  M  A  V  A  L  L  S  V  L  N  A  V  G  T  V  F  V  L  Y  Q  Q  R  E  D  S
 91   CTGCGAGGCGCCCTGATGGCCGTGGCGCTGCTGTCAGTGCTGAACGCCGTGGGCACCGTGTTCGTGCTGTACCAGCAGCGCGAGGACAGC

46   A  L  R  A  F  L  A  E  L  S  R  A  P  A  R  V  P  E  P  P  Q  D  P  M  S  A  A  R  N  K
181   GCCCTACGCGCCTTTCTAGCTGAATTAAGTCGTGCGCCAGCCCGAGTCCCCGAACCACCCCAGGACCCCATGAGTGCAGCGCGCAATAAG

76   R  S  H  G  G  E  P  A  S  H  I  R  A  E  S  Q  D  M  M  M  M  T  Y  S  M  V  P  I  R
271   CGCAGCCACGGCGGCGAGCCTGCCTCACACATCCGGGCGGAGAGCCAGGACATGATGATGATGACCTACAGCATGGTGCCGATCCGG

106   V  M  I  D  L  C  N  S  T  Q  G  I  C  L  T  G  P  P  P  G  P  P  P  G  A  G  G  L  P
361   GTGATGATAGACCTGTGCAACAGCACCCAGGGCATCTGCCTTACAGGACCTCCAGGACCTCCAGGAGCTGGTGGTTACCA

136   G  H  N  G  S  D  G  Q  P  G  L  Q  G  P  K  G  E  K  G  A  V  G  K  R  G  K  M  G  L  P
451   GGCCACAATGGATCAGATGGACAGCCTGGTCTCCAGGCCCCAAAAGGAGAAAAGGAGAGGGAAGCAGTTGGGAAGAGAGGAAAAATGGGGTTACCC

166   G  A  T  G  N  P  G  E  K  G  D  A  G  E  L  G  L  P  G  N  E  G  P  P  G  Q  K
541   GGAGCCACAGGAAATCCAGGGGAGAAAGGAGACGCTGGTGAACTGGGCCTACCTGGAAATGAGGGACCACCAGGACAGAAA
```

FIG. 3A

```
196        G  D  K  G  D  V  S  N  D  V  L  L  T  G  A  K  G  D  Q  G  P  P  P  G  P  P  G  P
631      GGAGACAAAGGAGACAAAGGAGATGTGTCCAATGACGTGCTTTTGACAGGTGCCAAGGTGACCAAGGGCCCCCTGGCCCACCTGGACCC

226        P  G  P  P  G  P  S  G  S  R  R  A  K  G  P  R  Q  P  N  S  F  T  N  Q  C  P  G  E  T  C
721      CCAGGGCCTCCAGGCCCTTCTGGAAGCAGAAGAGCCAAAGGCCCTCGGCAGCCAAATTCGTTCACCAACCAGTGTCCAGGGAGACGTGT

256        V  I  P  N  D  D  T  L  V  G  R  A  D  E  K  V  N  E  R  H  S  P  Q  T  E  P  M  I  T  S
811      GTCATACCCAATGATGATACCTTGGTGGGGAGAGCTGATGAGAAAGTCAATGAGCGCCATTCTCCACAAACAGAACCCATGATCACGTCC

286        I  G  N  P  A  Q  V  L  K  V  K  E  T  F  G  T  W  L  R  E  S  A  N  R  S  D  D  R  I  W
901      ATTGGTAACCCGGCCCAAGTCCTCAAAGTGAAAGAGACTTTTGGGACCTGGCTAAGAGAGTCTGCTAACAGGAGTGATGACCGCATTTGG

316        V  T  E  H  F  S  G  I  M  V  K  E  F  E  D  L  P  A  L  L  N  S  F  T  L  L  H  L  P
991      GTGACTGAACATTTTCAGGGCATCATGGTGAAGGAGTTTGAAGACCTGCCCGCCCTCCTGAATAGCAGCTTCACCCTCCTCCACCTCCCA

346        H  Y  F  H  G  C  G  H  A  V  Y  N  N  S  L  Y  Y  H  K  G  G  S  N  T  I  V  R  F  E  F
1081     CATTACTTCCATGGCTGTGCGGGCACGCTGTTTACAACAACTCTCTCTACTACCACAAAGGAGCTCCAACACCATAGTGAGATTTGAATTT

376        G  K  E  T  P  Q  T  L  K  L  E  D  A  L  Y  F  D  R  K  Y  L  F  A  N  S  K  T  Y  F  N
1171     GGGAAAGAGACACCTCAAACTCTGAAGCTTGAAGATGCTTTGTATTTTGATCGAAAATACCTCTTTGCGAATTCCAAGACTTACTTCAAC

406        I  A  V  D  E  K  G  L  W  I  I  Y  A  S  S  V  D  G  S  S  I  L  V  A  Q  L  D  E  R  T
1261     ATAGCAGTGGATGAGAAGGGCCTCTGGATTATCTACGCCTCGAGTGTGGATGGCTCAAGCATCCTTGTGGCACAGCTGGACGAGAGGACA
```

FIG. 3B

```
436   F  S  V  L  Q  H  I  N  T  T  Y  P  K  S  K  A  G  N  A  F  I  A  Q  G  I  L  Y  V  T  D
1351  TTCTGTGCTGCAGCACATCAATACCACATACCCCAAGTCCAAGGCTGGCAATGCCTTCATAGCTCAAGGGATCCTCTATGTCACGGAC

466   T  K  D  T  R  V  T  F  A  F  D  L  L  R  G  K  Q  I  N  A  N  F  G  L  R  M  S  Q  S  V
1441  ACAAAAGATACAAGGGTCACGTTTGCCTTTGATTTGTTACGAGGGAAGCAGATCAATGCAAACTTCGGTCTCAGAATGTCACAGTCTGTT

496   L  A  M  L  S  Y  N  M  R  D  Q  H  L  Y  S  W  E  D  G  H  L  M  L  Y  P  V  H  F  S  S
1531  CTTGCCATGTTGTCGTACAATATGAGAGACCAGCATTGTACTCGTGGGAAGACGGCCACCTGATGCTCTATCCTGTGCACTTTTCGTCA

526   T  A  P  S  Q  R  (SEQ ID NO:4)
1621  ACAGCACCCAGCCAGCAGCGGATAGGCCTGCAGTCGGCTCCCCTCATTATGCACCACACATTTCTGGGGTTTGACCAAGCCCAACGGAAAGAAG

1711  GCCTGTAAAGGATATCCAGATACTCAGAGCATACGCCCGTGTTACGGGCTTTTGTGCATGTGGCAAGTCCCCCTGTAAGCCAGGTTAACT

1801  AAAGGCTGGAAAGTTGAAATGGATAACATTGGTGACCCTGTCCCCTCTTCAAACTTAGCAAGTTAGTGCTCCCCCCTGACCTTAGTGT

1891  CCCCATCAGTAATATGAAACATCTGTGTGATTGCAGCATTTCCTATACCTATATGAAGTTCTGTGATTCTTGCCTGGTTATATATTAGAT

1981  TGCTTTCAGGTTTCTTTTTTTCTCCACATGTAAATGAGTTTACCTGCAGCTTGAGGGGTGTGCCTATCAGTGATGACGGACATTGT

2071  TTGGTGTTTAGGGAAAAAGCATTGTTCTTATGGCTTTTAAAGTATTATATATTATCCATAATTTGATATTTTTTTGAATACGCCCCTGC

2161  CACTACAGAATGATTATTGTTTCAGCTCCTAAGTACAAATCCAAGATTAATAAAAAAAAAACATGAATAGAAAAAAAAAAAAAAAAAAC

2251  TCGAGAGTATTAGTCGATGTAGGAAAAC (SEQ ID NO:3)
```

FIG. 3C

```
  1  GAATTCGGCACGAGGGGGCTTCTGGGGCGCCACGATTACTGTCCCCAACCCGCCTCGCCCAGACGGGTCTAAAGGCAGCTTGACTCACGACT

93  CTGCCACCAGCCCCACCACTCGCGCGAGGGTATAAAACCTGCCACTGCGGAGGAGGCCCAGTGCTGCCCTGAGTCGTTCGGCCTGAGCAC

M   T   R   A   A   E   R   G   Q   G   A   T   G   W   G   L   R   G   A   L   M   A   V   A   L   L   S   V
  1
183  AGAGACATGACCCGAGCCGCAGAGCGAGGCCAAGGGCTACAGGCTGGGGACTGCGGGCTGCGAGGGCACTGAGCGCGCTGATGGCCGTGCTGTCAGTG

L   N   A   V   G   T   V   F   V   L   Y   Q   W   R   E   L   S   A   A   L   R   A   L   E   A   Q   H   G   Q   E
 29
273  CTGAACGCCGTGGGCACCGTGTTCGTGCTGTACCAGTGGCGCGAGCTGAGCGCGGCGCTGCGGGCACTGGAGGCGCAACACGGCCAGGAG

Q   R   E   D   S   A   L   R   A   F   L   A   E   L   S   R   A   P   A   R   V   P   E   P   P   Q   D   P   P   M   S
 59
363  CAGCGCGAGGACAGCGCCCTACGCGCCTTTCTAGCTGAATTAAGTCGTGCGCCAGCCCCGAGTCCCCGAACCACCCCAGACCCCCATGAGT

A   A   R   N   K   R   S   H   G   G   E   P   A   S   H   I   R   A   E   S   Q   D   M   M   M   M   T   Y   S
 89
453  GCAGCGCGCAATAAGCGCAGCCACGGCGGCGAGCCTGCGTCACACATCCGCGCGGAGAGCCAGGACATGATGATGATGACCTACAGC

M   V   P   I   R   V   M   I   D   L   C   N   S   T   Q   G   I   C   L   T   G   P   P   G   P   P   P   G   P   P   G
119
543  ATGGTGCCGATCCGGGTGATGATAGACCTGTGCAACAGCACCCAGGGCATCTGCCTTACAGGACCCCGGGCCACCAGGACCTCCAGGA

A   G   G   L   P   G   H   N   G   S   D   G   Q   P   G   L   Q   G   P   K   G   E   K   G   A   V   G   K   R   G
149
633  GCTGGTGGGTTACCAGGCCACAATGGCTCACAGATGACAGCCTGTCTCCAGGGCCCAAAAGGAGAGAAAAAGGAGCAGTTGGGAAGAGAGAGGA

K   M   G   L   P   G   A   T   G   N   P   G   E   K   G   D   A   G   E   L   G   L   P   G   N   E   G
179
723  AAAATGGGGTTACCCGGAGCCCACAGGAAATCCAGGGGAAAGGGAGAAGGGAGAAGGGAGATGCTGGTGAACTGGGCCTACCTGGAAATGAGGGA
```

FIG. 4A

| | | |
|---|---|---|
| 209 | P P G Q K G D K G D V S N D V L L T G A K G D Q G P P | |
| 813 | CCACCAGGACAGAAAGGAGACAAAGGAGATGTGTCCAATGACGTGCTTTTGACAGGTGCCAAAGGTGACCAAGGGCCCCCT | |
| 239 | G P P P G P P P G S R R A K G P R Q P N S F T N Q C | |
| 903 | GGCCCACCTGGACCCCCAGGGCCTCCAGGCGGTCCTGGAAGCAGAAGAGCCAAAGGCCCTCGGCAGCCAAATTCGTTCACCAACCAGTGT | |
| 269 | P G E T C V I P N D D T L V G R A D E K V N E R H S P Q T E | |
| 993 | CCAGGGGAGACGTGTGTCATACCCAATGATGATACCTTGGTGGGGAGAGCTGATGAGAAAGTCAATGAGCGCCATTCTCCACAAACAGAA | |
| 299 | P M I T S I G N P A Q V L K V K E T F G T W L R E S A N R S | |
| 1083 | CCCATGATCACGTCCATTGGTAACCCGGCCCAAGTCCTCAAGGTGAAAGAGACTTTTGGGACCTGGCTAAGAGAGTCTGCTAACAGGAGT | |
| 329 | D D R I W V T E H F S G I M V K E F E D L P A L L N S S F T | |
| 1173 | GACGACCGGCATTGGGTGACTGAACATTTTTCAGGCATCATGGTGAAGGAGTTTGAAGACTTGCCCGCCCTCCTGAATAGCAGCTTCACC | |
| 359 | L L H P H Y F H G C G H A V Y N S L Y Y H K G G S N T I | |
| 1263 | CTCCTCCACCTCCCACATTACTTCCATGGCTGCGGCACGCTGTTTACAACTCTCTACTACCACAAAGGAGCTCCAACACCATA | |
| 389 | V R F F G K E T P Q T L K L E D A L Y F D R K Y L F A N S | |
| 1353 | GTGAGATTTGAATTTGGGAAAGAGACACCTCAAACTCTGAAGCTTGAAGATGCTTTGTATTTTGATCGAAAATACCTCTTTGCGAATTCC | |
| 419 | K T Y F N I A V D E K G L W I I Y A S S V D G S S I L V A Q | |
| 1443 | AAGACTTACTTCAACATAGCAGTGGATGAGAAGGGCCTCTGGATTATCTACGCCTCGAGTGTGGATGGCTCAAGCATCCTTGTGGCACAG | |

FIG. 4B

```
449   L   D   E   R   T   F   S   V   L   R   H   I   N   T   T   Y   P   K   S   K   A   G   N   A   F   I   A   Q   G   I
1533  CTGGACGAGAGGACATTCTCTGTCGCGGCACATCAATACCACATACCCCAAGTCCAAGGCTGGCAATGCCTTCATAGCTCAAGGGATC

479   L   Y   V   T   D   T   K   D   T   R   V   T   F   A   F   D   L   L   R   G   K   Q   I   N   A   N   F   G   L   R
1623  CTCTATGTCACGGACACCAAAGATACAAGGGTCACGTTTGCCTTTGATTGTTACGAGGAAGCAGATCAATGCAAACTTCGGTCTCAGA

509   M   S   Q   S   V   L   A   M   L   S   Y   N   M   R   D   Q   H   L   Y   S   W   E   D   G   H   L   M   L   Y   P
1713  ATGTCACAGTCTGTGTTCTTGCCATGTTGTCGTACAATATGAGAGACCAGCATTTGTACTCGTGGGAAGACGGCCACCTGATGCTCTATCCT

539   V   H   F   S   S   T   A   P   S   Q   R   (SEQ ID NO:6)
1803  GTGCACTTTTCGTCAACAGCACCCAGCCAGCCTGCAGTCGGCCTCCCCATTATGCACCACACATTTCTGGGTTTGACCAAG

1893  CCCAACGGAAAGAAGGCCTGTAAAGGATATCCAGATACTCAGAGCCATACGCCCGTGCTACGGGCTCTTGTGCATGTGGCAAGTCCCCCTG

1983  TAAGCCAGGTTAGCTAGAGGCTGGAAGTTGAAATGATAACATCTGGTGACCCTTGGTCTCCCTCTTCAAACTTAGCAAGTTAGTGTCCCC

2073  CCTGACCTTAGTGTCCCCATCAGTAATGTCTTCCTCTACCTATATGAAGTTCTGTGATTCTTGCCT

2163  GGTTATATATTAGATTGCTTTCTGGTTTCTTTTTTTTCTCCACATGTAAATGAGTTTACCTGCAGCTTGAGGGGTGTGCCTATCAGTG

2253  ATGACGGACATTTGTTTGGTGTTTAGGGAAGATGCATTGTCTCTTATGGCTTCTAAAGTATTATATATTATCCATAATTTGATATTTTCTC

2343  TGAATACGCACCTGCCACTACAGAATGATTATTGTTTCAGCTCCCTAAGTACAAATCCAAAAAAAAAAAAAAAAA (SEQ ID NO: 5)
```

FIG. 4C

```
  1                                                                      M   T   R   A   A   E   R   G   Q   G   A   T   G   W   G   L   R
  1   TCAGTGCTGCCCTGAGCCGCCCCGGCCTGAGCACGCAGACATGACCCGAGCCGCAGAGCGGGAGGCCAAGGGCGAGGCTGGGGGCTGCGC

18       G   A   L   V   A   I   A   L   L   S   A   L   N   A   A   G   T   V   F   V   L   C   Q   W   R   G   L   S   A   A
 91   GGCGCCCTGGTGGCCATAGCGCTGCTGTCCGCACTGAACGCCGCGGGCACCGTGTTCGTGCTGTGCCAGTGGCGGGGGTTAAGCGCGGCG

48       L   R   A   L   E   A   Q   R   G   R   E   Q   R   E   D   S   A   L   R   A   F   L   A   E   L   S   R   A   P   G
181   CTACGGGCGCTGGAGGCTCAACGCGGCCGAGAGCAGCGCGGAGGACAGCGCCCTACGGGCCTTTCTGGCCGAATTGAGTCGTGCCGGGC

78       R   V   P   E   P   S   Q   D   P   M   S   A   A   R   N   K   R   S   H   N   G   E   P   A   S   H   I   R   A   E
271   CGGGTCCCCGAACCATCCCAGGACCCCATGAGCGCAGCGCGCAACAAGCGCAGCCACAACGGCGAGCCTGCTCACACATCCGTGCGGAG

108       S   Q   D   M   M   M   M   T   Y   S   M   V   P   I   R   V   M   I   D   L   C   N   S   T   Q   G   I   C   L
361   AGCCAGGACATGATGATGATGACCTACTCCATGGTGCCGATTCGAGTGATGATAGACCTGTGCAACAGTACCCAGGGCATCTGCCTC

138       T   G   P   P   G   P   P   P   G   A   G   G   L   P   G   H   N   G   S   D   G   Q   P   P   G   L   Q   G   P
451   ACAGGACCACCGGGCCCACCAGGAGCCGGTGGGCTACCAGGAGACCTTCCAGGAGCACCACAATGGACAGCCTGGTCTCCAGGGCCCA

168       K   G   E   K   G   A   I   G   K   R   G   K   M   G   L   P   G   A   T   G   N   P   G   E   K   G   E   K   G   D
541   AAAGGAGAAAAAGGAGCAATTGGCAAGAGAGGGAAAATGGGGTTACCTGGAGCCACCGGAAATCCAGGGGAGAAAGGAGAAAGGAGAT
```

FIG. 5A

| | | |
|---|---|---|
| 198 | A G E L G L P G N E G P P G Q K G D K G D V S N D V L | |
| 631 | GCTGGTGAACTGGGTCTACCTGGAAATGAGGGCCCACCAGGGCAGAAAGGTGACAAGGAGACAAAGGAGAGACGTGTCCAATGACGTGCTT | |
| 228 | L T G A K G D D Q G P P P G P P P G P P P G S R R S K G | |
| 721 | TTGACAGGTGCCAAAGGTGACCAAGGTCCCCCCTGGCCCTCCAGGCCCTCCTGGAAGCAGAAGATCCAAAGGC | |
| 258 | P R P P N V F N S Q C P G E T C V I P N D D T L V G R A D E | |
| 811 | CCTCGGCCACCAAACGTGTTCAACAGCCAGTGTCCAGGGAGACGTGTCATACCCAATGATGATACCTTGGTGGGAAGAGCTGATGAG | |
| 288 | K A N E R H S P Q T E S M I T S I G N P A Q V L K V R E T F | |
| 901 | AAAGCAAATGAACGCCATTCACCACAACAGAATCTATGATCACTTCCATTGGCAACCCAGCCCAAGTCCTAAAAGTGAGAGAGACTTTT | |
| 318 | G T W M R E S A N K S D D R I W V T E H F S G I M V K E F K | |
| 991 | GGGACTTGGATGAGAGAGTCTGCTAACAAAAGTGACGACCGCATTTGGGTGACTGAACATTTTCAGGCATCATGGTGAAGGAGTTCAAA | |
| 348 | D L P A L L N S S F T L L H P H Y F H G C G H A V Y N N S | |
| 1081 | GACCTGCCGGCGCTCCTCAATAGCAGCTTCACACTCCTCCACCCACATTATTCCACGCTGTGGGCACGCTGTTTACAACAACTCT | |
| 378 | L Y Y H K G G S N T I V R F E F G K E T P Q T L K L E N A L | |
| 1171 | CTCTACTACCACAAAGGAGGCTCCAACACCATAGTGAGATTTGAATTTGGGAAAGAGACACCTCAGACTCTGAAGCTGGAAAATGCTTTG | |
| 408 | Y F D R K Y L F A N S K T Y F N I A V D E K G I W I I Y A S | |
| 1261 | TATTTGATCGAAAATACCTCTTTGCAAATTCCAAGACTTACTTCAACATAGCAGTGGATGAGAAGGGCATCTGGATTATCTACGCTTCA | |

FIG. 5B

```
438   S  V  D  G  S  S  I  L  V  A  Q  L  D  E  R  T  F  S  V  T  Q  H  I  N  T  T  Y  P  K  S
1351  AGTGTGGATGGCTCAAGCATCCTTGTAGCACAGCTGGATGAGAGGACATTCTCCGTGACACAGCACATCAACACACCCCAAATCC

468   K  A  G  N  A  F  I  A  R  G  I  L  Y  V  T  D  T  K  D  T  R  V  T  F  A  F  D  L  L  G
1441  AAGGCTGGCAATGCCTTCATAGCCCGAGGAATCCTCTATGTCACAGACACCAAAGATACGAGGGTCACGTTTGCCTTTGATTTGTTAGGA

498   G  K  Q  I  N  A  N  F  D  F  R  M  S  Q  S  V  L  A  M  L  S  Y  N  M  R  D  Q  H  L  Y
1531  GGAAAGCAAATCAATGCAAACTTTGATTTCAGAATGTCCCAGTCTGTTCTTGCCATGCTGTCATACAACATGAGAGATCAGCATTTATAC

528   S  W  E  D  G  H  L  M  L  Y  P  V  Q  F  L  S  A  A  S  S  Q  R   (SEQ ID NO:8)
1621  TCGTGGGAAGATGGCCATCTGATGCTCTATCCTGTGCAGTTTCTGTCAGGCGGCATCAAGTCAGGGGTTCCCTGGCTGTCTGCTC

1711  CCTCTCTATACTCCACATTGTCTAGGGTTTGGTCAAGCCCAACAGAAAGCTAGCCGGTAAAGATACCCAGGCACTCGGAGCGTAAGCCC

1801  ATGCCACGGGCTCTTGCACAAGCGGCAGTCCGCTCAAGCCAGGTGTTGAAATAGCTACAGATTAGAAATGGATGTGGAAGAGATCTG

1891  GTGACCCAGTATCCCTCCTTCAAACTCAGCAAGTTAGCTCTCCCCCGACCGTAGCCGTCCCCATAGGTAATACGAAACATCTGGGTATGACT

1981  GACATTTCCTCTTCCTAGATGAAATTCTGTGATTCTTGCCTGATTATATATTAGAAGTCTTTCTGATTCTTTTTTTTTCTCCACAT

2071  GTAAGTGAGCTTACTTGCAGCTTGAGGGGTGGGCCTTTCAGTGATGACTTATTTGGTATTTAGGAAGGTGCACTGGCTCTTATGGCTTC

2161  TAAGGTTTTATTTTATTCATAATTTGTTATTTCTCTGAATATTCACCTACCACTACAGAATGATCATTGTTTCAGCTCCTAAACACAA

2251  ATCCAAGATTAATAAACAAACAAACAAACAAACCATGAATAGATACAGGCTCAGAACTCTAAATGGAGCTGCATCAGGCCCATCTAG
```

FIG. 5C

2341 ATGCTGTCAATTTCTGATCATATATGTTTGCTGCTGGGAAAGTAAACAGGATATCTTCAGTTCGTGGTCCCTTTGCCAAGGCCATGGGAT
2431 TGTTATCAGAGTGTCAAACACTAAGTGGCCAATAATCTGTTAGAAGCATGAAACATGATGTTTTTCAGAAAACAGGCACCATTTAT
2521 ACTTACTGTTAGAATGAGGGAAGGCAATTGGCTCAAAGGCCAAAGTCAGCTTAGCTCTTTTCCTGTACCATGCATCCCTGCACCTAA
2611 GAATCTCGCCTCAGAGTGTGTCAGCAGTGAAGCAGAGCCGCTCTGTAAATCCTGAACCATTACTGCCTGGCCTTTACAGAAAGAAAGAAA
2701 AAAAAATGTTGACCTTTCATCTAAGGACAGGGAACGAGCCAGGTTCTCAGAAGGGCTCACTCCCTGAGTCTGGTTAGCTTTTACGGAC
2791 TGACAGGGCAGCATTTTATGTGGCTTGGGCTTGCAGAGGGAACAGTAAGGACACAGCATCAGATGGAGTAAGAGAACCTCCAGCCGTGGA
2881 GATGTTCACTCCCACGTGGTCCTCAAAGTTGGGTCTCTGTCCTCTCTTGGATAGCAAGGATCTAGTTTAATTGGTTCCTACAAGACCTTAAATA
2971 ACCACGTTCTCTGTCAACTCATTGAGTTCCAGGCAGGCTTGTGAGCTTCAAAGAGGAAGCTGTGGATTTCATGCCCCCCCCCGG
3061 AATATAGAAAAGACACTACAGAAACTGTCAGGAAAGACTGGCCAGCTGTTCCAAACCCACTCTCAGTGGGCCTGTGACCTGGTTTAGT
3151 TTTTTTAATAGAAGCATCTTGAGGCTTGGGGTATGCATTTAACTATTTAACTTCCCTGCCCTCTGAATAGATGTTTGCAGTTGGTCATCACAGCTGTTACT
3241 GGTGAACCTGTTGAGTTCTCAAGTCATGGGTCCCAAAGCTTCCCACTTCTTGATTAGATGTTTGCAGTTGGTCATCACAGCTTTTA
3331 AAGATATTCTCTCAGATTCATTTGTTGCAATGTAGAGTTCTAAATGTTTCATCAGTGTATCTAATGAATGGTATTGTTCTTTAAAGTATT
3421 CAAATATGAGAGATACTGTTTCTGAGTGCCGGTAGACCTGGATATACATATAATTCCATTTTTTATTACTTAGTAGCATTGCTGAGAATAGA

FIG. 5D

```
3511  TACAATACTAATTGTACATACAAGCAAAATAGTTAGTTATTGAATTAGCTCTCATTTTAATATCTGAACTAGCAAATGTCTTAGCTTTCC
3601  TTTACTTTTTTCTTTCCTTTCCTTTCCTTTCCTTTCCTTTCTTTCTTTTCTTTTTTTAAAGCAATGTCTTTGT
3691  GTTCGCCCAGACTTATCACAAACTCCTGCTTCAGATTCCTGGTGCTGGGACCACAGGCACAGTGGCTCTTTGACTCTCTTAATTGTGTG
3781  TAAGGAATCATACATATACTCACGATTAGAGAAACTCGTCTGAAGATTTTGTTCTTTCATGGTGTTGTTCTTTCTTTCTTTCTTTCTTT
3871  CTTTCTTTCGTTATAGTGTAGTGGGATTAGAACAAGTAAGGTTGACTGGTGTTTAATGAATTTATCTTTGCAGAAGGAAAGGAATTAAGG
3961  TTTTATTCCTTTTCTTTGCAAACAGGACTTCATTCTATATCACTCACTGTGTTTCAGGCTCACTGCTAAAATAGTGTGCACATCTTAT
4051  ATTTTTAAATGAAGATAATAATCAACCCTGCTGTCACTTGTAGCCAAGCTGTTCTAAAAGCACTTCATTTATGTCTGTATGAAATCAAGT
4141  GATTCTCCAATTCCTCTGAAATCTAAAGTAGATACCATTATACTAGAAACCACACCTTCCAGCTTCAAAGGTAGGCCAGACTCAACATTT
4231  ACAAAGCATTTCTATTAACTAATAAGAGTCCAACTAAGGTTGCAGAGTTGGCTCTGCCTCAATGTATCATTGATCAATGTATCAGAGA
4321  ACGTGGTCCGGGCTGAATATTTCAGATCAATTCTGGTGCTGGGCTCATTCGAAGTCTTTTTACCCTCATAATCAAATGACAAGGTGAGAT
4411  GACAAATGAGGAAGCACAGTCCTTGAAAAGTCACTCGTCATCCTCCAAGCATAGCAAGTACCTTACTCAGGCATTGCCTGTCTGGTGTTG
4501  AGCTACCTGAAGGAAAAGTGGGGGTGGAGCTCTTCAGTTTTCATCAGTGCTGTGGCCTTATTTATCTCATAATCTCCCATCAGTAACCA
4591  CAGATTCTAAACGACCAGCAAGTGTAAGTAGTAAGTAAAATAAAATTATCCTGAAT  (SEQ ID NO:7)
```

FIG. 5E

```
    1                                            M  V  D  L  C  N  S  T  K  G  I  C  L  T
    1 GACCATTGTGTATGATTCGTTGTTGACTGCAGCATCACTAGATCCGAGTGATGGTGGACCTGTGCAACAGCACCAAGGGCATCTGCCTCACA

15   G  P  S  G  P  P  P  G  A  G  G  L  P  G  H  N  G  L  D  G  Q  P  P  G  Q  G  P  P  K
   93 GGACCTTCTGGACCAGGACCTCCGGGAGCCGGGGGTTGCCAGGACACAACGGATTGGATGGACAGCCTGTCCTCAGGGCCCAAAA

45   G  E  K  G  A  N  G  K  R  G  K  M  G  I  P  G  A  A  G  N  P  G  E  R  G  E  K  G  D  H
  183 GGAGAAAAAGGAGCAAATGGGAAGAGAGGAAAAATGGGGGATACCTGGAGCTGCAGGAAATCCAGGGGAAAAAGGGAGAAAAGGAGACCAT

75   G  E  L  G  L  Q  G  N  E  G  P  P  G  Q  K  G  E  K  G  D  K  G  D  V  S  N  D  V  L  L
  273 GGTGAACTGGGCCTGCAGGGAAATGAGGGCCCACCAGGCAGAAGGGAGAAAAGGGTGACAAAGGAGATGTGTCCAACGACGTGCTCCTG

105   A  G  A  K  G  D  Q  G  P  P  G  P  P  G  P  P  G  P  P  G  S  R  R  A
  363 GCAGGTGCCAAAGGTGACCAAGGCCCCCCAGGCCCCCCAGGTCCTCCAGGGCCCCCCAGGCCCCCCTGGAAGCAGAGAGCC

135   K  G  P  R  Q  P  S  M  F  N  G  Q  C  P  G  E  T  C  A  I  P  N  D  D  T  L  V  G  K  A
  453 AAAGGCCCTCGGCAGCCAAGCATGTTCAACGGCCAGTGCCCAGGTGAGACTTGTGCCATACCAAATGATACCTTGGTTGGAAAAGCT

165   D  E  K  A  S  E  H  H  S  P  Q  A  E  S  M  I  T  S  I  G  N  P  V  Q  V  L  K  V  T  E
  543 GATGAGAAAGCCAGTGAACACCATTCCCCACAAGCAGAATCATGATCACTTCCATTGAAACCCAGTGCAAGTACTGAAGTGACAGAG
```

FIG. 6A

| | | |
|---|---|---|
| 195 | T F G T W I R E S A N K S D D R I W V T E H F S G I M V K E | |
| 633 | ACATTTGGGACTTGGATAAGAGAGTCTGCTAACAAGAGTGATGATGACCGGATTTGGGTGACAGAGCATTTTCAGGCATCATGGTTAAGGAA | |
| 225 | F K D Q P S L L N G S Y T F I H L P Y Y F H G C H V A Y N | |
| 723 | TTCAAGGATCAGCCCTCACTTCTGAATGGCAGTTACACGTTCATCATCCACTTCCATATACTATTTCCATGGCTGTGGGCACGTTGCTTACAAC | |
| 255 | N S L Y Y H K G G S N T L V R F E F G Q E T S Q T L K L E N | |
| 813 | AACTCTCTCTACTACCACAAAGGGGGTTCTAATACCCTAGTGAGATTGAGAATTTGGCCAGGAGAAACATCCCAAACTCTGAAGCTTGAAAAT | |
| 285 | A L Y F D R K Y L F A N S K T Y F N L A V D E K G L W I I Y | |
| 903 | GCCTTGTATTTTGATCGTAAATACCTTTTTGCAAATTCCAAAACTTACTTCAATCTAGCTGTAGATGAAAAGGGCCTTTGGATTATCTAT | |
| 315 | A S S V D G S S I L V A Q L D E R T F S V V Q H V N T T Y P | |
| 993 | GCGTCAAGTGTGGACGGCTCGAGCATTCTTGTAGCACAACTGGATGAGAGGACATTCTCAGTGTGTGCAACACGTCAATACCACGTACCCT | |
| 345 | K S K A G N A F I A R G I L Y V T D T K D M R V T F A F D L | |
| 1083 | AAATCCAAGGCTGGCAACGCCTTCATTGCCCGAGGAATCCTCTATGTCACAGACACCAAAGATATGAGGGTCACATTGCCTTTGATTTG | |
| 375 | L G G K Q I N A N F D L R T S Q S V L A M L A Y N M R D Q H | |
| 1173 | TTAGGAGGAAAACAGATCAAATGCAAACTTTGATTTAAGAACTTCCCAGTCTGTTCTTGCCATGTTAGCATACAACATGAGAGATCAGCAT | |
| 405 | L Y S W E D G H L M L Y P V Q F L S T T L N Q (SEQ ID NO:10) | |
| 1263 | TTATATTCATGGAAGATGGCCATTTAATGCTTTATCCTGTGCAGTTTTTGTCAACTACCTTAAATCAGTGATGTGCTGCATTCGGCTCC | |

FIG. 6B

1353  CTTCAGCAAATTTCAGGGGTTTTCTGGGACCAGTTCTCCCCCAACAGGAAACTTGTTTTTTAACGTCAGCCAGATATTTAGAAAATAAC

1443  CTCAAAAGTGTTTATATGGTCAGTGAGCCCCGCTTAGTGAAATAGCAACAGATTGGAAGTTGAAATGGCTGAGATTGGTGATCTCCCCA

1533  CAGCTGGCTCTGCAAGTTACCTCTTTCTCCTTGGGCCTTAGTTTCCCCATTGGTAATCTGAATTGGCTAAGATGATTGGGAGATTTCT

1623  GTACCTGTAGGTAATTGGTGATTCTTGGTGGCTGCTCTCTTCACAACTTTTATGTATCTGCTTCTGTCGTTAGCTTTTTAGCCACAT

1713  GCTGACCAAATTTACCTTTGAGTTGATAAGTCCAGTGCTTGAGTAGTGAATCCCTCAGTGCTGACTTATATCTGTTCTTTGAAAAAAT

1803  GCATTGACTCTTTAAGACATCTAAAGTATCACATTATCCATAATTTATTGCTTTCTTTGCATCTGCACCTGCCACCACAGAATAACCAT

1893  TACCCTCAGCTGCTGATTGGGCAGCTCTGAGATTAGCAAAAGCCAGGACAGCTACACATGTTCAGTTTTTTTTTTTTTTTCAATAG

1983  GCTATTTTTTCTTTCTTATTTAAATAGAGAGAGTCTTGCTATGTTCCCAGGCTGGTCTTGAACTCCTGGGGCTCAAGTGATCC

2073  TCCTGCCTTGGCCTCCCAAAATGCTGGATTACAGGCATGTGCCTGGCCAGGTTCTTAATAAAACAGAATCATGATCTTCCAGTTC

2163  CCCCCAGTTTCTGATCATGTTGATTGTAGCTGTGATCATGAACACTGAATCCCCAGATCACTCTGACTTCTTATGCTTCCTGTGGA

2253  TCCACTATCAAAGTACTAAATGCTGTGTAAGTAGACGTTAATCTGGCTGGAACCATGGAAGCACTTTGCAGTGTTCAGAAGAGAGGCTC

2343  CATTTGTGCTATTATGTAGAACTGGGCCAGAGCCAGTCCATTGCCTGTTTTTTAAATAAGGTTTTACTGAGCACAGCCACACTCATTT

2433  GTTTATGCAGTACGGCCTGACATTGCTTTTGCTCTGCAACAGCAGAGTCGAGTCATTGCAACAAAGAGCATATGCCCCACAGTGCCTAA

FIG. 6C

```
2523  AATATTGACCAGTCTACCCCTTTATGAAAAGATTGCTGACTCCTGATAAAGAATATAAAGTGAGCCTGATTCTTGAAAAAATCAGAACC
2613  AGAGCCTGTTTTGTTTGTTCTAAACTAAGAAGCCGCATAGAGATGTGACTTGCGTTTTGAGTAGAGGGGAAGGCTGATAACGGCGTAAGA
2703  TGAAGTGGCCCTCCACAAAGGCTGGTTAGGGGACAGTTCTTTCTCTAACATAGTTTTAAAGGATGTGATCTGGTCCCCTTGGATGCCAGG
2793  AGAGAATCCAGTTGAACTTGCTCCTAAATGCTCTTAAATATGCATATTTCTGCCAACTCACTTCTTTAAACATCTTTCAGCCCAGCGCT
2883  GCGGCCCCGGGAAGGGCCACTGCGAATAGAGAGGAAGCTGGAAAAGTTCCTGGGGCTCTGCAGCCAGGAAGGGAACCAGGCAAATCTT
2973  ATGTAAAGATTTTCAGCAACTTGTCCCAATTTGTGTATTCTGAAACTTTCTCTTTGGGACCAAATTCATTCTCAATGGCCCTGAGTT
3063  CAATATATTATTAACAGCAGTATTTAAAACTTAGGGTTGAACTGGGCATGGTGGCACATAACTGCAATCCCAGCTACTTGGAGGCAGG
3153  GATGGGAGGATCACTTGAGGCCCAGAGATCTCAGGACCAGCCTAGAGAGATCCCATCTCAAAAATAAAATAAGAAATAAAACTTAGG
3243  GGATATACAGATTTAAATATTCAAATCTCCCCTGCTCCCCCAGGCAGCTGTTAATGACTTGTTTGTTGTTCTCAATATG
3333  ATGGCTATTTGAAACTTCACCTACTTTCATTAGATTGGTTGTACCATGTCACCTTAGCTTTTAAAAATACTCTTTCAGATTCACGTTC
3423  TCTAACAAAGAGTCTCATGTTCAAGATCAATATGTCTAATAAGCGCTGGTGTCCTTTTAAAGTATTTAAATATATATGTTGCTGTTGCTG
3513  AATACAGGAGACCAGTTAGGAATATAGTTTCATAATAATGTACATACAATTGTATATAAGGTAGCAACCAAAGAGGTTGTT
3603  AATTAGCCACATATTCCTTTAGAAAAATGTTTCAGAAACCTCAGTCTTGATATCTGAGCTATCTGGGCTCCCTTACTTGTGAGTAAGGA
```

FIG. 6D

```
3693  TCATGCTCACCACTGAGAAGCTTACACCGGGACTTTTTTCTTTTTTTTGCTATGACAGAGTAATGCTAACGTAAGGACA
3783  ACTGAGTTTGATCAGTGTTTAATCGCAGTGGGTAATCTTATCTGATGTCTTTAAAAGTGAAAAGGATTAAGATTTTATTCTTTCTTGTA
3873  AACATTACTTGATTTTTAAAGAAGTTTGGGCTCACTGCTAAAATAGAGTATACAACTGAAGTTTTTAAGTCAAGATACTGTTTTAGG
3963  AGTTTACCCTCTCATTATAACCAAAGTTGCTCTAAAACACTTTCCAAATATCTGCACTTCTGATGTCAGAATCAAACCAGATAATTCTC
4053  TAATTCTTCTTTAATCTAAAGTAGATAGCTTCCCACTGAAAGTAAACAAACCATCCCTCCCAACCTCAAAGCTAGGCCACACTCTATT
4143  TCAAGGCATTTCTTTCAGCTGATAAGGTGTCCTCCTGAAGCCAAGTAGGTGTTCGTGTCTCCAAGTATCGTTAAGCACAGGTGCTATG
4233  ACAGAAAAAGTTCTGGGGTGGAAGTTTAAGATGAGGAGTTCTGATCTTAGGCATCTTAACAGTCAGTCACAAGGTGAAAAGTCAAATGAAACA
4323  GTACAATTCTTGATGAGTGAGGTGTCATCTTCCAACACACAGAGGAGCGTTTGGCTATGATCATCTGATGGCAAGTGAAGGAGAAATGA
4413  GTGATAGGGCTTTGCGTTTTCATCCAGATGCTGTGGCCCCTGTGTTTCACAGCATTAAGAGCCATAATTCCCAACCTGCACAGATCCTGAA
4503  CAACAAATGAATAACGATGAATGTCTTTTGGTTGTAATTAACAGTCAAATAAATAATCATTGCTGAGCACAATCACCAAAAAAAAAA
4593  AAAAAAAAAAAAAAAAAAAAAAAAAAAAAAAAAAAAAAAAAGAAAAAAAAAAAAAAAAAACA  (SEQ ID NO:9)
```

FIG. 6E

```
  1  M  A  R  G  A  E  G  G  R  G  D  A  G  W  G  L  R  G  A  L  A  A  V  A  L  L  S  A  L  N
  1  ATGGCCCGAGGCGCTGAGGGAGGCCGTGGGGACGCGGGGTGGGGGCTGCGTGGGGCCCTGGCTGCTGTGGCCCTGCTGTCCGCTCTCAAC

31  A  A  G  T  V  F  A  L  C  Q  W  R  G  L  S  S  A  L  R  A  L  E  A  Q  R  G  R  E  Q  R
 91  GCTGCGGGCACGGTGTTCGCCCTGTGCCAGTGGCGGGGACTGAGCTCGGCGCTGCGGGCTTTGGAGGCCCGGCGCGGGAGCAGCGC
```

FIG. 7A

```
 61  E  D  S  A  L  R  S  F  L  A  E  L  S  R  A  P  R  G  A  S  A  P  P  Q  D  P  A  S  S  A
181  GAGGACAGTGCCCTGCGCTCCTTCCTGGCCGAGTTGAGCCGCGCGCCGCGGGCGTCCGCCACCACCCCAAGACCCGGCCAGCTCAGCT

91  R  N  K  R  S  H  S  G  E  P  A  P  H  I  R  A  E  S  H  D  M  L  M  M  T  Y  S  M  V
271  CGCAACAAGCGCAGCCACAGCGGCGAGCCCGCGCCACATATCCGCGCCGAGAGCCATGACATGCTGATGATGACTACTCCATGGTG

121  P  I  R  V  M  V  D  L  C  N  S  T  K  G  I  C  L  T  G  P  S  G  P  P  P  G  P  A  G
361  CCGATCCGAGTGATGGTGGACCTGTGCAACAGCACCAAGGGCATCTGCCTCACAGGACCTTCTGGACCACCAGGACCTCCGGGAGCCGGC

151  G  L  P  G  H  N  G  L  D  G  Q  P  P  Q  G  P  K  G  E  K  G  A  N  G  K  R  G  K  M
451  GGGTTGCCAGGACACAACGGATTGGACGGCCTGCTCCTCAGGGCCCAAAAGGAGCCAAAAGGAGCAAATGGAAAAAGAGGAAAAATG

181  G  I  P  G  A  A  G  N  P  G  E  R  G  E  K  G  D  H  G  E  L  G  L  Q  G  N  E  G  P  P
541  GGGATACCTGGAGCTGCAGGAAATCCAGGGGAGAAAAGGGGAGAAAAGGAGACCATGGGCCTGAACTGTGAACTGGGCCAGGGAAATGAGGGCCCACCA

211  G  Q  K  G  E  K  G  D  K  G  D  V  S  N  D  V  L  L  A  G  A  K  G  D  Q  G  P  P  G  P
631  GGGCAGAAGGGAGAAAAGGGTGACAAAGGAGATGTGTCCAACGACGTGCTCCTGGCAGGTGCCAAAGGTGACCAAGGCCCACCCGGTCCA

241  P  G  P  P  G  P  P  G  P  P  G  S  R  R  A  K  G  P  R  Q  P  P  S  M  F  N  G  Q
721  CCTGGGCCCCCAGGCCCTCCAGGTCCTCCAGGGCCCCCTGGAAGCAGAAGACCAAAGGCCCTCGGCAGCCAAGCATGTTCAACGGCCAG

271  C  P  G  E  T  C  A  I  P  N  D  D  T  L  V  G  K  A  D  E  K  A  S  E  H  H  S  P  Q  A
811  TGCCCAGGTGAGACTTGTGCCATACCAAATGATGATACCTTGGTTGGAAAAGCTGATGAGAAAGCCAGTGAACACCATTCCCCACAAGCA
```

FIG. 7B

```
301  E  S  M  I  T  S  I  G  N  P  V  Q  V  L  K  V  T  E  T  F  G  T  W  I  R  E  S  A  N  K
901  GAATCCATGATCACTTCCATTGGAAACCCAGTGCAAGTACTGAAAGTGACAGAGACATTTGGGACTTGGATAAGAGAGTCTGCTAACAAG

331  S  D  D  R  I  W  V  T  E  H  F  S  G  I  M  V  K  E  F  K  D  Q  P  S  L  L  N  G  S  Y
991  AGTGATGACCGGATTTGGGTGACAGAGCATTTTCAGGCATCATGGTTAAGGAATTCAAGGATCAGCCCTCACTTCTGAATGGCAGTTAC

361  T  F  I  H  L  P  Y  F  H  G  C  G  H  V  A  Y  N  N  S  L  Y  Y  H  K  G  G  S  N  T
1081 ACGTTCATCCACCTTCCATACTATTCCATGGCTGTGGGCACGTTGCTTACAACAACTCTCTACTACCACAAAGGGGTTCTAATACC

391  L  V  R  F  E  F  G  Q  E  T  S  Q  T  L  K  L  E  N  A  L  Y  F  D  R  K  Y  L  F  A  N
1171 CTAGTGAGATTTGAATTGGCCAGGAAACATCCCAAACTCTGAAGCTTGAAATGCCTTGTATTTGATCGAAAATACCTTTTTGCAAAT

421  S  K  T  Y  F  N  L  A  V  D  E  K  G  L  W  I  I  Y  A  S  S  V  D  G  S  S  I  L  V  A
1261 TCCAAAACTTACTTCAATCTAGCTGTAGATGAAAAGGGCCTTTGGATTATCTATGCTTCAAGTGTGGACGGCTCGAGCATTCTTGTAGCA

451  Q  L  D  E  R  T  F  S  V  V  Q  H  V  N  T  T  Y  P  K  S  K  A  G  N  A  F  I  A  R  G
1351 CAACTGGATGAGAGGACATTCTCAGTGGTGCAACACGTCAATACCACGTACCCTAAATCCAAGGCTGGCAACGCCTTCATTGCCCGAGGA

481  I  L  Y  V  T  D  T  K  D  M  R  V  T  F  A  F  D  L  L  G  G  K  Q  I  N  A  N  F  D  L
1441 ATCCTCTATGTCACAGACACCAAAGATATGAGGGTCACATTTGCCTTTGATTGTTAGGAGGAAACAGATCAATGCAAACTTTGATTTA

511  R  T  S  Q  S  V  L  A  M  L  A  Y  N  M  R  D  Q  H  L  Y  S  W  E  D  G  H  L  M  L  Y
1531 AGAACTTCCCAGTCTGTTCTTGCCATGTTAGCATACAACATGAGAGATCAGCATTTATATTCATGGGAAGATGGCCATTTAATGCTTTAT
```

FIG. 7C

541  P  V  Q  F  L  S  T  T  L  N  Q    (SEQ ID NO:12)
1621 CCTGTGCAGTTTTGTCAACTACCTTAAATCAGTGATGTGCTGCATTCGGCTCCCTTCAGCAAATTTCAGGGGTTTCTGGGACCAGTTC
1711 TCCCCCAACAGGAAACTTGTTTTTTTAACGTCAGCCAGATATTTAGAAAATAACCTCAAAAGTGTTTATATGGTCAGTGAGCCCGCTTA
1801 GTGAAATAGCAACAGATTGGAAGTTGAAATCTCCCCACAGCTGGCTCTGCAAGTTACCTCTTCTCCTTGGGC
1891 CTTAGTTTCCCCATTGGTAATCTGAATTGGCTAAGATGATTGGGAGATTTCTGTACCTGTAGGTAATTGGTGTGATTCTTGGTGGCTGC
1981 TCTTCTCACAACTTTTATGTATCTGCTTCTCGTCGTTAGCTTTTTTAGCCACACATGCTGACCAAATTTACCTTTGAGTTGATAAGTCCAGT
2071 GGCTTGAGTAGTGAATCCCTCAGTGCTGACTTATATCTGTTCTTTGAAAAAAATGCATTGACTCTTTAAGACATCTAAAGTATCACATTA
2161 TCCATAATTATTGCTTTTCTTTGCATCTGCACCTGCCACCACAGAATAACCATTACCCTCAGCTGCTGATTGGGCAGCTCTGAGATTAG
2251 CAAAAGCCAGGACAGCTACACATGTTCAGGTTTTTTTTTTTTTTTTCTTTCTTTATTTTAAATAGAGAGA
2341 GAGTCTTGCTATGTTTCCCAGGCTGGTCTTGAACTCCTGACCTCAAGTGATCCTCCTGCCTTGGCCTCCCAAAATGCTGATTACAGGC
2431 ATGTGTGCCTGGCCCAGGTTTCTTAATAAAACAGAATCATGATCTTCCCAGTTCCCCCAGTTCTGATCATGTTGATTGTAGCTGTGG
2521 ATCATGAACACTGAATCCCAGATCACTCTGACTTCTTATGCTTCCCGTGGATCCACTATCAAAGTACTAAATGCTGTGTAAGTAGAC
2611 GTTAATCTGGCTGGAACCATGGGAAGCACTTTGCAGTGTTCAGAAGAGAGGCTCCATTTGTGGCTATTATGTAGAACTGGGCCAGAGCCA

FIG. 7D

2701 GTCCATTGCCTGTGTTTTTAAATAAGGTTTTACTGAGCACAGCCACACTCATTGTTTATGCAGTACGGCCTGACATTGCTTTGCTCTG

2791 CAACAGCAGAGTCGAGTCATTGCAACAAAGAGAGCATATGGCCCCACAGTGCCTAAAAATATTGACCAGCTACCCCTTTATGGAAAAAGATTG

2881 CTGACTCCTGATAAAGAATAAAGTGAGCCTGATTCTTGAAAAAATCAGAACCAGAGCCTGTTTTGTTTTGTTCTAAACTAAGAAGCCG

2971 CATAGGATGTGACTTGCGTTTGAGTAGAGGGAAGGCTGATAACGGCGTAAGATGAAGTGGCCCTCCACAAAGGCTGGTTAGGGACAG

3061 TTCTTTCTCTAACATAGTTTTAAAGGATGTGATCTGGTCTCCCCTTGGATGCCAGGAGAGAATCCAGTTGAACTTGCTCCTAAATGCTCTTA

3151 AATATGCATATTTCTGCAACTCACTCTTCTTAAACATCTTTCAGCCCAGGCGCTGCGGCCCCGGGAAGGGCCACTGCGAATAGAGAGAA

3241 GCTGGAAAAGTTCCTGGGGCTCTGCAGCCAGGAAGGGGAACCAGGGCAAATCTTATGTAAAGATTTTCAGCAACTTGTCCCAATTGTG

3331 TGTATTCTGAAACTTTCTCTTGGGACCAAATTCATTCTCAATGGCCCTGAGTTCAATATATATTAACAGCAGTATTTTAAAACTTAGG

3421 GTTGAACTGGGCATGTGGCACATAACTGCAATCCCAGCTACTTTGGAGGCAGGATGGGAGGATCACTTGAGGCCAGGATCTCAGGACC

3511 AGCCTAGAGAGATCCCATCTCTAAAAAATAAAGATATAAGAAAATAAAACTTAGGGGATATACAGATTTAAATATTCAAATCTCCCTGCTC

3601 CCCTGAAAGTCCCCAGCAGCTGTAATGACTTGTTGTTGTGTTCTCAATATGATGGCTATTTGAACTTCACCTACTTTTCATTAGAT

3691 TGGTTGTACCATGTCACCTTAGCTTTTAAAAATACTCTTTTCAGATTCACGTTCTCTAACAAAGAGTCTCATGTTCAAGATCAATATGTC

3781 TAATAAGCGCTGGTGTCCTTTTAAAGTATTTAAATATATATGTTGCTGTTGCTGAATACAGGAGACCAGGTTAGGAATATAGTTTCATAA

FIG. 7E

```
3871  TAATAGTACATACAATACTAATTGTATATAAGTAGCAACCAAAAGAGGTTGTTAATTAGCACATATTCCTTTTAGAAAAATGTTCAGA
3961  AACCTCAGTCTTGATATCTGAGCTATCTGGGCTCCCTTACTTGTGAGTAAGGATCATGCTCACCACTGGAGAAGCTTACACCGGACTT
4051  TTTTTCTTTTTCTTTTTTTTGCTATGACAGAGTAAGTCTAACGTAAGGACAACTGAGTTTGATCAGTGTTAATCGCAGTGGGTAAT
4141  CTTATCTGATTGTCTTTAAAGTGAAAAGGATTAAGATTTTATTCTTCTGTAAACATTACTTGATTTTTTAAAGAAGTTTTGGGCTCA
4231  CTGCTAAAATAGAGTATACAACTGAATGTTTTAAGTCAAGATACTGTTTTAGGAGTTTACCCTCTCATTATAACCAAAGTTGCTCTAA
4321  AACACTTTCCAAATATCTGCACTTCTGATGTCAGAATCAAACCAGATAATTCTCTAATTCTTCTTTAATCTAAAGTAGATAGCTTCCCAC
4411  TGGAAAGTAAACAAAACCATCCCTCCCAACCTCAAAGCTAGGCCACACTCTATTTCAAGGCATTTCTTTCAGCTGATAAGGTGTCCTCC
4501  TGAAGCCAAGTAGGTGGTTCTGGTCTCCAAGTATCGTTAAGCACAGGTCTATGACAGAGAAAAGTTCTGGGGTGGAAGTTTAAGATGAG
4591  GAGTTCTGATCTTAGGCATCTTAACAGTCACAAGGTGAAAAGTCAAATGAAACAGTACAATTCTTGATGAGTGAGGTGTCATCTTCCAAC
4681  CACACAGAGGACGTTTGGCTATGATCATCTGATGGCAAGTGAAGGAGAAATGAGTGATAGGGCTTTGCGTTTCATCCAGATGCTGTGG
4771  CCCTGTGTTTCACAGCATTAAGAGCCATAATTTCCAACCTGCACAGATCCTGAACAACAAATGAATAACGATGAATGTCTTTTGGTTGT
4861  AATTTAACAAGTCAAATAAATAATCATTGCTGAGCACACAATCACCAAAAAAAAAAAAAAAAAAAAAAAAAAAAAAAAAAAAAAAAAA
4951  AAAAAAGAAAAAAAAAAAAAAAAAAACA (SEQ ID NO:11)
```

FIG. 7F

```
              1               15 16           30 31           45 46           60 61           75 76           90
1 rFP-1a      MTRAAERGQGATGWG LRGALMAVALLSVLN AVGTVFVLYQRELS AALRALEAQHGQEQR EDSALRAFLAELSRA PARVPEPPQDPMSAA  90
2 rGliomedin  MTRAAERGQGATGWG LRGALMAVALLSVLN AVGTVFVLYQRELS AALRALEAQHGQEQR EDSALRAFLAELSRA PARVPEPPQDPMSAA  90
3 rFP-1b      MTRAAERGQGATGWG LRGALMAVALLSVLN AVGTVFVLYQQ--- -------------R  EDSALRAFLAELSRA PARVPEPPQDPMSAA  72
4 mCRG-L2     MTRAAERGQGATGWG LRGALVAIALLSAIN AAGTVFVLCQWRGLS AALRALEAQRGREQR EDSALRAFLAELSRA PGRVPEPSQDPMSAA  90
5 hCRG-L2     --------------- --------------- --------------- --------------- --------------- ---------------   0
6 hFP-1       MARGAEGGRGDAGWG LRGALAAVALLSALN AAGTVFALCQWRGLS SALRALEAQRGREQR EDSALRSFLAELSRA PRGASAPPQDPASSA  90

91              105 106          120 121          135 136          150 151          165 166          180
1 rFP-1a      RNKRSHGGEPASHIR AESQDMMMMTYSMV PIRVMIDLCNSTQGI CLTGPPGPPGPPGAG GLPGHNGSDGQPGLQ GPKGEKGAVGKRGKM 180
2 rGliomedin  RNKRSHGGEPASHIR AESQDMMMMTYSMV PIRVMIDLCNSTQGI CLTGPPGPPGPPGAG GLPGHNGSDGQPGLQ GPKGEKGAVGKRGKM 180
3 rFP-1b      RNKRSHGGEPASHIR AESQDMMMMTYSMV PIRVMIDLCNSTQGI CLTGPPGPPGPPGAG GLPGHNGSDGQPGLQ GPKGEKGAVGKRGKM 162
4 mCRG-L2     RNKRSHNGEPASHIR AESQDMMMMTYSMV PIRVMIDLCNSTQGI CLTGPPGPPGPPGAG GLPGHNGSDGQPGLQ GPKGEKGAIGKRGKM 180
5 hCRG-L2     --------------- -------------- ----MVDLCNSTKGI CLTGPSGPPGPPGAG GLPGHNGLDGQPGPQ GPKGEGANGKRGKM   56
6 hFP-1       RNKRSHSGEPAPHIR AESHDMLMMTYSMV PIRVMVDLCNSTKGI CLTGPSGPPGPPGAG GLPGHNGLDGQPGPQ GPKGEKGANGKRGKM 180

181             195 196          210 211          225 226          240 241          255 256          270
1 rFP-1a      GLPGATGNPGEKGEK GDAGELGLPGNEGPP GQKGDKGDKGDVSND VLLTGAKGDQGPPGP PGPPGPPGPPG--- -S RRAKGPRQPNSFTNQ 267
2 rGliomedin  GLPGATGNPGEKGEK GDAGELGLPGNEGPP GQKGDKGDKGDVSND VLLTGAKGDQGPPGP PGPPGPPGPPG--- -S RRAKGPRQPNSFTNQ 267
3 rFP-1b      GLPGATGNPGEKGEK GDAGELGLPGNEGPP GQKGDKGDKGDVSND VLLTGAKGDQGPPGP PGPPGPPGPPG--- -S RRAKGPRQPNSFTNQ 249
4 mCRG-L2     GLPGATGNPGEKGEK GDAGELGLPGNEGPP GQKGDKGDKGDVSND VLLTGAKGDQGPPGP PGPPGPPGPPG--- -S RRSKGPRPPNVFNSQ 267
5 hCRG-L2     GIPGAAGNPGERGEK GDHGELGLQGNEGPP GQKGEKGDKGDVSND VLLAGAKGDQGPPGP PGPPGPPGPPGPPGS RRAKGPRQPSMFNGQ 146
6 hFP-1       GIPGAAGNPGERGEK GDHGELGLQGNEGPP GQKGEKGDKGDVSND VLLAGAKGDQGPPGP PGPPGPPGPPGPPGS RRAKGPRQPSMFNGQ 270
```

FIG. 8A

```
              271         285 286                300 301               315 316               330 331               345 346               360
1 rFP-1a      CPGETCVIPNDDTLV GRADEKVNERHSPQT EPMITSIGNPAQVLK VKETFGTWLRESANR SDDRIWTEHFSGIM VKEFEDLPALLNSSF      357
2 rGliomedin  CPGETCVIPNDDTLV GRADEKVNERHSPQT EPMITSIGNPAQVLK VKETFGTWLRESANR SDDRIWTEHFSGIM VKEFEDLPALLNSSF      357
3 rFP-1b      CPGETCVIPNDDTLV GRADEKVNERHSPQT EPMITSIGNPAQVLK VKETFGTWLRESANR SDDRIWTEHFSGIM VKEFEDLPALLNSSF      339
4 mCRG-L2     CPGETCVIPNDDTLV GRADEKANERHSPQT ESMITSIGNPAQVLK VRETFGTWMRESANK SDDRIWTEHFSGIM VKEFKDLPALLNSSF      357
5 hCRG-L2     CPGETCAIPNDDTLV GKADEKASEHHSPQA ESMITSIGNPVQVLK VTETFGTWIRESANK SDDRIWTEHFSGIM VKEFKDQPSLLNGSY      236
6 hFP-1       CPGETCAIPNDDTLV GKADEKASEHHSPQA ESMITSIGNPVQVLK VTETFGTWIRESANK SDDRIWTEHFSGIM VKEFKDQPSLLNGSY      360

361         375 376                390 391               405 406               420 421               435 436               450
1 rFP-1a      TLLHLPHYFHGCGHA VYNNSLYYHKGGSNT IVRFEFGKETPQTLK LEDALYFDRKYLFAN SKTYFNIAVDEKGLW IIYASSVDGSSILVA      447
2 rGliomedin  TLLHLPHYFHGCGHA VYNNSLYYHKGGSNT IVRFEFGKETPQTLK LEDALYFDRKYLFAN SKTYFNIAVDEKGLW IIYASSVDGSSILVA      447
3 rFP-1b      TLLHLPHYFHGCGHA VYNNSLYYHKGGSNT IVRFEFGKETPQTLK LEDALYFDRKYLFAN SKTYFNIAVDEKGLW IIYASSVDGSSILVA      429
4 mCRG-L2     TLLHLPHYFHGCGHA VYNNSLYYHKGGSNT IVRFEFGKETPQTLK LENALYFDRKYLFAN SKTYFNIAVDEKGIW IIYASSVDGSSILVA      447
5 hCRG-L2     TFIHLPYYFHGCGHV AYNNSLYYHKGGSNT LVRFEFGQETSQTLK LENALYFDRKYLFAN SKTYFNLAVDEKGLW IIYASSVDGSSILVA      326
6 hFP-1       TFIHLPYYFHGCGHV AYNNSLYYHKGGSNT LVRFEFGQETSQTLK LENALYFDRKYLFAN SKTYFNLAVDEKGLW IIYASSVDGSSILVA      450

451         465 466                480 481               495 496               510 511               525 526               540
1 rFP-1a      QLDERTFSVLQHINT TYPKSKAGNAFIAQG ILYVTDTKDTRVTFA FDLLRGKQINANFGL RMSQSVLAMLSYNMR DQHLYSWEDGHLMLY      537
2 rGliomedin  QLDERTFSVLRHINT TYPKSKAGNAFIAQG ILYVTDTKDTRVTFA FDLLRGKQINANFGL RMSQSVLAMLSYNMR DQHLYSWEDGHLMLY      537
3 rFP-1b      QLDERTFSVLQHINT TYPKSKAGNAFIAQG ILYVTDTKDTRVTFA FDLLRGKQINANFGL RMSQSVLAMLSYNMR DQHLYSWEDGHLMLY      519
4 mCRG-L2     QLDERTFSVTQHINT TYPKSKAGNAFIARG ILYVTDTKDTRVTFA FDLLRGKQINANFDF RMSQSVLAMLSYNMR DQHLYSWEDGHLMLY      537
5 hCRG-L2     QLDERTFSVVQHINT TYPKSKAGNAFIARG ILYVTDTKDMRVTFA FDLLGGKQINANFDL RTSQSVLAMLAYNMR DQHLYSWEDGHLMLY      416
6 hFP-1       QLDERTFSVVQHVNT TYPKSKAGNAFIARG ILYVTDTKDMRVTFA FDLLGGKQINANFDL RTSQSVLAMLAYNMR DQHLYSWEDGHLMLY      540
```

FIG. 8B

```
                541
1 rFP-1a        PVHFSSTAPSQR    549 - SEQ ID NO: 2
2 rGliomedin    PVHFSSTAPSQR    549 - SEQ ID NO: 4
3 rFP-1b        PVHFSSTAPSQR    531 - SEQ ID NO: 6
4 mCRG-L2       PVQFLSAASSQR    549 - SEQ ID NO: 8
5 hCRG-L2       PVQFLSTTLNQ-    427 - SEQ ID NO: 10
6 hFP-1         PVQFLSTTLNQ-    551 - SEQ ID NO: 12
```

1. rat FP-1a
2. rat gliomedin (AAP22419)
3. rat FP-1b
4. mouse CRG-L2 (NP_796324)
5. human likely ortholog of mouse cancer related gene - liver 2 (CRG-L2): (NP_861454)
6. hypothetical human FP-1 full length

FIG. 8C

|   | 1 | 15 | 16 | 30 | 31 | 45 | 46 | 60 | 61 | 75 | 76 | 90 |   |
|---|---|---|---|---|---|---|---|---|---|---|---|---|---|
| 1 FP-1a | ATGACCCGAGCCGCA | GAGCGAGGCCAAGGG | GCTACAGGCTGGGGA | CTGCGAGGCGCCCTG | ATGGCCCGTGGCGCTG | CTGTCAGTGCTGAAC | 90 |
| 2 rGliomedin | ATGACCCGAGCCCGCA | GAGCGAGGCCAAGGG | GCTACAGGCTGGGGA | CTGCGAGGCGCCCTG | ATGGCCGTGGCGCTG | CTGTCAGTGCTGAAC | 90 |
| 3 hFP-1 | ATGGCCCGAGGCGCT | GAGGGAGGCCCGTGGG | GACGCGGGTTGGGGC | CTGCGTGGCGCCCTG | GCGGCCCGTGGCGCTG | CTCTCGGGCTCAAC | 90 |
| 4 hCrgl2 | ------ | ------ | ------ | ------ | ------ | ------ | 0 |
| 5 FP-1b | ATGACCCGAGCCGCA | GAGCGAGGCCAAGGG | GCTACAGGCTGGGGA | CTGCGAGGCGCCCTG | ATGGCCGTGGCGCTG | CTGTCAGTGCTGAAC | 90 |
| 6 mCRG-L2 | ATGACCCGAGCCGCA | GAGCGAGGCCAAGGG | GCTACAGGCTGGGGG | CTGCGCGGCGCCCCTG | GTGGCCATAGCGCTG | CTGTCCGCACTGAAC | 90 |

FIG. 9A

```
1 FP-1a      GCCGTGGGCACCGTG TTCGTGCTGTACCAG TGGCGCGAGCTGAGC GCGGCGCTGCGGGCA CTTGGAGGCGCAACAC GGCCAGGAGCAGCGC      180
2 rGliomedin GCCGTGGGCACCGTG TTCGTGCTGTACCAG TGGCGCGAGCTGAGC GCGGCGCTGCGGGCA CTTGGAGGCGCAACAC GGCCAGGAGCAGCGC      180
3 hFP-1      GCTGCGGGCACGGTG TTCGCGCTGTGCCAG TGGCGCGGGGCTGAGC TCGCGCTGCGGGCT TTGGAGGCGCGGGCGG GGCCGGGAGCAGCGC     180
4 hCrgl2     ---------------  ---------------  ---------------  ---------------  ---------------  ---------------        0
5 FP-1b      GCCGTGGGCACCGTG TTCGTGCTGTACCAG ---------------  ---------------  ---------------  ----------CAGCGC     126
6 mCRG-L2    GCCGCGGGCACCGTG TTCGTGCTGTGCCAG TGGCGGGGGTTAAGC GCGGCGCTACGGGCG CTTGGAGGCTCAACGC GGCCGAGAGCAGCGC      180

181             195 196         210 211             225 226         240 241             255 256         270
1 FP-1a      GAGGACAGCGCCCTA CGGCCCTTTCTAGCT GAATTAAGTCGTGCG CCAGCCCGAGTCGTG GAACCACCCCAGGAC CCCATGAGTGCAGCG      270
2 rGliomedin GAGGACAGCGCCCTA CGCGCCTTTCTAGCT GAATTAAGTCGTGCG CCAGCCCGAGTCGTG GAACCACCCCAGGAC CCCATGAGTGCAGCG      270
3 hFP-1      GAGGACAGTGCCCTG CGTCCTCCTCCTGGCC GAGTTGAGTCGCCGCG CCGCGCCCGAGTCGTCC GCACCACCCCAAGAC CCGGCCCAGTCAGCT   270
4 hCrgl2     ---------------  ---------------  ---------------  ---------------  ---------------  ---------------        0
5 FP-1b      GAGGACAGCGCCCTA CGGGCCCTTTCTAGCT GAATTAAGTCGTGCC CCAGCCCCGAGTCGCC GAACCACCCCGAGTCCCC CCCATGAGTGCAGCG   216
6 mCRG-L2    GAGGACAGCGCCCCTA CGCGCCCCCCTA    GAATTGAGTCGTGCC CCGGGCCCGGGGTCCCC GAACCATCCCAGGAC CCCATGAGCGCAGCG    270

271             285 286         300 301             315 316         330 331             345 346         360
1 FP-1a      CGCAATAAGCCAGC CACGGGCGGCGAGCCT GCGTCACACATCCGC GCGGAGAGCCAGGAC ATGATGATGATGATG ACCTACAGCATGGTG      360
2 rGliomedin CGCAATAAGCCAGC CACGGGCGGCGAGCCT GCGTCACACATCCGC GCGGAGAGCCAGGAC ATGATGATGATGATG ACCTACAGCATGGTG      360
3 hFP-1      CGCAACAAGCCCAGC CACAGCGGCGAGCCC GCGCCCGCATATCCGC GCCGAGAGCCATGAC ATGCTGATGATGATG ACCTACTCCATGGTG     360
4 hCrgl2     ---------------  ---------------  ---------------  ---------------  ---------------  ---------------        0
5 FP-1b      CGCAATAAGCCCAGC CACGGCGGCGAGCCT GCGTCACACATCCGC GCGGAGAGCCAGGAC ATGATGATGATGATG ACCTACAGCATGGTG      306
6 mCRG-L2    CGCAACAAGCCCAGC CACAACGGCGAGCCT GCGTCACACATCCGT GCGGAGAGCCAGGAC ATGATGATGATGATG ACCTACTCCATGGTG      360
```

FIG. 9B

|   | 361 | 375 376 | 390 391 | 405 406 | 420 421 | 435 436 | 450 | |
|---|---|---|---|---|---|---|---|---|
| 1 FP-1a | CCGATCCGGGTGATG | ATAGACCTGTGCAAC | AGCACCCAGGGCATC | TGCCTTACAGGACCA | CCGGGCCCACCAGGA | CCTCCAGGAGCTGGT | 450 | |
| 2 rGliomedin | CCGATCCGGGTGATG | ATAGACCTGTGCAAC | AGCACCCAGGGCATC | TGCCTTACAGGACCA | CCGGGCCCACCAGGA | CCTCCAGGAGCTGGT | 450 | |
| 3 hFP-1 | CCGATCCGAGTGATG | GTGGACCTGTGCAAC | AGCACCAAGGGCATC | TGCCTCACAGGACCT | TCTGGACCACCAGGA | CCTCCGGGAGCCGGC | 450 | |
| 4 hCrgl2 | --------ATG | GTGGACCTGTGCAAC | AGCACCAAGGGCATC | TGCCTCACAGGACCT | TCTGGACCACCAGGA | CCTCCGGGAGCCGGC | 78 | |
| 5 FP-1b | CCGATCCGGGTGATG | ATAGACCTGTGCAAC | AGCACCCAGGGCATC | TGCCTTACAGGACCA | CCGGGCCCACCAGGA | CCTCCAGGAGCTGGT | 396 | |
| 6 mCRG-L2 | CCGATTCGAGTGATG | ATAGACCTGTGCAAC | AGTACCCAGGGCATC | TGCCTCACAGGACCA | CCGGGCCCACCAGGA | CCTCCAGGAGCCGGC | 450 | |

|   | 451 | 465 466 | 480 481 | 495 496 | 510 511 | 525 526 | 540 | |
|---|---|---|---|---|---|---|---|---|
| 1 FP-1a | GGGTTACCAGGCCAC | AATGGATCAGATGGA | CAGCCTGGTCTTCCAG | GGCCCAAAAGGAGAA | AAAGGAGCAGTTGGG | AAGAGAGGAAAAATG | 540 | |
| 2 rGliomedin | GGGTTACCAGGCCAC | AATGGATCAGATGGA | CAGCCTGGTCTTCCAG | GGCCCAAAAGGAGAA | AAAGGAGCAGTTGGG | AAGAGAGGAAAAATG | 540 | |
| 3 hFP-1 | GGGTTGCCAGGACAC | AACGGATTGGATGGA | CAGCCTGGTCTCCAG | GGCCCAAAAGGAGAA | AAAGGAGCAAATGGA | AAAAGAGGAAAAATG | 540 | |
| 4 hCrgl2 | GGGTTGCCAGGACAC | AATGGATCAGATGGA | CAGCCTGGTCTCCAG | GGCCCAAAAGGAGAA | AAAGGAGCAAATGGA | AAAAGAGGAAAAATG | 168 | |
| 5 FP-1b | GGGTTACCAGGCCAC | AATGGATCAGATGGA | CAGCCTGGTCTTCCAG | GGCCCAAAAGGAGAA | AAAGGAGCAGTTGGG | AAGAGAGGAAAAATG | 486 | |
| 6 mCRG-L2 | GGGTTACCAGGCCAC | AATGGATCAGATGGA | CAGCCTGGTCTCTCCAG | GGCCCAAAAGGAGAA | AAAGGAGCAATTGGC | AAGAGAGGAAAAATG | 540 | |

|   | 541 | 555 556 | 570 571 | 585 586 | 600 601 | 615 616 | 630 | |
|---|---|---|---|---|---|---|---|---|
| 1 FP-1a | GGGTTACCCGGAGCC | ACAGGAAAATCCAGGG | GAAAAGGGAGAGAAG | GGAGATGCTGGTGAA | CTGGGCCTACCTGGA | AATGAGGGACCACCA | 630 | |
| 2 rGliomedin | GGGTTACCCGGAGCC | ACAGGAAAATCCAGGG | GAAAAGGGAGAGAAG | GGAGATGCTGGTGAA | CTGGGCCTACCTGGA | AATGAGGGACCACCA | 630 | |
| 3 hFP-1 | GGGATACCTGGAGCT | GCAGGAAAATCCAGGG | GAAAAGGGAGAAAAG | GGAGACCATGGTGAA | CTGGGCCTGCCAGGGA | AATGAGGGACCACCA | 630 | |
| 4 hCrgl2 | GGGATACCTGGAGCT | GCAGGAAAATCCAGGG | GAAAAGGGAGAAAAG | GGAGACCATGGTGAA | CTGGGCCTGCCAGGGA | AATGAGGGACCACCA | 258 | |
| 5 FP-1b | GGGTTACCCGGAGCC | ACAGGAAAATCCAGGG | GAAAAGGGAGAGAAG | GGAGATGCTGGTGAA | CTGGGCCTACCTGGA | AATGAGGGACCACCA | 576 | |
| 6 mCRG-L2 | GGGTTACCTGGAGCC | ACCGGAAAATCCAGGG | GAAAAGGGAGAAAAG | GGAGATGCTGGTGAA | CTGGGTCTACCTGGA | AATGAGGGCCCACCA | 630 | |

FIG. 9C

```
           631            645 646            660 661            675 676            690 691            705 706            720
1 FP-1a     GGACAGAAAGGAGAC AAAGGAGACAAAGGA GATGTGTCCAATGAC GTGCTTTTGACAGGT GCCAAAGGTGACCAA GGGCCCCCTGGCCCA 720
2 rGliomedin GGACAGAAAGGAGAC AAAGGAGACAAAGGA GATGTGTCCAATGAC GTGCTTTTGACAGGT GCCAAAGGTGACCAA GGGCCCCCTGGCCCA 720
3 hFP-1     GGGCAGAAGGGAGAA AAGGGTGACAAAGGA GATGTGTCCAACGAC GTGCTCCTGGCAGGT GCCAAAGGTGACCAA GGCCACCCGGTCCA  720
4 hCrgl2    GGGCAGAAGGGAGAA AAGGGTGACAAAGGA GATGTGTCCAACGAC GTGCTCCTGGCAGGT GCCAAAGGTGACCAA GGCCACCCGGTCCA  348
5 FP-1b     GGACAGAAAGGAGAC AAAGGAGACAAAGGA GATGTGTCCAATGAC GTGCTTTTGACAGGT GCCAAAGGTGACCAA GGGCCCCCTGGCCCA 666
6 mCRG-L2   GGGCAGAGAAGTGAC AAGGGAGACAAAGGA GACGTGTCCAATGAC GTGCTTTTGACAGGT GCCAAAGGTGACCAA GGTCCCCCTGGCCCC 720

721            735 736            750 751            765 766            780 781            795 796            810
1 FP-1a     CCTGGACCCCCAGGG CCTCCAGGCCCTTC- --------------- --TGGAAGC AGAAGAGCCAAAGGC CCTCGGCAGCCAAAT TCGTTCACCAACCAG 801
2 rGliomedin CCTGGACCCCCAGGG CCTCCAGGCCCTTC- --------------- --TGGAAGC AGAAGAGCCAAAGGC CCTCGGCAGCCAAAT TCGTTCACCAACCAG 801
3 hFP-1     CCTGGGCCCCCAGGC CCTCCAGGTCCTCCA --------------- --TGGAAGC AGAAGAGCCAAAGGC CCTCGGCAGCCAAGC ATGTTCAACGGCCAG 810
4 hCrgl2    CCTGGGCCCCCAGGC CCTCCAGGTCCTCCA GGGCCCCCTGGCCCA GGGCCCCCTGGCCCA AGAAGAGCCAAAGGC CCTCGGCAGCCAAGC ATGTTCAACGGCCAG 438
5 FP-1b     CCTGGACCCCCAGGG CCTCCAGGCCCTTC- --------------- --TGGAAGC AGAAGAGCCAAAGGC CCTCGGCAGCCAAAT TCGTTCACCAACCAG 747
6 mCRG-L2   CCTGGACCTCCAGGG CCTCCAGGCCCTCC- --------------- --TGGAAGC AGAAGATCCAAAGGC CCACCACCAAAAAC GTGTTCAACAGCCAG 801

811            825 826            840 841            855 856            870 871            885 886            900
1 FP-1a     TGTCCAGGGGGAGACG TGTGTCATACCCAAT GATGATACCCTTGGTG GGGAGAGCTGATGAG AAAGTCAATGAGCGC CATTCTCCACAAACA 891
2 rGliomedin TGTCCAGGGGGAGACG TGTGTCATACCCAAT GATGATACCCTTGGTG GGGAGAGCTGATGAG AAAGTCAATGAGCGC CATTCTCCACAAACA 891
3 hFP-1     TGCCCAGGTGAGACT TGTGTCATACCCAAT GATGATACCCTTGGTT GGAAAAGTGATGAG AAAGCCAGTGAACAC CATTCCCCACAAGCA 900
4 hCrgl2    TGCCCAGGTGAGACT TGTGTCATACCCAAT GATGATACCCTTGGTT GGAAAAGTGATGAG AAAGCCAGTGAACAC CATTCCCCACAAGCA 528
5 FP-1b     TGTCCAGGGGGAGACG TGTGTCATACCCAAT GATGATACCCTTGGTG GGGAGAGCTGATGAG AAAGTCAATGAGCGC CATTCTCCACAAACA 837
6 mCRG-L2   TGTCCAGGGGGAGACG TGTGTCATACCCAAT GATGATACCCTTGGTG GGAAGAGCTGATGAG AAAGCAAATGAACGC CATTCACCACAAACA 891
```

FIG. 9D

| | 901 | 915 916 | 930 931 | 945 946 | 960 961 | 975 976 | 990 | |
|---|---|---|---|---|---|---|---|---|
| 1 FP-1a | GAACCCATGATCACG | TCCATTGGTAACCCG | GCCCAAGTCCTCAAA | GTGAAAGAGACTTTT | GGGACCTGGCTAAGA | GAGTCTGCTAACAGG | | 981 |
| 2 rGliomedin | GAACCCATGATCACG | TCCATTGGTAACCCG | GCCCAAGTCCTCAAG | GTGAAAGAGACTTTT | GGGACCTGGCTAAGA | GAGTCTGCTAACAGG | | 981 |
| 3 hFP-1 | GAATCCATGATCACT | TCCATTGGAAACCCA | GTGCAAGTACTGAAA | GTGACAGAGACATTT | GGGACTTGGATAAGA | GAGTCTGCTAACAAG | | 990 |
| 4 hCrgl2 | GAATCCATGATCACT | TCCATTGGAAACCCA | GTGCAAGTACTGAAA | GTGACAGAGACATTT | GGGACTTGGATAAGA | GAGTCTGCTAACAAG | | 618 |
| 5 FP-1b | GAACCCATGATCACG | TCCATTGGTAACCCG | GCCCAAGTCCTCAAA | GTGAAAGAGACTTTT | GGGACCTGCTAAGA | GAGTCTGCTAACAGG | | 927 |
| 6 mCRG-L2 | GAATCATGATCACT | TCCATTGGCAACCCA | GCCCAAGTCCTAAAA | GTGAGAGAGACTTTT | GGGACTTGGATGAGA | GAGTCTGCTAACAAA | | 981 |

| | 991 | 1005 1006 | 1020 1021 | 1035 1036 | 1050 1051 | 1065 1066 | 1080 | |
|---|---|---|---|---|---|---|---|---|
| 1 FP-1a | AGTGATGACCGCATT | TGGGTGACTGAACAT | TTTTCAGGCATCATG | GTGAAGGAGTTTGAA | GACCTGCCCGCCCTC | CTGAATAGCAGCTTC | | 1071 |
| 2 rGliomedin | AGTGACGACCGCATT | TGGGTGACTGAACAT | TTTTCAGGCATCATG | GTGAAGGAGTTTGAA | GACCTGCCCGCCCTC | CTGAATAGCAGCTTC | | 1071 |
| 3 hFP-1 | AGTGATGACCGGATT | TGGGTGACAGAGCAT | TTTTCAGGCATCATG | GTTAAGGAATTCAAG | GATCAGCCCTCACTT | CTGAATGGCAGTTAC | | 1080 |
| 4 hCrgl2 | AGTGATGACCGGATT | TGGGTGACAGAGCAT | TTTTCAGGCATCATG | GTTAAGGAATTCAAG | GATCAGCCCTCACTT | CTGAATGGCAGTTAC | | 708 |
| 5 FP-1b | AGTGATGACCGCATT | TGGGTGACTGAACAT | TTTTCAGGCATCATG | GTGAAGGAGTTTCAAG | GACCTGCCCGCCCTC | CTGAATAGCAGCTTC | | 1017 |
| 6 mCRG-L2 | AGTGACGACCGCATT | TGGGTGACTGAACAT | TTTTCAGGCATCATG | GTGAAGGAGTTCAAA | GACCTGCCCGCGCTC | CTCAATAGCAGCTTC | | 1071 |

| | 1081 | 1095 1096 | 1110 1111 | 1125 1126 | 1140 1141 | 1155 1156 | 1170 | |
|---|---|---|---|---|---|---|---|---|
| 1 FP-1a | ACCCTCCTCCACCTC | CCATTACTTCCAT | GGCTGCGGGCACGCT | GTTACAACAACTCT | CTCTACTACCACAAA | GGAGGCTCCAACACC | | 1161 |
| 2 rGliomedin | ACCCTCCTCCACCTC | CCACATTACTTCCAT | GGCTGCGGGCACGCT | GTTACAACAACTCT | CTCTACTACCACAAA | GGAGGCTCCAACACC | | 1161 |
| 3 hFP-1 | ACGTTCATCACCCTT | CCATACTATTTCCAT | GGCTGTGGGCACGTT | GCTTACACAACAACTCT | CTCTACTACCACAAA | GGGGGTTCTAATACC | | 1170 |
| 4 hCrgl2 | ACGTTCATCCACCTT | CCATATATTCCAT | GGCTGTGGGCACGTT | GCTTACACAACAACTCT | CTCTACTACCACAAA | GGGGGTTCTAATACC | | 798 |
| 5 FP-1b | ACCCTCCTCCACCTC | CCACATTACTTCCAT | GGCTGCGGGCACGCT | GTTACAACAACTCT | CTCTACTACCACAAA | GGAGGCTCCAACACC | | 1107 |
| 6 mCRG-L2 | ACACTCCTCCACCTC | CCACATTATTCCAC | GGCTGTGGGCACGCT | GTTACAACAACTCT | CTCTACTACCACAAA | GGAGGCTCCAACACC | | 1161 |

FIG. 9E

|   |      | 1171       | 1185 1186  | 1200 1201  | 1215 1216  | 1230 1231  | 1245 1246  | 1260 |      |
|---|------|------------|------------|------------|------------|------------|------------|------|------|
| 1 | FP-1a       | ATAGTGAGATTTGAA | TTTGGGAAAGAGACA | CCTCAAACTCTGAAG | CTTGAAGATGCTTTG | TATTTTGATCGAAAA | TACCTCTTTTGCGAAT | | 1251 |
| 2 | rGliomedin  | ATAGTGAGATTTGAA | TTTGGGAAAGAGACA | CCTCAAACTCTGAAG | CTTGAAGATGCTTTG | TATTTTGATCGAAAA | TACCTCTTTTGCGAAT | | 1251 |
| 3 | hFP-1       | CTAGTGAGATTTGAA | TTTGGCCAGGAAACA | TCCCAAACTCTGAAG | CTTGAAAATGCCTTG | TATTTTGATCGAAAT | TACCTCTTTTGCAAAT | | 1260 |
| 4 | hCrgl2      | CTAGTGAGATTTGAA | TTTGGCCAGGAAACA | TCCCAAACTCTGAAG | CTTGAAAATGCCTTG | TATTTTGATCGAAAA | TACCTTTTTGCAAAT | | 888 |
| 5 | FP-1b       | ATAGTGAGATTTGAA | TTTGGGAAAGAGACA | CCTCAAACTCTGAAG | CTTGAAGATGCTTTG | TATTTTGATCGAAAA | TACCTCTTTTGCGAAT | | 1197 |
| 6 | mCRG-L2     | ATAGTGAGATTTGAA | TTTGGGAAAGAGACA | CCTCAGACTCTGAAG | CTGGAAAATGCTTTG | TATTTTGATCGAAAA | TACCTCTTTTGCAAAT | | 1251 |

|   |      | 1261       | 1275 1276  | 1290 1291  | 1305 1306  | 1320 1321  | 1335 1336  | 1350 |      |
|---|------|------------|------------|------------|------------|------------|------------|------|------|
| 1 | FP-1a       | TCCAAGACTTACTTC | AACATAGCAGTGGAT | GAGAAGGGCCTCTCG | ATTATCTACGCCTCG | AGTGTGGATGGCTCA | AGCATCCTTGTGGCA | | 1341 |
| 2 | rGliomedin  | TCCAAGACTTACTTC | AACATAGCAGTGGAT | GAGAAGGGCCTCTCG | ATTATCTACGCCTCG | AGTGTGGATGGCTCA | AGCATCCTTGTGGCA | | 1341 |
| 3 | hFP-1       | TCCAAAAACTTACTTC | AATCTAGCTGTGTAGAT | GAAAAAGGGCCTTTGG | ATTATCTATGCGTCA | AGTGTGGACGGCTCG | AGCATTCCTTGTAGCA | | 1350 |
| 4 | hCrgl2      | TCCAAAAACTTACTTC | AATCTAGCTGTGTAGAT | GAAAAGGGCCTTTGG | ATTATCTATGCGTCA | AGTGTGGACGGCTCG | AGCATTCCTTGTAGCA | | 978 |
| 5 | FP-1b       | TCCAAGACTTACTTC | AACATAGCAGTGGAT | GAGAAGGGCCTCTCG | ATTATCTACGCCTCG | AGTGTGGATGGCTCA | AGCATCCTTGTGGCA | | 1287 |
| 6 | mCRG-L2     | TCCAAGACTTACTTC | AACATAGCAGTGGAT | GAGAAGGGCATCTCG | ATTATCTACGCTTCA | AGTGTGGATGGCTCA | AGCATCCTTGTAGCA | | 1341 |

|   |      | 1351       | 1365 1366  | 1380 1381  | 1395 1396  | 1410 1411  | 1425 1426  | 1440 |      |
|---|------|------------|------------|------------|------------|------------|------------|------|------|
| 1 | FP-1a       | CAGCTGGACGAGAGG | ACATTCTCTGTGCTG | CAGCACATCAATAACC | ACATACCCAAGTCC | AAGGCTGGCAATGCC | TTCATAGCTCAAGGG | | 1431 |
| 2 | rGliomedin  | CAGCTGGACGAGAGG | ACATTCTCTGTGCTG | CGGCACATCAATAACC | ACATACCCAAGTCC | AAGGCTGGCAATGCC | TTCATAGCTCAAGGG | | 1431 |
| 3 | hFP-1       | CAACTGGATGAGAGG | ACATTCTCAGTGGTG | CAACACGTCAATAACC | ACGTACCCTAAATCC | AAGGCTGGCAACGCC | TTCATTGCCCGAGGA | | 1440 |
| 4 | hCrgl2      | CAACTGGATGAGAGG | ACATTCTCAGTGGTG | CAACACGTCAATAACC | ACGTACCCTAAATCC | AAGGCTGGCAACGCC | TTCATTGCCCGAGGA | | 1068 |
| 5 | FP-1b       | CAGCTGGACGAGAGG | ACATTCTCTGTGCTG | CAGCACATCAATAACC | ACATACCCCAAGTCC | AAGGCTGGCAATGCC | TTCATAGCTCAAGGG | | 1377 |
| 6 | mCRG-L2     | CAGCTGGATGAGAGG | ACATTCTCCGTGACA | CAGCACATCAACACC | ACATACCCCAAATCC | AAGGCTGGCAATGCC | TTCATAGCCCAGGGG | | 1431 |

FIG. 9F

|   | 1441 | 1455 1456 | 1470 1471 | 1485 1486 | 1500 1501 | 1515 1516 | 1530 |   |
|---|---|---|---|---|---|---|---|---|
| 1 FP-1a | ATCCTCTATGTCACG | GACACCAAAGATACA | AGGGTCACGTTTGCC | TTTGATTTGTTACGA | GGGAAGCAGATCAAT | GCAAACTTCGGTCTC | 1521 |
| 2 rGliomedin | ATCCTCTATGTCACG | GACACCAAAGATACA | AGGGTCACGTTTGCC | TTTGATTTGTTACGA | GGGAAGCAGATCAAT | GCAAACTTCGGTCTC | 1521 |
| 3 hFP-1 | ATCCTCTATGTCACA | GACACCAAAGATATG | AGGGTCACATTTGCC | TTTGATTTGTTAGGA | GGGAAACAGATCAAT | GCAAACTTTGATTTA | 1530 |
| 4 hCrgl2 | ATCCTCTATGTCACA | GACACCAAAGATATG | AGGGTCACATTTGCC | TTTGATTTGTTAGGA | GGGAAACAGATCAAT | GCAAACTTTGATTTA | 1158 |
| 5 FP-1b | ATCCTCTATGTCACG | GACACCAAAGATACA | AGGGTCACGTTTGCC | TTTGATTTGTTACGA | GGGAAGCAGATCAAT | GCAAACTTCGGTCTC | 1467 |
| 6 mCRG-L2 | ATCCTCTATGTCACA | GACACCAAAGATACG | AGGGTCACGTTTGCC | TTTGATTTGTTAGGA | GGAAAGCAAATCAAT | GCAAACTTTGATTTC | 1521 |

|   | 1531 | 1545 1546 | 1560 1561 | 1575 1576 | 1590 1591 | 1605 1606 | 1620 |   |
|---|---|---|---|---|---|---|---|---|
| 1 FP-1a | AGAATGTCACAGTCT | GTTCTTGCCATGTTG | TCGTACAATATGAGA | GACCAGCATTGTAC | TCGTGGGAAGACGGC | CACCTGATGCTCTAT | 1611 |
| 2 rGliomedin | AGAATGTCACAGTCT | GTTCTTGCCATGTTG | TCGTACAATATGAGA | GACCAGCATTGTAC | TCGTGGGAAGACGGC | CACCTGATGCTCTAT | 1611 |
| 3 hFP-1 | AGAACTTCCCAGTCT | GTTCTTGCCATGTTA | GCATACAACATGAGA | GATCAGCATTTATAT | TCATGGGAAGATGGC | CATTTAATGCTTTAT | 1620 |
| 4 hCrgl2 | AGAACTTCCCAGTCT | GTTCTTGCCATGTTA | GCATACAACATGAGA | GATCAGCATTTATAT | TCATGGGAAGATGGC | CATTTAATGCTTTAT | 1248 |
| 5 FP-1b | AGAATGTCACAGTCT | GTTCTTGCCATGTTG | TCGTACAATATGAGA | GACCAGCATTGTAC | TCGTGGGAAGACGGC | CACCTGATGCTCTAT | 1557 |
| 6 mCRG-L2 | AGAATGTCCCAGTCT | GTTCTTGCCATGCTG | TCATACAACATGAGA | GATCAGCATTATAC | TCGTGGGAAGATGGC | CATCTGATGCTCTAT | 1611 |

|   | 1621 | 1635 1636 | 1650 1651 |   |   |
|---|---|---|---|---|---|
| 1 FP-1a | CCTGTGCACTTTTCG | TCAACAGCACCCAGC | CAGCCGATAG | 1650 | – SEQ ID NO: 28 |
| 2 rGliomedin | CCTGTGCACTTTTCG | TCAACAGCACCCAGC | CAGCCGATAG | 1650 | – SEQ ID NO: 29 |
| 3 hFP-1 | CCTGTGCAGTTTTTG | TCAACTACCTTAAAT | CAGTGA--- | 1656 | – SEQ ID NO: 30 |
| 4 hCrgl2 | CCTGTGCAGTTTTTG | TCAACTACCTTAAAT | CAGTGA--- | 1284 | – SEQ ID NO: 31 |
| 5 FP-1b | CCTGTGCACTTTTCG | TCAACAGCACCCAGC | CAGCCGATAG | 1596 | – SEQ ID NO: 32 |
| 6 mCRG-L2 | CCTGTGCAGTTTCTG | TCAGCGGCATCAAGT | CAGCCGGTAG | 1650 | – SEQ ID NO: 33 |

FIG. 9G

```
1 FP-1a/b  RRAKGPRQPNSFTNQ CPGETCVIPNDDTLV GRADEKVNERHSPQT EPMITSIGNPAQVLK   312/320
2 hFP-1    RRAKGPRQPSMFNGQ CPGETCAIPNDDTLV GKADEKASEHHSPQA ESMITSIGNPVQVLK   314
3 OLF      GILAGVGIPVLLAES QYGKS---------- --------------- ---------------   20
                                  Region 1

1 FP-1a/b  VKETFGTWLRESAN- -RSDDRIWTEHFS-- -GIMVKEFEDLPALL NSS-FTLLHLPHYFH   367/385
2 hFP-1    VTETFGTWIRESAN- -KSDDRIWTEHFS-- -GIMVKEFKDQPSLL NGS-YTFIHLPYYFH   369
3 OLF      -----GAWMRDPLPN SMKAKRRWVMDGFAD VSRVLREYSSMSDFL DGVNKIKYYLPHAAS   75
                                  Region 3

1 FP-1a/b  GCGHAVYNNSLYYHK GGSNTIVRFEFGKET PQTLKLEDALYFDRK YLFAN-SKTYFNIAV   426/444
2 hFP-1    GCGHVAYNNSLYYHK GGSNTLVRFEFGQET SQTLKLENALYFDRK YLFAN-SKTYFNLAV   429
3 OLF      GTGNVVYNGSLYFNK FGSHSIVRYELETGV QVKEELLPEAGYNDC FPYAWGGHSDIDLAV   135
                                                         Region 5

1 FP-1a/b  DEKGLWIIYASSVDG SSILVAQLDERTFSV LQHINTTYPKSKAGN AFIAQGILYVTDTKD   486/504
2 hFP-1    DEKGLWIIYASSVDG SSILVAQLDERTFSV VQHVNTTYPKSKAGN AFIARGILYVTDTKD   489
3 OLF      DENGLWIYATEQNA GKIVISKLNPATLFV ENTWNTEYNKRSAAN AFMICGVLYVTKSAN   195
                                  Region 6                    Region 7

1 FP-1a/b  ---TRVTFAFDLLRG KQINANFGLRMSQSV LAMLSYNMRDQHLYS WEDGHLMLYPVHFSS   SEQ ID NO: 36
2 hFP-1    ---MRVTFAFDLLGG KQINANFDLRTSQSV LAMLAYNMRDQHLYS WEDGHLMLYPVQFLS   543/561
3 OLF      SLGTKITYAYDTNTG KTIPLDIPFYNPYQY ISMLDYNPLDRKLYA WDNGHLLSYDIRLEE   546
                      Region 8                              Region 9          255
                                                                              SEQ ID NO: 37
                                                                              SEQ ID NO: 38
```

GAPDH

FP-1

EB

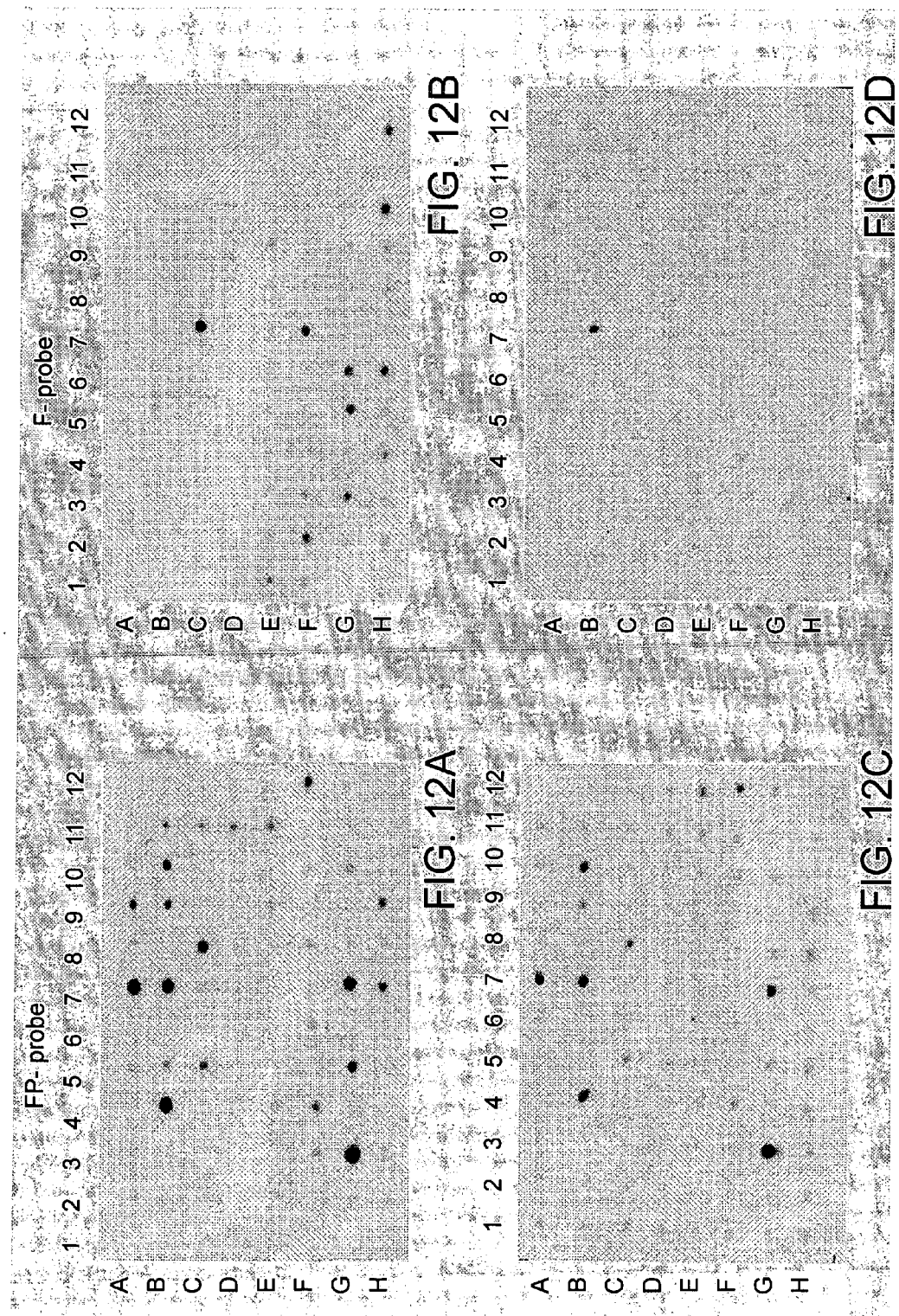

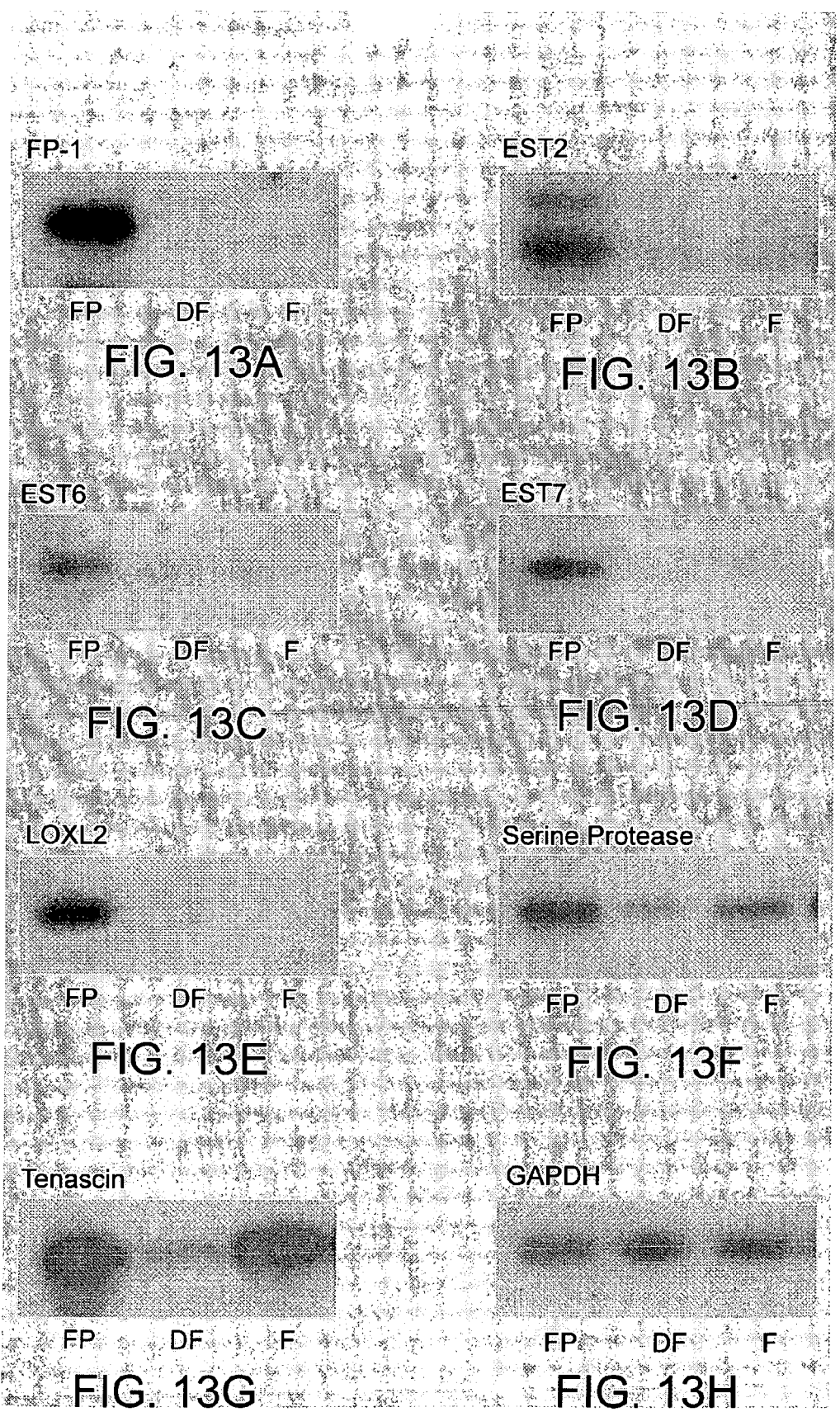

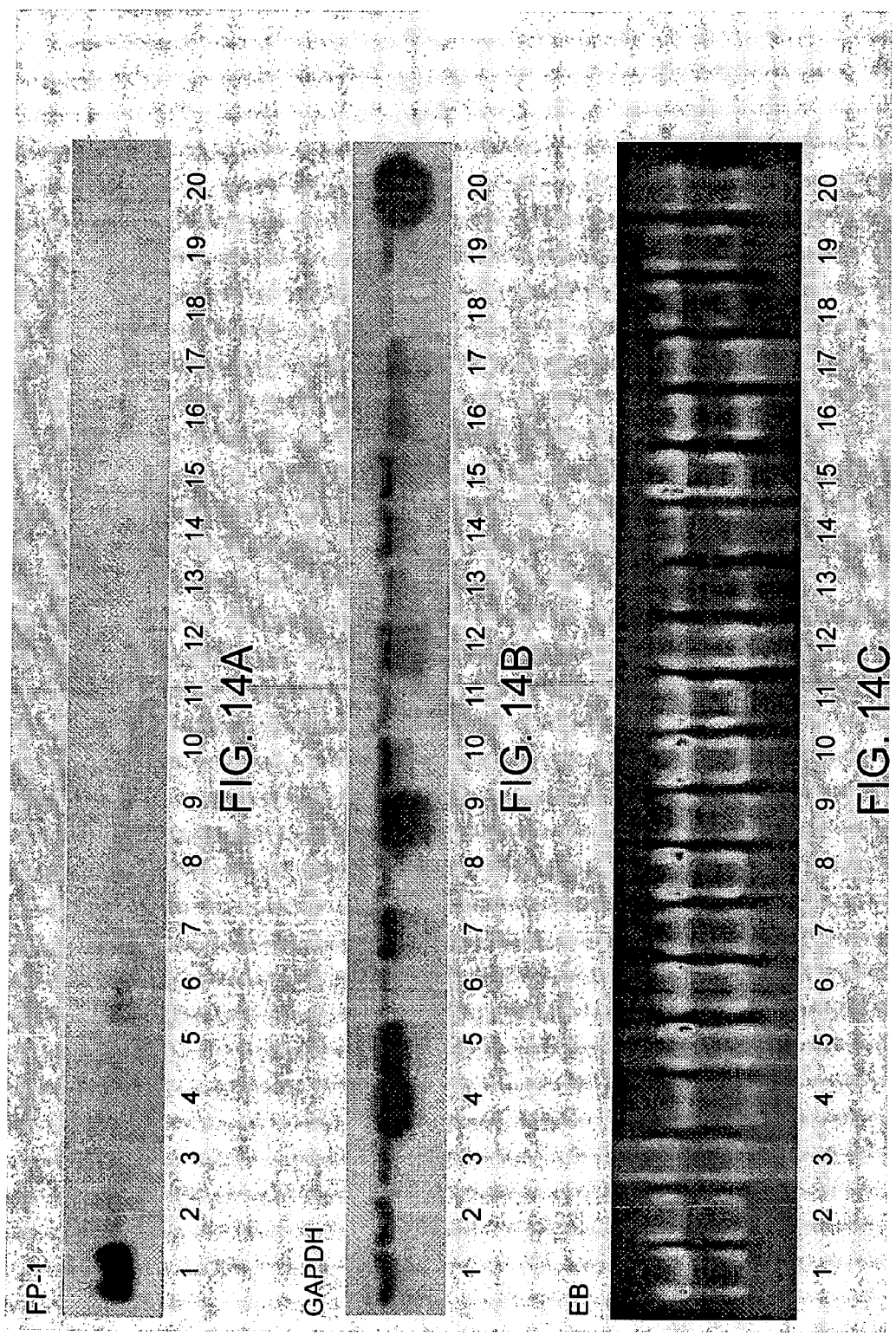

```
  1       M  T  R  A  A  E  R  G  Q  G  A  T  G  W  G
  1   ACGCGGGGAGTGCTGCCCTGAGTCGTTCGGCCTGAGCACAGAGACATGACCCGAGCCGCAGAGCGAGGCCAAGGGGCTACAGGCTGGGGA

16   L  R  G  A  L  M  A  V  A  L  L  S  V  L  N  A  V  G  T  V  F  V  L  Y  Q  W  R  E  L  S
 91   CTGCGAGGCGCCCTGATGGCCGTGGCCCTGCTGTCAGTGCTGAACGCCGTGGGCACCGTGTTCGTGCTGTACCAGTGGCGGAGCTGAGC

46   A  A  L  R  A  L  E  A  Q  H  G  Q  E  Q  R  E  D  S  A  L  R  A  F  L  A  E  L  S  R  A
181   GCGGGCGCTGCGGGCACTGGAGGCGCAACACGGCCAGGAGCAGCGCCTACGCGCCTTTCTAGCTGAATTAAGTCGTGCG

Epitope 1
 76   P  A  R  V  P  E  P  P  Q  D  P  M  S  A  A  R  N  K  R  S  H  G  G  E  P  A  S  H  I  R
271   CCAGCCCGAGTCCCCGAACCACCCCAGGACCCCATGAGTGCAGCGCGCAATAAGCGCAGCCACGGCGGGCGAGCCTGCTCACACATCCGC 106   A  E  S  Q  D  M  M  M  M  T  Y  S  M  V  P  I  R  V  M  I  D  L  C  N  S  T  Q  G  I
361   GCGGAGAGCCAGGACATGATGATGATGACCTACAGCATGGTGCCGATCCGGGTGATAGACCTGTGCAACAGCACCCAGGGCATC 136   C  L  T  G  P  P  P  G  P  P  P  G  P  P  P  G  A  G  G  L  P  G  H  N  G  S  D  G  Q  P  G  L  Q
451   TGCCTTACAGGACCCGGGCCCACCAGGACCTCCAGGAGCTGGTGGTTACCAGGCCACACCAATGATCAGATGACAGCCTGGTCTCCAG 166   G  P  K  G  E  K  G  A  V  G  K  R  G  K  M  G  L  P  G  A  T  G  N  P  G  E  K  G  E  K
541   GGCCCAAAAGGAGAAAAGGAGAAAAGGAGCAGTTGGGAAGAGAGAAAAAATGGGGTTACCCGGAGCCACAGAGAATCCAGGGAAAAGGGAGAGAAG
```

FIG. 15A

```
196  G  D  A  G  E  L  G  L  P  G  N  E  G  P  P  P  G  Q  K  G  D  K  G  D  K  G  D  V  S  N  D
631  GGAGATGCTGGTGAACTGGGCCTACCTGGGAAATGAGGGACCACCAGGACAAAGGAGACAAAGGAGATGTGTCAATGAC
                                                                        Epitope 2
226  V  L  L  T  G  A  K  G  D  Q  G  P  P  P  G  P  P  P  G  P  P  P  S  G  S  R  R  A
721  GTGCTTTTGACAGGTGCCAAAGTGACCAAGGGCCCCCCTGGCCCACTGGACCCCCTGGACCCCTGGACCCCTCTGGAAGCAGAAGAGCC
                      Epitope 3
256  K  G  P  R  Q  P  N  S  F  T  N  Q  C  P  G  E  T  C  V  I  P  N  D  D  T  L  V  G  R  A
811  AAAGGCCCTCGGCAGCCAAATTCGTTCACCAACCAGTGTCCAGGGGAGACGTGTGTCATACCCAATGATGATACCTTGGTGGGAGAGCT
286  D  E  K  V  N  E  R  H  S  P  Q  T  E  P  M  I  T  S  I  G  N  P  A  Q  V  L  K  V  K  E
901  GATGAGAAAGTCAATGAGCGCCATTCTCCACAAACAGAACCCATGATCACGTCCATTGGTAACCCGGCCCAAGTCCTCAAAGTGAAAGAG
                                Epitope 4
316  T  F  G  T  W  L  R  E  S  A  N  R  S  D  D  R  I  W  V  T  E  H  F  S  G  I  M  V  K  E
991  ACTTTTGGGACCTGGCTAAGAGAGTCTGCTAACAGGAGTGATGACCGCATTTGGGTGACTGAACATTTTCAGGCATCATGGTGAAGGAG
346  F  E  D  L  P  A  L  L  N  S  S  F  T  L  L  H  L  P  H  Y  F  H  G  C  G  H  A  V  Y  N
1081 TTTGAAGACCTGCCCGCCCTCCTGAATAGCAGCTTCACCCTCCTCCACTTACTTCCACATTACTTCCATGGCTGCGGGCACGCTGTTTACAAC
                            Epitope 5
376  N  S  L  Y  Y  H  K  G  G  S  N  T  I  V  R  F  F  F  G  K  E  T  P  Q  T  L  K  L  E  D
1171 AACTCTCTCTACTACCACAAAGGAGGCTCCAACACCATAGTGAGATTTGAATTTGGGAAAGAGACACCTCAAACTCTGAAGCTTGAAGAT
```

FIG. 15B

```
406   A  L  Y  F  D  R  K  Y  L  F  A  N  S  K  T  Y  F  N  I  A  V  D  E  K  G  L  W  I  I  Y
1261  GCTTTGTATTTGATCGAAAATACCTCTTTGCGAATTCAAGACTTACTTCAACATAGCAGTGGATGAGAAGGGCCTCTGGATTATCTAC

436   A  S  S  V  D  G  S  S  I  L  V  A  Q  L  D  E  R  T  F  S  V  L  Q  H  I  N  T  T  Y  P
1351  GCCTCGAGTGTGGATGGCTCAAGCATCCTTGTGGCACAGCTGGACGAGAGACATTCTCTGTGCTGCAGCACATCAATACCACATACCCC

466   K  S  K  A  G  N  A  F  I  A  Q  G  I  L  Y  V  T  D  T  K  D  T  R  V  T  F  A  F  D  L
1441  AAGTCCAAGGCTGGCAATGCCTTCATAGCTCAAGGGATCCTCTATGTCACGGACACAAAAGATACAAGGGTCACGTTTGCCTTTGATTTG

496   L  R  G  K  Q  I  N  A  N  F  G  L  R  M  S  Q  S  V  L  A  M  L  S  Y  N  M  R  D  Q  H
1531  TTACGAGGAAGCAGATCAATGCAAACTTCGGTCTCAGAATGTCACAGTCTGTTCTTGCCATGTTGTCGTACAATATGAGAGACCAGCAT

526   L  Y  S  W  E  D  G  H  L  M  L  Y  P  V  H  F  S  S  T  A  P  S  Q  R        (SEQ ID NO:2)
1621  TTGTACTCGTGGGAAGACGGCCACCTGATGCTCTATCCTGTGCACTTTCGTCAACAGCACCCAGCGCCTGCAGTCGGCTC

1711  CCTCATTATGCACCACACATTTCTGGGGTTTGACCAAGCCCAACGGAAAGAAGGCCTGTAAAGGATATCCAGATACTCAGAGCATACGC
1801  CCGTGTTACGGGCTTTTGTGCATGTGGCAAGTCCCCTGTAAGCCAGTTAACTAAGGCTGGAAAGTTGAAATGGATAACATTGGTGA
1891  CCCTTGGTCCCTCTTCAAACTTAGCAGTTAGTGCTCCCCCTGACCTTAGTGTCCCCATCAGTAATATGAAACATCTGTGATTGCAG
1981  CATTTCCTATACCTATATGAAGTTCTGTAGTTCTTGCCTGGTTATATATTAGAATTGCTTTCAGTTTCTTTTTTTTTCTCCACATGTAA
2071  ATGAGTTTACCTGCAGCTTGAGGGGTGTGCCTATCAGTGATGACGGACATTTGTTGGTGTTTAGGGAAAAAGCATTGTTCTTATGGCT
2161  TTTAAAGTTATTATATATTATCCATAATTTGATATTTTTTTTGAATACGCCCCTGCCACTACAGAATGATTATTGTTTCAGTCCTAAGTA
2251  CAAATCCAAGATTAATAAAAAAAAAAAAACATGAATAGAAAAAAAAAAACTCGAGAGTATTAGTCGATGTAGGAAAAC   (SEQ ID NO:1)
```

FIG. 15C

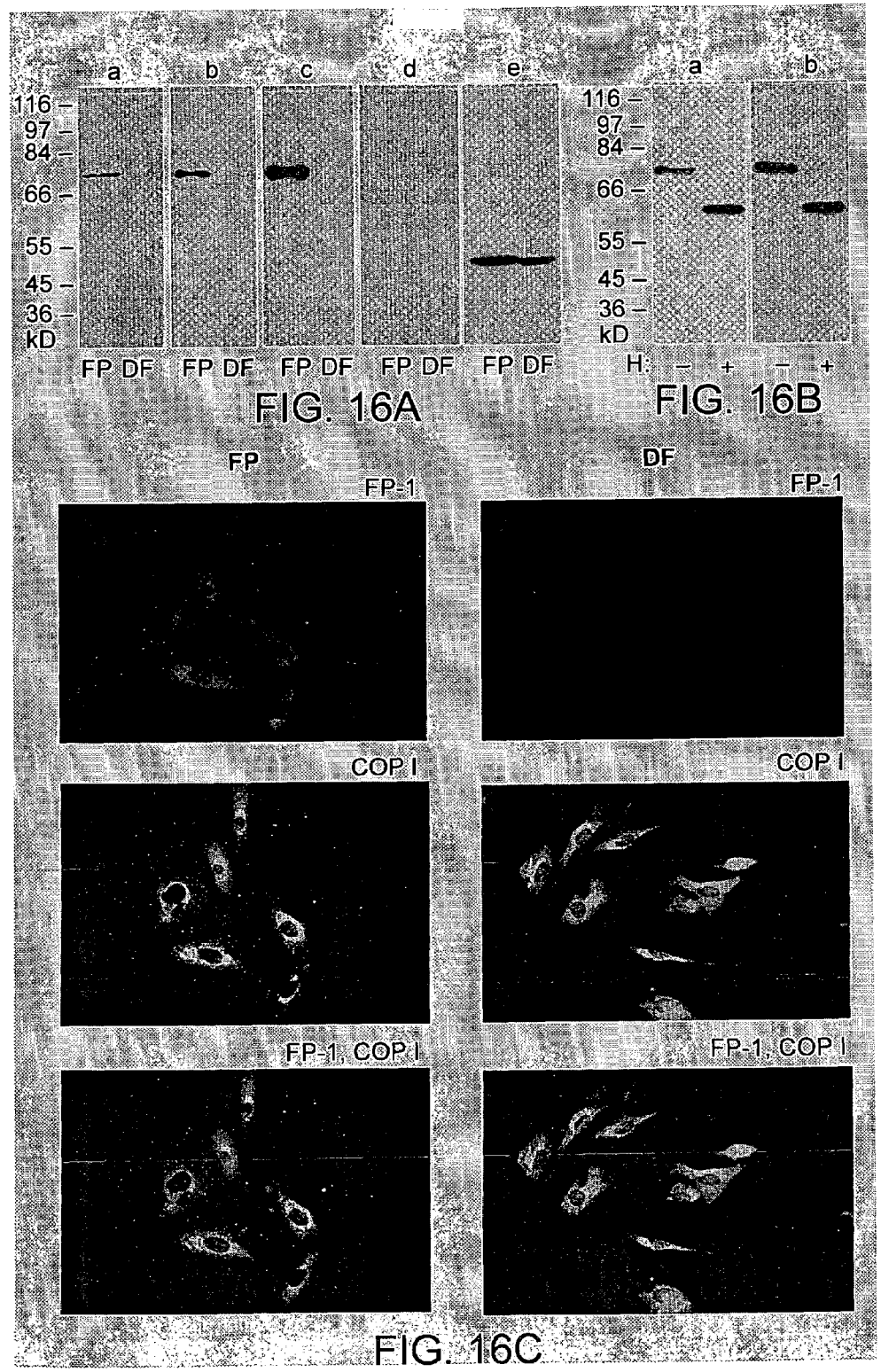

COMPOSITIONS FOR CONTROLLING HAIR GROWTH

CROSS REFERENCE TO RELATED APPLICATIONS

This application claims the benefit of U.S. Provisional Application No. 60/558,341, filed Mar. 31, 2004, now abandoned, the contents of which are hereby incorporated by reference in its entirety.

BACKGROUND OF THE INVENTION (a) Field of the Invention

The present invention relates to the field of dermatology. More specifically, the present invention relates to compositions and methods for modulating hair growth.

(b) Background

Although hair growth disorders are not life threatening, their impact on social interactions and on an individual's psychological well being is undeniable. Thus, effective methods of treating hair growth disorders are greatly desired.

One of the most common hair disorders is alopecia, where humans begin losing scalp hair at the temples and on the crown of their head as they age. Although this type of hair loss is predominantly found in males, it is also present in a certain proportion of women. Alopecia can also be induced by chemical agents or physical agents (e.g., during anti-cancer chemotherapy), and the condition also results from specific disease states.

Another type of hair growth disorder results from abnormally accentuated hair growth. For example, hirsutism is manifested as excessive androgen-dependent hair growth in women, whereas hypertrichosis is an increase in androgen-independent hair growth (Bertolino et al., "Disorders of epidermal appendages and related disorders," in *Dermatology in General Medicine,* 4th ed., pp. 671–695, Fitzpatrick et al., eds. (McGraw-Hill, 1993)).

A traditional treatment for alopecia is hair transplantation. This typically involves transplanting plugs of natural hair from areas of the scalp where hair is growing to bald or thinning areas of the scalp. This procedure is costly, time-consuming, painful, and does not provide a sufficient remedy in all cases. Electrical stimulus has been suggested as an alternative way to promote hair growth (see, e.g., U.S. Pat. No. 5,800,477 and references cited therein); however, such methods are of questionable efficacy.

Other methods for stimulating hair growth comprise the use of various chemicals or drugs, mud preparations, and plant extracts (see, e.g., U.S. Pat. Nos. 5,798,341, 5,767,152, 5,753,713, 5,750,107, 5,741,816, 5,739,111, 5,723,149, 5,679,378, 5,674,497, 5,663,160, 5,656,300, 5,643,898, 4,139,619, and references cited therein). There are two compounds currently in clinical use to treat alopecia: finasteride, sold as PROPECIA®, and minoxidil, marketed as ROGAINE®. A drawback of finasteride is that it can only be used by men. Furthermore, its use can result in sexual side effects such as a decreased desire for sex, difficulty in achieving erection, and a decrease in the amount of semen. Minoxidil is a vasodilatory drug which can have side effects in some patients. Similarly, mud preparations and plant extracts can produce unwelcome side effects in various patients and are of questionable efficacy. Moreover such treatments require a normal scalp with no local abrasions, dermatitis, or sunburn, rendering such methods unavailable to many individuals.

In addition to these hair growth disorders, individuals may also desire to increase, decrease, or prevent hair growth purely for cosmetic reasons. As a result, there is immense interest in the development of effective cosmetic and clinical treatments. Yet, most, if not all, of the known methods to control hair growth have several drawbacks.

For example, various procedures have been used to remove unwanted hair from the groin area, legs and face including shaving, electrolysis, use of depilatory creams, waxing, plucking and therapeutic anti-androgens, see, e.g., U.S. Pat. No. 6,093,748. However, these traditional methods have various drawbacks associated with them. For example, shaving can cause nicks, cuts and undesirable stubble. Although electrolysis keeps a treated area free of hair for prolonged periods of time, it can be expensive, painful, and may leave scarring in some cases. Depilatory creams have a high potential to irritate the skin. Waxing and plucking can cause pain, discomfort and poor removal of short hair. Finally, anti-androgens can have undesirable side effects.

Thus, alternative methods for controlling hair growth are needed.

SUMMARY OF THE INVENTION

The follicular papilla, a cluster of mesenchymal cells at the base of the hair follicle, plays an essential role in hair growth. It has been discovered that various genes are selectively expressed in follicular papilla compared to the neighboring dermal fibroblasts cells. For example, it has been discovered that follicular papilla-1 (FP-1) is selectively expressed in follicular papilla compared to dermal fibroblasts cells. This discovery has been exploited to develop the present invention, which relates to nucleic acids and proteins that control hair growth; compositions that control hair growth; compositions for isolating follicular papilla cells; methods for controlling hair growth; methods for repairing hair follicles; methods for screening for, or identifying, agents that control hair growth; methods for diagnosing hair disorders; and methods of diagnosing cancers.

In one aspect, the invention provides an isolated polynucleotide comprising the DNA sequence of rat FP-1. In some embodiments, the sequence of the rat FP-1 comprises SEQ ID NO:1 or SEQ ID NO:3. In additional embodiments, the invention provides an isolated polynucleotide that is the complement of the polynucleotide comprising SEQ ID NO:1 or SEQ ID NO:3.

In another embodiment, the invention provides a recombinant vector comprising any of the polynucleotides of this aspect of the invention. In a further embodiment, the invention provides a host cell comprising a recombinant vector of this aspect.

In a still further embodiment, the invention provides a method of preparing a substantially purified polypeptide encoded by a recombinant vector of this aspect. In this method, host cells transformed or transfected with a recombinant vector according to the invention are cultured under conditions conducive to the synthesis of the polypeptide. The polypeptide, in substantially purified form, is then isolated from the host cells. In another embodiment, the invention provides an isolated polypeptide comprising the amino acid sequence encoded by a polynucleotide having the DNA sequence of rat FP-1 (SEQ ID NO:1 or SEQ ID NO:3). In some embodiments, this polypeptide comprises SEQ ID NO:2 or SEQ ID NO:4.

In a still further embodiment, an antibody that specifically binds rat FP-1 (SEQ ID NO:2 or SEQ ID NO:4), is provided.

In yet another embodiment, an antibody that binds both a polypeptide comprising SEQ ID NO: 2 and a polypeptide comprising SEQ ID NO: 12, is provided. In another embodiment, the invention provides an antibody that binds both a polypeptide comprising SEQ ID NO: 4 and a polypeptide comprising SEQ ID NO:12.

In another aspect of the invention, an isolated polynucleotide consisting of SEQ ID NO:1 or SEQ ID NO:3 is provided. In one embodiment, the isolated polynucleotide is the complement of any of the polynucleotides of this aspect. In another embodiment, a recombinant vector comprising any of the polynucleotides of this aspect is provided. In a further embodiment, a host cell comprising a recombinant vector of this aspect is provided.

In another embodiment, the invention provides a method of preparing a substantially purified polypeptide encoded by a recombinant vector comprising the polynucleotide consisting of SEQ ID NO:1 or SEQ ID NO:3. In this method, host cells transformed or transfected with the recombinant vector are cultured under conditions conducive to the synthesis of the polypeptide. The polypeptide is then recovered in substantially purified form from the host cells.

In yet a further embodiment of this aspect of the invention, an isolated polypeptide (SEQ ID NO:2) comprising the amino acid sequence encoded by the polynucleotide consisting of the DNA sequence of rat FP-1 (SEQ ID NO:1) is provided. In a further embodiment of this aspect, the invention provides an isolated polypeptide (SEQ ID NO:4) comprising the amino acid sequence encoded by the polynucleotide consisting of the DNA sequence of rat FP-1 (SEQ ID NO:3).

The invention also provides an isolated polynucleotide comprising the DNA sequence of human FP-1. In one embodiment, the sequence of the human FP-1 comprises SEQ ID NO:1. In an additional embodiment, the invention provides an isolated polynucleotide that is the complement of the polynucleotide comprising SEQ ID NO:11. In another embodiment, the invention provides a recombinant vector comprising any of the polynucleotides of this aspect of the invention. In a further embodiment, the invention provides a host cell comprising the recombinant vector of this aspect.

In a still further embodiment, the invention provides a method of preparing a substantially purified polypeptide encoded by the recombinant vector of this aspect. In this method, host cells transformed or transfected with the recombinant vector according to the invention are cultured under conditions conducive to the synthesis of the polypeptide. The polypeptide, in substantially purified form, is then isolated from the host cells.

In another embodiment, the invention provides an isolated polypeptide comprising the amino acid sequence encoded by the polynucleotide having the DNA sequence of human FP-1 (SEQ ID NO:11). In one embodiment, this polypeptide comprises SEQ ID NO:12. In a still further embodiment, an antibody that specifically binds human FP-1 (SEQ ID NO:12), is provided. In yet another embodiment, an antibody that binds both a polypeptide comprising SEQ ID NO: 2 and a polypeptide comprising SEQ ID NO:12 is provided.

In still another embodiment, the invention provides an antibody that binds both a polypeptide comprising SEQ ID NO: 4 and a polypeptide comprising SEQ ID NO:12.

The invention also provides an isolated polynucleotide comprising a nucleic acid sequence that encodes a polypeptide comprising the amino acid sequence of rat FP-1 (SEQ ID NO:2 or SEQ ID NO:4). In one embodiment, the polynucleotide comprises a nucleic acid sequence that encodes a polypeptide comprising amino acids 34 to 549 of SEQ ID NO:2 or amino acids 34 to 531 of SEQ ID NO:4. In another embodiment, the isolated polynucleotide is the complement of any of the polynucleotides of this aspect. In another embodiment, a recombinant vector is provided which comprises any of the polynucleotide of this aspect. In a further embodiment, a host cell comprising a recombinant vector comprising any of the polynucleotides of this aspect is provided. In a still further embodiment, the invention provides a method of preparing a substantially purified polypeptide encoded by a recombinant vector comprising any of the polynucleotides of this aspect. In this method, cells transformed or transfected with the recombinant vector according to the invention are cultured under conditions conducive to the synthesis of the polypeptide. The polypeptide is then recovered in substantially purified form from the cells.

The invention also provides an isolated polynucleotide comprising a nucleic acid sequence that encodes a polypeptide comprising the amino acid sequence of human FP-1 (SEQ ID NO:12). In one embodiment, the polynucleotide comprises a nucleic acid sequence that encodes a polypeptide comprising amino acid 34 to 551 of SEQ ID NO:12. In another embodiment, the isolated polynucleotide is the complement of any of the polynucleotides of this aspect. In another embodiment, a recombinant vector is provided which comprises any of the polynucleotide of this aspect. In a further embodiment, a cell comprising a recombinant vector comprising any of the polynucleotides of this aspect is provided.

In a still further embodiment, the invention provides a method of preparing a substantially purified polypeptide encoded by a recombinant vector comprising the polynucleotide of this aspect. In this method, cells transformed or transfected with the recombinant vector according to the invention are cultured under conditions conducive to the synthesis of the polypeptide. The polypeptide is then recovered in substantially purified form from the cells.

In yet another aspect, the invention provides an isolated polynucleotide comprising a nucleic acid sequence that is homologous to SEQ ID NO:1 or SEQ ID NO:3, wherein the isolated polynucleotide molecule encodes a protein that controls hair growth. In some embodiments, the isolated polynucleotide of this aspect has about 80%, about 85%, about 90%, or about 95% identity to SEQ ID NO:1 or SEQ ID NO:3. In another embodiment, the isolated polynucleotide is the complement of any of the polynucleotides of this aspect of the invention. In another embodiment, a recombinant vector comprising a polynucleotide of this aspect is provided. The invention also provides a cell comprising the recombinant vector having any of the polynucleotides of this aspect.

Also provided is a method of preparing a substantially purified polypeptide encoded by a recombinant vector of this aspect of the invention. In this method, cells transformed or transfected with the recombinant vector are cultured under conditions conducive to the synthesis of the polypeptide. The polypeptide is then recovered in substantially purified form from the cells. In yet a further embodiment of this invention, an isolated polypeptide of this aspect, is provided. In a still further embodiment of the invention, an antibody that specifically binds an isolated polypeptide comprising the amino acid sequence encoded by the polynucleotide of the invention is provided.

In yet another aspect, the invention provides an isolated polynucleotide comprising a nucleic acid sequence that is homologous to SEQ ID NO:11, wherein the isolated polynucleotide molecule encodes a protein that controls hair growth. In some embodiments, the isolated polynucleotide of this aspect is about has about 80%, about 85%, about 90%, or about 95% identity to SEQ ID NO:11. In another embodiment, the isolated polynucleotide is the complement of any of the polynucleotides of this aspect of the invention. In another embodiment, a recombinant vector comprising any of the polynucleotides of this aspect is provided. The invention also provides a cell comprising a recombinant vector having any of the polynucleotides of this aspect.

Also provided is a method of preparing a substantially purified polypeptide encoded by a recombinant vector of this aspect of the invention. In this method, cells transformed or transfected with the recombinant vector are cultured under conditions conducive to the synthesis of the polypeptide. The polypeptide is then recovered in substantially purified form from the cells. In yet a further embodiment, the isolated polypeptide of this aspect of the invention is provided. In a still further embodiment of the invention, an antibody that specifically binds an isolated polypeptide comprising the amino acid sequence encoded by the polynucleotide of this aspect is provided.

In another aspect, the invention provides an isolated polynucleotide comprising a nucleic acid sequence that is homologous to a nucleic acid sequence that encodes a polypeptide comprising SEQ ID NO:2 or SEQ ID NO:4, wherein the isolated polynucleotide molecule encodes a protein that controls hair growth. In some embodiments, the isolated polynucleotide of this aspect has about 80%, about 85%, about 90%, or about 95% identity to a nucleic acid sequence that encodes a polypeptide comprising SEQ ID NO:2 or SEQ ID NO:4. In one embodiment of this aspect, the invention provides an isolated polynucleotide that is the complement of any of the polynucleotides of this aspect. In another embodiment, a recombinant vector of this aspect is provided. In a further embodiment, the invention provides a host cell comprising a recombinant vector having any of the polynucleotides of this aspect.

In yet another embodiment, a method of preparing a substantially purified polypeptide encoded by a recombinant vector of this aspect is provided. The method comprises culturing host cells transformed or transfected with a recombinant vector according to the invention under conditions conducive to the synthesis of the polypeptide. The polypeptide is then recovered in substantially purified form from the host cells. In yet a further embodiment of this invention, an isolated polypeptide comprising the amino acid sequence encoded by a polynucleotide of this aspect, is provided.

In a still further embodiment, the invention provides an antibody that specifically binds an isolated polypeptide of this aspect of the invention.

In another aspect, the invention provides an isolated polynucleotide comprising a nucleic acid sequence that is homologous to a nucleic acid sequence that encodes a polypeptide comprising SEQ ID NO:12, wherein the isolated polynucleotide molecule encodes a protein that controls hair growth. In some embodiments, the isolated polynucleotide of this aspect has about 80%, about 85%, about 90%, or about 95% identity to a nucleic acid sequence that encodes a polypeptide comprising SEQ ID NO:12. In one embodiment of this aspect, the invention provides an isolated polynucleotide that is the complement of any of the polynucleotides of this aspect. In another embodiment, a recombinant vector of this aspect is provided. In a further embodiment, the invention provides a host cell comprising a recombinant vector having any of the polynucleotides of this aspect.

In a still further embodiment, a method of preparing a substantially purified polypeptide encoded by a recombinant vector of this aspect is provided. The method comprises culturing host cells transformed or transfected with a recombinant vector according to the invention under conditions conducive to the synthesis of the polypeptide. The polypeptide is then recovered in substantially purified form from the host cells. In yet a further embodiment of this invention, an isolated polypeptide comprising the amino acid sequence encoded by a polynucleotide of this aspect, is provided.

In yet another embodiment, the invention provides an antibody that specifically binds an isolated polypeptide of this aspect of the invention.

In an additional aspect of the invention, an isolated polynucleotide that specifically hybridizes under highly stringent conditions to a complement of a polynucleotide sequence comprising SEQ ID NO:1 or SEQ ID NO:3, wherein the polynucleotide sequence encodes a protein that controls hair growth is provided. In one embodiment, an isolated polynucleotide that is the complement of any of the polynucleotides of this aspect is provided. In another embodiment, the invention provides a recombinant vector comprising a polynucleotide of this aspect. In a further embodiment, a host cell comprising a recombinant vector comprising any of the polynucleotides of this aspect of the invention is provided. In a still further embodiment, the invention provides a method of preparing a substantially purified polypeptide encoded by a recombinant vector according to the invention. The method comprises culturing host cells transformed or transfected with the recombinant vector under conditions conducive to the synthesis of the polypeptide of the invention. The polypeptide is then recovered in substantially purified form from the host cells. In yet a further embodiment of this invention, an isolated polypeptide comprising the amino acid sequence encoded by any of the polynucleotides of this aspect is provided. In a still further embodiment, the invention provides an antibody that specifically binds an isolated polypeptide comprising the amino acid sequence encoded by a polynucleotide according to this aspect.

The invention also provides an isolated polynucleotide that specifically hybridizes under highly stringent conditions to a complement of a polynucleotide sequence comprising SEQ ID NO:11, wherein the polynucleotide sequence encodes a protein that controls hair growth. In one embodiment, an isolated polynucleotide that is the complement of any of the polynucleotides of this aspect is provided. In another embodiment, the invention provides a recombinant vector comprising a polynucleotide of this aspect. In a further embodiment, a host cell comprising a recombinant vector comprising any of the polynucleotides of this aspect of the invention is provided.

In a still further embodiment, the invention provides a method of preparing a substantially purified polypeptide encoded by a recombinant vector according to the invention. The method comprises culturing host cells transformed or transfected with the recombinant vector under conditions conducive to the synthesis of the polypeptide of the invention. The polypeptide is then recovered in substantially purified form from the host cells. In yet a further embodiment of this invention, an isolated polypeptide comprising the amino acid sequence encoded by any of the polynucleotides of this aspect is provided.

In a still further embodiment, the invention provides an antibody that specifically binds an isolated polypeptide comprising the amino acid sequence encoded by a polynucleotide according to this aspect.

The present invention also encompasses an isolated polynucleotide molecule that specifically hybridizes under highly stringent conditions to a complement of a polynucleotide sequence comprising a nucleotide sequence that encodes a polypeptide having SEQ ID NO:2, SEQ ID NO:4 or SEQ ID NO:12, wherein the polynucleotide sequence encodes a protein that controls hair growth. In one embodiment, the present invention provides an isolated polynucleotide that is the complement of any of the polynucleotides of this aspect. In another embodiment, a recombinant vector comprising a polynucleotide molecule of this aspect is provided. In a further embodiment, the invention provides a host cell comprising a recombinant vector comprising any of the polynucleotides of this aspect.

In a still further embodiment, the invention provides a method of preparing a substantially purified polypeptide encoded by a recombinant vector comprising a polynucleotide molecule according to this aspect. In this method, host cells transformed or transfected with the recombinant vector are cultured under conditions conducive to the synthesis of the polypeptide according to the invention. The polypeptide is then recovered in substantially purified form from the host cells. In yet a further embodiment of this invention, an isolated polypeptide comprising the amino acid sequence encoded by the polynucleotide sequence comprising an isolated polynucleotide molecule of this aspect is provided.

In a still further embodiment, the invention provides an antibody that specifically binds an isolated polypeptide comprising the amino acid sequence encoded by any of the polynucleotides of this aspect.

The invention also provides a process for isolating a polynucleotide, comprising hybridizing a polynucleotide selected from the group consisting of polynucleotides having SEQ ID NO:1, SEQ ID NO:3, and SEQ ID NO:11 to genomic DNA under highly stringent conditions and isolating the DNA that hybridizes to the polynucleotide selected from the group consisting of polynucleotides having SEQ ID NO:1, SEQ ID NO:3, and SEQ ID NO:11. In one embodiment of this aspect of the invention, an isolated polynucleotide is prepared according to the process of this aspect of the invention. In another embodiment, an isolated polynucleotide that is the complement of the polynucleotide molecule of this aspect of the invention is provided. In another embodiment, a recombinant vector comprising the polynucleotide molecule of this aspect of the invention is provided. In a further embodiment, a host cell comprising the recombinant vector comprising the polynucleotide molecule of this aspect of the invention is provided.

In a still further embodiment, a method of preparing a substantially purified polypeptide encoded by the recombinant vector of this aspect of the invention, comprising culturing host cells transformed or transfected with the recombinant vector under conditions conducive to the synthesis of the polypeptide, and recovering a substantially purified polypeptide from the host cells, is provided. In yet a further embodiment of this invention, an isolated polypeptide comprising the amino acid sequence encoded by the polynucleotide sequence of this aspect of the invention is provided.

In a still further embodiment, an antibody that specifically binds the isolated polypeptide of this aspect of the invention is provided.

In another aspect, the invention provides a method for increasing or decreasing hair growth, or changing the texture/structure (i.e., rough, smooth, fragile, curly, etc.) of the hair shaft of a subject. In this method, an effective amount of a composition comprising at least any one of the polynucleotides according to the invention is administered to a subject in need thereof. In one embodiment, the method comprises administering a polynucleotide encoding the human homolog of FP-1 (SEQ ID NO:11) to a subject in need thereof. In another embodiment, the method comprises administering to a subject in need thereof a polynucleotide having SEQ ID NO:11; and a second agent. The second agent is any substance that can control hair growth or can assist the polypeptide encoded by a polynucleotide of the invention to control hair growth. In an another embodiment, the method comprises administering a polynucleotide characterized by the nucleic acid sequence of SEQ ID NO:1 with or without a second agent.

In a further aspect, the invention provides another method for increasing or decreasing hair growth, or changing the texture/structure (i.e., rough, smooth, fragile, curly, etc.) of the hair shaft of a subject. In this method, a formulation comprising a polypeptide encoded by any of the polynucleotides according to the invention is administered to the subject in an amount effective to control hair growth. In one embodiment, the method comprises administering to the subject, a polypeptide encoded by a polynucleotide comprising the human homolog of FP-1 (SEQ ID NO:12). In another embodiment, the method comprises administering to a subject, a polypeptide comprising amino acids 34 to 551 of SEQ ID NO:12. In a further embodiment, the subject is administered a polypeptide encoded by any of the nucleic acid molecules according to the invention; and a second agent. The second agent is any substance that can control hair growth or any substance that can assist the polypeptide of the invention to control hair growth.

In yet another aspect, the invention provides a method for controlling hair growth, comprising contacting the skin of a subject with a composition comprising an effective amount of a protein selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12, and any combination thereof. In one embodiment of this aspect of the invention, the hair follicle of a subject is contacted with the composition of this aspect. In another embodiment of this aspect, the follicular papilla of the subject is contacted with the composition according to the invention. In a further embodiment, the skin of a subject is contacted with a composition comprising an effective amount of a protein selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12; and a second agent. The second agent is any substance that can control hair growth or any substance that can assist the polypeptides selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12, to control hair growth.

In a further aspect of the invention, the invention provides a method of treating a subject with a hair growth disorder. In this method, a pharmaceutical composition comprising a pharmaceutically acceptable carrier, and a hair growth-promoting amount of any of the polynucleotides of the invention is administered to the subject. In one embodiment, the method comprises administering a polynucleotide encoding the human homolog of FP-1 (SEQ ID NO:11), and a pharmaceutically acceptable carrier to a subject in need thereof. In a different method, a pharmaceutical composition comprising a pharmaceutically acceptable carrier, and a hair growth-promoting amount of any of the polypeptides of the invention is administered to the subject. In one embodiment the polypeptide comprises an amino acid sequence selected from the group consisting of polypeptides having SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, amino acids 34 to 551 of SEQ ID NO:12.

In yet another aspect of the invention, a method of identifying an agent that modulates hair growth is provided. In one embodiment, skin, isolated follicular papilla cells, or an isolated hair follicle is contacted with a test agent. The expression of FP-1 in follicular papilla is then measured. If the test agent increases the expression of FP-1 in the isolated follicular papilla cells, or the follicular papilla of the isolated hair follicle or of the skin compared to those not contacted with the test agent, the agent is determined to stimulate hair growth. If on the other hand, the test agent decreases the expression of FP-1 in the isolated follicular papilla cells, or the follicular papilla of the isolated hair follicle or of the skin compared to those not contacted with the test agent, the agent is determined to inhibit hair growth.

The invention also provides methods for screening or identifying agents that modulate the ability of FP-1 to control hair growth. The method includes contacting FP-1 with a test agent. In this aspect, a test agent is a substance that is thought to be effective in modulating the activity of FP-1. The method includes determining if the test agent modulates the activity of FP-1. Accordingly, the agent is tested in in vitro hair growth assays to determine its ability to modulate hair growth by FP-1. The test agent is classified as an agent that stimulates hair growth if it increases the ability of FP-1 to promote hair growth, whereas the test agent is determined to be an inhibitor of hair growth if it decreases the activity of FP-1.

The invention also provides a method for stimulating hair growth in a subject, comprising contacting the skin of the subject with an amount of an agent that increases the expression of FP-1 in the follicular papilla. In some embodiments of this aspect, the hair follicle or the follicular papilla of the subject is contacted with the agent. In a further embodiment, the invention provides a method for stimulating hair growth in a subject, comprising contacting the skin of the subject with an amount of an agent that increases the expression of FP-1 in the follicular papilla; and a second agent. The second agent is any substance that controls hair growth or any substance that can assist the polypeptide of the invention to increase hair growth.

The present invention also provides a method for treating alopecia. The method comprises administering to a subject in need thereof an effective amount of FP-1, or an agent that increases the expression of FP-1 in follicular papilla of the subject. In one embodiment, the subject's skin is contacted with FP-1, or an agent that increases the expression of FP-1 in the follicular papilla of the subject. In a particular embodiment, contact with FP-1 or the agent alters the duration of the anagen in the subject. In another specific embodiment, contact with FP-1 or the agent converts telogen follicles into anagen follicles. In yet another embodiment, contact with FP-1 or the agent reverses miniaturization. In a still further embodiment, contact with FP-1 or the agent generates new hair follicles. In an additional embodiment, the method comprises administering to a subject in need thereof an effective amount of FP-1, or an agent that increases the expression of FP-1 in follicular papilla; and a second agent.

In another aspect, the present invention provides methods of diagnosing hair disorders in a subject. The method comprises collecting a blood or tissue sample from the subject and detecting the level of FP-1 expression in the sample. If the FP-1 expression is lower or higher than in blood or tissue samples from a control subject who does not have a hair disorder, the subject is determined to have a hair disorder.

The present invention also provides a method for transplanting hair in a subject. In this method, hair follicles or grafts are contacted with a polynucleotide selected from the group consisting of polynucleotides having SEQ ID NO:1, SEQ ID NO:3, SEQ ID NO:5, SEQ ID NO:7, SEQ ID NO:9, and SEQ ID NO:11, or contacted with a polypeptide selected from the group consisting of polypeptides comprising SEQ ID NO:2, amino acids 34 to 549 of SEQ ID NO:2, SEQ ID NO:4, amino acids 34 to 531 of SEQ ID NO:4, SEQ ID NO:6, amino acids 34 to 549 of SEQ ID NO:6, SEQ ID NO:8, amino acids 34 to 549 of SEQ ID NO:8, SEQ ID NO:10, SEQ ID NO:12, and amino acids 34 to 551 of SEQ ID NO:12. The contacted hair grafts or follicles are then transplanted to a predetermined bald or thinning area of the subject. The method of this aspect of the invention may further comprise contacting the hair follicles or grafts with additional substance(s) that control hair growth.

In yet another aspect, the invention provides a method for inhibiting hair growth of a subject, comprising contacting a hair follicle with an effective amount of an agent that decreases the expression of FP-1 in follicular papilla or inhibits the activity of FP-1. In some embodiments, the hair follicle is contacted by contacting the skin or the follicular papilla of a subject. In further embodiments, the agent that decreases the expression of FP-1 in follicular papilla or inhibits the activity of FP-1 is an antibody, a mutant form of FP-1, a ribozyme, an siRNA, an antisense molecule, or a small molecule inhibitor. In a further embodiment, the method of this aspect comprises contacting a hair follicle with an effective amount of an agent that decreases the expression of FP-1 in follicular papilla or inhibits the activity of FP-1; and an inhibitor of hair growth.

The invention also provides compositions comprising an antibody that binds FP-1 attached to a surface. In one embodiment, the surface is a solid phase surface. In another embodiment, the surface is a cell surface. In yet another embodiment the solid phase surface is a bead. In a still further embodiment the bead is selected from the group consisting of biodegradable beads, magnetic beads and latex beads.

In a further aspect, the present invention provides a method of identifying and isolating follicular papilla cells. In this method, a mixture of cells from the skin or hair follicles is contacted with an antibody that specifically binds to FP-1. In one embodiment, the antibody that binds FP-1 is coupled to a surface. These FP-1 antibody-bound cells are isolated from the unbound cells. The cells that bind an antibody that specifically binds to FP-1 are determined to be follicular papilla cells.

In another aspect, the invention provides a method for screening or validation of drugs for hair growth disorders. The method comprises contacting isolated follicular papilla cells, isolated hair follicles, or skin, and treating any of these with a test drug (e.g., chemical, compound, peptide, protein, DNA, etc.) and determining whether the test drug changes the expression level of FP-1 (RNA or protein) in the isolated follicular papilla cells, isolated hair follicles, or skin. The change in the expression levels of FP-1 is an indicator of the utility of the test drug for use in increasing or decreasing hair growth, or in regulating the texture/structure of the hair of a subject. If the test drug increases FP-1 expression it indicates that the test drug is effective in promoting hair growth. If, on the other hand, the test drug decreases FP-1 expression, the test agent is effective in inhibiting hair growth.

In an additional aspect the present invention provides methods of diagnosing cancers. The method comprises isolating blood from a subject and measuring the level of FP-1. If the level of FP-1 is higher than that in the normal population, the subject is determined to be at a risk of developing or having developed a cancer. In another embodiment, the method comprises obtaining a tissue biopsy from a subject. The tissue is then tested for expression of FP-1. If the level of FP-1 is higher than in normal tissues, the subject is determined to be at a risk of developing or having developed a cancer. In one embodiment the tissue is obtained from the skin. In another embodiment the tissue is from the hair follicle. In yet another embodiment the tissue is from the liver. In a further embodiment, the tissue is from the brain. In an even further embodiment the tissue is from the testes. In an additional embodiment the tissue is from the muscle (e.g., skeletal muscle). In a further embodiment the tissue is from the placenta.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 2 is a schematic representation of the nucleic acid (SEQ ID NO:1) and corresponding amino acid sequence of rat FP-1 (SEQ ID NO:2).

FIG. 3 is a schematic representation of the nucleic acid (SEQ ID NO:3) and corresponding amino acid sequence of an alternatively spliced rat FP-1 (SEQ ID NO:4).

FIG. 4 is a schematic representation of the nucleic acid (SEQ ID NO:5) and corresponding amino acid sequence (SEQ ID NO:6) of rat gliomedin.

FIG. 5 is a schematic representation of the nucleic acid (SEQ ID NO:7) and corresponding amino acid sequence (SEQ ID NO:8) of mouse cancer related gene-liver 2 (mCrg-L2).

FIG. 6 is a schematic representation of the nucleic acid (SEQ ID NO:9) and corresponding amino acid sequence (SEQ ID NO:10) of a human homolog of cancer related gene-liver 2 (hCrg-L2).

FIG. 7 is a schematic representation of a nucleic acid encoding human FP-1 (SEQ ID NO:11) and the corresponding amino acid sequence (SEQ ID NO:12).

FIG. 8 is a schematic representation of an alignment of the amino acid sequences of the rat FP-1 sequences of the present invention (SEQ ID NOS: 2 (FP-1a) and 4 (FP-1b)), rat gliomedin (SEQ ID NO: 6), mouse cancer related gene-liver 2 (SEQ ID NO: 8), the human homolog of the mouse cancer related gene-liver 2 (SEQ ID NO: 10), and the human homolog of FP-1 (SEQ ID NO: 12).

FIG. 9 is a schematic representation of an alignment of the coding regions of the nucleic acid sequences of the rat FP-1 sequences of the present invention (SEQ ID NOS: 28 (FP-1a) and 32 (FP-1b)), rat gliomedin (SEQ ID NO: 29), mouse cancer related gene-liver 2 (SEQ ID NO: 33), the human homolog of the mouse cancer related gene-liver 2 (SEQ ID NO: 31), and the human homolog of FP-1 (SEQ ID NO: 30).

FIG. 10C is a schematic representation of an amino acid sequence alignment of the olfactomedin domains of rat FP-1a and b (SEQ ID NO: 36), human FP-1 (SEQ ID NO: 37) and the olfactomedin-like domain (SEQ ID NO: 38) (OLF: NCBI Conserved Domain Database, gnl/CDD/8214, pfam02191). The seven regions of conservation in olfactomedin-related proteins (Regions 1, 3, and 5–9) as defined by Klein and Green (*Mol. Cell. Prot.*, 1.5:394–403, 2002) are underlined.

FIG. 11A is a photographic representation of a Southern Blot analysis performed using follicular papilla-specific cDNAs (FP-) as probes. Lane 1: subtracted follicular papilla cDNA; lane 2: nonsubtracted follicular papilla cDNA; lane 3: subtracted fibroblast cDNA; and lane 4: nonsubtracted fibroblast cDNA.

FIG. 12A is a photographic representation of a nylon membrane dotted with a cDNA array from randomly picked clones of the follicular papilla-specific subtracted library hybridized with the follicular papilla-specific cDNA (FP-probe). The following clones were used as negative controls: H1: a human homolog of a mouse testis-specific gene, and H2: human semenogelin II, which is specific to seminal vesicles.

FIG. 12B is a photographic representation of a duplicate of the cDNA array shown in FIG. 12A, but hybridized with the fibroblast-specific cDNA (F-probe).

FIG. 12C is a photographic representation of a nylon membrane dotted with a bacterial colony array from randomly picked clones of the follicular papilla-specific subtracted library hybridized with the follicular papilla-specific cDNA (FP-probe). The following clones were used as negative controls: H1: a human homolog of a mouse testis-specific gene, and H2: human semenogelin II, which is specific to seminal vesicles.

FIG. 12D is a photographic representation of a duplicate of the bacterial colony array shown in FIG. 12A, but hybridized with the fibroblast-specific cDNA (F-probe).

FIG. 13A is a photographic representation of a Southern blot hybridized with an FP-1 probe. FP: PCR-amplified double-stranded cDNAs of follicular papilla cells, F: PCR-amplified double-stranded cDNAs of fibroblasts (1:1:1 mixture of diaphragm, esophagus and stomach fibroblasts), and DF: PCR-amplified double-stranded cDNAs of dermal fibroblasts.

FIG. 13B is a photographic representation of the Southern blot hybridized with an EST2 probe.

FIG. 13C is a photographic representation of the Southern blot hybridized with an EST6 probe.

FIG. 13D is a photographic representation of the Southern blot hybridized with an EST7 probe.

FIG. 13E is a photographic representation of the Southern blot hybridized with a lysyl oxidase-like 2 (LOXL2) probe.

FIG. 13F is a photographic representation of the Southern blot hybridized with a serine protease probe.

FIG. 13G is a photographic representation of a Southern blot hybridized with a tenascin c probe.

FIG. 13H is a photographic representation of the Southern blot hybridized with a GAPDH probe.

FIG. 14A is a photographic representation of a Northern blot hybridized with an FP-1 probe. Five micrograms of total RNA of cultured rat vibrissa follicular papilla cells (lane 1) and dermal fibroblasts (lane 2) and 10 μg of total RNA of 18 rat tissues (lane 3–20) were separated electrophoretically in a denaturing gel and subjected to Northern blot analysis. Lane1: cultured follicular papilla cells; Lane 2: cultured dermal fibroblasts; Lane 3: skin; Lane 4: diaphragm; Lane 5: esophagus; Lane 6: stomach; Lane 7: brain; Lane 8: lung; Lane 9: heart; Lane 10: liver; Lane 1: spleen; Lane 12: kidney; Lane 13: bladder; Lane 14: intestine; Lane 15: colon; Lane 16: ovary; Lane 17: uterus; Lane 18: prostate; Lane 19: testis; and Lane 20: skeletal muscle.

FIG. 14B is a photographic representation of the Northern blot hybridized with a GAPDH probe.

FIG. 14C is a photographic representation of the gel stained with ethidium bromide.

FIG. 15 is a schematic representation of the cDNA (SEQ ID NO:1) and peptide sequence (SEQ ID NO:2) of the most full-length rat FP-1. The full-length FP-1 cDNA is 2332 bp, with a 1647 bp coding region that encodes a protein having 549 amino acids. Five peptide regions used to generate antisera are underlined and labeled epitopes 1 to 5. The N-terminal 33 amino acid residues of SEQ ID NO:2, which serve as a putative signal peptide, are indicated in bold and underlined. Amino acids 139–222 and 230–251 of SEQ ID NO:2 are homologous to collagen triple helix repeats. A region comprising amino acids 253–543 of SEQ ID NO:2 is homologous to an olfactomedin-related domain. Putative N-glycosylation sites are outlined in bold and underlined.

FIG. 16A is a photographic representation of a Western blot to test the antisera raised to FP-1. Total proteins of cultured rat vibrissa follicular papilla cells (FP) and dermal fibroblasts (DF) were separated electrophoretically on an SDS/polyacrylamide gel. Numbers on the left denote the positions of size markers in kilodalton (kDa). Immunoblots were performed using three separate FP-1 antisera (anti-epitopes 1, 2, and 3, panel a, b, c, respectively), pre-immune serum (panel d), and anti-β-tubulin antibody (panel e).

FIG. 16B is a photographic representation of a Western blot performed to test whether FP-1 was glycosylated. Total proteins of cultured rat vibrissa follicular papilla cells were digested with endoglycosidase-H (+) or left undigested (−) and the proteins were separated electrophoretically on an SDS/polyacrylamide gel. Immunoblotting was performed using two FP-1 antisera (anti-epitopes 2 and 3, panel a and b, respectively).

FIG. 16C is a photographic representation of immunofluorescent staining of FP-1 and COP I in cultured follicular papilla cells. Cultured rat vibrissa follicular papilla cells (FP) and fibroblasts (DF) at passage 4 were double stained with FP-1 rabbit antiserum (anti-epitope 3) and anti-COP I mouse monoclonal antibody.

DETAILED DESCRIPTION OF THE INVENTION

The patents and scientific literature cited herein establishes the knowledge that is available to those with skill in the art. The issued U.S. patents, published and allowed applications, and references cited herein are hereby incorporated by reference in their entirety. Unless otherwise defined, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

The present invention relates to compositions and methods for modulating hair growth. Specifically, the present invention is based on the discovery of a protein, follicular papilla-1 (FP-1), which exhibits highly selective expression in the follicular papilla of the hair follicle. Significantly, the mouse FP-1 gene has been localized to a region of the mouse chromosome that has been implicated in a number of hair-related disorders. These discoveries have been exploited to develop the present invention, which relates to proteins and polynucleotides that control hair growth; compositions that control hair growth; compositions and methods for identifying and isolating follicular papilla cells; methods of controlling hair growth; methods for screening for agents that control hair growth; methods of diagnosing hair disorders; and methods of diagnosing cancers.

Figure 1A:
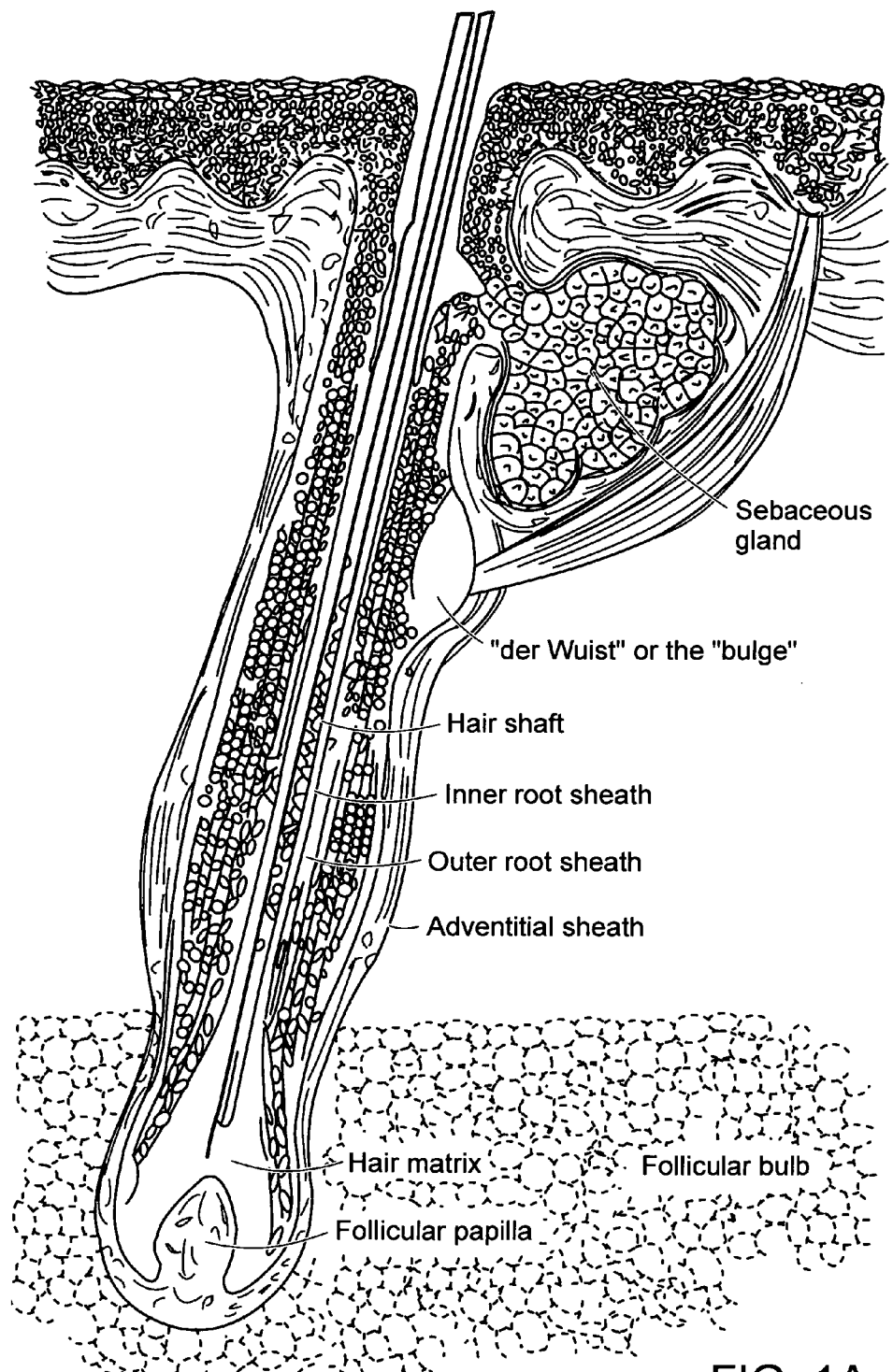
FIG. 1A is a diagrammatic representation of a human hair follicle in anagen.
Figure 1B:
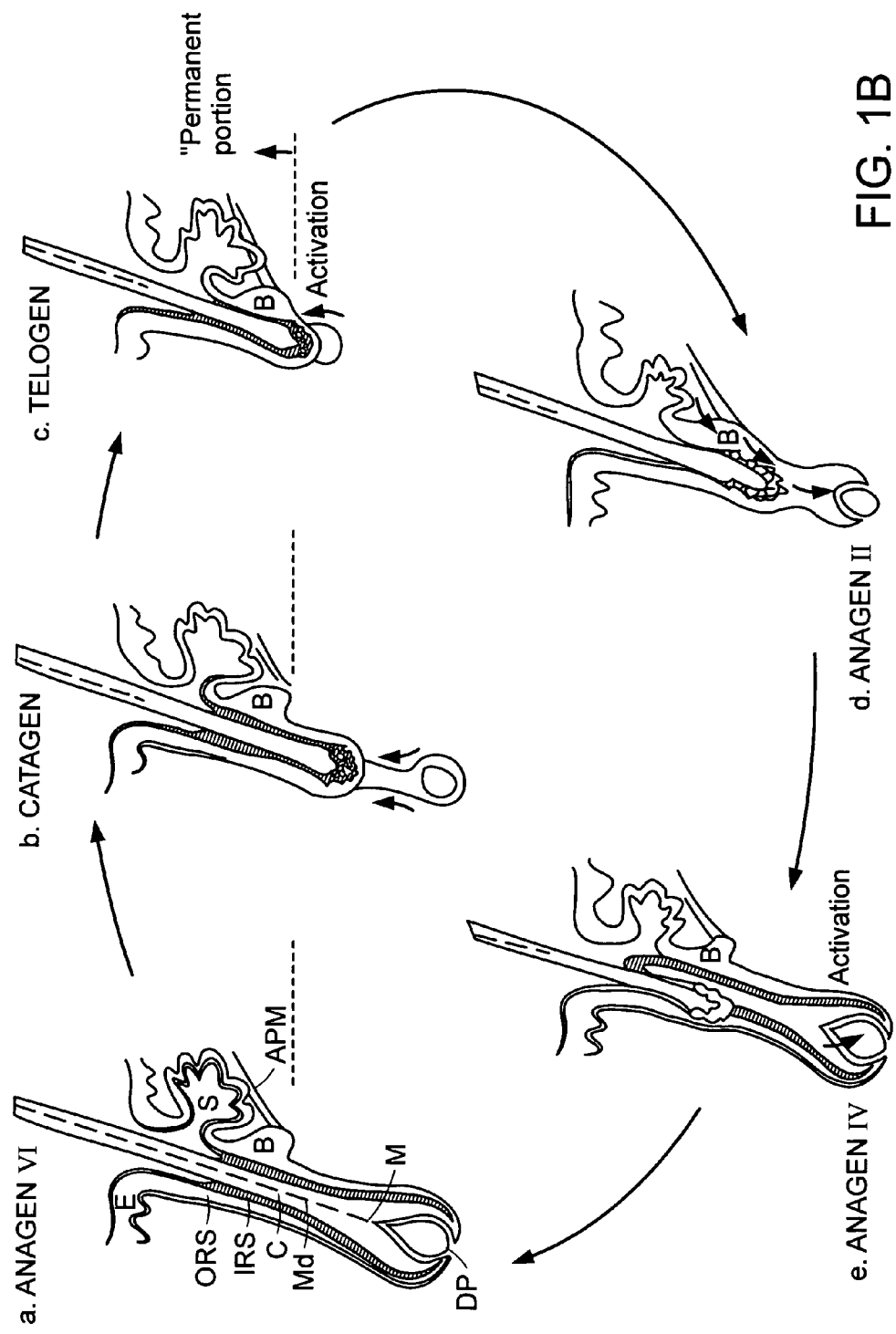
FIG. 1B is a diagrammatic representation of the different stages of a hair follicle cycle.

The outer surface of the hand, limb and body is covered by the epidermis, which is elaborated into a number of specialized appendages. One of the most prominent of these appendages is the hair follicle (FIG. 1A) which produces the hairs that fulfill a number of functions including thermoregulation, collecting sensory information, protection against environmental trauma, social communication, and mimicry (Stenn et al., *Physiol. Rev.* 81:449–494, 2001). Hair follicles have prolific growth characteristics and exhibit a complexity of differentiation (see, FIG. 1B). After initial embryonic morphogenesis, the hair follicle undergoes repeated cycles of regression and regeneration throughout the lifetime of an organism (Porter, *J. Anat.*, 202:125–131, 2003).

Hair follicle morphogenesis is governed by a series of inductive signals between epidermal keratinocytes committed to hair follicle specific differentiation and the mesenchymal cells that form the follicular papilla (Hardy, *Trends Genet.*, 8:55–61, 1992). Hair follicle precursors are first seen as thickenings or placodes in an otherwise uniform surface epithelium. These placodes send signals to the underlying dermis, causing the clustering of a group of cells—the dermal condensate—that will eventually form the follicular papilla. A second dermal signal from the dermal condensate to the follicular epithelium directs the proliferation and downgrowth of follicular epithelial cells into the dermis. These interactions eventually result in the morphogenesis of the hair bulb, in which keratinocytes rapidly proliferate and differentiate into six distinct cell populations, forming the medulla, cortex, and cuticle of the hair shaft, as well as the cuticle, Huxle and Henle layers of the inner root sheath (Bertolino et al., "Differentiation of the hair shaft," in *Differentiation of the Hair Shaft*, pp. 21–37, Olsen EA (ed.), McGraw Hill, Inc. New York, 1994). The inner root sheath separates the hair shaft from the outer root sheath, which forms the external concentric layer of epithelial cells in the hair follicle (Botchkarev et al., *J. Exp. Zool. Mol. Dev. Evol.*, 298(1):164–180, 2003).

In humans, the formation of hair follicles takes place during embryogenesis, and no new hair follicles form after birth. However, the hair follicle is a highly dynamic structure, which undergoes remodeling throughout the life of a mammal, in a cycle of growth (anagen), regression (catagen), rest (telogen), and shedding (exogen) (Muller-Rover et al., *J. Invest. Dermatol.*, 117:3–15, 2001; Cotsarelis et al., *Trends Mol. Med.*, 7(7):293–301, 2001). During catagen, much of the follicle undergoes programmed cell death. The hair bulb shrinks and pulls away from the mesenchymal cluster of follicular papilla cells, which it previously enveloped. The whole hair follicle then retracts upwards toward the epidermal surface. During this retraction, it undergoes a carefully controlled remodeling to form a shortened structure that significantly, maintains its close association with the follicular papilla. After a period of rest in this shortened form, a signal that is thought to be from the follicular papilla initiates the next anagen phase (Porter, *J. Anat.*, 202:125–131, 2003). Follicular regeneration requires the activation of rarely cycling epithelial stem cells located in the permanent, bulge region of the follicle (Cotsarelis et al., *Cell*, 61:1329–1337, 1990). Stem cell progeny form a new follicle matrix during early anagen, and the hair shaft and inner root sheath are derived from these relatively undifferentiated matrix cells (Oshima et al., *Cell*, 104:233–245, 2001).

It has been well established that follicular papilla cells of the hair follicle play a key role in controlling hair growth. First, the diameter and length of the hair fiber appears to be directly proportional to the size of the follicular papilla (Elliott et al., *J. Invest. Dermatol.*, 113:873–877, 1999). Second, the surgical removal of the lower half of the rat vibrissa follicle results in follicular degeneration which can be prevented if one implants a follicular papilla, or a pellet of cultured follicular papilla cells, at the bottom of the damaged follicle. Implantation of dermal fibroblasts, which are embryologically closely related to the follicular papilla cells, fail to support hair growth thus establishing the importance of follicular papilla cells in maintaining the viability of the upper follicle (Oliver, *J. Embryol. Exp. Morphol.*, 15:331–347, 1966); Jahoda et al., *Nature*, 311: 560–562, 1984). Like the vibrissa, the human follicle has also been shown to regenerate an active hair bulb after follicular amputation (Kim et al., *Dermatol. Surg.*, 21(4): 312–313, 1995). Third, follicular papilla cells implanted under the interfollicular epidermis can induce the formation of new hair follicles; the structure of the induced follicle resembles the original follicle of the follicular papilla (Jahoda, C. A., *Development*, 115:1103–1109, 1992); Reynolds, A. J. et al., *Nature*, 402:33–34, 1999). Fourth, when cultured keratinocytes were combined with follicular papilla cells and grafted onto a nude (athymic) mouse, hair follicles were generated; however, no hair grew when cultured keratinocytes that were mixed with dermal fibroblasts were grafted onto nude mice (Kamimura et al., *J. Invest. Dermatol.*, 109(4):534–40, 1997). Fifth, Jahoda et al. recently showed trans-species hair induction by human scalp follicular papilla cells, but not dermal fibroblasts (Jahoda et al., *Exp. Dermatol.*, 10(4):229–37, 2001). Sixth, minoxidil has been shown to upregulate the synthesis and secretion of VEGF by cultured follicular papilla cells thus providing a possible explanation of the minoxidil stimulation of hair growth (Lachgar et al., *Br. J. Dermatol.*, 138:407–411, 1998). Finally, recent data indicate that hair follicular epithelial stem cells reside in the bulge, and that the interaction between follicular papilla and bulge during telogen may play a role in activating the stem cells allowing the follicle to enter into a new anagen (Cotsarelis et al., *Cell*, 61:1329–1337, 1990; Taylor et al., *Cell*, 102:451–461, 2000). Taken together, these results clearly indicate that follicular papilla cells, unlike their closely related dermal fibroblasts, are endowed with a unique capacity to maintain and to support the growth of the hair follicle.

Given the important role of the follicular papilla in regulating the morphogenesis of the hair follicle, it is of interest to define the molecular basis for why the follicular papilla cells, but not their closely related dermal fibroblasts, support hair growth. Accordingly, a rat follicular papilla-specific subtractive cDNA library was constructed to identify polynucleotides that were selectively expressed in the follicular papilla. The most abundant cDNA that was isolated from this library was named follicular papilla-1 (FP-1). This cDNA was then used to identify the full length rat cDNA.

The rat FP-1 polynucleotide (FIG. 2, SEQ ID NO:1) encodes a protein of 549 amino acids (FIG. 2, SEQ ID NO:2). A second cDNA (FIG. 3, SEQ ID NO:3), which likely corresponds to an alternatively spliced product of the rat FP-1 gene, encodes a protein of 531 amino acids (FIG. 3, SEQ ID NO:4). A search of the GENBANK® database for other FP-1 related proteins led to the discovery of rat gliomedin (FIG. 4, Accession Number AAP22419; SEQ ID NO:6), a mouse protein named cancer related gene-liver 2 (Crg-L2) (FIG. 5, Graveel et al., Oncogene, 22:1730–1736, 2003; Accession Number NP_796324; SEQ ID NO: 8), and a human protein named likely ortholog of mouse cancer related gene-liver 2 (FIG. 6, Accession Number NP_861454; SEQ ID NO:10). An alignment of the rat, mouse, and human sequence (FIG. 8) indicated a high level of homology between these proteins. Interestingly, the human sequence listed in GENBANK® lacks the N-terminal region that is conserved between the mouse and the rat. Thus, it is likely that the human sequence listed in GENBANK® is an incomplete amino acid sequence. Accordingly, the present invention provides the amino acid sequence corresponding to a full-length human FP-1 protein (FIG. 7, SEQ ID NO:12). These rat (SEQ ID NOS: 2, 4, 6), mouse (SEQ ID NO: 8) and human (SEQ ID NOS:10 and 12) proteins, and any portions, derivatives, or variants thereof, are collectively referred to herein as "FP-1 proteins." The rat, mouse, and human FP-1 proteins have an N-terminal signal peptide sequence (FIG. 15) of about 33 amino acids (see for example, amino acids 1 to 33 of SEQ ID NO:2).

Figures 10A, 10B:
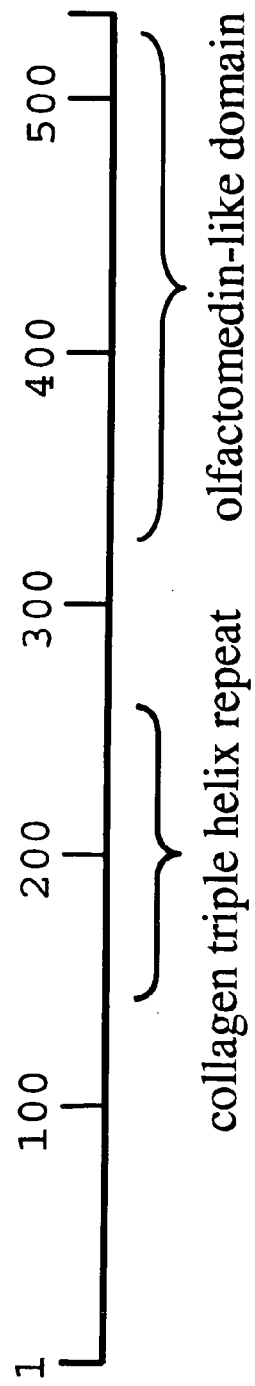
FIG. 10A is a diagrammatic representation of the location of the collagen triple helix repeat and olfactomedin-related domains of FP-1.
FIG. 10B is a schematic representation of an amino acid sequence alignment of the two regions (underlined) of rat FP-1a and b (SEQ ID NO: 34) and human FP-1 (SEQ ID NO: 35) that are homologous to the collagen triple helix repeat.

All the FP-1 proteins also possess amino acid sequences (see, e.g., amino acid 139–222 and 230–251 of SEQ ID NO:2) that are homologous to collagen triple helix repeat (20 copies) and several collagen family members such as collagen types IV, XIII and XV (FIG. 10B). Collagens are generally extracellular structural proteins involved in the formation of connective tissue structure. Collagen triple helix repeats contain 20 copies of the G-X-Y repeat (wherein G is glycine; X is any amino acid residue, but is frequently proline; and Y is any amino acid residue, but is frequently hydroxyproline) that forms a triple helix. Collagens are post-translationally modified by proline hydroxylase to form the hydroxyproline residues.

The FP-1 proteins are further characterized by the presence of an olfactomedin-related domain (see, e.g., amino acids 253–543 of SEQ ID NO:2). This domain was first identified in olfactomedin, which is an extracellular matrix glycoprotein specifically expressed in olfactory neuroepithelium (Snyder et al., Biochem., 30(38):9143–153, 1991). Olfactomedin forms homopolymers through disulfide bonds and carbohydrate interactions (Bal et al., Biochemistry, 32(4):1047–53, 1993) and has been suggested to influence the growth and differentiation of chemosensory olfactory cilia (Yokoe et al., Proc. Natl. Acad. Sci. USA 90:4655–4659, 1993). In addition to olfactomedin, this domain is also found in a wide variety of proteins such as amassin, noelin, myocilin, and tiarin. Interestingly, the olfactomedin domain is primarily found in extracellular proteins. Olfactomedin domain-containing proteins have been reported to possess at least seven amino acid segments of conservation (regions 1, 3, and 5 through 9) (Green et al., Mol. Cell. Prot., 1.5:394–403, 2002). These seven segments are also conserved in FP-1 proteins (see, FIG. 10C).

FP-1 proteins also have six potential glycosylation sites (FIG. 15, amino acids 130, 156, 252, 326, 354 and 461 of SEQ ID NO:2). When cell extracts having FP-1 are treated with endoglycosidase H, the molecular weight of rat FP-1 decreased from 72 kDa to roughly 60 kDa. Thus, FP-1 is a glycoprotein.

A survey of various rat tissues using Northern blot analysis indicated that FP-1 is expressed at an extremely high level in cultured rat vibrissa follicular papilla cells, and can be detected at low levels in the stomach and ovary. However, FP-1 was not detectable in the diaphragm, esophagus, stomach, brain, lung, heart, liver, spleen, kidney, bladder, intestine, colon, uterus, prostate, testis, and skeletal muscle (see, FIG. 14).

FP-1 is an extracellular matrix protein. The extracellular matrix of the follicular papilla undergoes cyclic changes such that it is completely degraded and removed during catagen, and then resynthesized and deposited in early to late anagen. These changes are important for the hair follicle cycle and thus hair growth. Thus, at least in part, FP-1 regulates hair growth by modulating the extracellular matrix of the hair follicle. Cross-species fluorescent in situ hybridization (FISH) on mouse chromosomes using rat FP-1 cDNA indicated that FP-1 is located on mouse chromosome 9 in the B-C region. This was confirmed by a BLAST search performed using rat FP-1 cDNA against the mouse genomic database after the completion of the Mouse Genome Program. Importantly, this region has three hair-related mutants, including rough fur (ruf), rough coat (rc) and fur deficient (fd).

The present invention provides isolated polynucleotides encoding FP-1. The polynucleotides of the invention can be DNA or RNA molecules that are single-stranded or double-stranded. The polynucleotides can include, but are not limited to, RNA, cDNA, genomic DNA, semisynthetic DNA or RNA, and chemically synthesized DNA or RNA sequences.

The polynucleotides comprise the sequences set forth as SEQ ID NO:1, SEQ ID NO:3 or SEQ ID NO:11. The invention also provides a nucleic acid sequence that encodes a polypeptide comprising SEQ ID NO:2, SEQ ID NO:4, or SEQ ID NO:12.

Alternatively, the isolated polynucleotides of the invention comprise a nucleic acid sequence that is homologous to any one of SEQ ID NO:1, SEQ ID NO:3 or SEQ ID NO:11. By "homologous" is meant a polynucleotide that has at least about 70%, at least about 80%, at least about 90%, at least about 95%, or at least about 98% nucleotide sequence identity to a given nucleotide sequence, which can be determined by any standard nucleotide sequence identity algorithms such as, but not limited to, the GCG program (Devereux et al., Nucl. Acids Res., 12(1): 387, 1984), BLASTN (GENBANK®), and FASTA (Altschul et al., J. Mol. Biol., 215:403, 1990). For example, the invention provides an isolated polynucleotide comprising a nucleic acid sequence that has about 90%, or about 95% nucleic acid sequence identity to SEQ ID NO:1, SEQ ID NO:3, or SEQ ID NO:11, wherein the isolated polynucleotide molecule encodes a protein that controls hair growth. By "controls hair growth" is meant to increase or decrease hair growth, or change the texture/structure of the hair shaft (e.g., rough, smooth, fragile, curly, etc.), relative to hair growth or hair texture in skin, hair follicles or follicular papilla not contacted with a polynucleotide, polypeptide, agent or composition of the invention. Some useful methods for determining whether FP-1 increases or decreases hair growth are described in the Examples below as well as in Philpott et al., Whole Hair Follicle Culture, in *Dermatologic Clinics* (Whiting D., ed.) 14(4): 595–607 (1966) and the references cited therein; and Wilson et al., *Differentiation* 55:127–136 (1994). Hair texture and structure can be assessed by direct visual study or by microscopy.

The polynucleotides of the invention alternatively comprise a nucleic acid sequence that is homologous to a nucleic acid sequence that encodes a polypeptide comprising SEQ ID NO:2, SEQ ID NO:4 or SEQ ID NO:12. For example, the polynucleotide may comprise a nucleic acid sequence that has about 90%, or about 95% nucleic acid sequence identity to a nucleic acid sequence that encodes a polypeptide comprising SEQ ID NO:2, SEQ ID NO:4 or SEQ ID NO:12, wherein the isolated polynucleotide molecule encodes a protein that increases or decreases hair growth, or changes hair texture.

The isolated polynucleotide of the invention specifically hybridize under moderately stringent or highly stringent conditions to a complement of a polynucleotide sequence comprising SEQ ID NO:1, SEQ ID NO:3 or SEQ ID NO:11, wherein the polynucleotide sequence encodes a protein that controls hair growth. As used herein, the phrase "specifically hybridizing" means the ability of a nucleic acid molecule to recognize another nucleic acid sequence by forming base pairs with it through hydrogen bonding, under moderately or highly stringent hybridization conditions. By "moderately stringent conditions" is meant hybridization to filter-bound DNA in 0.5 M NaHPO4, 7% sodium dodecyl sulfate (SDS), 1 mM EDTA at 65° C., and washing in 0.2×SSC/0.1% SDS at 42° C. (see, Ausubel et al. (eds.), *Current Protocols in Molecular Biology, Vol. I*, 1989, Green Publishing Associates, Inc., and John Wiley & Sons, Inc., New York at p. 2.10.3). By "highly stringent conditions" is meant hybridization to filter-bound DNA in 0.5 M NaHPO4, 7% sodium dodecyl sulfate (SDS), 1 mM EDTA at 65° C., and washing in 0.1×SSC/0.1% SDS at 68° C. (Ausubel et al., supra). The polynucleotides of the invention specifically hybridize under moderately stringent or highly stringent conditions to a complement of a polynucleotide sequence comprising a nucleotide sequence that encodes a polypeptide having SEQ ID NO:2, SEQ ID NO:4 or SEQ ID NO:12, wherein the polynucleotide sequence encodes a protein that increases or decreases hair growth, or changes hair texture.

Additionally, the invention provides an isolated polynucleotide that is the complement of the polynucleotide comprising any of the polynucleotides of the previous aspects.

The polynucleotides of the invention may be produced by hybridizing the polynucleotide having SEQ ID NO:1, SEQ ID NO:3 or SEQ ID NO:11 to genomic DNA under moderately stringent or highly stringent hybridization conditions and isolating the DNA polynucleotide hybridized to the polynucleotide having SEQ ID NO:1, SEQ ID NO:3 or SEQ ID NO:11. The genomic DNA can be from any eukaryotic organism including mammals, especially humans. Methods of hybridizing a polynucleotide to genomic DNA are well known in the art (Sambrook et al., *Molecular Cloning: A Laboratory Manual*, Third Edition, Cold Spring Harbor Laboratory Press).

The polynucleotides of the invention can be modified by the addition of flanking sequences such as, but not limited to, restriction enzyme recognition sequences, adaptors, nucleic acid sequences encoding epitopes recognized by antibodies (e.g., His, Flag, Myc, HA, MBP, GST) and nucleic acid sequences encoding proteins that permit detection of the fusion protein (e.g., GFP). Methods of adding or ligating desired DNA sequences to a DNA sequence of interest are well known in the art (Sambrook et al., ibid.).

The polynucleotides of the invention can also be mutated to generate polynucleotides that encode mutant FP-1 proteins. A polynucleotide sequence can be mutated by, for example, introducing one or more point mutations (e.g., a missense or nonsense mutation) or by inserting or deleting one or more bases. Any technique for mutagenesis known in the art can be used, including but not limited to, chemical mutagenesis, in vitro site-directed mutagenesis, PCR-based overlap extension, and PCR-based megaprimer mutagenesis. Methods of generating mutations in a DNA sequence are well within the skill of one of ordinary skill in the art (see, Sambrook et al., supra, Hutchinson et al., *J. Biol. Chem.*, 253:6551, 1978; Ho et al., *Gene*, 77:51–59, 1989; Sarkar et al., *Biotechniques*, 8:404–407, 1990; and Stratagene's QuikChange® Kit).

The invention provides oligonucleotides that hybridize to any of the aforementioned polynucleotides of the present invention, or that hybridize to a polynucleotide molecule having a nucleotide sequence that is the complement of any of the aforementioned polynucleotides of the invention. Such oligonucleotide molecules are at least about 10 nucleotides in length, at least about 20 nucleotides in length, at least about 30 nucleotides in length or at least about 40 nucleotides in length, and hybridize to one or more of the aforementioned polynucleotide molecules under moderately or highly stringent hybridization conditions. For shorter oligonucleotide molecules, an example of highly stringent conditions includes washing in 6×SSC/0.5% sodium pyrophosphate at about 37° C. for about 14-base oligonucleotides, at approximately 48° C. for about 17 bp oligonucleotides, at approximately 55° C. for about 20 bp oligonucleotides and at approximately 60° C. for about 23–40 base oligonucleotides. Hybridization conditions can of course be appropriately adjusted as known in the art, depending upon the particular oligonucleotide molecules utilized.

The oligonucleotides of the present invention are useful in a variety of purposes, including as primers in amplifying a FP-1 encoding polynucleotide, or as antisense molecules useful in regulating expression of FP-1 genes and gene products. A "gene product" means a product encoded by a gene, including the transcribed RNA message (including exons and introns), the spliced messenger RNA (mRNA), and the translated protein product encoded by the respective mRNA. Amplification of FP-1 polynucleotides can be carried out using suitably designed oligonucleotide molecules in conjunction with standard techniques, such as the polymerase chain reaction (PCR).

The present invention also provides recombinant cloning and expression vectors comprising any of the polynucleotide molecules of the invention. The choice of the vector and/or expression control sequences to which any of the polynucleotides of the present invention is operably linked depends directly, as well known in the art, on the functional properties desired, e.g., protein expression, and the host cell to be transformed. The regulatory sequences that are used for modulating the expression of an operably linked, protein-encoding sequence are known in the art and include, but are not limited to, inducible promoters, constitutive promoters, enhancers, and other regulatory elements known in the art that serve to drive and/or regulate expression of the polynucleotide coding sequences. The inducible promoter may be readily controlled, such as being responsive to a nutrient in the host cell's medium.

The vectors of the invention containing a polynucleotide according to the invention can include a prokaryotic replicon, i.e., a DNA sequence having the ability to direct autonomous replication and maintenance of the recombinant DNA molecule extra-chromosomally in a prokaryotic host cell, such as a bacterial host cell, transformed therewith. Such replicons are well known in the art. In addition, vectors that include a prokaryotic replicon may also include a gene whose expression confers a detectable marker such as drug resistance. Typical bacterial drug resistance genes are those that confer resistance to ampicillin, chloramphenicol, kanamycin or tetracycline. Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase, and permits transcription to occur. Promoter sequences compatible with bacterial hosts are typically provided in plasmid vectors containing convenient restriction sites for insertion of a polynucleotide or any fragment thereof of the present invention. Typical non-limiting prokaryotic vector plasmids include pUC8, pUC9, pBR322, pBR329 (BioRad Laboratories), pKK223-2 (Clontech), pSE280, pSE380, pSE420, pTrx-Fus, pRSET, pBAD/HisABC, pTrcHis (Invitrogen), pET-3, pET-11, pCAL-n-EK, pCAL-n (Stratagene), pFLAG-1, pFLAG-ATS, pFLAG-CTS, pFLAGShift(12) (Kodak), pET-14b, pET-15b, pET-30LIC, pET-32LIC (Novagen), pMC1871, pRIT2T and pKK223-3 (Pharmacia).

Suitable yeast vectors for use in the present invention are described in U.S. Pat. No. 6,291,212, and include YRp7 (Struhl et al., *Proc. Natl. Acad. Sc. USA*, 76: 1035–1039, 1978), YEp13 (Broach et al., *Gene*, 8:121–133, 1979), pJDB249 and pJDB219 (Beggs, *Nature*, 275:104–108, 1978). Such vectors generally include a selectable marker, which may be one of any number of genes that exhibit a dominant phenotype for which a phenotypic assay exists to enable transformants to be selected. Non-limiting examples of selectable markers include those that complement host cell auxotrophy, provide antibiotic resistance or enable a cell to utilize specific carbon sources, and include LEU2 (Broach et al. ibid.), URA3 (Botstein et al., *Gene*, 8:17, 1979), HIS3 (Struhl et al., ibid.) or POT1 (Kawasaki and Bell, EP 171142). Other suitable selectable markers include the CAT gene, which confers chloramphenicol resistance on yeast cells. Examples of promoters for use in yeast include promoters from yeast glycolytic genes (Hitzeman et al., *J. Biol. Chem.*, 225:12073–12080, 1980; Alber and Kawasaki, *J. Mol. Appl. Genet.*, 1:419–434, 1982; Kawasaki, U.S. Pat. No. 4,599,311) or alcohol dehydrogenase genes (Young et al., in *Genetic Engineering of Microorganisms for Chemicals*, Hollander et al., (eds.), p. 355, Plenum, N.Y., 1982; Ammerer, *Meth. Enzymol.* 101: 192–201, 1983). Non-limiting examples of yeast promoters include the TPI1 promoter and the ADH promoter. The yeast expression vector may further comprise a transcriptional terminator such as the TPI1 terminator (Alber and Kawasaki, ibid.).

In addition to yeast, polynucleotides of the present invention can be expressed in filamentous fungi, for example, strains of the fungi *Aspergillus*. Examples of useful promoters include those derived from *Aspergillus nidulans* glycolytic genes, such as the ADH3 promoter (McKnight et al., *EMBO J.*, 4:2093–2099, 1985) and the tpiA promoter. An example of a suitable terminator is the ADH3 terminator (McKnight et al., ibid.). The expression units utilizing such components may be cloned into vectors that are capable of insertion into the chromosomal DNA of *Aspergillus*.

Expression vectors compatible with mammalian cells can also be used to express the polynucleotides of the present invention. Eukaryotic cell expression vectors are well known in the art and are available from several commercial sources. Typically, such vectors are provided containing convenient restriction sites for insertion of the desired polynucleotide or any fragment thereof. Such vectors may further include a selectable marker that is effective in a eukaryotic cell, preferably a drug resistance selection marker. A useful drug resistance marker is the gene whose expression results in neomycin resistance, i.e., the neomycin phosphotransferase (neo) gene (Southern et al., *J. of Mol. and Appl. Genet.*, 1(4):327–341, 1982). Alternatively, the selectable marker can be present on a separate plasmid, and the two vectors are introduced by co-transfection of the host cell, and selected by culturing in the appropriate drug for the selectable marker. Mammalian expression vectors for use in carrying out the present invention will include a promoter capable of directing the transcription of a cloned gene or cDNA. Such promoters include viral promoters (e.g., the major late promoter from adenovirus 2 (Kaufman and Sharp, *Mol. Cell. Biol.*, 2: 1304–1319, 1982) and the SV40 promoter (Subramani et al., *Mol. Cell. Biol.*, 1: 854–864, 1981) and cellular promoters (e.g., mouse metallothionein 1 promoter (Palmiter et al., *Science*, 222:809–814, 1983)). These expression vectors may further comprise enhancers. In addition, these expression vectors may also contain a set of RNA splice sites located downstream from the promoter and upstream from the polynucleotide encoding the protein. RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto et al., *Nuc. Acids Res.*, 9:3719–3730, 1981). The expression vectors may include a noncoding viral leader sequence, such as the adenovirus 2 tripartite leader, located between the promoter and the RNA splice sites. Non-limiting examples of eukaryotic expression vectors include pACT, pCI, pCI-neo, pCMVTN™ (Promega), pTet-On™, pTet-Off™, pMAM neo, IRES Bicistronic, pRetro-Off™, pRetro-On™ (Clontech), pWE1, pWE2, pWE3, pWE4 (ATCC®), pIND(SP1), pCDM8, pccDNA1.1, pcDNA3.1, pZeoSV2, pRcCMV2, pRcRSV, pTracer (Invitrogen Corp.), pSVL, pMSG (Pharmacia), pBPV-1/pML2d (International Biotechnologies, Inc.), pCMVScript™, pBK-CMV, and pBK-RSV (Stratagene).

Methods for constructing recombinant vectors are well known in the art, and any of these can be used to construct the vectors of the present invention. These methods include in vitro recombinant techniques, synthetic techniques, and in vivo genetic recombination (see e.g., Sambrook et al., supra, Ausubel et al., supra).

The present invention further provides host cells comprising a polynucleotide molecule or recombinant vector of the invention. Host cells useful in the practice of the invention include prokaryotic and eukaryotic cells such as mammalian, insect, fungal, plant, bacterial, viral and baculoviral cells. Appropriate host cells can be chosen that modify and process the gene product in the specific fashion desired. Different host cells have characteristic mechanisms for the translational and post-translational processing and modification (e.g., glycosylation, phosphorylation) of proteins. For example, expression in a bacterial system can be used to produce an unglycosylated protein product. Expression in mammalian cells can be used to ensure "native" processing of a protein product. Further, different vector/host expression systems can affect processing reactions to different degrees. Non-limiting examples of prokaryotic host cells include the *E. coli* trains HB101, JM101, DH5α, LE392, RR1, XL1-Blue and KW251. Non-limiting examples of eukaryotic host cells include, COS, 293, 293T, CHO, CV-1, Hela, NIH3T3, BHK, C33A, U20S, and primary follicular papilla cells.

The recombinant vector of the invention is transformed or transfected into one or more host cells of a substantially homogenous culture of cells. Methods of transforming and/or transfecting cells are well known in the art. The expression vector is generally introduced into host cells in accordance with known techniques such as e.g., by protoplast transformation, calcium phosphate precipitation, calcium chloride treatment, microinjection, electroporation, transfection by contact with recombined virus, liposome-mediated transfection, DEAE-dextran transfection, transduction, conjugation, or microprojectile bombardment. Selection of transformants can be conducted by standard procedures, such as by selecting for cells expressing a selectable marker, e.g., antibiotic resistance associated with the recombinant vector, as described above. Once the expression vector is introduced into the host cell, the integration and maintenance of the polynucleotides of the invention, either episomally or in the host cell chromosome can be confirmed by standard techniques, e.g., by Southern hybridization analysis, restriction enzyme analysis, PCR analysis, RT-PCR, or by immunological assays to detect the expected gene product. Host cells containing and/or expressing the recombinant polynucleotide of the invention can be identified by any approach known in the art, including: (i) DNA-DNA, DNA-RNA, or RNA-antisense RNA hybridization; (ii) detecting the presence of "marker" gene functions; (iii) assessing the level of transcription as measured by the expression of the mRNAs produced by the recombinant polynucleotide in the host cell; and (iv) detecting the presence of a mature polypeptide product as measured by, for example, an immunoassay.

Once a polynucleotide of the invention has been introduced into an appropriate host cell, the transformed host cell is cultured under conditions conducive to the maximum production of the polypeptide encoded by the recombinant polynucleotide. Such conditions typically include, e.g., growing cells to high density. Where the expression vector comprises an inducible promoter, appropriate induction conditions such as temperature shift, exhaustion of nutrients, and addition of gratuitous inducers (e.g., zinc chloride, analogs of carbohydrates such as IPTG, etc.) are employed as needed to induce expression. Where the expressed polypeptide is retained inside the host cells, the cells are harvested and lysed, and the polypeptide is isolated and purified from the lysate under extraction conditions known in the art to minimize protein degradation such as, e.g., at 4° C. and/or in the presence of protease inhibitors. Where the expressed polypeptide is secreted from the host cells, the nutrient medium can simply be collected and the polypeptide isolated therefrom.

The polypeptide can be isolated or substantially purified from cell lysates or culture medium, as appropriate, using standard methods including, but not limited to, any combination of the following methods: ammonium sulfate precipitation, gel filtration chromatography, ion exchange chromatography, HPLC, density centrifugation, affinity chromatography and immuno-affinity chromatography. If the polypeptide exhibits any measurable biological activity, increasing purity of the polypeptide preparation can be monitored at each step of the purification procedure by use of an appropriate assay. Whether or not the polypeptide exhibits biological activity, it can be detected at each step of the purification based on size or reactivity with an antibody raised to the polypeptide or by detection with an antibody that binds a fusion tag attached to the protein.

The present invention thus provides a substantially purified or isolated polypeptide encoded by a polynucleotide molecule of the present invention. As used herein, a polypeptide is "substantially purified" where the polypeptide constitutes the majority (i.e., at least about 50%) by weight of the material in a particular preparation.

The polypeptides useful in the method of the invention include rat FP-1 gene products comprising, consisting essentially of, or consisting of, the amino acid sequence of SEQ ID NO:2 or SEQ ID NO:4. In one embodiment, the polypeptide is a rat FP-1 gene product comprising, consisting essentially of, or consisting of amino acids 34 to 549 of SEQ ID NO:2. The polypeptide, alternatively, is a rat FP-1 gene product comprising, consisting essentially of, or consisting of amino acids 34 to 531 of SEQ ID NO:4. Any of the amino acid sequences lacking the signal peptide can further comprise an initiating methionine residue.

The present invention also provides an isolated polypeptide comprising the amino acid sequence encoded by any one of the polynucleotides of the invention. For example, the polypeptide is a human FP-1 gene product comprising, consisting essentially of, or consisting of SEQ ID NO:12. Alternatively, the polypeptide is a human FP-1 gene product comprising, consisting essentially of, or consisting of amino acid 34 to 551 of SEQ ID NO:12.

The substantially purified or isolated polypeptides of the present invention are useful for a variety of purposes, such as increasing or decreasing hair growth, changing hair texture, regulating the length of the anagen phase of the hair follicle cycle, screening for proteins or compounds that interact with FP-1 and alter its ability to control hair growth, and for raising antibodies directed to the polypeptide. Such compounds and antibodies can be used in therapeutic methods to treat or prevent hair disorders.

Also within the scope of the present invention are FP-1 proteins or FP-1 fusion proteins comprising one or more amino acid substitutions, insertions or deletions occur in the FP-1 proteins. Such proteins may function as dominant-negative forms of FP-1. The mutant FP-1 proteins or the polynucleotides coding them can be administered to a subject to inhibit or decrease hair growth. Mutant FP-1 encompassed by the invention include, but are not limited to, FP-1 proteins with a deletion or substitution of one or more amino acids in the collagen triple helix repeats, and FP-1 proteins with a deletion or substitution of one or more amino acids in the olfactomedin-related domain.

Non-limiting examples of mutations in the collagen triple helix repeats of FP-1 include, (i) deletion of amino acids 139–222 of SEQ ID NO:2 (or the corresponding region in SEQ ID NOS: 4, 6, 8, 10 and 12); (ii) deletion of amino acids 230–250 of SEQ ID NO:2 (or the corresponding region in SEQ ID NOS: 4, 6, 8, 10 and 12); (iii) deletion of amino acids 139–165 (or the corresponding t region in SEQ ID NOS: 4, 6, 8, 10 and 12); (iv) deletion of amino acids 166–195 (or the corresponding region in SEQ ID NOS: 4, 6, 8, 10 and 12); (v) deletion of amino acids 196–222 (or the corresponding region in SEQ ID NOS: 4, 6, 8, 10 and 12); (vi) mutations of one or more glycines in the region encompassing amino acids 139–222 of SEQ ID NO:2 (or the corresponding region in SEQ ID NOS: 4, 6, 8, 10 and 12) to any other amino acid; and (vii) mutations of one or more glycines in the region encompassing amino acids 230–250 of SEQ ID NO:2 (or the corresponding region in SEQ ID NOS: 4, 6, 8, 10 and 12) to any other amino acid. In one embodiment, the FP-1 proteins wth mutations in the collagen triple helix repeat region have decreased or no binding to collagen. Methods of determining binding between mutant FP-1 proteins and collagen can be performed using methods well known in the art. For example, the binding of FP-1 and its mutants to collagen type 1 or other types may be studied using well established methods including gel electrophoresis and affinity chromatography (Keller et al., *Biochim. Biophys. Acta*, 882(1): 1–5, 1986). The binding constant can be assessed using affinity co-electrophoresis as described by San Antonio et al. (*J. Cell Biol.*, 125(5): 1178–1188). This method can be used to compare the binding of FP-1 to procollagen or collagen fibrils in order to determine whether the binding is collagen assembly-dependent. Finally, the collagen domain that is responsible for the binding of FP-1 can be mapped using synthetic peptides or paryial collagen fragments made as recombinant proteins (Knight et al., *J. Biol. Chem.*, 273(50):33287–33294, 1998).

Non-limiting examples of mutations in the olfactomedin-related domain of FP-1 include, (i) deletion of amino acids 315–325 of SEQ ID NO:2 (or the corresponding region in SEQ ID NOS: 4, 6, 8, 10 and 12); (ii) deletion of amino acids 366–382 of SEQ ID NO:2 (or the corresponding region in SEQ ID NOS: 4, 6, 8, 10 and 12); (iii) deletion of amino acids 408–437 of SEQ ID NO:2 (or the corresponding region in SEQ ID NOS: 4, 6, 8, 10 and 12); (iv) deletion of amino acids 441–466 of SEQ ID NO:2 (or the corresponding region in SEQ ID NOS: 4, 6, 8, 10 and 12); (v) deletion of amino acids 468–484 of SEQ ID NO:2 (or the corresponding region in SEQ ID NOS: 4, 6, 8, 10 and 12); (vi) deletion of amino acids 487–494 of SEQ ID NO:2 (or the corresponding region in SEQ ID NOS: 4, 6, 8, 10 and 12); (vii) deletion of amino acids 519–539 of SEQ ID NO:2 (or the corresponding region in SEQ ID NOS: 4, 6, 8, 10 and 12); (viii) deletion of any combination of the amino acids listed above; (ix) mutation of one or more of G318, W320, R322, E323, G368, G370, A372, V373, Y374, N375, S377, L378, Y379, Y380, K382, F409, Y413, I424, A425, V426, D427, E428, G430, L431, W432, I433, I434, Y435, A436, I444, L445, V446, L449, T453, V456, N461, T462, Y464, K466, A469, N471, A472, F473, A475, G477, I478, L479, Y480, V481, T482, T484, T490, F491, A492, F493, D494, Y519, N520, D523, L526, Y527, W529, E530, D531, G532, H533, L534, Y537 and V539 of SEQ ID NO:2 (or the corresponding amino acid in SEQ ID NOS: 4, 6, 8, 10 and 12) to any other amino acid; (ix) FP-1 comprising a mutation at Y480 of SEQ ID NO:2 (or the corresponding amino acid in SEQ ID NOS: 4, 6, 8, 10 and 12) to any amino acid, for example, but not limited to, histidine and asparagine; (x) FP-1 comprising a mutation at A469 of SEQ ID NO:2 (or the corresponding amino acid in SEQ ID NOS: 4, 6, 8, 10 and 12) to any amino acid, for example, but not limited to, phenylalanine, tyrosine and aspartic acid; (xi) FP-1 comprising a mutation at Y480 of SEQ ID NO:2 (or the corresponding amino acid in SEQ ID NOS: 4, 6, 8, 10 and 12) to any amino acid, for example, but not limited to, histidine and asparagines; and (xii) FP-1 comprising a mutation at N519 of SEQ ID NO:2 (or the corresponding amino acid in SEQ ID NOS: 4, 6, 8, 10 and 12) to any amino acid, for example, but not limited to, lysine and arginine.

In addition, the invention encompasses FP-1 proteins with mutations at one or more of the glycosylation sites of FP-1 that prevent its glycosylation. In one embodiment, N130, N156, S252, N326, N354 and N461 are mutated to a different amino acid residue such as, but not limited to, glycine. Glycosylation of FP-1 and mutant FP-1 proteins can be assessed by comparing SDS-PAGE mobilities of the unmutated and mutated FP-1 proteins. N-glycosylation of each potential glycosylation site will increase the apparent SDS gel molecular weight by approximately 2 kD. Thus, the mutation of one such N-glycosylation site in FP-1 will decrease the molecular weight of FP-1 by 2 kD.

In addition, the invention encompasses FP-1 proteins, or any hair growth-controlling portion thereof, that are fusion proteins. A protein or peptide may be fused either at the N- or C-terminus of FP-1 proteins. In one embodiment, an FP-1 protein is fused to an epitope tag selected from the group consisting of His, Flag, Myc, HA, MBP and GST.

The present invention further provides polyclonal and monoclonal antibodies, or portions thereof, that bind to the polypeptides or peptide fragments of the invention, or to a homologous polypeptide or peptide fragment of the invention. The term "antibody" as used herein refers to immunoglobulin molecules and immunologically active portions of immunoglobulin molecules, i.e., molecules that contain an antigen binding site which specifically binds (immunoreacts with) an antigen, such as FP-1. Antigen-binding fragments are also intended to be designated by the term "antibody." Examples of binding fragments encompassed within the term antibody include Fab, Fd, Fv, dAb, F(ab')$_2$, and single chain Fv (scFv). For example, antibody fragments for use in the present invention are those which are capable of crosslinking their target antigen, e.g., bivalent fragments such as F(ab')$_2$ fragments. In another embodiment, an antibody fragment which does not itself crosslink its target antigen (e.g., a Fab fragment) can be used in conjunction with a secondary antibody which serves to crosslink the antibody fragment, thereby crosslinking the target antigen. An antibody of the invention is further intended to include bispecific and chimeric molecules having a desired binding portion (e.g., FP-1).

An antibody of the present invention is used to detect the polypeptides of the invention; as affinity reagents with which to purify the polypeptides of the invention; as reagents to isolate follicular papilla cells; or to control the activity of the polypeptide of the invention. In this context, "controls hair growth" is meant to increase or decrease hair growth relative to hair growth in skin, hair follicles or follicular papilla not contacted with an antibody of the invention. For example, an antibody that binds FP-1 controls the activity of FP-1 by increasing or decreasing its ability to control hair growth. Methods of determining whether FP-1 increases or decreases hair growth can be assayed using any of the methods described or used in the Examples.

Polyclonal antibodies can be obtained from immunized animals and tested for specificity using standard techniques (Harlow et al., *Antibodies: A Laboratory Manual*, Cold Spring Harbor Laboratory Press, 1988). Alternatively, monoclonal antibodies to any of the polypeptides of the invention can be prepared using any technique that provides for the production of antibody molecules by continuous cell lines in culture. These include, but are not limited to, the hybridoma technique originally described by Kohler and Milstein (*Nature*, 256:495–497, 1975); the human B-cell hybridoma technique (Kosbor et al., *Immunol. Today*, 4:72, 1983; Cote et al., *Proc. Natl. Acad. Sci. USA*, 80:2026–2030, 1983); and the EBV-hybridoma technique (Cole et al., *Monoclonal Antibodies and Cancer Therapy*, Alan R. Liss, Inc., pp. 77–96) and any other methods known in the art (Golding, *Monoclonal Antibodies: Principles and Practice*, Academic Press, 1996). Alternatively, techniques described for the production of single chain antibodies (e.g., U.S. Pat. No. 4,946,778) can be adapted to produce single chain antibodies to the polypeptides of the present invention.

An anti-FP-1 antibody or a fragment thereof may be attached or coupled to a surface (e.g., cell surface, beads etc.). Beads that are used in the invention include, but are not limited to biodegradable beads, magnetic beads, and polymer microbeads. An antibody or fragment thereof can be immobilized directly or indirectly by, for example, by a secondary antibody, to a surface, such as a tissue culture flask or bead (see, for e.g., U.S. Pat. Nos. 6,352,694 and 6,129,916). Alternatively, antibodies can be coupled to a surface, e.g., beads by crosslinking via covalent modification, using tosyl linkage. In one method, an antibody such as anti-FP-1 is in 0.05 M borate buffer, pH 9.5 and added to tosyl activated magnetic immunobeads (Dynal Inc., Great Neck, N.Y.) according to the manufacturer's instructions. After a 24 hr incubation at 22° C., the beads are collected and washed extensively. It is not essential that immunomagnetic beads be used, as other methods are also satisfactory.

In one embodiment of the invention, an FP-1 protein, or a portion of an FP-1 protein, or a modified form of an FP-1 protein, capable of modulating hair growth is localized on the surface of a cell. This can be accomplished by transfecting a cell with a polynucleotide encoding the FP-1 protein in a form suitable for its expression on the cell surface or alternatively by coupling an FP-1 protein to the cell surface.

The FP-1 proteins may be expressed on the surface of a cell by transfection of the cell with a polynucleotide encoding the FP-1 molecule in a form suitable for expression of the molecule on the surface of the cell. The terms "transfection" or "transfected with" refers to the introduction of exogenous nucleic acid into a mammalian cell and encompass a variety of techniques useful for introduction of nucleic acids into mammalian cells including electroporation, calcium-phosphate precipitation, DEAE-dextran treatment, lipofection, microinjection and infection with viral vectors. Suitable methods for transfecting mammalian cells can be found in Sambrook et al., (*Molecular Cloning: A Laboratory Manual*, 2nd Edition, Cold Spring Harbor Laboratory Press, 1989) and other laboratory textbooks. The nucleic acid to be introduced may be any nucleic acid encompassing a polynucleotide encoding FP-1, sense strand RNA encoding FP-1, or a recombinant expression vector containing a cDNA encoding FP-1. Expression of FP-1 on the surface of a cell can be accomplished, for example, by including the transmembrane domain of a protein that localizes to the cell surface in the nucleic acid sequence, or by including signals which lead to modification of the protein, such as a C-terminal inositol-phosphate linkage, that allows for association of the molecule with the outer surface of the cell membrane. Expression of the FP-1 protein on the surface of the cell can be confirmed by immunofluorescence staining of the cells. For example, cells may be stained with a fluorescently labeled monoclonal antibody reactive against the FP-1 molecule.

Alternatively, FP-1 proteins can be coupled to the cell surface by any of a variety of different methods. The terms "coupled" or "coupling" refer to a chemical, enzymatic or other means (e.g., antibody) by which the FP-1 molecule is linked to a cell such that the FP-1 molecule is present on the surface of the cell. For example, the FP-1 molecule can be chemically crosslinked to the cell surface using commercially available crosslinking reagents (Pierce, Rockford Ill.). Another approach to coupling an FP-1 molecule to a cell is to use a bispecific antibody, which binds both the FP-1 molecule and a cell-surface molecule on the cell. Fragments, mutants or variants of a FP-1 molecule can also be used. The level of FP-1 expressed on or coupled to the cell surface can be determined by FACS analysis.

The present invention also encompasses methods of isolating follicular papilla cells. Since FP-1 is a secreted extracellular matrix protein at least some of the protein remains associated with the cell surface of the follicular papilla cells. Thus, antibodies to FP-1 can be used to sort the cells that bind an antibody raised to FP-1 using methods well known in the art. Alternatively, a composition comprising an anti-FP-1 antibody attached to a surface can be used to selectively isolate follicular papilla cells from a mixed population of cells from the skin or hair follicle. In this method, a composition comprising an FP-1 antibody can be used to contact a mixed population of cells from the skin or hair follicle sample from which the follicular papilla cells are to be isolated. The follicular papilla cells that bind to the FP-1 antibody can be separated from the unbound cells by any method known in the art including, but not limited to, fractionation. The isolated follicular papilla cells may be useful for (i) inducing epidermis to form new hair follicles de novo; or (ii) improving the performance of existing hair follicles that may contain defective or fewer numbers of follicular papilla cells than normal hair follicles.

Also within the scope of the present invention are oligonucleotide sequences that include antisense oligonucleotides, ribozymes, and siRNAs that function to bind to, degrade and/or inhibit the translation of the mRNA encoded by the polynucleotides of the invention. Antisense RNAs can be designed based on principles established in the art (e.g., Schiavone et al., *Curr. Pharm. Des.*, 10(7):769–784, 2004; Sczakiel, *Antisense Nucl. Acid Drug Dev.*, 7(4):439–444, 1997; Stein, *Antisense Nucl. Acid Drug Dev.*, 8(2): 129–132, 1998; and Summerton et al., *Antisense Nucl. Acid Drug Dev.*, 7(3): 187–195, 1997). Methods for designing suitable siRNAs for a target gene are well known in the art (e.g., Elbashir et al., *Nature*, 411:494–498, 2001; Semizarov et al., *Proc. Natl. Acad. Sci. USA*, 100:6347–6352, 2003).

The antisense oligonucleotides, ribozymes and siRNAs of the present invention can be commercially obtained or prepared by known methods. These include techniques for chemical synthesis such as, e.g., by solid phase phosphoramidite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters.

Various modifications to any of the polynucleotides and oligonucleotides of the present invention can be introduced to increase intracellular stability and half-life. Possible modifications include, but are not limited to, the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

The present invention also provides pharmaceutical compositions or formulations comprising the polynucleotides, polypeptides, antisense molecules, ribozymes, siRNAs or antibodies of the present invention, as an active component. For example, a pharmaceutical composition may comprise a polynucleotide selected from the group consisting of SEQ ID NO:1, SEQ ID NO:3, SEQ ID NO:5, SEQ ID NO:7, SEQ ID NO:9, SEQ ID NO:11, and any combination thereof. The pharmaceutical composition may instead comprise a polypeptide selected from the group consisting of SEQ ID NO:2, SEQ ID NO:4, SEQ ID NO:6, SEQ ID NO:8, SEQ ID NO:10, SEQ ID NO:12, and any combination thereof. The pharmaceutical composition alternatively may comprise a polypeptide such as one having amino acids 34 to 549 of SEQ ID NO:2, 34 to 531 of SEQ ID NO:4, 34 to 549 of SEQ ID NO:6, 34 to 549 of SEQ ID NO:8, 34 to 427 of SEQ ID NO:10, and/or 34 to 551 of SEQ ID NO:12. The pharmaceutical composition may instead comprise an antibody that binds to FP-1. For example, the antibody may be one that specifically binds to human FP-1, or to both the rat and human FP-1 proteins. The pharmaceutical composition may alternatively comprise an antisense molecule that inhibits or prevents translation of FP-1 mRNA, an siRNA that blocks expression of an FP-1 mRNA, or a ribozyme that cleaves an FP-1 mRNA.

In addition to the FP-1 component of the composition, the therapeutic compositions of the present invention contain suitable pharmaceutically acceptable carriers, and may also comprise excipients and auxiliaries that facilitate processing of the active compounds into preparations, which can be used pharmaceutically for delivery to the site of action. Suitable formulations for parenteral administration include aqueous solutions of the active compounds in water-soluble form, for example, water-soluble salts. In one embodiment, the pharmaceutically acceptable carrier is phosphate buffered saline. In another embodiment, the carrier is water. In addition, suspensions of the active compounds as appropriate oily injection suspensions may be administered. Suitable lipophilic solvents or vehicles include, but are not limited to, fatty oils (e.g., sesame oil), or synthetic fatty acid esters (e.g., ethyl oleate), or triglycerides. Aqueous injection suspensions may contain substances which increase the viscosity of the suspension, for example, sodium carboxymethyl cellulose, sorbitol and dextran. Optionally, the suspension may also contain stabilizers. Liposomes can also be used to encapsulate the composition for delivery into the cell (e.g., U.S. Pat. Nos. 4,828,837 and 6,224,901).

The pharmaceutical formulations of the invention may be administered to a subject in need thereof using standard administration protocols. "A subject in need thereof," is used herein, to mean a mammalian subject who is determined by a health care provider, scientist, veterinarian, animal breeder, or other qualified person to be in need of increasing or decreasing hair growth. In the case of human subjects, the health care provider may determine that the subject is in need of controlling hair growth for health or cosmetic reasons. For non-mammalian subjects, a veterinarian or animal breeder may determine that a particular subject is in need of a pharmaceutical composition of the invention to increase hair growth, e.g., in wool or fur production.

The compositions of the present invention can be administered via topical, parenteral, subcutaneous, intravenous, intramuscular, intraperitoneal, transdermal, or buccal routes. For example, a composition is administered locally to a site via microinfusion, or by topical application in a cream, gel, lotion, ointment, salve, balm, aqueous solution or patch. Alternatively, or concurrently, administration may be by the oral route. Suitable formulations for oral administration include hard or soft gelatin capsules, pills, tablets, including coated tablets, elixirs, suspensions, syrups or inhalations and controlled release forms thereof. Indeed, all types of formulations may be used simultaneously to achieve systematic administration of the active ingredient. The dosage administered is dependent upon the age, health, and weight of the recipient, kind of concurrent treatment, if any, frequency of treatment, and the nature of the desired effect. The present invention further provides compositions containing one or more polypeptides of the invention. While individual needs vary, determination of optimal ranges of effective amounts of each composition of the invention is within the skill of the art. In one non-limiting example, dosages of protein for topical formulations comprise from about 0.1 ng to about 100 ng per ml of the formulation, from about 10 ng to about 50 ng, or about 30 ng.

The pharmaceutical formulations of the present invention can be provided alone, or in combination, or in sequential combination with other agents that modulate hair growth. As used herein, two agents are said to be administered in combination when the two agents are administered simultaneously or are administered independently in a way such that the agents will act at the same or almost the same time.

The use of gene therapy to administer the compositions of the invention is contemplated in one aspect of this invention. More specifically, the polynucleotides of the invention can be applied to the skin or scalp through the delivery of nucleic acid molecules. The delivery of nucleic acid molecules can be accomplished by any means known in the art. Gene delivery vehicles (GDVs) are available for delivery of polynucleotides to cells or tissue for expression. For example, a nucleic acid sequence of the invention can be administered either locally or systematically in a GDV. These constructs can utilize viral or non-viral vector approaches in vivo or ex viva. Expression of such coding sequence can be induced using endogenous mammalian or heterologous promoters. Expression of the coding sequence in vivo can be either constitutive or regulated. The invention includes gene delivery vehicles capable of expressing the contemplated polynucleotides. The gene delivery vehicle may be a viral vector such as, but not limited to, a retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picomavirus, poxvirus, togavirus viral vector (see generally, Jolly, *Cancer Gene Therapy*, 1:51–64, 1994; Kimura, *Human Gene Therapy*, 5:845–852, 1994; Connelly, *Human Gene Therapy*, 6:185–193, 1995; and Kaplitt, *Nature Genetics*, 6:148–153, 1994). Delivery of the gene therapy constructs of this invention into cells is not limited to the above-mentioned viral vectors. Other delivery methods and media may be employed such as nucleic acid expression vectors, polycationic condensed DNA linked or unlinked to killed adenovirus alone (Curiel, *Hum. Gene Ther.*, 3:147–154, 1992), ligand linked DNA (Wu, *J. Biol. Chem.*, 264:16985–16987, 1989), eukaryotic cell delivery vehicles cells (U.S. Pat. No. 6,015,686), deposition of photopolymerized hydrogel materials, hand-held gene transfer particle gun (U.S. Pat. No. 5,149,655), ionizing radiation (U.S. Pat. No. 5,206,152 and PCT Patent Publication No. WO 92/11033), nucleic charge neutralization or fusion with cell membranes. Additional approaches are described in Phillip, *Mol. Cell. Biol.,* 14:2411–2418, 1994 and in Woffendin, *Proc. Natl. Acad. Sci. USA,* 91:1581–585, 1994. Briefly, the nucleotide sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands. Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes, that can act as gene delivery vehicles are described in U.S. Pat. No. 5,422,120, PCT Patent Publication Nos. WO 95/13796, WO 94/23697, and WO 91/144445, and EP No. 524,968.

The polynucleotide molecules of the invention may be introduced into the skin or scalp using the injectable carrier alone. Liposomal preparations are preferred for methods in which in vitro transfections of cells obtained from the skin or scalp are carried out. The carrier preferably is isotonic, hypotonic, or weakly hypertonic, and has a relatively low ionic strength, such as provided by a sucrose solution. The preparation may further advantageously comprise a source of a cytokine which is incorporated into liposomes in the form of a polypeptide or as a polynucleotide. Alternatively, an even more prolonged effect can be achieved by introducing the DNA sequence into the cell by means of a vector plasmid having the DNA sequence inserted therein. The plasmid may further comprise a replicator.

It is possible to obtain long term administration of a polypeptide to the scalp by introducing a naked DNA sequence operatively coding for the polypeptide interstitially into the skin or scalp, whereby cells of the tissue produce the polypeptide for at least one month or at least 3 months, more preferably at least 6 months. In addition, a method for obtaining transitory expression of a polypeptide in the scalp can be achieved by introducing a naked mRNA sequence operatively coding for the polypeptide interstitially into the skin or scalp, whereby cells of the tissue produce the polypeptide for less than about 20 days, usually less than about 10 days, and often less than 3 or 5 days.

The polypeptides of the invention can also be administered to a patient via depot or transdermal technology. In one embodiment, a pharmaceutical composition comprising FP-1 and a pharmaceutically acceptable carrier are delivered to a subject using one of Alza's D-TRANS® patches, Alza's E-TRANS® systems, and ALZA's Macroflux® transdermal technology. In an alternative embodiment, a pharmaceutical composition comprising FP-1 and a pharmaceutically acceptable carrier are delivered to a subject using one of Alza's DUROS® implant or ALZAMER® Depot technologies.

The pharmaceutical compositions or formulations of the present invention can be used in modulating hair growth in several contexts. By "modulate hair growth" is meant to increase or decrease hair growth. Methods of measuring or assaying hair growth are described in the Examples below, and in Philpott et al., "Whole Hair Follicle Culture" in *Dermatological Clinics* 14(4): 595–607, 1996), and the references cited therein. The compositions comprising polynucleotides encoding FP-1 and FP-1 polypeptides are primarily intended for use in increasing or promoting hair growth, whereas compositions comprising mutant FP-1 polynucleotides or proteins, FP-1 ribozymes, FP-1 antisense molecules, FP-1 siRNAs, and antibodies raised to FP-1, are primarily intended for use in decreasing, or inhibiting hair growth.

Promoting hair growth or attenuating hair loss serves to combat the effects of alopecia in humans and other mammalian species. Conversely, retarding hair growth or promoting hair loss can combat the effects of hirsutism, hypertrichosis, and similar disorders of afflicted individuals. Additionally, the compositions of the invention can be employed to control hair growth in normal skin. Thus, for example, the compositions can be employed in wool or fur production (e.g., applied to alpaca, beaver, calf, chinchilla, coyote, ermine, fisher, fitch, fox, lamb, llama, lynx, marten, mink, muskrat, nutria, opossum, otter, raccoon, Russian squirrel, sable, sheep, and other fur- or wool-producing mammals), to increase hair growth thereby permitting greater net annual wool production or reducing the time needed to produce mature pelts. Alternatively, the compositions of the present invention can be employed to produce custom designs of bare skin or thin, thick, or variegated hair within pelts of treated animals.

The compositions of the present invention are utilized in the methods of the present invention, which include a method of controlling hair growth in a subject comprising administering a pharmaceutical composition of the invention to that subject. The present invention also provides a method for modulating hair growth comprising contacting the skin or hair follicle of a subject with a composition of the invention. Alternatively, the follicular papilla of a subject may be contacted with a pharmaceutical composition of the present invention. Any of these methods can further comprise administering a second agent that controls hair growth. Where it is desired to increase hair growth, the second agent is a substance that either increases hair growth or which assists the composition of the invention to increase hair growth. Where it is desired to decrease or prevent hair growth, the second agent is a substance that decreases hair growth or assists the composition of the invention to decrease hair growth. The compositions of the invention may be administered by any of the methods detailed above. For example, the composition is topically administered to the skin of a subject in an amount sufficient to achieve a dose of at least about 0.01 nmol, at least 0.1 nmol, or at least about 1 nmol per 2 cm by 4.5 cm skin surface area, up to a dose of about 100 nmol, 1,000 nmol, or 10,000 nmol or more per 2 cm×4.5 cm skin surface area.

The present invention also provides a method for transplanting hair in a subject in need thereof including the pretreatment of hair follicles or grafts to be transplanted. In a typical hair transplantation procedure, grafts of skin containing hair are removed from the back or sides of the scalp (donor area) of the individual and are transplanted to other areas, that is, the bald or thinning area (recipient area). To place the grafts onto these areas, a number of incisions are made in the scalp. The incisions are then cleaned and a graft is inserted into each incision. Hair transplantation includes a minigraft for placing only a small number of hairs into the incisions, a micrograft for placing a single hair in the incisions (also, referred to as one-haired minigraft), and a follicular unit hair transplantation.

FP-1 polynucleotides and proteins of the present invention can be used in the pretreatment of hair follicles or grafts before transplantation. Such treatment is contemplated to promote or accelerate hair implantation.

The present invention also relates to diagnostic assays such as quantitative and diagnostic assays for detecting levels of FP-1 protein in cells and tissues. FP-1 levels can be detected at the RNA or protein level. A diagnostic assay in accordance with the invention for detecting under-expression of FP-1 proteins compared to normal control tissue samples, are used to detect whether the subject is likely to develop a hair loss disorder. In one embodiment, the diagnostic assay is used for the prognosis of alopecia. Assay techniques that are used to determine levels of FP-1 proteins of the present invention, in a sample derived from a host, for example blood or scalp tissue, are well known to those of skill in the art. Such assay methods include, but are not limited to, immunoassays, radio-immunoassays, competitive-binding assays, Western Blot analysis, ELISA assays, and immunofluorescence assays. Accordingly, the present invention provides a method for diagnosing alopecia in a subject comprising collecting a blood or tissue sample from said subject and detecting FP-1 proteins in said sample.

Such diagnostic assays can also be used to diagnose cancers. Overexpression of FP-1 correlates with heightened risk for developing or having developed a cancer. In one embodiment, the invention provides a method to diagnose skin cancers (e.g., basal cell carcinoma, pilomatricoma). In other embodiments, the method permits diagnosis of liver cancers, cancers of the nervous system, stomach cancers, testicular cancer and ovarian cancer among others.

The present invention further provides methods of identifying agents that control hair growth. The method comprises contacting skin with a test agent ex vivo. A test agent may be any substance that is contemplated to potentially regulate hair growth. The method further comprises detecting or measuring the expression of FP-1 in the follicular papilla. If the test agent is found to increase expression of FP-1 in the follicular papilla it is determined to be an agent that stimulates hair growth. If, however, the test agent decreases the expression of FP-1 in the follicular papilla it is determined to be an inhibitor of hair growth.

Also contemplated are methods to identify agents that interact with FP-1 and modulate its ability to control hair growth. Methods of identifying other proteins that interact with FP-1 include, but are not limited to, immuno-precipitation and two-hybrid assays (Sambrook et al., cited supra; Fields et al., *Nature*, 340(6230):245–246, 1989; and Fields et al., *Trends Genet.*, 10(8):286–92, 1994).

The present invention also encompasses the production of transgenic non-human animals that express FP-1 protein or FP-1 fusion protein encoding construct of the instant invention. Animals, which contain exogenous DNA sequences in their genome, are referred to as transgenic animals. The successful production of transgenic, non-human animals has been described in a number of patents and publications, such as, for example U.S. Pat. Nos. 6,291,740; 6,281,408; and 6,271,436.

The most widely used method for the production of transgenic animals is the microinjection of DNA into the pronuclei of fertilized embryos (Wall et al., *J. Cell. Biochem.*, 49:113, 1992). Other methods for the production of transgenic animals include the infection of embryos with retroviruses or with retroviral vectors. Infection of both pre- and post-implantation mouse embryos with either wild-type or recombinant retroviruses has been reported (Jaenisch, *Proc. Natl. Acad. Sci. USA*, 73:1260, 1976; Jaenisch et al., *Cell*, 24:519, 1981; Stuhlmann et al., *Proc. Natl. Acad. Sci. USA*, 81:7151, 1984; Jahner et al., *Proc. Natl. Acad. Sci. USA*, 82:6927, 1985; Van der Putten et al., *Proc. Natl. Acad. Sci. USA*, 82:6148–6152, 1985; Stewart et al., *EMBO J.*, 6:383–388, 1987).

An alternative means for infecting embryos with retroviruses is the injection of virus or virus-producing cells into the blastocoele of mouse embryos (Jahner, D. et al., *Nature* 298:623, 1982). The introduction of transgenes into the germline of mice has been reported using intrauterine retroviral infection of the midgestation mouse embryo (Jahner et al., supra, 1982). Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos (PCT International Application WO 90/08832; and Haskell and Bowen, *Mol. Reprod. Dev.*, 40:386, 1995). PCT International Application WO 90/08832 describes the injection of wild-type feline leukemia virus B into the perivitelline space of sheep embryos at the 2 to 8 cell stage. Fetuses derived from injected embryos were shown to contain multiple sites of integration.

The ability to alter the genetic make-up of animals, such as domesticated mammals including cows, pigs, goats, horses, cattle, and sheep, allows a number of commercial applications. In the context of the present invention, FP-1 transgenic animals are useful as models to study hair growth, as well as to test drugs, compounds, etc. for use in regulating hair growth.

Without further description, a person of ordinary skill in the art can, using the preceding description and the following illustrative examples, make and utilize the present invention and practice the disclosed methods. The following working examples therefore are not to be construed as limiting in any way the remainder of the disclosure.

EXAMPLES

Example 1

Materials and Methods

I. Cell Culture (a) Follicular Papilla

Vibrissa follicles were isolated individually from the lip region of 4–6 months old male Wistar rats (Charles River). To expose follicular papilla, the lower part of the follicle was opened by a 20 gauge needle. About 35–40 follicular papillae were microdissected from each rat, The isolated follicular papillae were placed in 1 ml Chang's medium (Irvine Scientific) with 100 units/ml penicillin and 100 µg/ml streptomycin in a 35 mm petri plate, and left undisturbed in a 37° C., 5% $CO_2$ incubator for 4 days. Under these conditions most of the papillae formed outgrowths (Jahoda and Oliver, *Br. J. Dermatol.*, 105(6):623–627, 1981; Jahoda and Oliver, *J. Embryol. Exp. Morphol.*, 79:211–24, 1984; Warren et al., *J. Invest. Dermat.*, 98:693–699, 1992). The culture medium was changed every 3 days. Ten to twelve days later, the cells were treated with 0.125% trypsin and 0.01% EDTA in phosphate-buffer saline, and the dissociated single cells were then plated in Dulbecco's Modified Eagle's Medium (DMEM) containing 10% fetal bovine serum (FBS), 100 units/ml penicillin and 100 µg/ml streptomycin. Sub-confluent cells were fed every 3 days by removing old medium and adding fresh medium warmed to 37° C.

(b) Rat Dermal Fibroblasts

Rat dermal fibroblasts were cultured by explant outgrowth from small pieces (<1 mm$^3$) of interfollicular dermis from the same lip skin tissue, from which the vibrissa follicles had been removed. The primary culture and subculture conditions were the same as described above. Rat stomach, esophagus and thoracoabdominal diaphragm tissues were minced thoroughly to <1 mm$^3$ and placed in 1 ml DMEM containing 10% FBS, 100 units/ml penicillin and 100 µg/ml streptomycin in a 30 mm petri plate. After being undisturbed for a few days, fibroblasts grew out from these tissues. The subculture conditions were the same as described above. All experiments were carried out using the fourth passage of the cultured cells. One passage constituted a 1:3 dilution of subculture.

II. Subtractive cDNA Library

Total RNA of cultured cells was isolated by a system using guanidine thiocyanate and CSB (citrate/sarcosine/β-mercaptoethanol) as denaturing buffer followed by phenol extraction (The RNAgents® Total RNA Isolation System, Promega). Poly A+ RNA was separated from the total RNA using a biotinylated oligo (dT) selection with the MagneSphere® mRNA isolation system (Promega).

Cultured rat vibrissa follicular papilla-specific subtractive cDNA library was constructed using the PCR-select™ cDNA subtraction Kit (Clontech) according to the manufacturer's instructions (Diatchenko et al., *Proc. Natl. Acad. Sci. USA*, 93(12):6025–6030, 1996). For the first strand cDNA synthesis, 2 µg of cultured rat vibrissa follicular papilla cell poly A+ RNA (the "tester") and 2 µg of a mixture (1:1:1) of cultured rat stomach, esophagus and diaphragm fibroblasts poly A+ RNA were reverse-transcribed using MMLV reverse transcriptase (Gibco). The second stranded cDNA was synthesized with a 20× enzyme cocktail containing DNA polymerase 1 (6 U/µl), RNase H (0.25 U/µl), *E. coli* DNase ligase (1.2 U/µl), and T4 DNA polymerase (1.5 U/µl). The double strand cDNA obtained was phenol extracted and ethanol precipitated. After digesting with Rsa I, the tester (follicular papilla) cDNA was divided into two subpopulations, which were ligated with two different adaptors. The two subpopulations (about 15 ng each) were then hybridized with an excess amount of the driver (3 types of fibroblasts) cDNA (about 470 ng), after which they were combined. Without denaturing the DNA hybrids, the mixture of the two primary hybridization samples was hybridized again with freshly denatured driver cDNA (about 310 ng). To enrich and amplify the differentially expressed sequences, two rounds of selective PCR were performed in both subtracted and unsubtracted cDNA (tester cDNAs ligated with two different adaptors) using primers that anneal to the adaptors sequences. The PCR products were cloned into the pCRII TA cloning vector, which was then transformed into TOP10F' cells (Invitrogen).

In order to perform differential screening later, a reverse subtraction (a rat fibroblast-specific subtractive cDNA library) was also performed by the same PCR-select™ cDNA subtraction technique as described above. In the reverse subtraction, a mixture of the 3 types of fibroblast (cultured rat stomach, esophagus and diaphragm fibroblasts) served as the "tester" and follicular papilla as the "driver."

III. Differential Screening a. cDNA Array

Bacterial colonies were randomly picked from the follicular papilla-specific subtracted library and cultured overnight at 37° C. with shaking. To amplify the cDNA inserts, PCR was performed using adaptor-specific primers (Clontech). After denaturing with 0.6 N NaOH, the PCR products were transferred onto a Hybond™-XL nylon membrane (Amersham Pharmacia Biotech). Two identical blots were prepared for hybridizing with follicular papilla-specific subtracted library (FP probe) and fibroblast-specific subtracted library (F probe). The blots were neutralized with 0.5 M Tris-HCl (pH 7.5) for 2–4 min. and washed with H$_2$O. DNA was cross-linked to the membrane by UV light.

b. Colony Array

The same overnight cultures of the randomly picked bacterial clones were used to perform colony array. Each bacterial culture was transferred onto a Hybond™-XL nylon membrane (Amersham Pharmacia Biotech) placed on the LB/agar plate containing kahamycin. Two identical blots were prepared for hybridizing with the follicular papilla-specific subtracted library (FP probe) and fibroblast-specific subtracted library (F probe). After culturing overnight at 37° C., the blots were denatured with 0.5 M NaOH, 1.5 M NaCl for 4 min, neutralized with 0.5 M Tris-HCl (pH 7.5), 1.5 M NaCl for 4 min, and air dried for 30 min. The DNA was fixed to the membrane by baking at 80° C. for 2 hrs.

c. Preparation of the Subtracted cDNA Probes

The amplified PCR products of the subtracted cDNAs were purified with the NucleoTrap® PCR purification kit (Clontech), and underwent restriction enzyme digestion to remove the adaptor sequences. Three restriction enzymes were used one after another in the following order: Rsa I at 37° C. for 1 hr, Sma I at room temperature for 1 hr, and Eag I at 37° C. for 1 hr. After separation from the adaptor using the NucleoTrap® PCR purification kit (Clontech), the cDNAs were then labeled with ($\alpha$-$^{32}$P) dCTP by the Multiprime™ DNA labeling system (Amersham Pharmacia Biotech). The specific activity of the labeled probe was determined by using a scintillation counter. The total counts per probe was greater than 10$^7$ cpm.

d. Hybridization with the Subtracted cDNA Probes

The blots of the cDNA array and colony array were hybridized at 60° C. over night with the labeled subtracted cDNA probes in Church solution (0.25 M Na$_2$HPO$_4$ (pH 7.2), 1 mM EDTA, 7% SDS, and 1% BSA). Equal amounts (about 3.5×10$^7$ cpm) of the labeled follicular papilla-specific cDNA probe (FP probe) and fibroblast-specific cDNA probe (F probe) were used in an equal amount (7.5 ml) of Church hybridization solution for every two identical colony array or cDNA array blots. Two cDNA fragments were used as hybridization negative controls: (i) a mouse testis-specific gene (GenBank® Accession No. X52128), and (ii) a human semenogelin II (GeneBank® Accession No. ANM81652), which is specific to seminal vesicles.

IV. Virtual Northern

1 µg of total RNA from cultured follicular papilla cells, fibroblasts (diaphragm, esophagus, and stomach fibroblasts in a 1:1:1 mixture), and dermal fibroblasts were separately reverse transcribed to first-strand cDNAs. Double strand cDNA (ds cDNA) was synthesized and then amplified by PCR according to the SMART™ cDNA synthesis technique (Clontech). The optimal number of PCR cycles was titrated to ensure that the ds cDNA synthesis remained in the exponential phase of amplification. The PCR-amplified ds cDNA was electrophoresed on a 1% agarose gel, and then transferred onto a Hybond™-XL nylon membrane (Amersham Pharmacia Biotech). The filter was subjected to hybridization using the procedure used for Northern blot hybridization.

V. 5' RACE (Rapid Amplification of cDNA Ends) of FP-1

5' race of FP-1 was performed according to the manufacturer's instructions (Clontech). 1 µg of poly A+ RNA from the cultured rat vibrissa follicular papilla cells was reverse transcribed into first-strand cDNA. Using the first-strand cDNA as a template, the primary PCR was performed with the Universal Primer (Clontech) and a FP-1 specific primer. The thermal cycling program was as follows: 5 cycles of 94° C., 5 sec; 72° C., 3 min.; 5 cycles of 94° C., 5 sec; 70° C., 10 sec; 72° C., 3 min.; 23 cycles of 94° C., 5 sec; 68° C., 10 sec; 72° C., 3 min. The primary PCR product was diluted to 1:50 and used as a template in the secondary PCR. The second PCR was primed with the Universal Nested Primer (Clontech) and a FP-1 specific nested primer. The thermal cycling program was as follows: 20 cycles of 94° C., 5 sec; 68° C., 10 sec; 72° C., 3 min. The nucleotide sequences of the FP-1 primer and the FP-1 nested primer were: 5' CCCAGTTCACCAGCATCTCCCTTCTCTC 3' (SEQ ID NO:13) and 5' GTCTATCATCACCCGGATCGGCACCAT 3' (SEQ ID NO:14), respectively. The PCR product from the second PCR reaction was ligated into a TA cloning vector (Invitrogen). Individual clones were sequenced.

VI. Western Blot and Deglycosylation

Cultured cells were dissolved in lysis buffer (1% NP40, 1% deoxycholic acid, 0.1% SDS, 150 mM NaCl, 50 mM Tris-HCl (pH 7.4), 2 mM EDTA and freshly added protease inhibitor). After centrifugation at 14,000 rpm for 20 min at 4° C., the soluble proteins were quantified using a BCA kit (Pierce). 50 μg of the total proteins were resolved on a 12% polyacrylamide gel according to standard procedures (Laemmli, 1970). The separated proteins were transferred electrophoretically to an MSI-nitrocellulose membrane (Towbin et al., *Proc. Natl. Acad. Sci. USA*, 76:4350–4354, 1979; Burnette, *Anal. Biochem.*, 112:195–203, 1981). The membrane was incubated with primary antibodies and HRP-conjugated secondary antibody. Optimal concentration of the primary antibodies was determined by titration: anti-DP1 rabbit serum G320 (1:10,000), anti-β-tubulin mouse monoclonal antibody (Sigma) (1:2,000). The reaction was visualized by an enhanced chemiluminescence detection kit (Pierce) according to the manufacturer's instruction.

VII. Deglycosylation Reaction

For the deglycosylation reaction, about 250 μg total proteins was incubated with the Endo-H reaction buffer (50 mM NaAc (pH 5.5), 0.1% SDS) at room temperature for 20 min, and then digested with 10 mU Endo-H (Roche) in the same reaction buffer in the presence of freshly added 0.05% $NaN_3$ and 10 mM EDTA at 37° C. over night (Kobata, *Anal. Biochem.*, 100(1): 1–14, 1979; Trimble and Maley, *Anal. Biochem.*, 141 (2):515–22, 1984). Total cell lysate that went through the above procedure, but without the addition of Endo-H was used as the intact glycoprotein control. Samples were stored at −20° C. before being analyzed by Western blotting.

VIII. Endo H Digestion

Half of 100 mm plate cell lysate (about 250 μg total proteins) was incubated with Endo H reaction buffer (20 mM $Na_3PO_4$ (pH 7.5), 0.02% $NaN_3$, 0.1% SDS, 50 mM β-mercaptoethanol) at room temperature for 20 min, and then digested by 30 mU Endo H (Roche) in the same reaction buffer with freshly added 0.75% Nonidet P-40 at 37° C. over night (Tanner et al., *J. Virol.*, 62(12):4452–64, 1988). Total cell lysate that went through the above procedure, but without Endo H was used as the intact glycoprotein control. Samples were stored at −20° C. before being analyzed by Western blot.

IX. FP-1 Antibodies

Five different regions of rat FP-1 (SEQ ID NO:2), which were predicted to be hydrophilic and to be more antigenic than other regions in FP-1 according to several computer algorithms, including one that predicts hydropathy, were selected to produce antibodies to rat FP-1. These five regions of FP-1 included amino acids 87–102, 247–262, 276–297, 321–333, and 392–405 of SEQ ID NO:2.

The synthesized peptides were purified by reverse-phase high performance liquid chromatography (HPLC) and their purity was examined by mass spectrometry. A cysteine residue was placed at either the N- or C-terminus of each peptide to facilitate conjugation to the carrier protein, Keyhole Limpet Hemosyanin (KLH). For each conjugated peptide, two rabbits were immunized by subcutaneous injection of 100 μg of peptide in Freund's complete adjuvant. This primary immunization was followed by booster injections at 2-week intervals. The titer of the antisera was checked by ELISA after 3 booster injections (Genemed Synthesis).

Table I summarizes the information relating to the five polyclonal rabbit anti-rat FP-1 antibodies.

TABLE 1

| Antibody | Epitope | IB dilution | IF dilution | Mismatch/ Total aa Mouse | Mismatch/ Total aa human |
|---|---|---|---|---|---|
| G311 | 1 | 1:1,000 | n.d. | 0/16 | 3/16 |
| G312 | 2 | 1:2,000 | 1:200 | 8/22 | 1/16 |
| G320 | 3 | 1:10,000 | 1:1,000 | 0/22 | 5/22 |
| G324 | 5 | 1:500 | n.d. | 1/14 | 3/14 |
| G325 | 4 | n.d. | n.d. | 2/13 | 1/13 |

Key:
IB = immunoblot
IF = immunofluorescence
n.d. = not determined
Mismatch/Total aa = the number of amino acids that are different between the rat and mouse FP-1, or rat and human FP-1, in the peptide sequences recognized by the rat FP-1 antibodies.

X. Immunofluorescence Staining

Culture cells grown on glass cover slips (12 mm, Fisher) were fixed with cold 1:1 methanol/acetone for 20 min. and then air-dried. Fresh tissues were embedded in OCT medium (Sakura Finetek) in liquid nitrogen and sectioned into 7–8 μm according to standard procedures. The sections were fixed with cold 1:1 methanol/acetone for 10 min and air-dried.

Cover slips with cultured cells or slides with frozen sections were incubated with primary antibodies. Optimal concentration of the primary antibodies was determined by titration: anti-FP1 rabbit serum G320 (1:1,000), anti-β-COP mouse monoclonal antibody (Sigma) (1:80). After washing, the cover slips or slides with PBS for 5 min. three times, the cover slip or slide was incubated with fluorescein FITC or rhodamine conjugated secondary antibody (Molecular Probes, Eugene, Oreg.), mounted with aqueous mounting medium with anti-fading agents (Biomeda, Foster City, Calif.), and examined under a fluorescence microscope (Zeiss, Thornwood, N.Y.).

XI. Fluorescent In Situ Hybridization (FISH)

Lymphocytes were isolated from mouse spleen and cultured at 37° C. in RPMI 1640 medium supplemented with 15% fetal calf serum, 3 μg/ml concanavalin A, 10 μg/ml lipopolysaccharide and $5 \times 10^{-5}$ M mercaptoethanol. After 44 hr, the cultured lymphocytes were treated with 0.18 mg/ml BrdU for an additional 14 hr. The synchronized cells were washed and recultured at 37° C. for 4 hr in α-MEM with thymidine (2.5 μg/ml). Cells were harvested and chromosome slides were made by standard procedures including hypotonic treatment, fixation and air-drying (See DNA Biotech). For probe preparation, a 2.1 kb rat FP-1 cDNA fragment was amplified by PCR using the plasmid of the longest FP-1 positive clone (obtained from screening the follicular papilla cDNA library) as template and primers flanking the cDNA insert on the vector plasmid. The DNA probe was biotinylated with dATP at 15° C. for 1 hr (Gibco BRL BioNick labeling kit, Gaithersburg, Md.) (Heng et al., *Proc. Natl. Acad. Sci. USA,* 89(20):9509–13, 1992). The procedure for FISH was performed according to published methods (Heng et al., ibid; Heng and Tsui, *Chromosoma,* 102(5):325–32, 1993).

Example 2

Identification of Follicular Papilla-Specific Genes by Subtraction cDNA Library

Figure 11A:
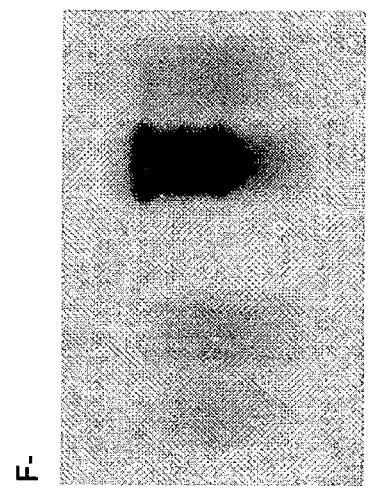
FIG. 11A is a photographic representation showing the enrichment of follicular papilla-specific cDNAs in the follicular papilla subtraction library. Specifically.
Figure 11B:
FIG. 11B is a photographic representation of a Southern Blot analysis performed using fibroblasts-specific cDNAs (F-) as probes. Lane 1: subtracted follicular papilla cDNA; lane 2: nonsubtracted follicular papilla cDNA; lane 3: subtracted fibroblast cDNA; and lane 4: nonsubtracted fibroblast cDNA.
Figure 11C:
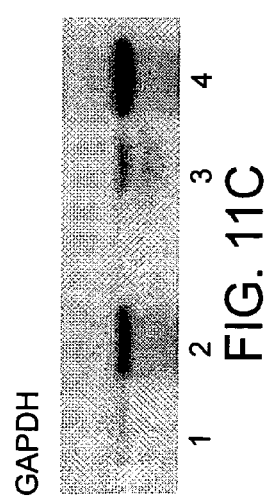
FIG. 11C is a photographic representation of a Southern Blot analysis performed using a GAPDH probe. Lane 1: subtracted follicular papilla cDNA; lane 2: nonsubtracted follicular papilla cDNA; lane 3: subtracted fibroblast cDNA; and lane 4: nonsubtracted fibroblast cDNA.
Figure 11D:
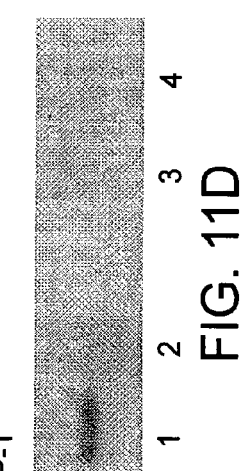
FIG. 11D is a photographic representation of a Southern Blot analysis performed using an FP-1 probe. Lane 1: subtracted follicular papilla cDNA; lane 2: nonsubtracted follicular papilla cDNA; lane 3: subtracted fibroblast cDNA; and lane 4: nonsubtracted fibroblast cDNA.
Figure 11E:
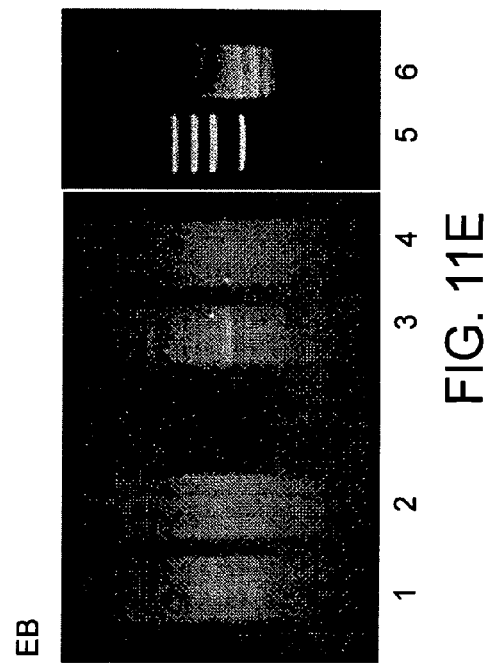
FIG. 11E is a photographic representation of an ethidium bromide stained gel in which the subtracted and nonsubtracted cDNAs of cultured rat follicular papilla cells, rat fibroblasts and human skeletal muscle control were separated electrophoretically. Lane 1: subtracted follicular papilla cDNA; lane 2: nonsubtracted follicular papilla cDNA; lane 3: subtracted fibroblast cDNA; lane 4: nonsubtracted fibroblast cDNA; lane 5: subtracted control (human skeletal muscle cDNA mixed with φX174/Hae III, and then subtracted with a human skeletal muscle cDNA); and lane 6: nonsubtracted control (human skeletal muscle cDNA).

To identify genes that are expressed preferentially in follicular papilla cells, a follicular papilla-specific subtraction cDNA library was constructed. Common messages were eliminated by hybridizing the cDNAs of cultured rat vibrissa follicular papilla cells ("tester") with those of fibroblasts that had been grown under identical culture conditions ("driver"). To examine the subtraction efficiency, a series of Southern blots were performed using the following probes: (1) follicular papilla-specific cDNAs, (2) fibroblast-specific cDNAs, (3) GAPDH, a housekeeping gene, and (4) FP-1, a novel gene identified from the subtraction library. The results showed a greater than 10 fold enrichment of FP-1 in the subtracted follicular papilla library (FIG. 11D), and a greater than 20 fold reduction of GAPDH in both the subtracted follicular papilla-specific library (FIG. 11C). These data indicated that a greater than 200 fold enrichment of the differentially expressed follicular papilla messages had been achieved. Indeed, when the follicular papilla-specific cDNAs were used as the probe (FP- probe), the signals of subtracted follicular papilla cDNAs (FIG. 11A, lane 1) were much stronger than those of subtracted fibroblast cDNAs (FIG. 11A, lane 3). On the contrary, when the fibroblast-specific cDNAs were used as a probe (F– probe), the signals of subtracted fibroblast cDNAs (FIG. 11B, lane 3) were much stronger than those of subtracted follicular papilla cDNAs (FIG. 11B, lane 1). These data indicated that the follicular papilla-specific cDNAs were enriched using the subtraction technique.

To identify the follicular papilla-specific clones in the subtracted library, a differential screening method was used. Randomly picked clones from the follicular papilla-specific subtracted library were hybridized with the follicular papilla-specific cDNAs (F-probe) and fibroblast-specific cDNAs (F-probe) (FIG. 12). Clones representing differentially expressed poly A+ species in follicular papilla cells were expected to give strong signals with the FP-probe but weak or no signals with the F-probe (FIG. 12). Clones were considered as "follicular papilla-specific" only when the difference in signal intensity (FP/F) was greater than or equal to 5 fold. By screening 465 randomly picked clones from the follicular papilla-specific subtracted library, about 60 follicular papilla-specific clones representing 9 ESTs and 25 known sequences were obtained.

To minimize the chance of eliminating follicular papilla-specific messages, a mixture of diaphragm, esophagus and stomach fibroblast cDNAs were used as the "driver" to construct the follicular papilla-specific subtraction library. To verify that the clones identified from the subtraction library were really differentially expressed in follicular papilla cells compared to dermal fibroblasts, virtual Northern blots were carried out by hybridizing PCR-amplified cDNAs from cultured cells with some of the identified clones, including EST1 (later named as FP-1), EST2, EST6, EST7, lysyl oxidase-like 2 (LOXL2), serine protease, and tenascin c. The results showed that all the cDNA clones examined by virtual Northern blots were indeed expressed at higher levels in follicular papilla cells than in the (non-dermal) fibroblast mixture (FIG. 13), again indicating the success of the subtraction. When cultured follicular papilla cells were tested against dermal fibroblasts, six out of the seven genes were found to be expressed at higher levels in follicular papilla cells than in dermal fibroblasts; only one, tenascin c, showed about equal intensity in these two cell types (FIG. 13). These data proved the follicular papilla-specificity of the genes identified from the subtraction library. From a gene expression profile point of view, the difference between follicular papilla and various types of fibroblasts was greater than the difference among the different fibroblasts.

Example 3

FP-1, a Novel Follicular Papilla Marker

Among the 25 known genes and 9 EST sequences that had been identified from the follicular papilla-specific subtraction library, EST1 (Genbank® Accession Number A1574756) was most abundant, represented by 8 independent clones. The expression level of this EST in cultured rat vibrissa follicular papilla cells was greater than 30 fold higher than that in cultured rat dermal fibroblasts (FIGS. 13 and 14). To further characterize this cDNA, its tissue distribution was examined in 18 rat tissues including skin, diaphragm, esophagus, stomach, brain, lung, heart, liver, spleen, kidney, bladder, intestine, colon, ovary, uterus, prostate testis, and skeletal muscle. This EST was only detected at relatively low levels in stomach and ovary, while the other 16 tissues were negative (FIG. 14A). Since these data indicated that this clone was preferentially expressed in follicular papilla, it was named "FP-1."

To obtain the full-length cDNA sequence of FP-1, a cDNA phage library of cultured rat vibrissa follicular papilla cells was screened, and a 5' RACE (rapid amplification of cDNA ends) was also performed. The full-length FP-1 cDNA was 2332 bp, which had a 1647 bp coding region encoding 549 amino acids (FIG. 15). FP-1's N- and C-terminus amino acid sequences have domains homologous to collagen triple helix repeat and an olfactomedin-like domain, respectively (FIG. 15). Computer analysis of the FP-1 protein sequence revealed that the N-terminal 31 amino acid residues of FP-1 is a signal peptide (FIG. 15), and that FP-1 has 6 potential glycosylation sites (FIG. 15).

Example 4

Immunoblotting and Immunofluorescence Studies

To examine the protein expression pattern of FP-1, five polyclonal antibodies against FP-1 were generated (the five epitopes are indicated in FIG. 15). Immunoblot analysis showed that three of the FP-1 antisera (anti-epitopes 1, 2, and 3) recognized a single protein band of about 72 kDa in cultured rat follicular papilla cell lysate, with no detectable signals in cultured fibroblast cell lysate (FIG. 16A). Immunofluorescent staining of cultured follicular papilla cells at passage 4 using the FP-1 antisera showed very strong cytoplasmic signals in follicular papilla cells, but negative signals in fibroblasts (FIG. 16C). These data verified that FP-1 was preferentially expressed in cultured follicular papilla cells compared to fibroblasts. Staining of COP I, a Golgi complex marker, overlapped with FP-1 staining, even though FP-1 staining had a broader area (FIG. 16C).

Consistent with the presence of several potential N-glycosylation sites, FP-1 is a glycoprotein. After digestion with endoglycosidase-H, the molecular weight of FP-1 decreased to 60 kDa (FIG. 6B).

Example 5

Temporal Expression of FP-1

To analyze at what time point FP-1 expression was turned on in follicular papilla cells under cultured conditions, immunofluorescent staining was performed using primary cultures 4, 7, and 10 days after microdissection. Starting from day 4, all the cells of the whole colony derived from a follicular papilla were FP-1 positive, whereas cultured fibroblasts were always FP-1 negative (data not shown). Staining was not performed at earlier time points.

Example 6

Survey of Existing FP-1 Mouse Mutants

Since FP-1 is abundantly expressed in follicular papilla cells, which are essential for hair growth, tests were done to determine whether the gene localized to any of the loci corresponding to the 196 mouse mutants that had a hair-related phenotype in the Jackson Laboratory database (Bar Harbor, Me.).

Figures 17A, 17B, 17C, 17D:
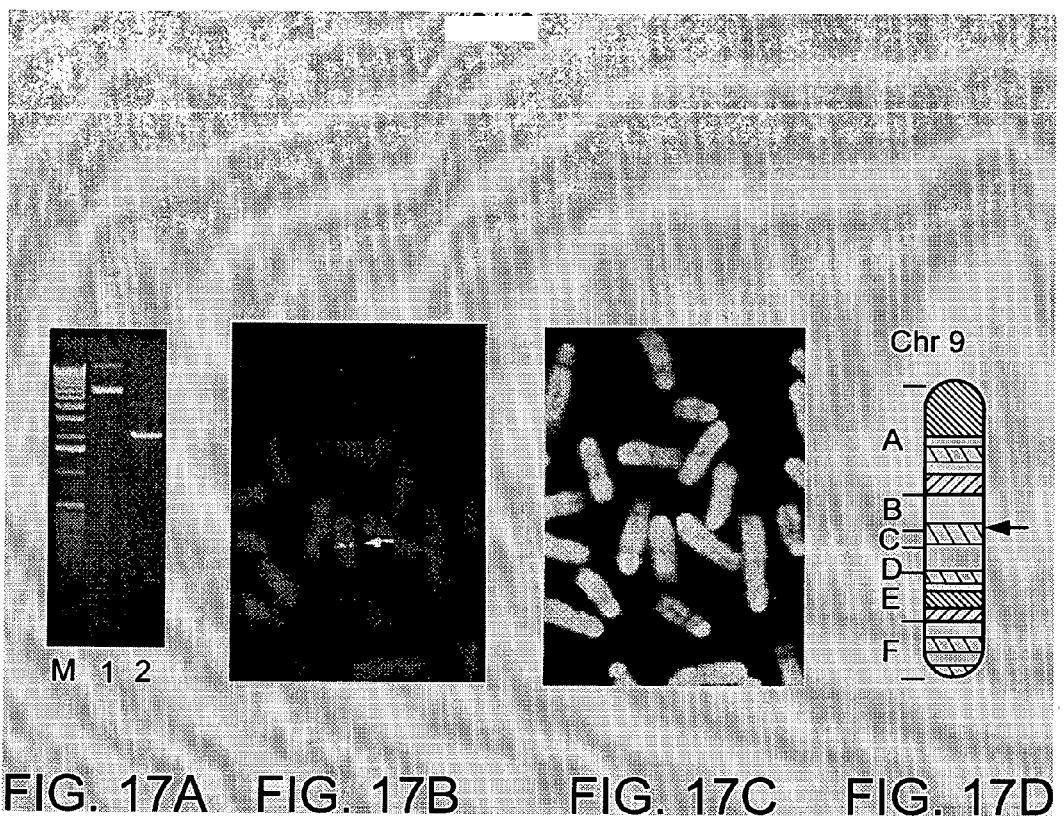
FIG. 17A is a photographic representation of an ethidium bromide-stained gel showing the probe used for fluorescent in situ hybridization (FISH). A 2.1 kb rat FP-1 cDNA fragment (lane 2) was amplified by PCR using the plasmid containing the longest FP-1 clone (lane1) as template.
FIG. 17B is a photographic representation of a biotin-labeled rat FP-1 probe localizing specifically to a mouse chromosome (arrow).
FIG. 17C is a photographic representation of DAPI staining of mouse chromosomes confirming that mouse FP-1 gene is localized on chromosome 9.
FIG. 17D is a diagrammatic representation of mouse chromosome 9 showing the position of the FP-1 gene as the 9B-C region (arrow).

To determine whether FP-1 mapped to any of these existing mouse hair mutants, a cross-species fluorescent in situ hybridization (FISH) on mouse chromosomes using rat FP-1 cDNA as a probe was performed. The FISH analysis indicated that FP-1 was on mouse chromosome 9 B-C region (FIG. 17). Significantly, there are 3 hair-related mutants, including rough fur (ruf), rough coat (rc), and fur deficient (fd) in this region.

To examine whether there were any gross changes in the FP-1 gene in these 3 mouse mutants, a genomic Southern blot was performed. After digestion with 7 different restriction enzymes, the genomic DNA of homozygous and heterozygous mutants and their background strains (considered as wild type to the mutations) were compared. A size change greater than 1 kb due to insertion or deletion, which occurs frequently in the mouse genome, could in theory be detectable by this approach. However, no significant difference in the FP-1 sequence was found in all the 3 mutants suggesting that there was no deletion or insertion of a big DNA fragment (greater than 1 kb) within the genomic region close to FP-1 in these mutants (data not shown). Of course, it must be remembered that this finding does not rule out the possibility that there are other mutations in any of these genes, which cannot be detected by this approach.

Example 7

Immunolocalization of FP-1

To investigate FP-1 localization in hair follicles in vivo, indirect immunofluorescence staining of the depilated mouse back skin using FP-1 antiserum was performed. Back skin of C57BL/6 mice was collected on different days after depilation, snap-frozen, and cryo-sectioned. The sections were fixed with 1:1 methanol/acetone (4° C.), air-dried, and stained by indirect immunofluorescence using the tyramide signal amplification (TSA) system (Perkin Elmer). Polyclonal G320 antibody was used for staining at a dilution of 1:5,000 to 1:20,000. As a control, a preimmune serum at a comparable concentration, and an FP-1 antibody that was blocked by a peptide that bound the FP-1 antibody (the original antigen used to generate the G320 antibody) was used. Specifically, the peptide blocking experiments were performed, using the G320 antibody pre-incubated at 25° C. with the FP-1 peptide having the sequence PNDDTLV-GRADEKVNERHSPQT (aa 276–297 of rat FP-1; SEQ ID NO:27). The antibody:peptide ratio for the blocking experiment was 1:4, and the antibody was incubated with the peptide for 45 minutes before the FP-1 antibody was used to stain the sections in the control experiments.

Figure 18:
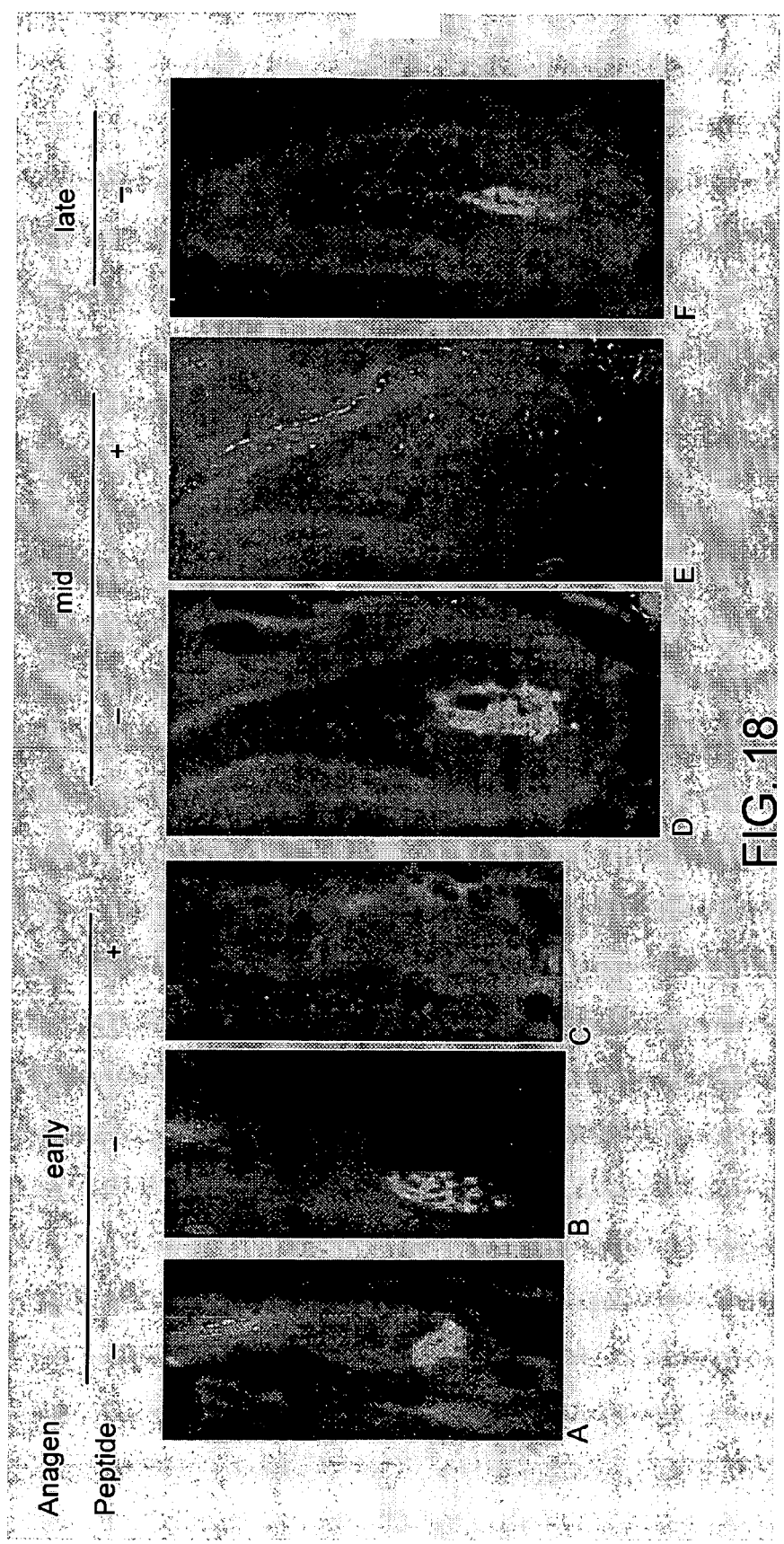
FIG. 18A is a photographic representation of immunofluorescent staining of FP-1 on C57BL/6 mouse back skin at 3 days after hair depilation.
FIG. 18B is a photographic representation of immunofluorescent staining of FP-1 on C57BL/6 mouse back skin at 5 days after hair depilation.
FIG. 18C is a photographic representation of immunofluorescent staining of FP-1 on C57BL/6 mouse back skin at 5 days after hair depilation. In this case, note that the FP-1 antiserum was pre-adsorbed with peptide antigen prior to staining.
FIG. 18D is a photographic representation of immunofluorescent staining of FP-1 on C57BL/6 mouse back skin at 8 days after hair depilation.
FIG. 18E is a photographic representation of immunofluorescent staining of FP-1 on C57BL/6 mouse back skin at 8 days after hair depilation. In this case, note that the FP-1 antiserum was pre-adsorbed with peptide antigen prior to staining.
FIG. 18F is a photographic representation of immunofluorescent staining of FP-1 on C57BL/6 mouse back skin at 12 days after hair depilation.

FP-1 was strongly expressed in the follicular papillae during the anagen phase (FIG. 18), but not in the catagen and telogen phases of the hair cycle (data not shown). This hair-cycle dependent expression pattern strongly suggested that FP-1 is involved in the control of hair growth. No staining was noted in the epidermis and other skin cells.

To analyze FP-1 expression in the follicular papilla cells under the cultured conditions, we performed immunofluorescent staining using primary cultures 4, 7 and 10 days after plating. Starting from day 4, all the cells of the whole colony derived from a follicular papilla were FP-1 positive, whereas FP-1 was barely detectable in cultured fibroblasts (FIG. 16B).

Example 8

Inhibition of FP-1 Function in Mouse Skin by Antibodies

Purified polyclonal or monoclonal antibodies that specifically bind to FP-1 are used to block FP-1 activity in the hair follicle in vivo. As a control, peptide-blocked FP-1 antibody prepared as described in Example 7, is used. For example, antibodies are purified using commercial kits, and used at several concentrations (i.e., 1 µg/ml to 1 mg/ml) and based on titration studies the concentration of antibody to be used in the experiments outlined below is determined.

Mice that are around day 35 of life are in a prolonged telogen phase. In the first experiment, mice around day 38 of life are anesthetized, and each of the mice are implanted intraperitoneally with two Alzet osmotic minipumps (Model 2001; Alza Corp., Palo Alto, Calif.). The minipumps are each loaded with 200 µl of FP-1 antibody, or peptide-blocked FP-1 in phosphate buffered saline (PBS) at the concentration determined by the titration studies. The FP-1 antibody, or preimmune antibody, or peptide-blocked FP-1 antibody, is provided systemically for approximately 14 days. The hair of the mice are plucked on day 42 (Wilson et al., *Differentiation*, 55:127–136, 1994). Mice are then sacrificed every 2 days for 17 days and the length of the hair from the dermal papilla to the skin surface is measured. The FP-1 antibody treated and control mice are compared to check whether there are differences in hair growth. Hair growth can be assessed based on the elongation rate of the hair fibers that is measured by clipping the fibers that are exposed on the skin surface. In addition, the hair cycle is analyzed by using histological methods to determine whether the follicle is in anagen, catagen, or telogen (Wilson et al., *Differentiation*, 55:127–136, 1994).

In the second experiment, 200 µl of FP-1 antibody, or the preimmune antibody, or the peptide-blocked FP-1 antibody, at the concentration identified in the titration experiments are injected subcutaneoulsly every 2 days for 15 days (Cotsarelis et al., *Cell* 61:1329–1337, 1990; Taylor et al., *Cell* 102:451–461, 2000). At the end of the subcutaneous injections, mice are sacrificed every 3 days for 15 days and the length of the hair fibers that are exposed on the skin surface is measured as mentioned above, and the length of the follicule from the dermal papilla to the skin surface is measured by histological examination. The FP-1 antibody-treated and control mice are compared to check whether there are differences in hair growth.

In both experiments described above, the FP-1 antibodies bind and neutralize FP-1 thus blocking its in vivo activity. In contrast, the preimmune antibodies and peptide-blocked FP-1 antibody do not impair the in vivo activity of FP-1.

Blocking FP-1 activity using neutralizing FP-1 antibodies results in inhibition of hair growth. However, the peptide-blocked FP-1 antibody (or pre-immune sera or control antibodies that are raised against intracellular antigens such as keratins, if used in the above experiments) show minimal, if any, effects on hair growth. Immunolocalization studies show that mouse skin of FP-1 antibody-treated mice has antibody staining in the extracellular matrix zone of the follicular papilla.

Example 9

Inhibition of FP-1 in Cultured Rat Vibrissa Follicular Papilla Cells

FP-1 expression is inhibited in cultured rat vibrissa follicular papilla cells using inhibitory agents such as antibodies to FP-1, antisense molecules, ribozymes and/or siRNA molecules directed to rat FP-1.

Prediction of suitable siRNA targets and siRNAs are possible using many different sources, (see, for example "siRNA Selection Program," Whitehead Institute for Biomedical Research, 2003; Ambion's siRNA Target Finder, etc.). Examples of siRNA target sequences and sense and antisense strand siRNAs for use in this experiment include:

```
(i) Target Sequence:
5' AATTAAGTCGTGCGCCAGCCC 3',    (SEQ ID NO:15)
(corresponding to 257–279 of SEQ ID NO:1);

Sense Strand siRNA:
5' UUAAGUCGUGCGCCAGCCCtt 3';    (SEQ ID NO:16)

Antisense strand siRNA:
5' GGGCUGGCGCACGACUUAAtt 3';    (SEQ ID NO:17)
and (ii) Target Sequence:
5' AATGATGATACCTTGGTGGGG 3',    (SEQ ID NO:18)
(corresponding to 874–896 of SEQ ID NO:1);

Sense Strand siRNA:
5' UGAUGAUACCUUGGUGGGGtt 3';    (SEQ ID NO:19)

Antisense strand siRNA:
5' CCCCACCAAGGUAUCAUCAtt 3';    (SEQ ID NO:20)
and (iii) Target Sequence:
5' AATGAGCGCCATTCTCCACAA 3',    (SEQ ID NO:21)
(corresponding to 913–935 of SEQ ID NO:1);

Sense Strand siRNA:
5' UGAGCGCCAUUCUCCACAAtt 3';    (SEQ ID NO:22)
```

```
-continued
Antisense strand siRNA:
5' UUGUGGAGAAUGGCGCUCAtt 3';    (SEQ ID NO:23)
and (iv) Target Sequence:
5' AACCCATGATCACGTCCATTG 3',    (SEQ ID NO:24)
(corresponding to 938–960 of SEQ ID NO:1);

Sense Strand siRNA:
5' CCCAUGAUCACGUCCAUUGtt 3';    (SEQ ID NO:25)

Antisense strand siRNA:
5' CAAUGGACGUGAUCAUGGGtt 3'.    (SEQ ID NO:26)
```

Methods of using siRNA to knock down expression of a target gene are well known in the art (Kittler et al., *Semin. Cancer Biol.*, 13(4):259–65, 2003; Scherr et al., *Curr. Med. Chem.*, 10(3):245–56, 2003; and Hudson et al., *Trends Cell Biol.*, 12(6):281–7, 2002).

After treatment of cells with a FP-1 inhibitory agent that inhibits or prevents expression of FP-1, the expression of FP-1 mRNA is tested by Northern blot analysis using well-established methods (Sambrook et al., cited supra). FP-1 protein levels are tested using Western blot analysis using antibodies to FP-1.

The effect of inhibiting FP-1 on the morphological and proliferative properties of the follicular cells is also tested. Neutralizing antibodies to FP-1, FP-1 antisense molecules, FP-1 ribozymes and FP-1 siRNA molecules are expected to cause the cultured rat vibrissa cells to aggregate and suppress their growth. Immunolocalization of FP-1 antibody is expected to show it binding to both the cell surface and the extracellular matrix that is deposited on the plastic dish surface. It is also expected that preimmune sera from healthy rabbits, control antisense, ribozyme and siRNA molecules show no effects on the morphology and growth properties of the cultured vibrissa cells.

Example 10

Isolation of Follicular Papilla Cells from Skin

Rat vibrissa and mouse pelage follicular papilla are surgically isolated as described in Example 1 and dissociated into single cells by trypsinization. The rat follicular papillae are minced and treated with 0.2% trypsin in PBS at 37° C. with stirring for 30–45 minutes. The loosened tissues will be pipetted several times to suspend the cells. The single cells that are released by this procedure will be counted and mixed with an equal volume of DMEM medium containing 10% calf serum that inhibits trypsin. These cells are then treated with rabbit antibodies to FP-1 (see, Example 1), followed by fluorescein-conjugated goat anti-rabbit-IgG antibody (Jackson Laboratories). The cell-surface fluorescein-labeled, FP-1 positive cells are then isolated by fluorescein-activated cell sorting.

Alternatively, magnetic beads (4.5 µm; DYNABEADS® from DYNAL® or MACSiBead™ from Miltenyi Biotec) that are precoated with sheep anti-rabbit IgG antibody are used to adsorb rabbit anti-FP-1 antibodies, which are then used for isolating follicular papilla cells. A dissociated, single cell suspension (as obtained above) containing a mixture of follicular papilla cells and other non-follicular papilla cells (such as the dermal fibroblasts) are mixed with the FP-1 coupled magnetic beads. The FP-1 antibody-coupled magnetic beads coated with the adherent cells are then separated from the non-adherent cells by applying a magnetic field (e.g., OPTICELL® magnetic separation, or magnetic plate, Dynal, Inc., Lake Success, N.Y.). The magnetic beads are then washed with phosphate buffered saline (PBS). Finally, the cells that have bound to the FP-1 antibodies are dissociated by a brief treatment with low pH buffer or with 0.05% trypsin in PBS, or other suitable conditions. The cells that are bound by FP-1 antibody are follicular papilla cells.

Example 11

Hair Reconstitution Experiments

The nude mouse graft model system originally described by Lichti et al. (*J. Invest. Dermatol.*, 101:124–129S, 1993) is used for testing the role of FP-1 in regulating hair growth. In this system, a mixture of epidermal and dermal cell preparations from newborn mice are grafted onto the backs of athymic nude mouse hosts, resulting in the in vivo reconstitution of hair follicles (Lichti et al., ibid; Weinberg et al., *J. Invest. Dermatol.*, 100:229–236, 1993). Neutralizing antibodies to FP-1 (monoclonal or polyclonal antibodies), that are either perfused into the athymic nude mice system via injection of the antibody into either the left ventricle or a tail vein, or injected subcutaneously, inhibit the reconstitution of the hair follicle.

In a different approach, cultured follicular papilla cells are transfected with either FP-1 cDNA (a/b). It is expected that such FP-1 over-expressing FP cells are particularly active in supporting hair reconstitution in the athymic nude mouse hosts. In striking contrast, it is expected that follicular papilla cells transfected with antisense FP-1 cDNA, or an FP-1 cDNA encoding a dominant negative FP-1 protein, or siRNA that inhibits or prevents expression of FP-1 have a diminished ability to support hair reconstitution in athymic nude mouse hosts. Hair growth can be measured using methods as described in Chamberlain et al., *Australasian J. Dermat.*, 44:10–18, 2003.

Example 12

Determination of Mitogenic Activity of Recombinant FP-1

Isolated human hair follicles are maintained in individual wells of 24-well multiwell plates containing 1 ml of KBM media (Clonetics) supplemented with 100 U/ml penicillin, 10 ng/ml hydrocortisone, 75 µg/ml bovine pituitary extract in an atmosphere of 5% $CO_2$/95% air.

The cell growth of hair follicles is measured by colorimetric MTS assays (Bunger et al., *Artif. Organs.*, 26(2): 111–116, 2002; and Vorauer et al., *J. Biochem. Biophys. Methods*, 32(2):85–96, 1996). Specifically, FP-1 is added to culture media at different concentrations at different concentrations (from about 10 ng/ml, about 30 ng/ml, about 100 ng/ml, and about 1 µg/ml), and the isolated human hair follicles are incubated in these media with human FP-1 for 48 hrs before measuring by MTS assay.

A single hair follicle is then plated in a 96-well microtiter per well (see, Philpott et al., supra; Philpott et al., *J. Dermatol. Sci.* 7 Suppl, S55–72; and Philpott et al., *J Invest Dermatol.*, 102:857–861); and proliferation is measured 4 hr later using a calorimetric MTS assay according to the manufacturer's suggestions (Promega). In each experiment, observations (n=8 hair follicles per group) are performed and the values are reported as mean+/−standard error (S.E.).

In the proliferation assay, the negative control is evaluated using untreated hair follicle cells.

The addition of FP-1 results in dose-dependent stimulation of human hair follicle cells.

Example 13

Liposome-Mediated Delivery of FP-1 to Hair Follicles

To achieve targeted delivery of FP-1 to hair follicles, the following protocol is carried out.

Liposomes are prepared by sonication. About 20 mg of egg phosphatidycholine is rotary evaporated with a vacuum drier from a chloroform solution to form a thin film on the walls of a 5 ml round-bottomed flask for about 1 hr. The dried thin film phospholipid is suspended in about 0.5 ml phosphate buffered saline (pH 7.4) on a vortex mixer and then is sonicated with a Branson probe-type sonicator fitted with a microtip at power level 3 for about 8 min. Then 0.5 ml of a solution of mouse FP-1 protein (10 mg/ml) is entrapped with the above suspension by sonication for about an additional 4 min. Liposomes are separated from the non-entrapped FP-1 by gel-filtration on a Sepharose 4B column equilibrated with phosphate buffered saline.

Pieces of outbred white-haired mouse skin derived from 1 to 2 week-old animals (about 2×5×2 mm each) is harvested under a dissection microscope. The samples are then histocultured on collagen-gel supported sponges as described U.S. Pat. No. 6,224,901. Liposome interaction with the skin is initiated after about 24 hrs of histoculture. Mouse skin histocultures are incubated for about 12 hrs with liposomes. As a control, a solution of "free" FP-1 at the same concentration as is used in the liposome preparation is also incubated for about 12 hrs with pieces of the histocultured skin.

Example 14

Liposome-Mediated Delivery of Nucleic Acid to Hair Follicles

About 50 ng of an expression vector comprising DNA encoding mouse FP-1 is purified for liposomal delivery to cultured mouse cells.

Liposomes are prepared by freezing and thawing. About 20 mg of egg phosphatidylcholine (EPC) is rotary evaporated with a vacuum drier from a chloroform solution to form a thin film on the walls of a 5 ml round-bottomed flask for about 1 hr. The dried film phospholipid is suspended in about 0.5 ml phosphate buffered saline solution at a pH of about 7.4 in a vortex mixer and is then sonicated with a Branson probe-type sonicator fitted with a microtip at power level 3 for about 8 min. The 0.5 ml of FP-1 DNA solution is added to the above suspension by extensive vortexing for about 1 minute and is followed by freezing and thawing. Liposomes are separated from the non-entrapped DNA by gel-filtration on a Sepharose 4B column that is equilibrated with PBS. About 50 µl calcein (about 10 mg/ml) is added into the solution in order to mark the liposomes during the separation.

Pieces of outbred white-haired-mouse skin (about 1×5×2 mm) derived from 1 to 5-week-old animals are harvested under a dissection microscope and then histocultured on collagen-gel-supported sponges as described in U.S. Pat. No. 6,224,901. Liposome interaction with the skin is initiated after about 24 hrs of histoculture. Mouse skin histocultures are then incubated for about 44 hrs with liposomes.

As a control, a solution of naked DNA (lacking any inserted cDNA) at the same concentration is used in the liposome preparation and is also incubated with skin histocultures. The effects of the liposome-delivered FP-1 cDNA, or antisense RNA, or siRNA, on hair growth is assessed by measuring the length of the hair fibers exposed on the skin surface, and by measuring the length of the follicle in the skin by histology as mentioned in Example 10.

Example 15

Effect of Expressing FP-1 On Mammalian Hair Growth

An expression cassette is created, placing the entire cDNA for the murine FP-1 gene under the control of the HCMV immediate early promoter/enhancer and linked to the poladenylation sequence from SV40. This cassette is subcloned by standard methods into the deleted E1 region of an E1-/E3-adenovirus vector. Recombinant viruses are isolated, and correct insertion of the expression cassette is verified by Southern hybridization and DNA sequence analysis. The recombinant vector (termed AdFP1) is thereafter purified and grown to high titer.

Groups of 2 to 4, 7 g, 3-week-old C57 Bl/6 mice are injected intradermally with $1 \times 10^8$ pfu of either AdFP1, a control E1-/E3-vector lacking the FP-1 cDNA, or a sham injection of saline. After seven days, skin in the area of injection is removed from the injected animals, as well as naive animals, and is analyzed.

Northern hybridization of the excised skin patches reveals the presence of elevated levels of FP-1 mRNA in skin patches injected with AdFP1 but not in sham-injected patches, naive patches, or patches injected with the E1-/E3-control adenoviral vector. Blots of mRNA from the various skin patches are also probed for the expression of hair-specific gene expression, specifically the hair-specific keratin gene (ghHb-1), that is expressed mainly during anagen, which is the growing phase of the hair follicle. Northern blots reveals the presence of some ghHb-1 mRNA in all excised skin patches; however, the level of ghHb-1 signal is more pronounced in the skin injected with AdFP1 than in sham-injected patches, naive patches, and patches injected with the E1-/E3-control adenoviral vector. The excised skin patches above are visually examined to assess the effect of each treatment on hair growth in the area. To permit such evaluation, the mice are treated carefully during the protocol so as not to induce hair growth by the manner in which they are handled generally. Hair growth is assessed by measuring the length of the hair fibers exposed on the skin surface, and by measuring the length of the follicle in the skin by histology as mentioned in Example 10

Melanogenesis, a pigment synthesis process that occurs in association with hair growth, is evaluated using digital image analysis. Specifically, light is passed through the excised patches and the intensity of transmitted light is measured by determining the average gray scale of a digitally collected image of the transmitted light. The optical density (relative light adsorbance) at the injection site is compared with the optical density of the same skin patch at a site distant from the injection site. This analysis is expected to reveal that the optical density of the excised skin patches that are injected with AdFP1 is consistently greater at the site of injection than distal from the injection or that is observed anywhere in sham-injected patches, naive patches, and patches injected with the E1-/E3-control adenoviral vector.

The growth phase of the hair follicle cycle is associated with morphologic changes in follicles including an increase in size of the follicle, which can be recognized as an increase in the area of the follicle relative to total dermal/epidermal area. To evaluate hair follicle size, digital images of cross sections of skin patches are collected and analyzed by integrating the number of pixels occupied by either hair follicles or by total dermis/epidermis. The quotient of the two measurements gives the percentage of area occupied by hair follicles. This analysis is expected to reveal that the percentage of skin represented by mature hair follicles is consistently greater in the excised skin patches that are injected with AdFP1 than that is observed in sham-injected patches; naive patches, and patches injected with the E1-/E3-control adenoviral vector.

These results indicate that transfer of a gene encoding an FP-1 protein promotes hair growth in the skin. That follicular area increases suggests the presence of larger hair follicles in anagen phase that were actively producing hair shafts. This result is important given the fact that alopecia is often correlated with increased likelihood of finding hair follicles in telogen phase, and that AdFP1 apparently induces anagen within a population of hair follicles initially in telogen.

Example 16

Identification of the FP-1 Regulatory Elements

The promoter of the mouse FP-1 gene is isolated by screening a mouse genomic library using PCR methods (Auch et al., *Nuc. Acids Res.,* 18: 6743–6744, 1990; and Garces et al., *Methods Mol. Biol.,* 161:3–8, 2001). Several overlapping clones are isolated and characterized by restriction mapping and partial sequencing. Combination of these data and the available mouse genomic sequence database allows the identification of the genomic clones having the longest 5'-upstream sequence. A segment of 3 to 6 kb 5'-upstream sequence is inserted into a suitable restriction site upstream from a lacZ reporter gene (Lin et al., *Proc. Natl. Acad. Sci USA,* 92:679–683, 1995; Mercer et al., *Neuron* 7:703–716, 1991; Peschon et al., *Proc. Natl. Acad. Sci. USA,* 84:5316–5319, 1987). The fusion gene is excised by using suitable restriciton enzymes, gel-purified and microinjected into fertlized mouse eggs, which are implanted into CD-1 foster mothers. The lacZ transgene is identified by Southern blot analysis of the tail DNA. Positive founder mice are back crossed with C57BL/6J×DBA2 F1 hybrids to generate hemizygous animals that are used for studying transgene expression. The promoter activities of the 5'-upstream sequence of various lengths ranging from 1 kb to 5 or 6 kb is tested to compare their expression pattern to identify the minimal sequence that achieves follicular papilla-specific expression of the lacZ reporter gene.

Example 17

Construction of FP-1 Transgenic Mice

FP-1 transgenic mice, which overexpress FP-1, or derivatives (e.g., any of the coding regions of FP-1 smaller than the full length), mutants, or variants thereof, in a follicular papilla-specific manner are constructed by operably linking a promoter that is follicular papilla-specific (for example, the promoter of the FP-1 gene, or the promoter of versican (Kishimoto, J., R. Ehama, et al., *Proc. Natl. Acad. Sci. USA*, 96 (13): 7336–41, 1999) to a FP-1 cDNA, or any portion thereof. The generation of such transgenic mice is done using standard techniques (Joyner, *Gene Targeting*, Oxford University Press, New York, 2000, (*Practical Approach Series*, 212), i-xviii).

For example, an appropriate fusion gene, comprising any follicular papilla-specific promoter operably linked to a mouse or rat FP-1 full-length cDNA, is first constructed. The fusion gene is excised from the construction vector, gel purified, and microinjected into fertilized mouse eggs (from F1 hybrids of c57BL/6J×DBA2), which can then be implanted into CDE-1 foster mothers. The transgene is identified by Southern blot analysis of tail cDNA using the mouse FP-1 cDNA as probe. Positive founder mice can be back crossed with c57BL/6J×DBA2 F1 hybrids to generate hemizygous and later homozygous mice. Over-expression of FP-1, which is normally expressed transiently during the anagen (or growing) phase of the hair cycle, prolongs the anagen phase of the hair cycle leading to longer hair fibers.

Example 18

Construction of FP-1 Knock-Out Mice

The ablation of the FP-1 gene in mice is done using standard techniques. Briefly, genomic clones of mouse FP-1 gene are isolated from a 129/Ola mouse P1 genomic library. A targeting vector can be designed to delete the third and fourth exons of the FP-1 gene; this vector can contain four portions: an approximately 3–5 kb mouse FP-1 fragment upstream of exon 2, a neomycin-resistance gene (neo) driven by the phosphoglycerate kinase (PGK) promoter in the opposite direction of exon 2 of FP-1, a 3 to 5 kb mouse FP-1 genomic fragment of exon 4 to be eliminated, and a thymidine kinase (tk) gene of herpes simplex virus driven by the PGK promoter (Joyner, *Gene Targeting*, Oxford University Press, New York, 2000 (*Practical Approach Series*; 212), i-xviii; Ramirez-Solis et al., *Methods Enzymol.*, 225:855–878, 1993). The linearized vector is electroporated into 129/SvEv embryonic stem cell line W4, and the neo-positive and tk-negative transformants are selected using G418 (240 mg/ml) and gancyclovir (2 mM). The embryonic stem (ES) cell colonies that harbor the correct homologous recombination events are detected by Southern blotting and by long-range PCR using primers. The confirmed ES cell clones are amplified and aggregated with eight cell stage embryos of Swiss Webster mice, and implanted into pseudopregnant females. Chimeric mice from two ES cell lines that are germline-transmitting are bred with SW mice to yield hybrid homozygotes, or mated with 129/SvEv mice to yield inbred 129/SvEv FP-1-knockout mice.

Example 19

Screening Tissue Sections of Cancer Patients and Cancer Cell Lines for FP-1 Expression Levels Frozen sections and paraffin sections of various normal and various abnormal tissues including tumors are prepared by standard techniques (Hu et al., *J. Cell Biol.*, 151:961–972, 2000; Deng et al., *J. Cell Biol.*, 159:685–694, 2002; and Chen et al., *Proc. Natl. Acad. Sci. USA*, 100: 14012–14017, 2003) and are stained immunohistochemically using rabbit antibodies to FP-1 (G320 at 1:10,000; G311 at 1:1,000; and G312 at 1:2,000) followed by visualization using secondary goat-anti-rabbit antibodies that have been conjugated with peroxidase or fluorescein.

Cancer cell lines representing cancers of, for example, skin (e.g., basal cell carcinoma), stomach, ovary, liver, brain, etc. are used to prepare RNA. RNA is separated on a gel and is transferred to a filter for Northern analysis (Sanger et al., *Proc. Natl. Acad. Sci USA.*, 74:5463–5467, 1977). Filters with mRNAs from these cell lines are hybridized with a probe to FP-1. In those instances where the cell lines are derived from mouse cell lines, a mouse FP-1 probe is used; where rat cell lines are use, rat FP-1 probe is used; and where human cell lines are used, a human FP-1 probe is used.

FP-1 is found to be overexpressed in several cancer cell lines.

Example 20

Monoclonal Antibodies that Specifically Bind FP-1

Balb/c mice are immunized with rat or human FP-1 antigen with weekly injections of 200 to 500 µg of recombinant FP-1 protein over a period of 3 to 4 months. Mice showing high serum titers of anti-FP-1 antibodies as determined by ELISA assay against recombinant FP-1, are identified and the spleens of the mice removed. Spleen cells are fused with the mouse myeloma SP2/0 (ATCC® Accession No. CRL-8006) in accordance with the protocol described in Enfield, D. A. et al. *EMBO J.* 7:711, 1988.

Assays for FP-1 specificity are accomplished by ELISA assays against recombinant FP-1. The cell line producing an FP-1 antibody demonstrating the highest binding for recombinant FP-1 while having the least non-specific binding to an unrelated protein is selected.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated polynucleotide comprising a nucleic acid sequence selected from the group consisting of SEQ ID NO:1 and SEQ ID NO: 3.

2. An isolated polynucleotide comprising a nucleic acid sequence encoding a polypeptide comprising an amino acid sequence selected from the group consisting of SEQ ID NO:2, amino acids 34 to 549 of SEQ ID NO:2, SEQ ID NO:4 and amino acids 34 to 531 of SEQ ID NO:4.

3. An isolated polynucleotide that is the complement of the polynucleotide of claim 1.

4. An isolated polynucleotide that is the complement of the polynucleotide of claim 2.

5. A recombinant vector comprising the polynucleotide of claim 1.

6. A recombinant vector comprising the polynucleotide of claim 2.

7. A transformed host cell comprising the recombinant vector of claim 5.

8. A transformed host cell comprising the recombinant vector of claim 6.

9. A method of preparing a substantially purified polypeptide encoded by the recombinant vector of claim 5, the method comprising culturing host cells transformed with the recombinant vector under conditions conducive to the synthesis of the polypeptide, and recovering the substantially purified polypeptide from the host cells.

10. A method of preparing a substantially purified polypeptide encoded by the recombinant vector of claim 6, the method comprising culturing host cells transformed with the recombinant vector under conditions conducive to the synthesis of the polypeptide, and recovering the substantially purified polypeptide from the host cells.

11. The isolated polynucleotide of claim 1, comprising the nucleic acid sequence of SEQ ID NO:1.

12. The isolated polynucleotide of claim 1, comprising the nucleic add sequence of SEQ ID NO:3.

13. The isolated polynudeotide of claim 2, comprising the nucleic acid sequence encoding the polypeptide comprising the amino acid sequence of SEQ ID NO:2.

14. The isolated polynucleotide of claim 2, comprising the nucleic add sequence encoding the polypeptide comprising amino adds 34 to 549 of SEQ ID NO:2.

15. The isolated polynucleotide of claim 2, comprising the nucleic add sequence encoding the polypeptide comprising the amino acid sequence of SEQ ID NO:4.

16. The isolated polynucleotide of claim 2, comprising the nucleic add sequence encoding the polypeptide comprising amino acids 34 to 531 of SEQ ID NO:4.

17. The recombinant vector of claim 5, wherein the vector is a cloning vector or an expression vector.

18. The recombinant vector of claim 6, wherein the vector is a cloning vector or an expression vector.

19. The host cell of claim 7, wherein the cell is a prokaryotic cell or a eukaryotic cell.

20. The host cell of claim 8, wherein the cell is a prokaryotic cell or a eukaryotic cell.

21. The recombinant vector of claim 17, wherein the expression vector is a prokaryotic cell expression vector or a eukaryotic cell expression vector.

22. The recombinant vector of claim 18, wherein the expression vector is a prokaryotic cell expression vector or a eukaryotic cell expression vector.

* * * * *

SEQUENCE LISTING

```
<160> NUMBER OF SEQ ID NOS: 38

<210> SEQ ID NO 1
<211> LENGTH: 2332
<212> TYPE: DNA
<213> ORGANISM: Rattus sp.
<220> FEATURE:
<221> NAME/KEY: CDS
```

-continued

<222> LOCATION: (46)..(1692)

<400> SEQUENCE: 1

```
acgcggggag tgctgccctg agtcgttcgg cctgagcaca gagac atg acc cga gcc      57
                                                  Met Thr Arg Ala
                                                    1 gca gag cga ggc caa ggg gct aca ggc tgg gga ctg cga ggc gcc ctg        105
Ala Glu Arg Gly Gln Gly Ala Thr Gly Trp Gly Leu Arg Gly Ala Leu
  5              10                  15                  20 atg gcc gtg gcg ctg ctg tca gtg ctg aac gcc gtg ggc acc gtg ttc        153
Met Ala Val Ala Leu Leu Ser Val Leu Asn Ala Val Gly Thr Val Phe
             25                  30                  35 gtg ctg tac cag tgg cgc gag ctg agc gcg gcg ctg cgg gca ctg gag        201
Val Leu Tyr Gln Trp Arg Glu Leu Ser Ala Ala Leu Arg Ala Leu Glu
         40                  45                  50 gcg caa cac ggc cag gag cag cgc gag gac agc gcc cta cgc gcc ttt        249
Ala Gln His Gly Gln Glu Gln Arg Glu Asp Ser Ala Leu Arg Ala Phe
     55                  60                  65 cta gct gaa tta agt cgt gcg cca gcc cga gtc ccc gaa cca ccc cag        297
Leu Ala Glu Leu Ser Arg Ala Pro Ala Arg Val Pro Glu Pro Pro Gln
 70                  75                  80 gac ccc atg agt gca gcg cgc aat aag cgc agc cac ggc ggc gag cct        345
Asp Pro Met Ser Ala Ala Arg Asn Lys Arg Ser His Gly Gly Glu Pro
 85                  90                  95                 100 gcg tca cac atc cgc gcg gag agc cag gac atg atg atg atg acc            393
Ala Ser His Ile Arg Ala Glu Ser Gln Asp Met Met Met Met Met Thr
                105                 110                 115 tac agc atg gtg ccg atc cgg gtg atg ata gac ctg tgc aac agc acc        441
Tyr Ser Met Val Pro Ile Arg Val Met Ile Asp Leu Cys Asn Ser Thr
            120                 125                 130 cag ggc atc tgc ctt aca gga cca ccg ggc cca cca gga cct cca gga        489
Gln Gly Ile Cys Leu Thr Gly Pro Pro Gly Pro Pro Gly Pro Pro Gly
        135                 140                 145 gct ggt ggg tta cca ggc cac aat gga tca gat gga cag cct ggt ctc        537
Ala Gly Gly Leu Pro Gly His Asn Gly Ser Asp Gly Gln Pro Gly Leu
    150                 155                 160 cag ggc cca aaa gga gaa aaa gga gca gtt ggg aag aga gga aaa atg        585
Gln Gly Pro Lys Gly Glu Lys Gly Ala Val Gly Lys Arg Gly Lys Met
165                 170                 175                 180 ggg tta ccc gga gcc aca gga aat cca ggg gaa aag gga gag aag gga        633
Gly Leu Pro Gly Ala Thr Gly Asn Pro Gly Glu Lys Gly Glu Lys Gly
                185                 190                 195 gat gct ggt gaa ctg ggc cta cct gga aat gag gga cca cca gga cag        681
Asp Ala Gly Glu Leu Gly Leu Pro Gly Asn Glu Gly Pro Pro Gly Gln
            200                 205                 210 aaa gga gac aaa gga gac aaa gga gat gtg tcc aat gac gtg ctt ttg        729
Lys Gly Asp Lys Gly Asp Lys Gly Asp Val Ser Asn Asp Val Leu Leu
        215                 220                 225 aca ggt gcc aaa ggt gac caa ggg ccc cct ggc cca cct gga ccc cca        777
Thr Gly Ala Lys Gly Asp Gln Gly Pro Pro Gly Pro Pro Gly Pro Pro
    230                 235                 240 ggg cct cca ggc cct tct gga agc aga aga gcc aaa ggc cct cgg cag        825
Gly Pro Pro Gly Pro Ser Gly Ser Arg Arg Ala Lys Gly Pro Arg Gln
245                 250                 255                 260 cca aat tcg ttc acc aac cag tgt cca ggg gag acg tgt gtc ata ccc        873
Pro Asn Ser Phe Thr Asn Gln Cys Pro Gly Glu Thr Cys Val Ile Pro
                265                 270                 275 aat gat gat acc ttg gtg ggg aga gct gat gag aaa gtc aat gag cgc        921
Asn Asp Asp Thr Leu Val Gly Arg Ala Asp Glu Lys Val Asn Glu Arg
            280                 285                 290
```

```
cat tct cca caa aca gaa ccc atg atc acg tcc att ggt aac ccg gcc    969
His Ser Pro Gln Thr Glu Pro Met Ile Thr Ser Ile Gly Asn Pro Ala
        295                 300                 305 caa gtc ctc aaa gtg aaa gag act ttt ggg acc tgg cta aga gag tct   1017
Gln Val Leu Lys Val Lys Glu Thr Phe Gly Thr Trp Leu Arg Glu Ser
310                 315                 320 gct aac agg agt gat gac cgc att tgg gtg act gaa cat ttt tca ggc   1065
Ala Asn Arg Ser Asp Asp Arg Ile Trp Val Thr Glu His Phe Ser Gly
325                 330                 335                 340 atc atg gtg aag gag ttt gaa gac ctg ccc gcc ctc ctg aat agc agc   1113
Ile Met Val Lys Glu Phe Glu Asp Leu Pro Ala Leu Leu Asn Ser Ser
                345                 350                 355 ttc acc ctc ctc cac ctc cca cat tac ttc cat ggc tgc ggg cac gct   1161
Phe Thr Leu Leu His Leu Pro His Tyr Phe His Gly Cys Gly His Ala
        360                 365                 370 gtt tac aac aac tct ctc tac tac cac aaa gga ggc tcc aac acc ata   1209
Val Tyr Asn Asn Ser Leu Tyr Tyr His Lys Gly Gly Ser Asn Thr Ile
        375                 380                 385 gtg aga ttt gaa ttt ggg aaa gag aca cct caa act ctg aag ctt gaa   1257
Val Arg Phe Glu Phe Gly Lys Glu Thr Pro Gln Thr Leu Lys Leu Glu
390                 395                 400 gat gct ttg tat ttt gat cga aaa tac ctc ttt gcg aat tcc aag act   1305
Asp Ala Leu Tyr Phe Asp Arg Lys Tyr Leu Phe Ala Asn Ser Lys Thr
405                 410                 415                 420 tac ttc aac ata gca gtg gat gag aag ggc ctc tgg att atc tac gcc   1353
Tyr Phe Asn Ile Ala Val Asp Glu Lys Gly Leu Trp Ile Ile Tyr Ala
                425                 430                 435 tcg agt gtg gat ggc tca agc atc ctt gtg gca cag ctg gac gag agg   1401
Ser Ser Val Asp Gly Ser Ser Ile Leu Val Ala Gln Leu Asp Glu Arg
        440                 445                 450 aca ttc tct gtg ctg cag cac atc aat acc aca tac ccc aag tcc aag   1449
Thr Phe Ser Val Leu Gln His Ile Asn Thr Thr Tyr Pro Lys Ser Lys
        455                 460                 465 gct ggc aat gcc ttc ata gct caa ggg atc ctc tat gtc acg gac aca   1497
Ala Gly Asn Ala Phe Ile Ala Gln Gly Ile Leu Tyr Val Thr Asp Thr
470                 475                 480 aaa gat aca agg gtc acg ttt gcc ttt gat ttg tta cga ggg aag cag   1545
Lys Asp Thr Arg Val Thr Phe Ala Phe Asp Leu Leu Arg Gly Lys Gln
485                 490                 495                 500 atc aat gca aac ttc ggt ctc aga atg tca cag tct gtt ctt gcc atg   1593
Ile Asn Ala Asn Phe Gly Leu Arg Met Ser Gln Ser Val Leu Ala Met
                505                 510                 515 ttg tcg tac aat atg aga gac cag cat ttg tac tcg tgg gaa gac ggc   1641
Leu Ser Tyr Asn Met Arg Asp Gln His Leu Tyr Ser Trp Glu Asp Gly
        520                 525                 530 cac ctg atg ctc tat cct gtg cac ttt tcg tca aca gca ccc agc cag   1689
His Leu Met Leu Tyr Pro Val His Phe Ser Ser Thr Ala Pro Ser Gln
        535                 540                 545 cga taggcctgca gtcggctccc tcattatgca ccacacattt tctggggttt        1742
Arg gaccaagccc aacggaaaga aggcctgtaa aggatatcca gatactcaga gcatacgccc  1802
gtgttacggg cttttgtgca tgtggcaagt cccctgtaa gccaggttaa ctaaaggctg   1862
gaaagttgaa atggataaca tttggtgacc cttggtccct cttcaaactt agcaagttag  1922
tgctcccccc tgaccttagt gtccccatca gtaatatgaa acatctgtgt gattgcagca  1982
tttcctatac ctatatgaag ttctgtgatt cttgcctggt tatatattag attgcttca   2042 ggtttctttt ttttttctcc acatgtaaat gagtttacct gcagcttgag gggtgtgcct  2102
```

```
atcagtgatg acggacattt gtttggtgtt tagggaaaaa gcattgtttc ttatggcttt    2162
taaagtatta tattatccat aatttgatat ttttttttga atacgcccct gccactacag    2222
aatgattatt gttttcagct cctaagtaca aatccaagat taataaaaaa aaacatgaa     2282 tagaaaaaaa aaaaaaaaaa actcgagagt attagtcgat gtaggaaaac               2332
```

<210> SEQ ID NO 2
<211> LENGTH: 549
<212> TYPE: PRT
<213> ORGANISM: Rattus sp.

<400> SEQUENCE: 2

```
Met Thr Arg Ala Ala Glu Arg Gly Gln Gly Ala Thr Gly Trp Gly Leu
 1               5                  10                  15

Arg Gly Ala Leu Met Ala Val Ala Leu Leu Ser Val Leu Asn Ala Val
            20                  25                  30

Gly Thr Val Phe Val Leu Tyr Gln Trp Arg Glu Leu Ser Ala Ala Leu
        35                  40                  45

Arg Ala Leu Glu Ala Gln His Gly Gln Glu Gln Arg Glu Asp Ser Ala
    50                  55                  60

Leu Arg Ala Phe Leu Ala Glu Leu Ser Arg Ala Pro Ala Arg Val Pro
65                  70                  75                  80

Glu Pro Pro Gln Asp Pro Met Ser Ala Ala Arg Asn Lys Arg Ser His
                85                  90                  95

Gly Gly Glu Pro Ala Ser His Ile Arg Ala Glu Ser Gln Asp Met Met
           100                 105                 110

Met Met Met Thr Tyr Ser Met Val Pro Ile Arg Val Met Ile Asp Leu
        115                 120                 125

Cys Asn Ser Thr Gln Gly Ile Cys Leu Thr Gly Pro Pro Gly Pro Pro
    130                 135                 140

Gly Pro Pro Gly Ala Gly Gly Leu Pro Gly His Asn Gly Ser Asp Gly
145                 150                 155                 160

Gln Pro Gly Leu Gln Gly Pro Lys Gly Glu Lys Gly Ala Val Gly Lys
                165                 170                 175

Arg Gly Lys Met Gly Leu Pro Gly Ala Thr Gly Asn Pro Gly Glu Lys
            180                 185                 190

Gly Glu Lys Gly Asp Ala Gly Glu Leu Gly Leu Pro Gly Asn Glu Gly
        195                 200                 205

Pro Pro Gly Gln Lys Gly Asp Lys Gly Asp Lys Gly Asp Val Ser Asn
    210                 215                 220

Asp Val Leu Leu Thr Gly Ala Lys Gly Asp Gln Gly Pro Pro Gly Pro
225                 230                 235                 240

Pro Gly Pro Pro Gly Pro Gly Pro Ser Gly Ser Arg Arg Ala Lys
                245                 250                 255

Gly Pro Arg Gln Pro Asn Ser Phe Thr Asn Gln Cys Pro Gly Glu Thr
            260                 265                 270

Cys Val Ile Pro Asn Asp Asp Thr Leu Val Gly Arg Ala Asp Glu Lys
        275                 280                 285

Val Asn Glu Arg His Ser Pro Gln Thr Glu Pro Met Ile Thr Ser Ile
    290                 295                 300

Gly Asn Pro Ala Gln Val Leu Lys Val Lys Glu Thr Phe Gly Thr Trp
305                 310                 315                 320

Leu Arg Glu Ser Ala Asn Arg Ser Asp Asp Arg Ile Trp Val Thr Glu
                325                 330                 335
```

-continued

```
His Phe Ser Gly Ile Met Val Lys Glu Phe Glu Asp Leu Pro Ala Leu
            340                 345                 350
Leu Asn Ser Ser Phe Thr Leu Leu His Leu Pro His Tyr Phe His Gly
        355                 360                 365
Cys Gly His Ala Val Tyr Asn Asn Ser Leu Tyr Tyr His Lys Gly Gly
        370                 375                 380
Ser Asn Thr Ile Val Arg Phe Glu Phe Gly Lys Glu Thr Pro Gln Thr
385                 390                 395                 400
Leu Lys Leu Glu Asp Ala Leu Tyr Phe Asp Arg Lys Tyr Leu Phe Ala
                405                 410                 415
Asn Ser Lys Thr Tyr Phe Asn Ile Ala Val Asp Glu Lys Gly Leu Trp
            420                 425                 430
Ile Ile Tyr Ala Ser Ser Val Asp Gly Ser Ser Ile Leu Val Ala Gln
        435                 440                 445
Leu Asp Glu Arg Thr Phe Ser Val Leu Gln His Ile Asn Thr Thr Tyr
    450                 455                 460
Pro Lys Ser Lys Ala Gly Asn Ala Phe Ile Ala Gln Gly Ile Leu Tyr
465                 470                 475                 480
Val Thr Asp Thr Lys Asp Thr Arg Val Thr Phe Ala Phe Asp Leu Leu
                485                 490                 495
Arg Gly Lys Gln Ile Asn Ala Asn Phe Gly Leu Arg Met Ser Gln Ser
            500                 505                 510
Val Leu Ala Met Leu Ser Tyr Asn Met Arg Asp Gln His Leu Tyr Ser
        515                 520                 525
Trp Glu Asp Gly His Leu Met Leu Tyr Pro Val His Phe Ser Ser Thr
    530                 535                 540
Ala Pro Ser Gln Arg
545

<210> SEQ ID NO 3
<211> LENGTH: 2278
<212> TYPE: DNA
<213> ORGANISM: Rattus sp.
<220> FEATURE:
<221> NAME/KEY: CDS
<222> LOCATION: (46)..(1638)

<400> SEQUENCE: 3
acgcggggag tgctgccctg agtcgttcgg cctgagcaca gagac atg acc cga gcc      57
                                                Met Thr Arg Ala
                                                  1 gca gag cga ggc caa ggg gct aca ggc tgg gga ctg cga ggc gcc ctg      105
Ala Glu Arg Gly Gln Gly Ala Thr Gly Trp Gly Leu Arg Gly Ala Leu
  5                  10                  15                  20 atg gcc gtg gcg ctg ctg tca gtg ctg aac gcc gtg ggc acc gtg ttc      153
Met Ala Val Ala Leu Leu Ser Val Leu Asn Ala Val Gly Thr Val Phe
                 25                  30                  35 gtg ctg tac cag cag cgc gag gac agc gcc cta cgc gcc ttt cta gct      201
Val Leu Tyr Gln Gln Arg Glu Asp Ser Ala Leu Arg Ala Phe Leu Ala
             40                  45                  50 gaa tta agt cgt gcg cca gcc cga gtc ccc gaa cca ccc cag gac ccc      249
Glu Leu Ser Arg Ala Pro Ala Arg Val Pro Glu Pro Pro Gln Asp Pro
         55                  60                  65 atg agt gca gcg cgc aat aag cgc agc cac ggc ggc gag cct gcg tca      297
Met Ser Ala Ala Arg Asn Lys Arg Ser His Gly Gly Glu Pro Ala Ser
     70                  75                  80 cac atc cgc gcg gag agc cag gac atg atg atg atg acc tac agc          345
His Ile Arg Ala Glu Ser Gln Asp Met Met Met Met Thr Tyr Ser
```

```
His Ile Arg Ala Glu Ser Gln Asp Met Met Met Met Thr Tyr Ser
 85                  90                  95                 100 atg gtg ccg atc cgg gtg atg ata gac ctg tgc aac agc acc cag ggc     393
Met Val Pro Ile Arg Val Met Ile Asp Leu Cys Asn Ser Thr Gln Gly
                    105                 110                 115 atc tgc ctt aca gga cca ccg ggc cca cca gga cct cca gga gct ggt     441
Ile Cys Leu Thr Gly Pro Pro Gly Pro Pro Gly Pro Pro Gly Ala Gly
                120                 125                 130 ggg tta cca ggc cac aat gga tca gat gga cag cct ggt ctc cag ggc     489
Gly Leu Pro Gly His Asn Gly Ser Asp Gly Gln Pro Gly Leu Gln Gly
            135                 140                 145 cca aaa gga gaa aaa gga gca gtt ggg aag aga gga aaa atg ggg tta     537
Pro Lys Gly Glu Lys Gly Ala Val Gly Lys Arg Gly Lys Met Gly Leu
        150                 155                 160 ccc gga gcc aca gga aat cca ggg gaa aag gga gag aag gga gat gct     585
Pro Gly Ala Thr Gly Asn Pro Gly Glu Lys Gly Glu Lys Gly Asp Ala
165                 170                 175                 180 ggt gaa ctg ggc cta cct gga aat gag gga cca cca gga cag aaa gga     633
Gly Glu Leu Gly Leu Pro Gly Asn Glu Gly Pro Pro Gly Gln Lys Gly
                    185                 190                 195 gac aaa gga gac aaa gga gat gtg tcc aat gac gtg ctt ttg aca ggt     681
Asp Lys Gly Asp Lys Gly Asp Val Ser Asn Asp Val Leu Leu Thr Gly
                200                 205                 210 gcc aaa ggt gac caa ggg ccc cct ggc cca cct gga ccc cca ggg cct     729
Ala Lys Gly Asp Gln Gly Pro Pro Gly Pro Pro Gly Pro Pro Gly Pro
            215                 220                 225 cca ggc cct tct gga agc aga aga gcc aaa ggc cct cgg cag cca aat     777
Pro Gly Pro Ser Gly Ser Arg Arg Ala Lys Gly Pro Arg Gln Pro Asn
        230                 235                 240 tcg ttc acc aac cag tgt cca ggg gag acg tgt gtc ata ccc aat gat     825
Ser Phe Thr Asn Gln Cys Pro Gly Glu Thr Cys Val Ile Pro Asn Asp
245                 250                 255                 260 gat acc ttg gtg ggg aga gct gat gag aaa gtc aat gag cgc cat tct     873
Asp Thr Leu Val Gly Arg Ala Asp Glu Lys Val Asn Glu Arg His Ser
                    265                 270                 275 cca caa aca gaa ccc atg atc acg tcc att ggt aac ccg gcc caa gtc     921
Pro Gln Thr Glu Pro Met Ile Thr Ser Ile Gly Asn Pro Ala Gln Val
                280                 285                 290 ctc aaa gtg aaa gag act ttt ggg acc tgg cta aga gag tct gct aac     969
Leu Lys Val Lys Glu Thr Phe Gly Thr Trp Leu Arg Glu Ser Ala Asn
            295                 300                 305 agg agt gat gac cgc att tgg gtg act gaa cat ttt tca ggc atc atg    1017
Arg Ser Asp Asp Arg Ile Trp Val Thr Glu His Phe Ser Gly Ile Met
        310                 315                 320 gtg aag gag ttt gaa gac ctg ccc gcc ctc ctg aat agc agc ttc acc    1065
Val Lys Glu Phe Glu Asp Leu Pro Ala Leu Leu Asn Ser Ser Phe Thr
325                 330                 335                 340 ctc ctc cac ctc cca cat tac ttc cat ggc tgc ggg cac gct gtt tac    1113
Leu Leu His Leu Pro His Tyr Phe His Gly Cys Gly His Ala Val Tyr
                    345                 350                 355 aac aac tct ctc tac tac cac aaa gga ggc tcc aac acc ata gtg aga    1161
Asn Asn Ser Leu Tyr Tyr His Lys Gly Gly Ser Asn Thr Ile Val Arg
                360                 365                 370 ttt gaa ttt ggg aaa gag aca cct caa act ctg aag ctt gaa gat gct    1209
Phe Glu Phe Gly Lys Glu Thr Pro Gln Thr Leu Lys Leu Glu Asp Ala
            375                 380                 385 ttg tat ttt gat cga aaa tac ctc ttt gcg aat tcc aag act tac ttc    1257
Leu Tyr Phe Asp Arg Lys Tyr Leu Phe Ala Asn Ser Lys Thr Tyr Phe
        390                 395                 400
```

| | | | | | | | | | | | | | | | |
|---|---|---|---|---|---|---|---|---|---|---|---|---|---|---|---|
| aac | ata | gca | gtg | gat | gag | aag | ggc | ctc | tgg | att | atc | tac | gcc | tcg | agt | 1305 |
| Asn | Ile | Ala | Val | Asp | Glu | Lys | Gly | Leu | Trp | Ile | Ile | Tyr | Ala | Ser | Ser | |
| 405 | | | | | 410 | | | | | 415 | | | | | 420 | |

| | | | | | | | | | | | | | | | |
|---|---|---|---|---|---|---|---|---|---|---|---|---|---|---|---|
| gtg | gat | ggc | tca | agc | atc | ctt | gtg | gca | cag | ctg | gac | gag | agg | aca | ttc | 1353 |
| Val | Asp | Gly | Ser | Ser | Ile | Leu | Val | Ala | Gln | Leu | Asp | Glu | Arg | Thr | Phe | |
| | | | | 425 | | | | | 430 | | | | | 435 | | |

| | | | | | | | | | | | | | | | |
|---|---|---|---|---|---|---|---|---|---|---|---|---|---|---|---|
| tct | gtg | ctg | cag | cac | atc | aat | acc | aca | tac | ccc | aag | tcc | aag | gct | ggc | 1401 |
| Ser | Val | Leu | Gln | His | Ile | Asn | Thr | Thr | Tyr | Pro | Lys | Ser | Lys | Ala | Gly | |
| | | | 440 | | | | | 445 | | | | | 450 | | | |

| | | | | | | | | | | | | | | | |
|---|---|---|---|---|---|---|---|---|---|---|---|---|---|---|---|
| aat | gcc | ttc | ata | gct | caa | ggg | atc | ctc | tat | gtc | acg | gac | aca | aaa | gat | 1449 |
| Asn | Ala | Phe | Ile | Ala | Gln | Gly | Ile | Leu | Tyr | Val | Thr | Asp | Thr | Lys | Asp | |
| | | 455 | | | | | 460 | | | | | 465 | | | | |

| | | | | | | | | | | | | | | | |
|---|---|---|---|---|---|---|---|---|---|---|---|---|---|---|---|
| aca | agg | gtc | acg | ttt | gcc | ttt | gat | ttg | tta | cga | ggg | aag | cag | atc | aat | 1497 |
| Thr | Arg | Val | Thr | Phe | Ala | Phe | Asp | Leu | Leu | Arg | Gly | Lys | Gln | Ile | Asn | |
| | 470 | | | | | 475 | | | | | 480 | | | | | |

| | | | | | | | | | | | | | | | |
|---|---|---|---|---|---|---|---|---|---|---|---|---|---|---|---|
| gca | aac | ttc | ggt | ctc | aga | atg | tca | cag | tct | gtt | ctt | gcc | atg | ttg | tcg | 1545 |
| Ala | Asn | Phe | Gly | Leu | Arg | Met | Ser | Gln | Ser | Val | Leu | Ala | Met | Leu | Ser | |
| 485 | | | | | 490 | | | | | 495 | | | | | 500 | |

| | | | | | | | | | | | | | | | |
|---|---|---|---|---|---|---|---|---|---|---|---|---|---|---|---|
| tac | aat | atg | aga | gac | cag | cat | ttg | tac | tcg | tgg | gaa | gac | ggc | cac | ctg | 1593 |
| Tyr | Asn | Met | Arg | Asp | Gln | His | Leu | Tyr | Ser | Trp | Glu | Asp | Gly | His | Leu | |
| | | | | 505 | | | | | 510 | | | | | 515 | | |

| | | | | | | | | | | | | | | |
|---|---|---|---|---|---|---|---|---|---|---|---|---|---|---|
| atg | ctc | tat | cct | gtg | cac | ttt | tcg | tca | aca | gca | ccc | agc | cag | cga | 1638 |
| Met | Leu | Tyr | Pro | Val | His | Phe | Ser | Ser | Thr | Ala | Pro | Ser | Gln | Arg | |
| | | | 520 | | | | | 525 | | | | | 530 | | |

| | | | |
|---|---|---|---|
| taggcctgca | gtcggctccc | tcattatgca | ccacacattt tctggggttt gaccaagccc | 1698 |
| aacggaaaga | aggcctgtaa | aggatatcca | gatactcaga gcatacgccc gtgttacggg | 1758 |
| cttttgtgca | tgtggcaagt | cccctgtaa | gccaggttaa ctaaaggctg gaaagttgaa | 1818 |
| atggataaca | tttggtgacc | cttggtccct | cttcaaactt agcaagttag tgctcccccc | 1878 |
| tgaccttagt | gtccccatca | gtaatatgaa | acatctgtgt gattgcagca tttcctatac | 1938 |
| ctatatgaag | ttctgtgatt | cttgcctggt | tatatattag attgctttca ggtttctttt | 1998 |
| ttttttctcc | acatgtaaat | gagtttacct | gcagcttgag gggtgtgcct atcagtgatg | 2058 |
| acggacattt | gtttggtgtt | tagggaaaaa | gcattgtttc ttatggcttt taaagtatta | 2118 |
| tattatccat | aatttgatat | ttttttttga | atacgcccct gccactacag aatgattatt | 2178 |
| gttttcagct | cctaagtaca | aatccaagat | taataaaaaa aaaacatgaa tagaaaaaaa | 2238 |
| aaaaaaaaaa | actcgagagt | attagtcgat | gtaggaaaac | 2278 |

<210> SEQ ID NO 4
<211> LENGTH: 531
<212> TYPE: PRT
<213> ORGANISM: Rattus sp.

<400> SEQUENCE: 4

Met Thr Arg Ala Ala Glu Arg Gly Gln Gly Ala Thr Gly Trp Gly Leu
 1               5                  10                  15

Arg Gly Ala Leu Met Ala Val Ala Leu Leu Ser Val Leu Asn Ala Val
            20                  25                  30

Gly Thr Val Phe Val Leu Tyr Gln Gln Arg Glu Asp Ser Ala Leu Arg
        35                  40                  45

Ala Phe Leu Ala Glu Leu Ser Arg Ala Pro Ala Arg Val Pro Glu Pro
    50                  55                  60

Pro Gln Asp Pro Met Ser Ala Ala Arg Asn Lys Arg Ser His Gly Gly
65                  70                  75                  80

Glu Pro Ala Ser His Ile Arg Ala Glu Ser Gln Asp Met Met Met Met
                85                  90                  95

-continued

```
Met Thr Tyr Ser Met Val Pro Ile Arg Val Met Ile Asp Leu Cys Asn
            100                 105                 110
Ser Thr Gln Gly Ile Cys Leu Thr Gly Pro Pro Gly Pro Gly Pro
            115                 120                 125
Pro Gly Ala Gly Gly Leu Pro Gly His Asn Gly Ser Asp Gly Gln Pro
            130                 135                 140
Gly Leu Gln Gly Pro Lys Gly Glu Lys Gly Ala Val Gly Lys Arg Gly
145                 150                 155                 160
Lys Met Gly Leu Pro Gly Ala Thr Gly Asn Pro Gly Glu Lys Gly Glu
                165                 170                 175
Lys Gly Asp Ala Gly Glu Leu Gly Leu Pro Gly Asn Glu Gly Pro Pro
            180                 185                 190
Gly Gln Lys Gly Asp Lys Gly Asp Lys Gly Asp Val Ser Asn Asp Val
            195                 200                 205
Leu Leu Thr Gly Ala Lys Gly Asp Gln Gly Pro Pro Gly Pro Pro Gly
210                 215                 220
Pro Pro Gly Pro Pro Gly Pro Ser Gly Ser Arg Arg Ala Lys Gly Pro
225                 230                 235                 240
Arg Gln Pro Asn Ser Phe Thr Asn Gln Cys Pro Gly Glu Thr Cys Val
                245                 250                 255
Ile Pro Asn Asp Asp Thr Leu Val Gly Arg Ala Asp Glu Lys Val Asn
            260                 265                 270
Glu Arg His Ser Pro Gln Thr Glu Pro Met Ile Thr Ser Ile Gly Asn
            275                 280                 285
Pro Ala Gln Val Leu Lys Val Lys Glu Thr Phe Gly Thr Trp Leu Arg
290                 295                 300
Glu Ser Ala Asn Arg Ser Asp Asp Arg Ile Trp Val Thr Glu His Phe
305                 310                 315                 320
Ser Gly Ile Met Val Lys Glu Phe Glu Asp Leu Pro Ala Leu Leu Asn
            325                 330                 335
Ser Ser Phe Thr Leu Leu His Leu Pro His Tyr Phe His Gly Cys Gly
            340                 345                 350
His Ala Val Tyr Asn Asn Ser Leu Tyr Tyr His Lys Gly Gly Ser Asn
            355                 360                 365
Thr Ile Val Arg Phe Glu Phe Gly Lys Glu Thr Pro Gln Thr Leu Lys
            370                 375                 380
Leu Glu Asp Ala Leu Tyr Phe Asp Arg Lys Tyr Leu Phe Ala Asn Ser
385                 390                 395                 400
Lys Thr Tyr Phe Asn Ile Ala Val Asp Glu Lys Gly Leu Trp Ile Ile
                405                 410                 415
Tyr Ala Ser Ser Val Asp Gly Ser Ser Ile Leu Val Ala Gln Leu Asp
            420                 425                 430
Glu Arg Thr Phe Ser Val Leu Gln His Ile Asn Thr Thr Tyr Pro Lys
            435                 440                 445
Ser Lys Ala Gly Asn Ala Phe Ile Ala Gln Gly Ile Leu Tyr Val Thr
            450                 455                 460
Asp Thr Lys Asp Thr Arg Val Thr Phe Ala Phe Asp Leu Leu Arg Gly
465                 470                 475                 480
Lys Gln Ile Asn Ala Asn Phe Gly Leu Arg Met Ser Gln Ser Val Leu
                485                 490                 495
Ala Met Leu Ser Tyr Asn Met Arg Asp Gln His Leu Tyr Ser Trp Glu
            500                 505                 510
```

```
Asp Gly His Leu Met Leu Tyr Pro Val His Phe Ser Ser Thr Ala Pro
        515                 520                 525

Ser Gln Arg
    530

<210> SEQ ID NO 5
<211> LENGTH: 2416
<212> TYPE: DNA
<213> ORGANISM: Rattus sp.
<220> FEATURE:
<221> NAME/KEY: CDS
<222> LOCATION: (189)..(1835)

<400> SEQUENCE: 5
gaattcggca cgagggggggc ttctggggcg ccacgattac tgtccccaac ccgcctcgcc      60
agacgggtct aaaggcagct tgactcacga ctctgccacc agcccaccac tcgcgcgagg     120
gtataaaacc tgccactgcg ggaggaggcc cagtgctgcc ctgagtcgtt cggcctgagc     180 acagagac atg acc cga gcc gca gag cga ggc caa ggg gct aca ggc tgg     230
         Met Thr Arg Ala Ala Glu Arg Gly Gln Gly Ala Thr Gly Trp
           1               5                  10 gga ctg cga ggc gcc ctg atg gcc gtg gcg ctg ctg tca gtg ctg aac     278
Gly Leu Arg Gly Ala Leu Met Ala Val Ala Leu Leu Ser Val Leu Asn
 15                  20                  25                  30 gcc gtg ggc acc gtg ttc gtg ctg tac cag tgg cgc gag ctg agc gcg     326
Ala Val Gly Thr Val Phe Val Leu Tyr Gln Trp Arg Glu Leu Ser Ala
                 35                  40                  45 gcg ctg cgg gca ctg gag gcg caa cac ggc cag gag cag cgc gag gac     374
Ala Leu Arg Ala Leu Glu Ala Gln His Gly Gln Glu Gln Arg Glu Asp
             50                  55                  60 agc gcc cta cgc gcc ttt cta gct gaa tta agt cgt gcg cca gcc cga     422
Ser Ala Leu Arg Ala Phe Leu Ala Glu Leu Ser Arg Ala Pro Ala Arg
         65                  70                  75 gtc ccc gaa cca ccc cag gac ccc atg agt gca gcg cgc aat aag cgc     470
Val Pro Glu Pro Pro Gln Asp Pro Met Ser Ala Ala Arg Asn Lys Arg
     80                  85                  90 agc cac ggc ggc gag cct gcg tca cac atc cgc gcg gag agc cag gac     518
Ser His Gly Gly Glu Pro Ala Ser His Ile Arg Ala Glu Ser Gln Asp
 95                 100                 105                 110 atg atg atg atg atg acc tac agc atg gtg ccg atc cgg gtg atg ata     566
Met Met Met Met Met Thr Tyr Ser Met Val Pro Ile Arg Val Met Ile
                115                 120                 125 gac ctg tgc aac agc acc cag ggc atc tgc ctt aca gga cca ccg ggc     614
Asp Leu Cys Asn Ser Thr Gln Gly Ile Cys Leu Thr Gly Pro Pro Gly
            130                 135                 140 cca cca gga cct cca gga gct ggt ggg tta cca ggc cac aat gga tca     662
Pro Pro Gly Pro Pro Gly Ala Gly Gly Leu Pro Gly His Asn Gly Ser
        145                 150                 155 gat gga cag cct ggt ctc cag ggc cca aaa gga gaa aaa gga gca gtt     710
Asp Gly Gln Pro Gly Leu Gln Gly Pro Lys Gly Glu Lys Gly Ala Val
    160                 165                 170 ggg aag aga gga aaa atg ggg tta ccc gga gcc aca gga aat cca ggg     758
Gly Lys Arg Gly Lys Met Gly Leu Pro Gly Ala Thr Gly Asn Pro Gly
175                 180                 185                 190 gaa aag gga gag aag gga gat gct ggt gaa ctg ggc cta cct gga aat     806
Glu Lys Gly Glu Lys Gly Asp Ala Gly Glu Leu Gly Leu Pro Gly Asn
                195                 200                 205 gag gga cca cca gga cag aaa gga gac aaa gga gac aaa gga gat gtg     854
Glu Gly Pro Pro Gly Gln Lys Gly Asp Lys Gly Asp Lys Gly Asp Val
            210                 215                 220
```

```
tcc aat gac gtg ctt ttg aca ggt gcc aaa ggt gac caa ggg ccc cct      902
Ser Asn Asp Val Leu Leu Thr Gly Ala Lys Gly Asp Gln Gly Pro Pro
            225                 230                 235 ggc cca cct gga ccc cca ggg cct cca ggc cct cct gga agc aga aga      950
Gly Pro Pro Gly Pro Pro Gly Pro Pro Gly Pro Pro Gly Ser Arg Arg
    240                 245                 250 gcc aaa ggc cct cgg cag cca aat tcg ttc acc aac cag tgt cca ggg      998
Ala Lys Gly Pro Arg Gln Pro Asn Ser Phe Thr Asn Gln Cys Pro Gly
255                 260                 265                 270 gag acg tgt gtc ata ccc aat gat gat acc ttg gtg ggg aga gct gat     1046
Glu Thr Cys Val Ile Pro Asn Asp Asp Thr Leu Val Gly Arg Ala Asp
                275                 280                 285 gag aaa gtc aat gag cgc cat tct cca caa aca gaa ccc atg atc acg     1094
Glu Lys Val Asn Glu Arg His Ser Pro Gln Thr Glu Pro Met Ile Thr
            290                 295                 300 tcc att ggt aac ccg gcc caa gtc ctc aag gtg aaa gag act ttt ggg     1142
Ser Ile Gly Asn Pro Ala Gln Val Leu Lys Val Lys Glu Thr Phe Gly
        305                 310                 315 acc tgg cta aga gag tct gct aac agg agt gac gac cgc att tgg gtg     1190
Thr Trp Leu Arg Glu Ser Ala Asn Arg Ser Asp Asp Arg Ile Trp Val
    320                 325                 330 act gaa cat ttt tca ggc atc atg gtg aag gag ttt gaa gac ctg ccc     1238
Thr Glu His Phe Ser Gly Ile Met Val Lys Glu Phe Glu Asp Leu Pro
335                 340                 345                 350 gcc ctc ctg aat agc agc ttc acc ctc ctc cac ctc cca cat tac ttc     1286
Ala Leu Leu Asn Ser Ser Phe Thr Leu Leu His Leu Pro His Tyr Phe
                355                 360                 365 cat ggc tgc ggg cac gct gtt tac aac aac tct ctc tac tac cac aaa     1334
His Gly Cys Gly His Ala Val Tyr Asn Asn Ser Leu Tyr Tyr His Lys
            370                 375                 380 gga ggc tcc aac acc ata gtg aga ttt gaa ttt ggg aaa gag aca cct     1382
Gly Gly Ser Asn Thr Ile Val Arg Phe Glu Phe Gly Lys Glu Thr Pro
        385                 390                 395 caa act ctg aag ctt gaa gat gct ttg tat ttt gat cga aaa tac ctc     1430
Gln Thr Leu Lys Leu Glu Asp Ala Leu Tyr Phe Asp Arg Lys Tyr Leu
    400                 405                 410 ttt gcg aat tcc aag act tac ttc aac ata gca gtg gat gag aag ggc     1478
Phe Ala Asn Ser Lys Thr Tyr Phe Asn Ile Ala Val Asp Glu Lys Gly
415                 420                 425                 430 ctc tgg att atc tac gcc tcg agt gtg gat ggc tca agc atc ctt gtg     1526
Leu Trp Ile Ile Tyr Ala Ser Ser Val Asp Gly Ser Ser Ile Leu Val
                435                 440                 445 gca cag ctg gac gag agg aca ttc tct gtg ctg cgg cac atc aat acc     1574
Ala Gln Leu Asp Glu Arg Thr Phe Ser Val Leu Arg His Ile Asn Thr
            450                 455                 460 aca tac ccc aag tcc aag gct ggc aat gcc ttc ata gct caa ggg atc     1622
Thr Tyr Pro Lys Ser Lys Ala Gly Asn Ala Phe Ile Ala Gln Gly Ile
        465                 470                 475 ctc tat gtc acg gac acc aaa gat aca agg gtc acg ttt gcc ttt gat     1670
Leu Tyr Val Thr Asp Thr Lys Asp Thr Arg Val Thr Phe Ala Phe Asp
    480                 485                 490 ttg tta cga ggg aag cag atc aat gca aac ttc ggt ctc aga atg tca     1718
Leu Leu Arg Gly Lys Gln Ile Asn Ala Asn Phe Gly Leu Arg Met Ser
495                 500                 505                 510 cag tct gtt ctt gcc atg ttg tcg tac aat atg aga gac cag cat ttg     1766
Gln Ser Val Leu Ala Met Leu Ser Tyr Asn Met Arg Asp Gln His Leu
                515                 520                 525 tac tcg tgg gaa gac ggc cac ctg atg ctc tat cct gtg cac ttt tcg     1814
Tyr Ser Trp Glu Asp Gly His Leu Met Leu Tyr Pro Val His Phe Ser
            530                 535                 540
```

```
tca aca gca ccc agc cag cga taggcctgca gtcggctccc tcattatgca      1865
Ser Thr Ala Pro Ser Gln Arg
        545 ccacacattt tctggggttt gaccaagccc aacggaaaga aggcctgtaa aggatatcca  1925 gatactcaga gcatacgccc gtgctacggg ctcttgtgca tgtggcaagt cccctgtaa   1985 gccaggttag ctagaggctg gaagttgaaa tggataacat ctggtgaccc ttggtccctc  2045 ttcaaactta gcaagttagt gctcccccct gaccttagtg tccccatcag taatatgaaa  2105 catctgtgtg attgacagca tttcctctac ctatatgaag ttctgtgatt cttgcctggt  2165 tatatattag attgctttct ggtttctttt tttttctcc  acatgtaaat gagtttacct   2225 gcagcttgag gggtgtgcct atcagtgatg acggacattt gtttggtgtt tagggaagat  2285 gcattgtctc ttatggcttc taaagtatta tattatccat aatttgatat ttttctctga  2345 atacgcacct gccactacag aatgattatt gtttcagctc ctaagtacaa atccaaaaaa  2405 aaaaaaaaaa a                                                      2416
```

<210> SEQ ID NO 6
<211> LENGTH: 549
<212> TYPE: PRT
<213> ORGANISM: Rattus sp.

<400> SEQUENCE: 6

```
Met Thr Arg Ala Ala Glu Arg Gly Gln Gly Ala Thr Gly Trp Gly Leu
 1               5                  10                  15

Arg Gly Ala Leu Met Ala Val Ala Leu Leu Ser Val Leu Asn Ala Val
            20                  25                  30

Gly Thr Val Phe Val Leu Tyr Gln Trp Arg Glu Leu Ser Ala Ala Leu
        35                  40                  45

Arg Ala Leu Glu Ala Gln His Gly Gln Glu Gln Arg Glu Asp Ser Ala
    50                  55                  60

Leu Arg Ala Phe Leu Ala Glu Leu Ser Arg Ala Pro Ala Arg Val Pro
65                  70                  75                  80

Glu Pro Pro Gln Asp Pro Met Ser Ala Ala Arg Asn Lys Arg Ser His
                85                  90                  95

Gly Gly Glu Pro Ala Ser His Ile Arg Ala Glu Ser Gln Asp Met Met
            100                 105                 110

Met Met Met Thr Tyr Ser Met Val Pro Ile Arg Val Met Ile Asp Leu
        115                 120                 125

Cys Asn Ser Thr Gln Gly Ile Cys Leu Thr Gly Pro Pro Gly Pro Pro
    130                 135                 140

Gly Pro Pro Gly Ala Gly Gly Leu Pro Gly His Asn Gly Ser Asp Gly
145                 150                 155                 160

Gln Pro Gly Leu Gln Gly Pro Lys Gly Glu Lys Gly Ala Val Gly Lys
                165                 170                 175

Arg Gly Lys Met Gly Leu Pro Gly Ala Thr Gly Asn Pro Gly Glu Lys
            180                 185                 190

Gly Glu Lys Gly Asp Ala Gly Glu Leu Gly Leu Pro Gly Asn Glu Gly
        195                 200                 205

Pro Pro Gly Gln Lys Gly Asp Lys Gly Asp Lys Gly Asp Val Ser Asn
    210                 215                 220

Asp Val Leu Leu Thr Gly Ala Lys Gly Asp Gln Gly Pro Pro Gly Pro
225                 230                 235                 240

Pro Gly Pro Pro Gly Pro Pro Gly Pro Pro Gly Ser Arg Arg Ala Lys
```

```
                    245                 250                 255
Gly Pro Arg Gln Pro Asn Ser Phe Thr Asn Gln Cys Pro Gly Glu Thr
            260                 265                 270
Cys Val Ile Pro Asn Asp Asp Thr Leu Val Gly Arg Ala Asp Glu Lys
        275                 280                 285
Val Asn Glu Arg His Ser Pro Gln Thr Glu Pro Met Ile Thr Ser Ile
    290                 295                 300
Gly Asn Pro Ala Gln Val Leu Lys Val Lys Glu Thr Phe Gly Thr Trp
305                 310                 315                 320
Leu Arg Glu Ser Ala Asn Arg Ser Asp Asp Arg Ile Trp Val Thr Glu
                325                 330                 335
His Phe Ser Gly Ile Met Val Lys Glu Phe Glu Asp Leu Pro Ala Leu
            340                 345                 350
Leu Asn Ser Ser Phe Thr Leu Leu His Leu Pro His Tyr Phe His Gly
        355                 360                 365
Cys Gly His Ala Val Tyr Asn Asn Ser Leu Tyr Tyr His Lys Gly Gly
    370                 375                 380
Ser Asn Thr Ile Val Arg Phe Glu Phe Gly Lys Glu Thr Pro Gln Thr
385                 390                 395                 400
Leu Lys Leu Glu Asp Ala Leu Tyr Phe Asp Arg Lys Tyr Leu Phe Ala
                405                 410                 415
Asn Ser Lys Thr Tyr Phe Asn Ile Ala Val Asp Glu Lys Gly Leu Trp
            420                 425                 430
Ile Ile Tyr Ala Ser Ser Val Asp Gly Ser Ser Ile Leu Val Ala Gln
        435                 440                 445
Leu Asp Glu Arg Thr Phe Ser Val Leu Arg His Ile Asn Thr Thr Tyr
    450                 455                 460
Pro Lys Ser Lys Ala Gly Asn Ala Phe Ile Ala Gln Gly Ile Leu Tyr
465                 470                 475                 480
Val Thr Asp Thr Lys Asp Thr Arg Val Thr Phe Ala Phe Asp Leu Leu
                485                 490                 495
Arg Gly Lys Gln Ile Asn Ala Asn Phe Gly Leu Arg Met Ser Gln Ser
            500                 505                 510
Val Leu Ala Met Leu Ser Tyr Asn Met Arg Asp Gln His Leu Tyr Ser
        515                 520                 525
Trp Glu Asp Gly His Leu Met Leu Tyr Pro Val His Phe Ser Ser Thr
    530                 535                 540
Ala Pro Ser Gln Arg
545

<210> SEQ ID NO 7
<211> LENGTH: 4649
<212> TYPE: DNA
<213> ORGANISM: Mus sp.
<220> FEATURE:
<221> NAME/KEY: CDS
<222> LOCATION: (40)..(1686)

<400> SEQUENCE: 7
tcagtgctgc cctgagccgc ccggcctgag cacgcagac atg acc cga gcc gca        54
                                            Met Thr Arg Ala Ala
                                              1               5 gag cga ggc caa ggg gct aca ggc tgg ggg ctg cgc ggc gcc ctg gtg     102
Glu Arg Gly Gln Gly Ala Thr Gly Trp Gly Leu Arg Gly Ala Leu Val
             10                  15                  20 gcc ata gcg ctg ctg tcc gca ctg aac gcc gcg ggc acc gtg ttc gtg     150
```

```
                                                                         -continued Ala Ile Ala Leu Leu Ser Ala Leu Asn Ala Ala Gly Thr Val Phe Val
            25                  30                  35 ctg tgc cag tgg cgg ggg tta agc gcg gcg cta cgg gcg ctg gag gct            198
Leu Cys Gln Trp Arg Gly Leu Ser Ala Ala Leu Arg Ala Leu Glu Ala
            40                  45                  50 caa cgc ggc cga gag cag cgc gag gac agc gcc cta cgc gcc ttt ctg            246
Gln Arg Gly Arg Glu Gln Arg Glu Asp Ser Ala Leu Arg Ala Phe Leu
        55                  60                  65 gcc gaa ttg agt cgt gcg ccg ggc cgg gtc ccc gaa cca tcc cag gac            294
Ala Glu Leu Ser Arg Ala Pro Gly Arg Val Pro Glu Pro Ser Gln Asp
70                  75                  80                  85 ccc atg agc gca gcg cgc aac aag cgc agc cac aac ggc gag cct gcg            342
Pro Met Ser Ala Ala Arg Asn Lys Arg Ser His Asn Gly Glu Pro Ala
                90                  95                 100 tca cac atc cgt gcg gag agc cag gac atg atg atg atg acc tac                390
Ser His Ile Arg Ala Glu Ser Gln Asp Met Met Met Met Thr Tyr
               105                 110                 115 tcc atg gtg ccg att cga gtg atg ata gac ctg tgc aac agt acc cag            438
Ser Met Val Pro Ile Arg Val Met Ile Asp Leu Cys Asn Ser Thr Gln
               120                 125                 130 ggc atc tgc ctc aca gga cca ccg ggc cca cca gga cct cca gga gcc            486
Gly Ile Cys Leu Thr Gly Pro Pro Gly Pro Pro Gly Pro Pro Gly Ala
       135                 140                 145 ggc ggg tta cca ggc cac aat gga tca gat gga cag cct ggt ctc cag            534
Gly Gly Leu Pro Gly His Asn Gly Ser Asp Gly Gln Pro Gly Leu Gln
150                 155                 160                 165 ggc cca aaa gga gaa aaa gga gca att ggc aag aga gga aaa atg ggg            582
Gly Pro Lys Gly Glu Lys Gly Ala Ile Gly Lys Arg Gly Lys Met Gly
                170                 175                 180 tta cct gga gcc acc gga aat cca ggg gaa aag gga gaa aag gga gat            630
Leu Pro Gly Ala Thr Gly Asn Pro Gly Glu Lys Gly Glu Lys Gly Asp
                185                 190                 195 gct ggt gaa ctg ggt cta cct gga aat gag ggc cca cca ggg cag aaa            678
Ala Gly Glu Leu Gly Leu Pro Gly Asn Glu Gly Pro Pro Gly Gln Lys
       200                 205                 210 ggt gac aag gga gac aaa gga gac gtg tcc aat gac gtg ctt ttg aca            726
Gly Asp Lys Gly Asp Lys Gly Asp Val Ser Asn Asp Val Leu Leu Thr
215                 220                 225 ggt gcc aaa ggt gac caa ggt ccc cct ggc ccc cct gga cct cca ggg            774
Gly Ala Lys Gly Asp Gln Gly Pro Pro Gly Pro Pro Gly Pro Pro Gly
230                 235                 240                 245 cct cca ggc cct cct gga agc aga aga tcc aaa ggc cct cgg cca cca            822
Pro Pro Gly Pro Pro Gly Ser Arg Arg Ser Lys Gly Pro Arg Pro Pro
                250                 255                 260 aac gtg ttc aac agc cag tgt cca ggg gag acg tgt gtc ata ccc aat            870
Asn Val Phe Asn Ser Gln Cys Pro Gly Glu Thr Cys Val Ile Pro Asn
                265                 270                 275 gat gat acc ttg gtg gga aga gct gat gag aaa gca aat gaa cgc cat            918
Asp Asp Thr Leu Val Gly Arg Ala Asp Glu Lys Ala Asn Glu Arg His
        280                 285                 290 tca cca caa aca gaa tct atg atc act tcc att ggc aac cca gcc caa            966
Ser Pro Gln Thr Glu Ser Met Ile Thr Ser Ile Gly Asn Pro Ala Gln
       295                 300                 305 gtc cta aaa gtg aga gag act ttt ggg act tgg atg aga gag tct gct           1014
Val Leu Lys Val Arg Glu Thr Phe Gly Thr Trp Met Arg Glu Ser Ala
310                 315                 320                 325 aac aaa agt gac gac cgc att tgg gtg act gaa cat ttt tca ggc atc           1062
Asn Lys Ser Asp Asp Arg Ile Trp Val Thr Glu His Phe Ser Gly Ile
                330                 335                 340
```

```
atg gtg aag gag ttc aaa gac ctg ccg gcg ctc ctc aat agc agc ttc     1110
Met Val Lys Glu Phe Lys Asp Leu Pro Ala Leu Leu Asn Ser Ser Phe
        345                 350                 355 aca ctc ctc cac ctc cca cat tat ttc cac ggc tgt ggg cac gct gtt     1158
Thr Leu Leu His Leu Pro His Tyr Phe His Gly Cys Gly His Ala Val
    360                 365                 370 tac aac aac tct ctc tac tac cac aaa gga ggc tcc aac acc ata gtg     1206
Tyr Asn Asn Ser Leu Tyr Tyr His Lys Gly Gly Ser Asn Thr Ile Val
375                 380                 385 aga ttt gaa ttt ggg aaa gag aca cct cag act ctg aag ctg gaa aat     1254
Arg Phe Glu Phe Gly Lys Glu Thr Pro Gln Thr Leu Lys Leu Glu Asn
390                 395                 400                 405 gct ttg tat ttt gat cga aaa tac ctc ttt gca aat tcc aag act tac     1302
Ala Leu Tyr Phe Asp Arg Lys Tyr Leu Phe Ala Asn Ser Lys Thr Tyr
            410                 415                 420 ttc aac ata gca gtg gat gag aag ggc atc tgg att atc tac gct tca     1350
Phe Asn Ile Ala Val Asp Glu Lys Gly Ile Trp Ile Ile Tyr Ala Ser
                425                 430                 435 agt gtg gat ggc tca agc atc ctt gta gca cag ctg gat gag agg aca     1398
Ser Val Asp Gly Ser Ser Ile Leu Val Ala Gln Leu Asp Glu Arg Thr
            440                 445                 450 ttc tcc gtg aca cag cac atc aac acc aca tac ccc aaa tcc aag gct     1446
Phe Ser Val Thr Gln His Ile Asn Thr Thr Tyr Pro Lys Ser Lys Ala
    455                 460                 465 ggc aat gcc ttc ata gcc cga ggg atc ctc tat gtc aca gac acc aaa     1494
Gly Asn Ala Phe Ile Ala Arg Gly Ile Leu Tyr Val Thr Asp Thr Lys
470                 475                 480                 485 gat acg agg gtc acg ttt gcc ttt gat ttg tta gga gga aag caa atc     1542
Asp Thr Arg Val Thr Phe Ala Phe Asp Leu Leu Gly Gly Lys Gln Ile
            490                 495                 500 aat gca aac ttt gat ttc aga atg tcc cag tct gtt ctt gcc atg ctg     1590
Asn Ala Asn Phe Asp Phe Arg Met Ser Gln Ser Val Leu Ala Met Leu
                505                 510                 515 tca tac aac atg aga gat cag cat tta tac tcg tgg gaa gat ggc cat     1638
Ser Tyr Asn Met Arg Asp Gln His Leu Tyr Ser Trp Glu Asp Gly His
        520                 525                 530 ctg atg ctc tat cct gtg cag ttt ctg tca gcg gca tca agt cag cgg     1686
Leu Met Leu Tyr Pro Val Gln Phe Leu Ser Ala Ala Ser Ser Gln Arg
    535                 540                 545 tagggttccc tcggctgtct gctccctctc tatactccac attgtctagg gtttggtcaa   1746
gcccaacaga aagctagccg gtaaaggata cccaggcact cggagcgtaa gcccatgcca   1806
cgggctcttg cacaagcggc gagtccgctc taagccaggt tgttgaaata gctacagatt   1866
agaaatggat gtggaagaga tctggtgacc cagtatccct cctcaaactc agcaagttag   1926
ctctcccccg accgtagcgt ccccataggt aatacgaaac atctgggtat gactgacatt   1986
tcctcttcct agatgaaatt ctgtgattct tgcctgatta tatattagaa tgctttctgg   2046
attctttttt ttttttctcc acatgtaagt gagcttactt gcagcttgag gggtgggcct   2106
ttcagtgatg acttatttgg tatttaggga aggtgcactg gctcttatgg cttctaaggt   2166 tttatttat tcataaatttg ttatttttctc tgaatattca cctaccacta cagaatgatc   2226
attgttttca gctcctaaac acaaatccaa gattaataaa caaacaaaca aaccatgaat   2286
agatacaggc tcagaactct aaatggagct gcatcaggcc cataggccat ctagatgctg   2346
tcaatttctg atcatattgt ttgctgctgg gaaagtaaac aggatatctt cagttcgtgg   2406 tccctttgc caaggccatg ggattgttat cagagtgtca aacactaagt ggccaataat    2466
ctggttagaa gcatggaaac atgatggttt tttcagaaaa caggcaccat ttatacttac   2526
```

-continued

```
tgtttagaat gagggaaggc aattggctca aaggccaaag tcagcttagc tcttttttcct    2586
gtaccatcgc atccctgcac ctaagaatct cgcctcagag tgtgtcagca gtgaagcaga    2646
gccgctctgt aaatcctgaa ccattactgc ctggccttta cagaaagaaa gaaaaaaaaa    2706
tgttgacctt tcatctaagg acagggaacg agccaggttc tcagaagggc tcactccctg    2766
agtctggtta ggcttttttac ggactgacag gcagcatttt atgtggcttg ggctttggca    2826
gagggaacag gtaaggacag catcagatgg agtaagagaa cctccagccg tggagatgtt    2886
cactcccacg tggtcctcaa agttgggtct gtcctcttgg atagcaagga tctagtttaa    2946
ttggttccta caagacctta aataaccacg ttctctgtca actcattgag ttccaggcag    3006
gcctgtggag cttcaaagag gaagctgtgg atttcatcgc ccccccccc ccggaatata    3066
gaaaaagaca ctacagaaac tgtccaggaa agactggcca gctgttccaa acccactctc    3126
agtgggcctg tgacctggtt tagttttttt aatagaagca tcttgaggct tggggtatgc    3186
attttaacta tttaactttc cctgccctct gaaagcaccc aggcagctgt tactggtgaa    3246
cctgttgagt tctcaaggtc atgggtccca aagcttcccc acttcttgat tagatggttt    3306
tgcagttggt catcacagct tttaaagata ttctctcaga ttcatttgtt gcaatgtaga    3366
gttctaatgt ttcatcagtg tatctaatga atggtattgt tcttttaaag tattcaaata    3426
tgagatactg tttctgagtg cggtagacct ggatatacat ataattccat tttttttatta    3486
cttagtagca ttgctgagaa tagatacaat actaattgta catacaagca aaatagttta    3546
gttattgaat tagctcattt ttaatatctg aactagcaaa tgtcttagct ttcctttact    3606
tttttctttc ttttccttc ttttctcttc ttttcctttc tttcctttcc ttttcttttc    3666
ttttttttaa agcaatgtct ttgtgttcgc ccagacttat cacaaactcc tgcttcagat    3726
tcctgggtgc tgggaccaca ggcacagtgg ctctttgact ctcttaattg tgtgtaagga    3786
atcatacata tactcacgat tagagaaact cgtctgaaga ttttgtttct ttcatggtt    3846
gtttctttct ttcttctttt cttcttttct ttcgttatag tgtagtggga ttagaacaag    3906
taaggttgac tggtgtttaa tgaatttatc tttgcagaag gaaaggaatt aaggttttat    3966
tccttttctt gcaaacagga cttcattcta tatcactcaa cacagtgttt caggctcact    4026
gctaaaatag tgtgcacatc ttatattttt aaatgaagat agtaatcaac cctgctgtca    4086
cttgtagcca agctgttcta aaagcacttc atttatgtct gtatgaaatc aagtgattct    4146
ccaattcctc tgaaatctaa agtagatacc attatactag aaaccacacc ttccagcttc    4206
aaaggtaggc cagactcaac atttacaaag catttctatt aactaatata gagtccaact    4266
aaggttgcag agttggctct ggcctcaatg tatcatgtat caatgtatca gagaacgtgg    4326
tccgggctga atatttcaga tcaattctgg tgctgggctc attcgaagtc ttttttacct    4386
cataatcaaa tgacaaggtg agatgacaaa tgaggaagca cagtccttga aaagtcactc    4446
gtcatcctcc aagcatagca agtaccttac tcaggcattg cctgtctggt gttgagctac    4506
ctgaaggaaa agtgggggt ggagctcttc agttttcatc agtgctgtgg ccttattttat    4566
ctcataatct cccatcagta accacagatt ctaaacgacc agcaagtaac agttgtaagt    4626
agtaaaataa aattatcctg aat                                             4649
```

<210> SEQ ID NO 8
<211> LENGTH: 549
<212> TYPE: PRT
<213> ORGANISM: Mus sp.

<400> SEQUENCE: 8

```
Met Thr Arg Ala Ala Glu Arg Gly Gln Gly Ala Thr Gly Trp Gly Leu
  1               5                  10                  15

Arg Gly Ala Leu Val Ala Ile Ala Leu Leu Ser Ala Leu Asn Ala Ala
             20                  25                  30

Gly Thr Val Phe Val Leu Cys Gln Trp Arg Gly Leu Ser Ala Ala Leu
         35                  40                  45

Arg Ala Leu Glu Ala Gln Arg Gly Arg Glu Gln Arg Glu Asp Ser Ala
     50                  55                  60

Leu Arg Ala Phe Leu Ala Glu Leu Ser Arg Ala Pro Gly Arg Val Pro
 65                  70                  75                  80

Glu Pro Ser Gln Asp Pro Met Ser Ala Ala Arg Asn Lys Arg Ser His
                 85                  90                  95

Asn Gly Glu Pro Ala Ser His Ile Arg Ala Glu Ser Gln Asp Met Met
            100                 105                 110

Met Met Met Thr Tyr Ser Met Val Pro Ile Arg Val Met Ile Asp Leu
            115                 120                 125

Cys Asn Ser Thr Gln Gly Ile Cys Leu Thr Gly Pro Pro Gly Pro Pro
130                 135                 140

Gly Pro Pro Gly Ala Gly Gly Leu Pro Gly His Asn Gly Ser Asp Gly
145                 150                 155                 160

Gln Pro Gly Leu Gln Gly Pro Lys Gly Glu Lys Gly Ala Ile Gly Lys
                165                 170                 175

Arg Gly Lys Met Gly Leu Pro Gly Ala Thr Gly Asn Pro Gly Glu Lys
            180                 185                 190

Gly Glu Lys Gly Asp Ala Gly Glu Leu Gly Leu Pro Gly Asn Glu Gly
            195                 200                 205

Pro Pro Gly Gln Lys Gly Asp Lys Gly Asp Lys Gly Asp Val Ser Asn
210                 215                 220

Asp Val Leu Leu Thr Gly Ala Lys Gly Asp Gln Gly Pro Pro Gly Pro
225                 230                 235                 240

Pro Gly Pro Pro Gly Pro Pro Gly Pro Pro Gly Ser Arg Arg Ser Lys
                245                 250                 255

Gly Pro Arg Pro Pro Asn Val Phe Asn Ser Gln Cys Pro Gly Glu Thr
            260                 265                 270

Cys Val Ile Pro Asn Asp Asp Thr Leu Val Gly Arg Ala Asp Glu Lys
            275                 280                 285

Ala Asn Glu Arg His Ser Pro Gln Thr Glu Ser Met Ile Thr Ser Ile
            290                 295                 300

Gly Asn Pro Ala Gln Val Leu Lys Val Arg Glu Thr Phe Gly Thr Trp
305                 310                 315                 320

Met Arg Glu Ser Ala Asn Lys Ser Asp Asp Arg Ile Trp Val Thr Glu
                325                 330                 335

His Phe Ser Gly Ile Met Val Lys Glu Phe Lys Asp Leu Pro Ala Leu
            340                 345                 350

Leu Asn Ser Ser Phe Thr Leu Leu His Leu Pro His Tyr Phe His Gly
            355                 360                 365

Cys Gly His Ala Val Tyr Asn Asn Ser Leu Tyr Tyr His Lys Gly Gly
            370                 375                 380

Ser Asn Thr Ile Val Arg Phe Glu Phe Gly Lys Glu Thr Pro Gln Thr
385                 390                 395                 400

Leu Lys Leu Glu Asn Ala Leu Tyr Phe Asp Arg Lys Tyr Leu Phe Ala
                405                 410                 415
```

-continued

```
Asn Ser Lys Thr Tyr Phe Asn Ile Ala Val Asp Glu Lys Gly Ile Trp
            420                 425                 430

Ile Ile Tyr Ala Ser Ser Val Asp Gly Ser Ser Ile Leu Val Ala Gln
        435                 440                 445

Leu Asp Glu Arg Thr Phe Ser Val Thr Gln His Ile Asn Thr Thr Tyr
    450                 455                 460

Pro Lys Ser Lys Ala Gly Asn Ala Phe Ile Ala Arg Gly Ile Leu Tyr
465                 470                 475                 480

Val Thr Asp Thr Lys Asp Thr Arg Val Thr Phe Ala Phe Asp Leu Leu
                485                 490                 495

Gly Gly Lys Gln Ile Asn Ala Asn Phe Asp Phe Arg Met Ser Gln Ser
            500                 505                 510

Val Leu Ala Met Leu Ser Tyr Asn Met Arg Asp Gln His Leu Tyr Ser
        515                 520                 525

Trp Glu Asp Gly His Leu Met Leu Tyr Pro Val Gln Phe Leu Ser Ala
    530                 535                 540

Ala Ser Ser Gln Arg
545
```

<210> SEQ ID NO 9
<211> LENGTH: 4654
<212> TYPE: DNA
<213> ORGANISM: Homo sapiens
<220> FEATURE:
<221> NAME/KEY: CDS
<222> LOCATION: (51)..(1331)

<400> SEQUENCE: 9

```
gaccattgtg tatgattcgt tgttgactgc agcatcacta gatccgagtg atg gtg       56
                                                      Met Val
                                                        1 gac ctg tgc aac agc acc aag ggc atc tgc ctc aca gga cct tct gga    104
Asp Leu Cys Asn Ser Thr Lys Gly Ile Cys Leu Thr Gly Pro Ser Gly
        5                  10                  15 cca cca gga cct ccg gga gcc ggc ggg ttg cca gga cac aac gga ttg    152
Pro Pro Gly Pro Pro Gly Ala Gly Gly Leu Pro Gly His Asn Gly Leu
 20                  25                  30 gat gga cag cct ggt cct cag ggc cca aaa gga gaa aaa gga gca aat    200
Asp Gly Gln Pro Gly Pro Gln Gly Pro Lys Gly Glu Lys Gly Ala Asn
 35                  40                  45                  50 gga aaa aga gga aaa atg ggg ata cct gga gct gca gga aat cca ggg    248
Gly Lys Arg Gly Lys Met Gly Ile Pro Gly Ala Ala Gly Asn Pro Gly
             55                  60                  65 gaa agg gga gaa aag gga gac cat ggt gaa ctg ggc ctg cag gga aat    296
Glu Arg Gly Glu Lys Gly Asp His Gly Glu Leu Gly Leu Gln Gly Asn
         70                  75                  80 gag ggc cca cca ggg cag aag gga gaa aag ggt gac aaa gga gat gtg    344
Glu Gly Pro Pro Gly Gln Lys Gly Glu Lys Gly Asp Lys Gly Asp Val
     85                  90                  95 tcc aac gac gtg ctc ctg gca ggt gcc aaa ggt gac caa ggc cca ccc    392
Ser Asn Asp Val Leu Leu Ala Gly Ala Lys Gly Asp Gln Gly Pro Pro
100                 105                 110 ggt cca cct ggg ccc cca ggc cct cca ggt cct cca ggg ccc cct gga    440
Gly Pro Pro Gly Pro Pro Gly Pro Pro Gly Pro Pro Gly Pro Pro Gly
115                 120                 125                 130 agc aga aga gcc aaa ggc cct cgg cag cca agc atg ttc aac ggc cag    488
Ser Arg Arg Ala Lys Gly Pro Arg Gln Pro Ser Met Phe Asn Gly Gln
             135                 140                 145
```

-continued

| | |
|---|---|
| tgc cca ggt gag act tgt gcc ata cca aat gat gat acc ttg gtt gga<br>Cys Pro Gly Glu Thr Cys Ala Ile Pro Asn Asp Asp Thr Leu Val Gly<br>           150                155                160 | 536 |
| aaa gct gat gag aaa gcc agt gaa cac cat tcc cca caa gca gaa tcc<br>Lys Ala Asp Glu Lys Ala Ser Glu His His Ser Pro Gln Ala Glu Ser<br>165                  170                175 | 584 |
| atg atc act tcc att gga aac cca gtg caa gta ctg aaa gtg aca gag<br>Met Ile Thr Ser Ile Gly Asn Pro Val Gln Val Leu Lys Val Thr Glu<br>     180               185                190 | 632 |
| aca ttt ggg act tgg ata aga gag tct gct aac aag agt gat gac cgg<br>Thr Phe Gly Thr Trp Ile Arg Glu Ser Ala Asn Lys Ser Asp Asp Arg<br>195                  200                205              210 | 680 |
| att tgg gtg aca gag cat ttt tca ggc atc atg gtt aag gaa ttc aag<br>Ile Trp Val Thr Glu His Phe Ser Gly Ile Met Val Lys Glu Phe Lys<br>           215                220                225 | 728 |
| gat cag ccc tca ctt ctg aat ggc agt tac acg ttc atc cac ctt cca<br>Asp Gln Pro Ser Leu Leu Asn Gly Ser Tyr Thr Phe Ile His Leu Pro<br>           230                235                240 | 776 |
| tac tat ttc cat ggc tgt ggg cac gtt gct tac aac aac tct ctc tac<br>Tyr Tyr Phe His Gly Cys Gly His Val Ala Tyr Asn Asn Ser Leu Tyr<br>               245                250                255 | 824 |
| tac cac aaa ggg ggt tct aat acc cta gtg aga ttt gaa ttt ggc cag<br>Tyr His Lys Gly Gly Ser Asn Thr Leu Val Arg Phe Glu Phe Gly Gln<br>260                  265                270 | 872 |
| gaa aca tcc caa act ctg aag ctt gaa aat gcc ttg tat ttt gat cga<br>Glu Thr Ser Gln Thr Leu Lys Leu Glu Asn Ala Leu Tyr Phe Asp Arg<br>275                  280                285              290 | 920 |
| aaa tac ctt ttt gca aat tcc aaa act tac ttc aat cta gct gta gat<br>Lys Tyr Leu Phe Ala Asn Ser Lys Thr Tyr Phe Asn Leu Ala Val Asp<br>               295                300                305 | 968 |
| gaa aag ggc ctt tgg att atc tat gcg tca agt gtg gac ggc tcg agc<br>Glu Lys Gly Leu Trp Ile Ile Tyr Ala Ser Ser Val Asp Gly Ser Ser<br>           310                315                320 | 1016 |
| att ctt gta gca caa ctg gat gag agg aca ttc tca gtg gtg caa cac<br>Ile Leu Val Ala Gln Leu Asp Glu Arg Thr Phe Ser Val Val Gln His<br>325                  330                335 | 1064 |
| gtc aat acc acg tac cct aaa tcc aag gct ggc aac gcc ttc att gcc<br>Val Asn Thr Thr Tyr Pro Lys Ser Lys Ala Gly Asn Ala Phe Ile Ala<br>           340                345                350 | 1112 |
| cga gga atc ctc tat gtc aca gac acc aaa gat atg agg gtc aca ttt<br>Arg Gly Ile Leu Tyr Val Thr Asp Thr Lys Asp Met Arg Val Thr Phe<br>355                  360                365              370 | 1160 |
| gcc ttt gat ttg tta gga ggg aaa cag atc aat gca aac ttt gat tta<br>Ala Phe Asp Leu Leu Gly Gly Lys Gln Ile Asn Ala Asn Phe Asp Leu<br>               375                380                385 | 1208 |
| aga act tcc cag tct gtt ctt gcc atg tta gca tac aac atg aga gat<br>Arg Thr Ser Gln Ser Val Leu Ala Met Leu Ala Tyr Asn Met Arg Asp<br>           390                395                400 | 1256 |
| cag cat tta tat tca tgg gaa gat ggc cat tta atg ctt tat cct gtg<br>Gln His Leu Tyr Ser Trp Glu Asp Gly His Leu Met Leu Tyr Pro Val<br>               405                410                415 | 1304 |
| cag ttt ttg tca act acc tta aat cag tgatgtgctg cattcggctc<br>Gln Phe Leu Ser Thr Thr Leu Asn Gln<br>           420                425 | 1351 |
| ccttcagcaa atttcagggg ttttctggga ccagttctcc cccaacagga aacttgtttt | 1411 |
| tttaacgtca gccagatatt tagaaaataa cctcaaaagt gtttatatgg tcagtgagcc | 1471 |
| ccgcttagtg aaatagcaac agattggaag ttgaaatggc tgagatttgg tgatctcccc | 1531 |
| acagctggct ctgcaagtta cctctttctc cttgggcctt agtttcccca ttggtaatct | 1591 |

```
gaattggcta agatgattgg ggagattttc tgtacctgta ggtaatttgg tgattcttgg    1651
tggctgctct tctcacaact tttatgtatc tgcttctgtc gtttagcttt tttagccaca    1711
tgctgaccaa atttaccttt gagttgataa gtccagtggc ttgagtagtg aatccctcag    1771
tgctgactta tatcttgttc tttgaaaaaa tgcattgact ctttaagaca tctaaagtat    1831
cacattatcc ataatttatt gcttttcttt gcatctgcac ctgccaccac agaataacca    1891
ttaccctcag ctgctgattg ggcagctctg agattagcaa aagccaggga cagctacatg    1951
ttcaggtttt tttttttttt ttttttcaata ggctattttt tttcttttct tattttaaat    2011
agagagagag tcttgctatg tttcccaggc tggtcttgaa ctcctggggc tcaagtgatc    2071
ctcctgcctt ggcctcccaa aatgctggat tacaggcatg tgtgcctggc ccaggtttct    2131
taataaaaca gaatcatgat cttccaggtt cccccccagtt tctgatcatg ttgatttgta    2191
gctgtggatc atgaacactg aatccccaga tcactctgac ttcttatgct ctcctgtgg     2251 atccactatc aaagtactaa atgctgtgta agtagacgtt aatctggctg gaaccatggg    2311
aagcactttg cagtgttcag aagagaggct ccatttgtgg ctattatgta gaactgggcc    2371
agagccagtc cattgcctgt tttttttaaat aaggttttac tgagcacagc cacactcatt    2431
tgtttatgca gtacggcctg acattgcttt tgctctgcaa cagcagagtc gagtcattgc    2491
aacaaagagc atatggcccc acagtgccta aaatattgac cagctacccc tttatggaaa    2551
aagattgctg actcctgata aagaatataa agtgagcctg attcttgaaa aaatcagaac    2611
cagagcctgt tttgttttgt tctaaactaa gaagccgcat aggatgtgac ttgcgttttg    2671
agtagagggg aaggctgata acggcgtaag atgaagtggc cctccacaaa ggctggttag    2731
gggacagttc tttctctaac atagtttttaa aggatgtgat ctggtcccct tggatgccag    2791
gagagaatcc agttgaactt gctcctaaat gctcttaaat atgcatattt tctgccaact    2851
cacttcttta aacatctttc agcccagcgc tgcggccccg ggaagggcca ctgcgaatag    2911
agaggaagct ggaaaagttc ctgggctct gcagccagga aggggaacca gggcaaatct     2971
tatgtaaaga ttttttcagca acttgtccca atttgtgtgt attctgaaac tttctctttg    3031
ggaccaaatt cattctcaat ggccctgagt tcaatatatt attaacagca gtattttaaa    3091 acttaggggtt gaactgggca tggtggcaca taactgcaat cccagctact ttggaggcag    3151
ggatgggagg atcacttgag gccaggatct caggaccagc ctagagagat cccatctcta    3211
aaaaataaaa tataagaaaa taaaacttag gggatataca gatttaaata ttcaaatctc    3271
cctgctcccc tgaaagtccc caggcagctg ttaatgactt gtttgttgtg ttctcaatat    3331
gatggctatt tgaaacttca cctactttc attagattgg ttgtaccatg tcaccttagc     3391
ttttaaaaat actcttttca gattcacgtt ctctaacaaa gagtctcatg ttcaagatca    3451
atatgtctaa taagcgctgg tgtccttta aagtatttaa atatatatgt tgctgttgct      3511
gaatacagga gaccaggtta ggaatatagt ttcataataa tagtacatac aatactaatt    3571
gtatataagg tagcaaccaa aagaggttgt taattagcac atattccttt tagaaaaatg    3631
tttcagaaac ctcagtcttg atatctgagc tatctgggct cccttacttg tgagtaaggg    3691
atcatgctca ccactggaga agcttacacc gggactttt ttcttttttc tttttttttt     3751
gctatgacag agtaatgcta acgtaaggac aactgagttt gatcagtgtt taatcgcagt    3811
gggtaatctt atctgattgt ctttaaaagt gaaaaggatt aagatttat tctttcttgt      3871 aaacattact tgatttttta aagaagtttt gggctcactg ctaaaataga gtatacaact    3931
```

```
gaatgttttt aagtcaagat actgttttag gagtttaccc tctcatttat aaccaaagtt       3991
gctctaaaac actttccaaa tatctgcact tctgatgtca gaatcaaacc agataattct       4051
ctaattcttc tttaatctaa agtagatagc ttcccactgg aaagtaaaca aaaccatccc       4111
tcccaacctc aaagctaggc cacactctat ttcaaggcat tttctttcag ctgataaggt       4171
gtcctcctga agccaagtag gtggttctgg tctccaagta tcgttaagca caggtgctat       4231
gacagaaaaa gttctggggt ggaagtttta agatgaggag ttctgatctt aggcatctta       4291
acagtcacaa ggtgaaaagt caaatgaaac agtacaattc ttgatgagtg aggtgtcatc       4351
ttccaaccac acagaggacg ttttggctat gatcatctga tggcaagtga aggagaaatg       4411
agtgataggg ctttgcgttt tcatccagat gctgtggccc tgtgtttcac agcattaaga       4471
gccataattt ccaacctgca cagatcctga acaacaaatg aataacgatg aatgtctttt       4531
tggttgtaat ttaacaagtc aaataaataa tcattgctga gcacaatcac caaaaaaaaa       4591
aaaaaaaaaa aaaaaaaaaa aaaaaaaaaa aaaaaaaaaa aaagaaaaaa aaaaaaaaaa       4651
aca                                                                    4654
```

<210> SEQ ID NO 10
<211> LENGTH: 427
<212> TYPE: PRT
<213> ORGANISM: Homo sapiens

<400> SEQUENCE: 10

```
Met Val Asp Leu Cys Asn Ser Thr Lys Gly Ile Cys Leu Thr Gly Pro
  1               5                  10                  15

Ser Gly Pro Pro Gly Pro Pro Gly Ala Gly Gly Leu Pro Gly His Asn
             20                  25                  30

Gly Leu Asp Gly Gln Pro Gly Pro Gln Gly Pro Lys Gly Glu Lys Gly
         35                  40                  45

Ala Asn Gly Lys Arg Gly Lys Met Gly Ile Pro Gly Ala Ala Gly Asn
     50                  55                  60

Pro Gly Glu Arg Gly Glu Lys Gly Asp His Gly Glu Leu Gly Leu Gln
 65                  70                  75                  80

Gly Asn Glu Gly Pro Pro Gly Gln Lys Gly Glu Lys Gly Asp Lys Gly
                 85                  90                  95

Asp Val Ser Asn Asp Val Leu Leu Ala Gly Ala Lys Gly Asp Gln Gly
            100                 105                 110

Pro Pro Gly Pro Pro Gly Pro Pro Gly Pro Pro Gly Pro Pro Gly Pro
        115                 120                 125

Pro Gly Ser Arg Arg Ala Lys Gly Pro Arg Gln Pro Ser Met Phe Asn
    130                 135                 140

Gly Gln Cys Pro Gly Glu Thr Cys Ala Ile Pro Asn Asp Asp Thr Leu
145                 150                 155                 160

Val Gly Lys Ala Asp Glu Lys Ala Ser Glu His His Ser Pro Gln Ala
                165                 170                 175

Glu Ser Met Ile Thr Ser Ile Gly Asn Pro Val Gln Val Leu Lys Val
            180                 185                 190

Thr Glu Thr Phe Gly Thr Trp Ile Arg Glu Ser Ala Asn Lys Ser Asp
        195                 200                 205

Asp Arg Ile Trp Val Thr Glu His Phe Ser Gly Ile Met Val Lys Glu
    210                 215                 220

Phe Lys Asp Gln Pro Ser Leu Leu Asn Gly Ser Tyr Thr Phe Ile His
225                 230                 235                 240
```

```
Leu Pro Tyr Tyr Phe His Gly Cys Gly His Val Ala Tyr Asn Asn Ser
                245                 250                 255

Leu Tyr Tyr His Lys Gly Gly Ser Asn Thr Leu Val Arg Phe Glu Phe
            260                 265                 270

Gly Gln Glu Thr Ser Gln Thr Leu Lys Leu Glu Asn Ala Leu Tyr Phe
        275                 280                 285

Asp Arg Lys Tyr Leu Phe Ala Asn Ser Lys Thr Tyr Phe Asn Leu Ala
    290                 295                 300

Val Asp Glu Lys Gly Leu Trp Ile Ile Tyr Ala Ser Val Asp Gly
305                 310                 315                 320

Ser Ser Ile Leu Val Ala Gln Leu Asp Glu Arg Thr Phe Ser Val Val
                325                 330                 335

Gln His Val Asn Thr Thr Tyr Pro Lys Ser Lys Ala Gly Asn Ala Phe
            340                 345                 350

Ile Ala Arg Gly Ile Leu Tyr Val Thr Asp Thr Lys Asp Met Arg Val
        355                 360                 365

Thr Phe Ala Phe Asp Leu Leu Gly Gly Lys Gln Ile Asn Ala Asn Phe
    370                 375                 380

Asp Leu Arg Thr Ser Gln Ser Val Leu Ala Met Leu Ala Tyr Asn Met
385                 390                 395                 400

Arg Asp Gln His Leu Tyr Ser Trp Glu Asp Gly His Leu Met Leu Tyr
                405                 410                 415

Pro Val Gln Phe Leu Ser Thr Thr Leu Asn Gln
            420                 425

<210> SEQ ID NO 11
<211> LENGTH: 4976
<212> TYPE: DNA
<213> ORGANISM: Homo sapiens
<220> FEATURE:
<221> NAME/KEY: CDS
<222> LOCATION: (1)..(1653)

<400> SEQUENCE: 11 atg gcc cga ggc gct gag gga ggc cgt ggg gac gcg ggt tgg ggc ctg     48
Met Ala Arg Gly Ala Glu Gly Gly Arg Gly Asp Ala Gly Trp Gly Leu
  1               5                  10                  15 cgt ggc gcc ctg gcg gcc gtg gcg ctg ctc tcg gcg ctc aac gct gcg     96
Arg Gly Ala Leu Ala Ala Val Ala Leu Leu Ser Ala Leu Asn Ala Ala
                 20                  25                  30 ggc acg gtg ttc gcg ctg tgc cag tgg cgc ggg ctg agc tcg gcg ctg    144
Gly Thr Val Phe Ala Leu Cys Gln Trp Arg Gly Leu Ser Ser Ala Leu
             35                  40                  45 cgg gct ttg gag gcg cag cgg ggc cgg gag cag cgc gag gac agt gcc    192
Arg Ala Leu Glu Ala Gln Arg Gly Arg Glu Gln Arg Glu Asp Ser Ala
         50                  55                  60 ctg cgc tcc ttc ctg gcc gag ttg agc cgc gcg ccg cgc ggg gcg tcc    240
Leu Arg Ser Phe Leu Ala Glu Leu Ser Arg Ala Pro Arg Gly Ala Ser
 65                  70                  75                  80 gca cca ccc caa gac ccg gcc agc tca gct cgc aac aag cgc agc cac    288
Ala Pro Pro Gln Asp Pro Ala Ser Ser Ala Arg Asn Lys Arg Ser His
                 85                  90                  95 agc ggc gag ccc gcg ccg cat atc cgc gcc gag agc cat gac atg ctg    336
Ser Gly Glu Pro Ala Pro His Ile Arg Ala Glu Ser His Asp Met Leu
            100                 105                 110 atg atg atg acc tac tcc atg gtg ccg atc cga gtg atg gtg gac ctg    384
Met Met Met Thr Tyr Ser Met Val Pro Ile Arg Val Met Val Asp Leu
        115                 120                 125
```

```
tgc aac agc acc aag ggc atc tgc ctc aca gga cct tct gga cca cca    432
Cys Asn Ser Thr Lys Gly Ile Cys Leu Thr Gly Pro Ser Gly Pro Pro
    130                 135                 140 gga cct ccg gga gcc ggc ggg ttg cca gga cac aac gga ttg gat gga    480
Gly Pro Pro Gly Ala Gly Gly Leu Pro Gly His Asn Gly Leu Asp Gly
145                 150                 155                 160 cag cct ggt cct cag ggc cca aaa gga gaa aaa gga gca aat gga aaa    528
Gln Pro Gly Pro Gln Gly Pro Lys Gly Glu Lys Gly Ala Asn Gly Lys
                    165                 170                 175 aga gga aaa atg ggg ata cct gga gct gca gga aat cca ggg gaa agg    576
Arg Gly Lys Met Gly Ile Pro Gly Ala Ala Gly Asn Pro Gly Glu Arg
                180                 185                 190 gga gaa aag gga gac cat ggt gaa ctg ggc ctg cag gga aat gag ggc    624
Gly Glu Lys Gly Asp His Gly Glu Leu Gly Leu Gln Gly Asn Glu Gly
            195                 200                 205 cca cca ggg cag aag gga gaa aag ggt gac aaa gga gat gtg tcc aac    672
Pro Pro Gly Gln Lys Gly Glu Lys Gly Asp Lys Gly Asp Val Ser Asn
        210                 215                 220 gac gtg ctc ctg gca ggt gcc aaa ggt gac caa ggc cca ccc ggt cca    720
Asp Val Leu Leu Ala Gly Ala Lys Gly Asp Gln Gly Pro Pro Gly Pro
225                 230                 235                 240 cct ggg ccc cca ggc cct cca ggt cct cca ggg ccc cct gga agc aga    768
Pro Gly Pro Pro Gly Pro Pro Gly Pro Pro Gly Pro Pro Gly Ser Arg
                    245                 250                 255 aga gcc aaa ggc cct cgg cag cca agc atg ttc aac ggc cag tgc cca    816
Arg Ala Lys Gly Pro Arg Gln Pro Ser Met Phe Asn Gly Gln Cys Pro
                260                 265                 270 ggt gag act tgt gcc ata cca aat gat gat acc ttg gtt gga aaa gct    864
Gly Glu Thr Cys Ala Ile Pro Asn Asp Asp Thr Leu Val Gly Lys Ala
            275                 280                 285 gat gag aaa gcc agt gaa cac cat tcc cca caa gca gaa tcc atg atc    912
Asp Glu Lys Ala Ser Glu His His Ser Pro Gln Ala Glu Ser Met Ile
        290                 295                 300 act tcc att gga aac cca gtg caa gta ctg aaa gtg aca gag aca ttt    960
Thr Ser Ile Gly Asn Pro Val Gln Val Leu Lys Val Thr Glu Thr Phe
305                 310                 315                 320 ggg act tgg ata aga gag tct gct aac aag agt gat gac cgg att tgg   1008
Gly Thr Trp Ile Arg Glu Ser Ala Asn Lys Ser Asp Asp Arg Ile Trp
                    325                 330                 335 gtg aca gag cat ttt tca ggc atc atg gtt aag gaa ttc aag gat cag   1056
Val Thr Glu His Phe Ser Gly Ile Met Val Lys Glu Phe Lys Asp Gln
                340                 345                 350 ccc tca ctt ctg aat ggc agt tac acg ttc atc cac ctt cca tac tat   1104
Pro Ser Leu Leu Asn Gly Ser Tyr Thr Phe Ile His Leu Pro Tyr Tyr
            355                 360                 365 ttc cat ggc tgt ggg cac gtt gct tac aac aac tct ctc tac tac cac   1152
Phe His Gly Cys Gly His Val Ala Tyr Asn Asn Ser Leu Tyr Tyr His
        370                 375                 380 aaa ggg ggt tct aat acc cta gtg aga ttt gaa ttt ggc cag gaa aca   1200
Lys Gly Gly Ser Asn Thr Leu Val Arg Phe Glu Phe Gly Gln Glu Thr
385                 390                 395                 400 tcc caa act ctg aag ctt gaa aat gcc ttg tat ttt gat cga aaa tac   1248
Ser Gln Thr Leu Lys Leu Glu Asn Ala Leu Tyr Phe Asp Arg Lys Tyr
                    405                 410                 415 ctt ttt gca aat tcc aaa act tac ttc aat cta gct gta gat gaa aag   1296
Leu Phe Ala Asn Ser Lys Thr Tyr Phe Asn Leu Ala Val Asp Glu Lys
                420                 425                 430 ggc ctt tgg att atc tat gcg tca agt gtg gac ggc tcg agc att ctt   1344
Gly Leu Trp Ile Ile Tyr Ala Ser Ser Val Asp Gly Ser Ser Ile Leu
            435                 440                 445
```

```
gta gca caa ctg gat gag agg aca ttc tca gtg gtg caa cac gtc aat    1392
Val Ala Gln Leu Asp Glu Arg Thr Phe Ser Val Val Gln His Val Asn
    450                 455                 460 acc acg tac cct aaa tcc aag gct ggc aac gcc ttc att gcc cga gga    1440
Thr Thr Tyr Pro Lys Ser Lys Ala Gly Asn Ala Phe Ile Ala Arg Gly
465                 470                 475                 480 atc ctc tat gtc aca gac acc aaa gat atg agg gtc aca ttt gcc ttt    1488
Ile Leu Tyr Val Thr Asp Thr Lys Asp Met Arg Val Thr Phe Ala Phe
                485                 490                 495 gat ttg tta gga ggg aaa cag atc aat gca aac ttt gat tta aga act    1536
Asp Leu Leu Gly Gly Lys Gln Ile Asn Ala Asn Phe Asp Leu Arg Thr
            500                 505                 510 tcc cag tct gtt ctt gcc atg tta gca tac aac atg aga gat cag cat    1584
Ser Gln Ser Val Leu Ala Met Leu Ala Tyr Asn Met Arg Asp Gln His
        515                 520                 525 tta tat tca tgg gaa gat ggc cat tta atg ctt tat cct gtg cag ttt    1632
Leu Tyr Ser Trp Glu Asp Gly His Leu Met Leu Tyr Pro Val Gln Phe
    530                 535                 540 ttg tca act acc tta aat cag tgatgtgctg cattcggctc ccttcagcaa       1683
Leu Ser Thr Thr Leu Asn Gln
545             550
```

| | |
|---|---|
| atttcagggg ttttctggga ccagttctcc cccaacagga aacttgtttt tttaacgtca | 1743 |
| gccagatatt tagaaaataa cctcaaaagt gtttatatgg tcagtgagcc ccgcttagtg | 1803 |
| aaatagcaac agattggaag ttgaaatggc tgagatttgg tgatctcccc acagctggct | 1863 |
| ctgcaagtta cctctttctc cttgggcctt agtttcccca ttggtaatct gaattggcta | 1923 |
| agatgattgg ggagattttc tgtacctgta ggtaatttgg tgattcttgg tggctgctct | 1983 |
| tctcacaact tttatgtatc tgcttctgtc gtttagcttt tttagccaca tgctgaccaa | 2043 |
| atttaccttt gagttgataa gtccagtggc ttgagtagtg aatccctcag tgctgactta | 2103 |
| tatcttgttc tttgaaaaaa tgcattgact ctttaagaca tctaaagtat cacattatcc | 2163 |
| ataatttatt gcttttcttt gcatctgcac ctgccaccac agaataacca ttaccctcag | 2223 |
| ctgctgattg ggcagctctg agattagcaa agccaggga cagctacatg ttcaggtttt | 2283 |
| tttttttttt tttttcaata ggctatttt tttcttttct tattttaaat agagagagag | 2343 |
| tcttgctatg tttcccaggc tggtcttgaa ctcctgggc tcaagtgatc ctcctgcctt | 2403 |
| ggcctcccaa aatgctggat tacaggcatg tgtgcctggc ccaggtttct taataaaaca | 2463 |
| gaatcatgat cttccaggtt ccccccagtt tctgatcatg ttgatttgta gctgtggatc | 2523 |
| atgaacactg aatccccaga tcactctgac ttcttatgct tctcctgtgg atccactatc | 2583 |
| aaagtactaa atgctgtgta agtagacgtt aatctggctg gaaccatggg aagcactttg | 2643 |
| cagtgttcag aagagaggct ccatttgtgg ctattatgta aactgggcc agagccagtc | 2703 |
| cattgcctgt ttttttaaat aaggttttac tgagcacagc cacactcatt tgttatgca | 2763 |
| gtacggcctg acattgcttt tgctctgcaa cagcagagtc gagtcattgc aacaaagagc | 2823 |
| atatggcccc acagtgccta aaatattgac cagctacccc tttatggaaa agattgctg | 2883 |
| actcctgata agaatataa agtgagcctg attcttgaaa aaatcagaac cagagcctgt | 2943 |
| tttgttttgt tctaaactaa gaagccgcat aggatgtgac ttgcgttttg agtagagggg | 3003 |
| aaggctgata acggcgtaag atgaagtggc cctccacaaa ggctggttag gggacagttc | 3063 |
| tttctctaac atagttttaa aggatgtgat ctggtcccct tggatgccag gagagaatcc | 3123 |
| agttgaactt gctcctaaat gctcttaaat atgcatattt tctgccaact cacttcttta | 3183 |

| | | |
|---|---|---|
| aacatctttc agcccagcgc tgcggccccg ggaagggcca ctgcgaatag agaggaagct | 3243 | |
| ggaaaagttc ctggggctct gcagccagga aggggaacca gggcaaatct tatgtaaaga | 3303 | |
| tttttcagca acttgtccca atttgtgtgt attctgaaac tttctctttg ggaccaaatt | 3363 | |
| cattctcaat ggccctgagt tcaatatatt attaacagca gtattttaaa acttagggtt | 3423 | |
| gaactgggca tggtggcaca taactgcaat cccagctact ttggaggcag ggatgggagg | 3483 | |
| atcacttgag gccaggatct caggaccagc ctagagagat cccatctcta aaaataaaa | 3543 | |
| tataagaaaa taaaacttag gggatataca gatttaaata ttcaaatctc cctgctcccc | 3603 | |
| tgaaagtccc caggcagctg ttaatgactt gtttgttgtg ttctcaatat gatggctatt | 3663 | |
| tgaaacttca cctactttc attagattgg ttgtaccatg tcaccttagc ttttaaaaat | 3723 | |
| actcttttca gattcacgtt ctctaacaaa gagtctcatg ttcaagatca atatgtctaa | 3783 | |
| taagcgctgg tgtcctttta aagtatttaa atatatatgt tgctgttgct gaatacagga | 3843 | |
| gaccaggtta ggaatatagt ttcataataa tagtacatac aatactaatt gtatataagg | 3903 | |
| tagcaaccaa aagaggttgt taattagcac atattccttt tagaaaaatg tttcagaaac | 3963 | |
| ctcagtcttg atatctgagc tatctgggct cccttacttg tgagtaaggg atcatgctca | 4023 | |
| ccactggaga agcttacacc gggacttttt ttcttttttc ttttttttt gctatgacag | 4083 | |
| agtaatgcta acgtaaggac aactgagttt gatcagtgtt taatcgcagt gggtaatctt | 4143 | |
| atctgattgt cttaaaagt gaaaaggatt aagattttat tctttcttgt aaacattact | 4203 | |
| tgattttta aagaagtttt gggctcactg ctaaaataga gtatacaact gaatgttttt | 4263 | |
| aagtcaagat actgttttag gagtttaccc tctcatttat aaccaaagtt gctctaaaac | 4323 | |
| actttccaaa tatctgcact tctgatgtca gaatcaaacc agataattct ctaattcttc | 4383 | |
| tttaatctaa agtagatagc ttcccactgg aaagtaaaca aaaccatccc tcccaacctc | 4443 | |
| aaagctaggc cacactctat ttcaaggcat tttcttcag ctgataaggt gtcctcctga | 4503 | |
| agccaagtag gtggttctgg tctccaagta tcgttaagca caggtgctat gacagaaaaa | 4563 | |
| gttctggggt ggaagttta agatgaggag ttctgatctt aggcatctta acagtcacaa | 4623 | |
| ggtgaaaagt caaatgaaac agtacaattc ttgatgagtg aggtgtcatc ttccaaccac | 4683 | |
| acagaggacg ttttggctat gatcatctga tggcaagtga aggagaaatg agtgataggg | 4743 | |
| cttttgcgttt tcatccagat gctgtggccc tgtgtttcac agcattaaga gccataattt | 4803 | |
| ccaacctgca cagatcctga acaacaaatg aataacgatg aatgtctttt tggttgtaat | 4863 | |
| ttaacaagtc aaataaataa tcattgctga gcacaatcac caaaaaaaaa aaaaaaaaa | 4923 | |
| aaaaaaaaa aaaaaaaa aaaaaaaa aaagaaaaa aaaaaaaaa aca | 4976 | |

<210> SEQ ID NO 12
<211> LENGTH: 551
<212> TYPE: PRT
<213> ORGANISM: Homo sapiens

<400> SEQUENCE: 12

Met Ala Arg Gly Ala Glu Gly Gly Arg Gly Asp Ala Gly Trp Gly Leu
1               5                   10                  15

Arg Gly Ala Leu Ala Ala Val Ala Leu Leu Ser Ala Leu Asn Ala Ala
            20                  25                  30

Gly Thr Val Phe Ala Leu Cys Gln Trp Arg Gly Leu Ser Ser Ala Leu
        35                  40                  45

Arg Ala Leu Glu Ala Gln Arg Gly Arg Glu Gln Arg Glu Asp Ser Ala
    50                  55                  60

```
Leu Arg Ser Phe Leu Ala Glu Leu Ser Arg Ala Pro Arg Gly Ala Ser
 65                  70                  75                  80

Ala Pro Pro Gln Asp Pro Ala Ser Ser Ala Arg Asn Lys Arg Ser His
                 85                  90                  95

Ser Gly Glu Pro Ala Pro His Ile Arg Ala Glu Ser His Asp Met Leu
            100                 105                 110

Met Met Met Thr Tyr Ser Met Val Pro Ile Arg Val Met Val Asp Leu
            115                 120                 125

Cys Asn Ser Thr Lys Gly Ile Cys Leu Thr Gly Pro Ser Gly Pro Pro
130                 135                 140

Gly Pro Pro Gly Ala Gly Leu Pro Gly His Asn Gly Leu Asp Gly
145                 150                 155                 160

Gln Pro Gly Pro Gln Gly Pro Lys Gly Glu Lys Gly Ala Asn Gly Lys
                165                 170                 175

Arg Gly Lys Met Gly Ile Pro Gly Ala Ala Gly Asn Pro Gly Glu Arg
            180                 185                 190

Gly Glu Lys Gly Asp His Gly Glu Leu Gly Leu Gln Gly Asn Glu Gly
            195                 200                 205

Pro Pro Gly Gln Lys Gly Glu Lys Gly Asp Lys Gly Asp Val Ser Asn
210                 215                 220

Asp Val Leu Leu Ala Gly Ala Lys Gly Asp Gln Gly Pro Pro Gly Pro
225                 230                 235                 240

Pro Gly Pro Pro Gly Pro Pro Gly Pro Pro Gly Pro Pro Gly Ser Arg
                245                 250                 255

Arg Ala Lys Gly Pro Arg Gln Pro Ser Met Phe Asn Gly Gln Cys Pro
            260                 265                 270

Gly Glu Thr Cys Ala Ile Pro Asn Asp Asp Thr Leu Val Gly Lys Ala
            275                 280                 285

Asp Glu Lys Ala Ser Glu His His Ser Pro Gln Ala Glu Ser Met Ile
290                 295                 300

Thr Ser Ile Gly Asn Pro Val Gln Val Leu Lys Val Thr Glu Thr Phe
305                 310                 315                 320

Gly Thr Trp Ile Arg Glu Ser Ala Asn Lys Ser Asp Asp Arg Ile Trp
                325                 330                 335

Val Thr Glu His Phe Ser Gly Ile Met Val Lys Glu Phe Lys Asp Gln
            340                 345                 350

Pro Ser Leu Leu Asn Gly Ser Tyr Thr Phe Ile His Leu Pro Tyr Tyr
            355                 360                 365

Phe His Gly Cys Gly His Val Ala Tyr Asn Asn Ser Leu Tyr Tyr His
370                 375                 380

Lys Gly Gly Ser Asn Thr Leu Val Arg Phe Glu Phe Gly Gln Glu Thr
385                 390                 395                 400

Ser Gln Thr Leu Lys Leu Glu Asn Ala Leu Tyr Phe Asp Arg Lys Tyr
                405                 410                 415

Leu Phe Ala Asn Ser Lys Thr Tyr Phe Asn Leu Ala Val Asp Glu Lys
            420                 425                 430

Gly Leu Trp Ile Ile Tyr Ala Ser Val Asp Gly Ser Ser Ile Leu
            435                 440                 445

Val Ala Gln Leu Asp Glu Arg Thr Phe Ser Val Gln His Val Asn
450                 455                 460

Thr Thr Tyr Pro Lys Ser Lys Ala Gly Asn Ala Phe Ile Ala Arg Gly
465                 470                 475                 480
```

```
Ile Leu Tyr Val Thr Asp Thr Lys Asp Met Arg Val Thr Phe Ala Phe
            485                 490                 495

Asp Leu Leu Gly Gly Lys Gln Ile Asn Ala Asn Phe Asp Leu Arg Thr
            500                 505                 510

Ser Gln Ser Val Leu Ala Met Leu Ala Tyr Asn Met Arg Asp Gln His
            515                 520                 525

Leu Tyr Ser Trp Glu Asp Gly His Leu Met Leu Tyr Pro Val Gln Phe
    530                 535                 540

Leu Ser Thr Thr Leu Asn Gln
545                 550

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccagttcac cagcatctcc cttctctc                                        28

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtctatcatc acccggatcg gcaccat                                         27

<210> SEQ ID NO 15
<211> LENGTH: 21
<212> TYPE: DNA
<213> ORGANISM: Rattus sp.

<400> SEQUENCE: 15
aattaagtcg tgcgccagcc c                                               21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
uuaagucgug cgccagccct t                                               21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

```
<400> SEQUENCE: 17
gggcuggcgc acgacuuaat t                                              21

<210> SEQ ID NO 18
<211> LENGTH: 21
<212> TYPE: DNA
<213> ORGANISM: Rattus sp.

<400> SEQUENCE: 18
aatgatgata ccttggtggg g                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
ugaugauacc uuggugggt t                                               21

<210> SEQ ID NO 20
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
ccccaccaag guaucaucat t                                              21

<210> SEQ ID NO 21
<211> LENGTH: 21
<212> TYPE: DNA
<213> ORGANISM: Rattus sp.

<400> SEQUENCE: 21
aatgagcgcc attctccaca a                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
ugagcgccau ucuccacaat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
        Synthetic oligonucleotide
<220> FEATURE:
<223> OTHER INFORMATION: Description of Artificial Sequence: Synthetic
      oligonucleotide

<400> SEQUENCE: 23 uguggagaa uggcgcucat t                                           21

<210> SEQ ID NO 24
<211> LENGTH: 21
<212> TYPE: DNA
<213> ORGANISM: Rattus sp.

<400> SEQUENCE: 24
aacccatgat cacgtccatt g                                          21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
cccaugauca cguccauugt t                                          21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
caauggacgu gaucaugggt t                                          21

<210> SEQ ID NO 27
<211> LENGTH: 22
<212> TYPE: PRT
<213> ORGANISM: Rattus sp.

<400> SEQUENCE: 27

Pro Asn Asp Asp Thr Leu Val Gly Arg Ala Asp Glu Lys Val Asn Glu
 1               5                  10                  15

Arg His Ser Pro Gln Thr
            20

<210> SEQ ID NO 28
<211> LENGTH: 1650
<212> TYPE: DNA
<213> ORGANISM: Rattus sp.

<400> SEQUENCE: 28
atgacccgag ccgcagagcg aggccaaggg gctacaggct ggggactgcg aggcgccctg    60
atggccgtgg cgctgctgtc agtgctgaac gccgtgggca ccgtgttcgt gctgtaccag   120
tggcgcgagc tgagcgcggc gctgcgggca ctggaggcgc aacacggcca ggagcagcgc   180
```

-continued

```
gaggacagcg ccctacgcgc ctttctagct gaattaagtc gtgcgccagc ccgagtcccc      240
gaaccacccc aggaccccat gagtgcagcg cgcaataagc gcagccacgg cggcgagcct      300
gcgtcacaca tccgcgcgga gagccaggac atgatgatga tgatgaccta cagcatggtg      360
ccgatccggg tgatgataga cctgtgcaac agcacccagg gcatctgcct tacaggacca      420
ccgggcccac caggacctcc aggagctggt gggttaccag gccacaatgg atcagatgga      480
cagcctggtc tccagggccc aaaaggagaa aaggagcag ttgggaagag aggaaaaatg       540
gggttacccg gagccacagg aaatccaggg gaaagggag agaagggaga tgctggtgaa       600
ctgggcctac ctggaaatga gggaccacca ggacagaaag gagacaaagg agacaaagga     660
gatgtgtcca atgacgtgct tttgacaggt gccaaaggtg accaagggcc cctggccca     720 cctgaccccc agggcctcc aggcccttct ggaagcagaa gagccaaagg ccctcggcag      780
ccaaattcgt tcaccaacca gtgtccaggg gagacgtgtg tcatacccaa tgatgatacc     840
ttggtgggga gagctgatga gaaagtcaat gagcgccatt ctccacaaac agaacccatg     900
atcacgtcca ttggtaaccc ggcccaagtc ctcaaagtga agagacttt tgggacctgg     960 ctaagagagt ctgctaacag gagtgatgac cgcatttggg tgactgaaca tttttcaggc    1020
atcatggtga aggagtttga agacctgccc gccctcctga atagcagctt cacctcctc    1080 cacctcccac attacttcca tggctgcggg cacgctgttt acaacaactc tctctactac     1140
cacaaaggag gctccaacac catagtgaga tttgaatttg gaaagagac acctcaaact     1200 ctgaagcttg aagatgcttt gtatttgat cgaaaatacc tctttgcgaa ttccaagact     1260
tacttcaaca tagcagtgga tgagaagggc ctctggatta tctacgcctc gagtgtggat    1320
ggctcaagca tccttgtggc acagctggac gagaggacat tctctgtgct gcagcacatc    1380
aataccacat accccaagtc caaggctggc aatgccttca tagctcaagg gatcctctat    1440
gtcacggaca caaagatac aagggtcacg tttgcctttg atttgttacg agggaagcag      1500
atcaatgcaa acttcggtct cagaatgtca cagtctgttc ttgccatgtt gtcgtacaat    1560
atgagagacc agcatttgta ctcgtgggaa gacggccacc tgatgctcta tcctgtgcac    1620
ttttcgtcaa cagcacccag ccagcgatag                                     1650
```

<210> SEQ ID NO 29
<211> LENGTH: 1650
<212> TYPE: DNA
<213> ORGANISM: Rattus sp.

<400> SEQUENCE: 29

```
atgacccgag ccgcagagcg aggccaaggg gctacaggct ggggactgcg aggcgccctg      60
atggccgtgg cgctgctgtc agtgctgaac gccgtgggca ccgtgttcgt gctgtaccag    120
tggcgcgagc tgagcgcggc gctgcgggca ctggaggcgc aacacggcca ggagcagcgc    180
gaggacagcg ccctacgcgc ctttctagct gaattaagtc gtgcgccagc ccgagtcccc    240
gaaccacccc aggaccccat gagtgcagcg cgcaataagc gcagccacgg cggcgagcct    300
gcgtcacaca tccgcgcgga gagccaggac atgatgatga tgatgaccta cagcatggtg    360
ccgatccggg tgatgataga cctgtgcaac agcacccagg gcatctgcct tacaggacca    420
ccgggcccac caggacctcc aggagctggt gggttaccag gccacaatgg atcagatgga    480
cagcctggtc tccagggccc aaaaggagaa aaggagcag ttgggaagag aggaaaaatg     540
gggttacccg gagccacagg aaatccaggg gaaagggag agaagggaga tgctggtgaa     600
ctgggcctac ctggaaatga gggaccacca ggacagaaag gagacaaagg agacaaagga    660
```

```
gatgtgtcca atgacgtgct tttgacaggt gccaaaggtg accaagggcc cctggcccag      720
cctggacccc cagggcctcc aggccctcct ggaagcagaa gagccaaagg ccctcggcag      780
ccaaattcgt tcaccaacca gtgtccaggg gagacgtgtg tcatacccaa tgatgatacc      840
ttggtgggga gagctgatga gaaagtcaat gagcgccatt ctccacaaac agaacccatg      900
atcacgtcca ttggtaaccc ggcccaagtc ctcaaggtga aagagacttt tgggacctgg      960
ctaagagagt ctgctaacag gagtgacgac cgcatttggg tgactgaaca tttttcaggc     1020
atcatggtga aggagtttga agacctgccc gccctcctga atagcagctt caccctcctc     1080
cacctcccac attacttcca tggctgcggg cacgctgttt acaacaactc tctctactac     1140
cacaaaggag gctccaacac catagtgaga tttgaatttg ggaaagagac acctcaaact     1200
ctgaagcttg aagatgcttt gtattttgat cgaaaatacc tctttgcgaa ttccaagact     1260
tacttcaaca tagcagtgga tgagaagggc ctctggatta tctacgcctc gagtgtggat     1320
ggctcaagca tccttgtggc acagctggac gagaggacat tctctgtgct gcggcacatc     1380
aataccacat accccaagtc caaggctgga atgccttca tagctcaagg gatcctctat     1440
gtcacggaca ccaaagatac aagggtcacg tttgcctttg atttgttacg agggaagcag     1500
atcaatgcaa acttcggtct cagaatgtca cagtctgttc ttgccatgtt gtcgtacaat     1560
atgagagacc agcatttgta ctcgtgggaa gacggccacc tgatgctcta tcctgtgcac     1620
ttttcgtcaa cagcacccag ccagcgatag                                     1650

<210> SEQ ID NO 30
<211> LENGTH: 1656
<212> TYPE: DNA
<213> ORGANISM: Homo sapiens

<400> SEQUENCE: 30
atggcccgag cgctgaggg aggccgtggg gacgcgggtt ggggcctgcg tggcgccctg        60
gcggccgtgg cgctgctctc ggcgctcaac gctgcgggca cggtgttcgc gctgtgccag      120
tggcgcgggc tgagctcggc gctgcgggct ttggaggcgc agcggggccg ggagcagcgc      180
gaggacagtg ccctgcgctc cttcctggcc gagttgagcc gcgcgccgcg cggggcgtcc      240
gcaccacccc aagacccggc cagctcagct cgcaacaagc gcagccacag cggcgagccc      300
gcgccgcata tccgcgccga gagccatgac atgctgatga tgatgaccta ctccatggtg      360
ccgatccgag tgatggtgga cctgtgcaac agcaccaagg gcatctgcct cacaggacct      420
tctggaccac caggacctcc gggagccggc gggttgccag gacacaacgg attggatgga      480
cagcctggtc ctcagggccc aaaaggagaa aaggagcaa atggaaaaag aggaaaatg      540
gggatacctg gagctgcagg aaatccaggg gaaaggggag aaaagggaga ccatggtgaa      600
ctgggcctgc agggaaatga gggcccacca gggcagaagg gagaaaaggg tgacaaagga      660
gatgtgtcca acgacgtgct cctggcaggt gccaaaggtg accaaggccc acccggtcca      720
cctgggcccc caggccctcc aggtcctcca gggccccctg gaagcagaag agccaaaggc      780
cctcggcagc caagcatgtt caacggccag tgcccaggtg agacttgtgc cataccaaat      840
gatgatacct tggttggaaa agctgatgag aaagccagtg aacaccattc cccacaagca      900
gaatccatga tcacttccat tggaaaccca gtgcaagtac tgaaagtgac agagacattt      960
gggacttgga taagagagtc tgctaacaag agtgatgacc ggatttgggt gacagagcat     1020
ttttcaggca tcatggttaa ggaattcaag gatcagccct cacttctgaa tggcagttac     1080
```

-continued

```
acgttcatcc accttccata ctatttccat ggctgtgggc acgttgctta caacaactct    1140
ctctactacc acaaaggggg ttctaatacc ctagtgagat ttgaatttgg ccaggaaaca    1200
tcccaaactc tgaagcttga aaatgccttg tattttgatc gaaataacct ttttgcaaat    1260
tccaaaactt acttcaatct agctgtagat gaaaagggcc tttggattat ctatgcgtca    1320
agtgtggacg gctcgagcat tcttgtagca caactggatg agaggacatt ctcagtggtg    1380
caacacgtca ataccacgta ccctaaatcc aaggctggca acgccttcat tgcccgagga    1440
atcctctatg tcacagacac caaagatatg agggtcacat ttgcctttga tttgttagga    1500
gggaaacaga tcaatgcaaa cttttgattta agaacttccc agtctgttct tgccatgtta    1560
gcatacaaca tgagagatca gcatttatat tcatgggaag atggccattt aatgctttat    1620
cctgtgcagt ttttgtcaac taccttaaat cagtga                              1656
```

<210> SEQ ID NO 31
<211> LENGTH: 1284
<212> TYPE: DNA
<213> ORGANISM: Homo sapiens

<400> SEQUENCE: 31

```
atggtggacc tgtgcaacag caccaagggc atctgcctca caggaccttc tggaccacca      60
ggacctccgg gagccggcgg gttgccagga cacaacggat tggatggaca gcctggtcct     120
cagggcccaa aggagaaaa aggagcaaat ggaaaaagag gaaaatggg gataccttgga     180 gctgcaggaa atccagggga aaggggagaa aaggagacc atggtgaact gggcctgcag     240
ggaaatgagg gcccaccagg gcagaaggga gaaaagggtg acaaaggaga tgtgtccaac     300
gacgtgctcc tggcaggtgc caaggtgac caaggcccac ccggtccacc tgggccccca     360
ggccctccag gtcctccagg gccccctgga agcagaagag ccaaaggccc tcggcagcca     420
agcatgttca acggccagtg cccaggtgag acttgtgcca taccaaatga tgataccttg     480
gttgaaaaag ctgatgagaa agccagtgaa caccattccc cacaagcaga atccatgatc     540
acttccattg gaaacccagt gcaagtactg aaagtgacag agacatttgg gacttggata     600
agagagtctg ctaacaagag tgatgaccgg atttgggtga cagagcattt ttcaggcatc     660
atggttaagg aattcaagga tcagccctca cttctgaatg gcagttacac ggttcatccac     720 cttccatact atttccatgg ctgtgggcac gttgcttaca caactctct ctactaccac     780 aaaggggggtt ctaatacccct agtgagattt gaatttggcc aggaaacatc ccaaactctg     840
aagcttgaaa atgccttgta ttttgatcga aaataccttt ttgcaaattc caaaacttac     900
ttcaatctag ctgtagatga aaagggcctt tggattatct atgcgtcaag tgtggacggc     960
tcgagcattc ttgtagcaca actggatgag aggacattct cagtggtgca acacgtcaat    1020
accacgtacc ctaaatccaa ggctggcaac gccttcattg cccgaggaat cctctatgtc    1080
acagacacca agatatgag ggtcacattt gcctttgatt gttaggagg gaaacagatc    1140 aatgcaaact tgattttaag aacttccccag tctgttcttg ccatgttagc atacaacatg    1200
agagatcagc atttatattc atgggaagat ggccattttaa tgctttatcc tgtgcagttt    1260
ttgtcaacta ccttaaaatca gtga                                         1284
```

<210> SEQ ID NO 32
<211> LENGTH: 1596
<212> TYPE: DNA
<213> ORGANISM: Rattus sp.

<400> SEQUENCE: 32

```
atgacccgag ccgcagagcg aggccaaggg gctacaggct ggggactgcg aggcgccctg      60
atggccgtgg cgctgctgtc agtgctgaac gccgtgggca ccgtgttcgt gctgtaccag     120
cagcgcgagg acagcgccct acgcgccttt ctagctgaat taagtcgtgc gccagcccga     180
gtccccgaac cacccccagga ccccatgagt gcagcgcgca ataagcgcag ccacggcggc     240
gagcctgcgt cacacatccg cgcggagagc caggacatga tgatgatgat gacctacagc     300
atggtgccga tccgggtgat gatagacctg tgcaacagca cccagggcat ctgccttaca     360
ggaccaccgg gccaccagg acctccagga gctggtgggt taccaggcca caatggatca     420
gatggacagc ctggtctcca gggcccaaaa ggagaaaaag gagcagttgg aagagagga     480 aaaatggggt tacccggagc acaggaaat ccaggggaaa agggagagaa gggagatgct     540
ggtgaactgg gcctacctgg aaatgaggga ccaccaggac agaaaggaga caaggagac     600 aaggagatg tgtccaatga cgtgcttttg acaggtgcca aaggtgacca agggccccct     660
ggcccacctg gacccccagg gcctccaggc ccttctggaa gcagaagagc caaaggccct     720
cggcagccaa attcgttcac caaccagtgt ccagggagga cgtgtgtcat acccaatgat     780 gatacccttgg tggggagagc tgatgagaaa gtcaatgagc gccattctcc acaaacagaa     840
cccatgatca cgtccattgg taacccggcc caagtcctca agtgaaaga cttttggg     900 acctggctaa gagagtctgc taacaggagt gatgaccgca tttgggtgac tgaacatttt     960
tcaggcatca tggtgaagga gtttgaagac ctgcccgccc tcctgaatag cagcttcacc    1020
ctcctccacc tcccacatta cttccatggc tgcgggcacg ctgtttacaa caactctctc    1080
tactaccaca aaggaggctc caacaccata gtgagatttg aatttgggaa agagacacct    1140
caaactctga agcttgaaga tgcttttgtat tttgatcgaa atacctcctt tgcgaattcc    1200
aagacttact tcaacatagc agtggatgag aagggcctct ggattatcta cgcctcgagt    1260
gtggatggct caagcatcct tgtggcacag ctggacgaga ggacattctc tgtgctgcag    1320
cacatcaata ccacataccc caagtccaag gctggcaatg ccttcatagc tcaagggatc    1380
ctctatgtca cggacacaaa agatacaagg gtcacgtttg cctttgattt gttacgaggg    1440
aagcagatca atgcaaactt cggtctcaga atgtcacagt ctgttcttgc catgttgtcg    1500
tacaatatga gagaccagca tttgtactcg tgggaagacg gccacctgat gctctatcct    1560
gtgcactttt cgtcaacagc acccagccag cgatag                               1596
```

<210> SEQ ID NO 33
<211> LENGTH: 1650
<212> TYPE: DNA
<213> ORGANISM: Mus sp.

<400> SEQUENCE: 33

```
atgacccgag ccgcagagcg aggccaaggg gctacaggct gggggctgcg cggcgccctg      60
gtggccatag cgctgctgtc cgcactgaac gccgcgggca ccgtgttcgt gctgtgccag     120
tggcgggggt taagcgcggc gctacggcg ctggaggctc aacgcggccg agagcagcgc     180
gaggacagcg ccctacgcgc ctttctggcc gaattgagtc gtgcgccggg ccgggtcccc     240
gaaccatccc aggaccccat gagcgcagcg cgcaacaagc gcagccacaa cggcgagcct     300
gcgtcacaca tccgtgcgga gagccaggac atgatgatga tgatgaccta ctccatggtg     360
ccgattcgag tgatgataga cctgtgcaac agtacccagg gcatctgcct cacaggacca     420
ccgggcccac caggacctcc aggagccggc gggttaccag gccacaatgg atcagatgga     480
```

```
cagcctggtc tccagggccc aaaaggagaa aaaggagcaa ttggcaagag aggaaaaatg      540
gggttacctg gagccaccgg aaatccaggg gaaaagggag aaaagggaga tgctggtgaa      600
ctgggtctac ctggaaatga gggcccacca gggcagaaag gtgacaaggg agacaaagga      660
gacgtgtcca atgacgtgct tttgacaggt gccaaggtg accaaggtcc ccctggcccc       720
cctggacctc cagggcctcc aggccctcct ggaagcagaa gatccaaagg ccctcggcca       780
ccaaacgtgt tcaacagcca gtgtccaggg gagacgtgtg tcataccccaa tgatgatacc     840 ttggtgggaa gagctgatga gaaagcaaat gaacgccatt caccacaaac agaatctatg     900
atcacttcca ttggcaaccc agcccaagtc ctaaaagtga gagagacttt tgggacttgg      960
atgagagagt ctgctaacaa aagtgacgac cgcatttggg tgactgaaca ttttcaggc      1020 atcatggtga aggagttcaa agacctgccg gcgctcctca atagcagctt cacactcctc     1080
cacctcccac attatttcca cggctgtggg cacgctgttt acaacaactc tctctactac      1140
cacaaaggag gctccaacac catagtgaga tttgaatttg ggaaagagac acctcagact      1200
ctgaagctgg aaaatgcttt gtattttgat cgaaaatacc tctttgcaaa ttccaagact       1260
tacttcaaca tagcagtgga tgagaagggc atctggatta tctacgcttc aagtgtggat       1320
ggctcaagca tccttgtagc acagctggat gagaggacat tctccgtgac acagcacatc      1380
aacaccacat accccaaatc caaggctggc aatgccttca tagcccgagg gatcctctat     1440
gtcacagaca ccaaagatac gagggtcacg tttgcctttg atttgttagg aggaaagcaa      1500
atcaatgcaa actttgatt cagaatgtcc cagtctgttc ttgccatgct gtcatacaac       1560
atgagagatc agcatttata ctcgtgggaa gatggccatc tgatgctcta tcctgtgcag      1620
tttctgtcag cggcatcaag tcagcggtag                                        1650
```

<210> SEQ ID NO 34
<211> LENGTH: 117
<212> TYPE: PRT
<213> ORGANISM: Rattus sp.

<400> SEQUENCE: 34

```
Cys Leu Thr Gly Pro Pro Gly Pro Pro Gly Pro Pro Gly Ala Gly Gly
 1               5                  10                  15

Leu Pro Gly His Asn Gly Ser Asp Gly Gln Pro Gly Leu Gln Gly Pro
            20                  25                  30

Lys Gly Glu Lys Gly Ala Val Gly Lys Arg Gly Lys Met Gly Leu Pro
        35                  40                  45

Gly Ala Thr Gly Asn Pro Gly Glu Lys Gly Glu Lys Gly Asp Ala Gly
    50                  55                  60

Glu Leu Gly Leu Pro Gly Asn Glu Gly Pro Pro Gly Gln Lys Gly Asp
65                  70                  75                  80

Lys Gly Asp Lys Gly Asp Val Ser Asn Asp Val Leu Leu Thr Gly Ala
                85                  90                  95

Lys Gly Asp Gln Gly Pro Pro Gly Pro Pro Gly Pro Pro Gly Pro Pro
            100                 105                 110

Gly Pro Pro Gly Ser
        115
```

<210> SEQ ID NO 35
<211> LENGTH: 120
<212> TYPE: PRT
<213> ORGANISM: Homo sapiens

<400> SEQUENCE: 35

-continued

```
Cys Leu Thr Gly Pro Ser Gly Pro Pro Gly Pro Pro Gly Ala Gly Gly
  1               5                  10                  15

Leu Pro Gly His Asn Gly Leu Asp Gly Gln Pro Gly Pro Gln Gly Pro
             20                  25                  30

Lys Gly Glu Lys Gly Ala Asn Gly Lys Arg Gly Lys Met Gly Ile Pro
         35                  40                  45

Gly Ala Ala Gly Asn Pro Gly Glu Arg Gly Glu Lys Gly Asp His Gly
     50                  55                  60

Glu Leu Gly Leu Gln Gly Asn Glu Gly Pro Pro Gly Gln Lys Gly Glu
 65                  70                  75                  80

Lys Gly Asp Lys Gly Asp Val Ser Asn Asp Val Leu Leu Ala Gly Ala
                 85                  90                  95

Lys Gly Asp Gln Gly Pro Pro Gly Pro Gly Pro Gly Pro Gly Pro Pro
                100                 105                 110

Gly Pro Pro Gly Pro Pro Gly Ser
            115                 120
```

<210> SEQ ID NO 36
<211> LENGTH: 291
<212> TYPE: PRT
<213> ORGANISM: Rattus sp.

<400> SEQUENCE: 36

```
Arg Arg Ala Lys Gly Pro Arg Gln Pro Asn Ser Phe Thr Asn Gln Cys
  1               5                  10                  15

Pro Gly Glu Thr Cys Val Ile Pro Asn Asp Asp Thr Leu Val Gly Arg
             20                  25                  30

Ala Asp Glu Lys Val Asn Glu Arg His Ser Pro Gln Thr Glu Pro Met
         35                  40                  45

Ile Thr Ser Ile Gly Asn Pro Ala Gln Val Leu Lys Val Lys Glu Thr
     50                  55                  60

Phe Gly Thr Trp Leu Arg Glu Ser Ala Asn Arg Ser Asp Asp Arg Ile
 65                  70                  75                  80

Trp Val Thr Glu His Phe Ser Gly Ile Met Val Lys Glu Phe Glu Asp
                 85                  90                  95

Leu Pro Ala Leu Leu Asn Ser Ser Phe Thr Leu Leu His Leu Pro His
                100                 105                 110

Tyr Phe His Gly Cys Gly His Ala Val Tyr Asn Asn Ser Leu Tyr Tyr
            115                 120                 125

His Lys Gly Gly Ser Asn Thr Ile Val Arg Phe Glu Phe Gly Lys Glu
        130                 135                 140

Thr Pro Gln Thr Leu Lys Leu Glu Asp Ala Leu Tyr Phe Asp Arg Lys
145                 150                 155                 160

Tyr Leu Phe Ala Asn Ser Lys Thr Tyr Phe Asn Ile Ala Val Asp Glu
                165                 170                 175

Lys Gly Leu Trp Ile Ile Tyr Ala Ser Ser Val Asp Gly Ser Ser Ile
            180                 185                 190

Leu Val Ala Gln Leu Asp Glu Arg Thr Phe Ser Val Leu Gln His Ile
        195                 200                 205

Asn Thr Thr Tyr Pro Lys Ser Lys Ala Gly Asn Ala Phe Ile Ala Gln
    210                 215                 220

Gly Ile Leu Tyr Val Thr Asp Thr Lys Asp Thr Arg Val Thr Phe Ala
225                 230                 235                 240

Phe Asp Leu Leu Arg Gly Lys Gln Ile Asn Ala Asn Phe Gly Leu Arg
```

```
                    245                 250                 255
Met Ser Gln Ser Val Leu Ala Met Leu Ser Tyr Asn Met Arg Asp Gln
            260                 265                 270
His Leu Tyr Ser Trp Glu Asp Gly His Leu Met Leu Tyr Pro Val His
        275                 280                 285
Phe Ser Ser
    290

<210> SEQ ID NO 37
<211> LENGTH: 291
<212> TYPE: PRT
<213> ORGANISM: Homo sapiens

<400> SEQUENCE: 37

Arg Arg Ala Lys Gly Pro Arg Gln Pro Ser Met Phe Asn Gly Gln Cys
  1               5                  10                  15
Pro Gly Glu Thr Cys Ala Ile Pro Asn Asp Asp Thr Leu Val Gly Lys
             20                  25                  30
Ala Asp Glu Lys Ala Ser Glu His His Ser Pro Gln Ala Glu Ser Met
         35                  40                  45
Ile Thr Ser Ile Gly Asn Pro Val Gln Val Leu Lys Val Thr Glu Thr
     50                  55                  60
Phe Gly Thr Trp Ile Arg Glu Ser Ala Asn Lys Ser Asp Asp Arg Ile
 65                  70                  75                  80
Trp Val Thr Glu His Phe Ser Gly Ile Met Val Lys Glu Phe Lys Asp
                 85                  90                  95
Gln Pro Ser Leu Leu Asn Gly Ser Tyr Thr Phe Ile His Leu Pro Tyr
            100                 105                 110
Tyr Phe His Gly Cys Gly His Val Ala Tyr Asn Asn Ser Leu Tyr Tyr
        115                 120                 125
His Lys Gly Gly Ser Asn Thr Leu Val Arg Phe Glu Phe Gly Gln Glu
    130                 135                 140
Thr Ser Gln Thr Leu Lys Leu Glu Asn Ala Leu Tyr Phe Asp Arg Lys
145                 150                 155                 160
Tyr Leu Phe Ala Asn Ser Lys Thr Tyr Phe Asn Leu Ala Val Asp Glu
                165                 170                 175
Lys Gly Leu Trp Ile Ile Tyr Ala Ser Ser Val Asp Gly Ser Ser Ile
            180                 185                 190
Leu Val Ala Gln Leu Asp Glu Arg Thr Phe Ser Val Val Gln His Val
        195                 200                 205
Asn Thr Thr Tyr Pro Lys Ser Lys Ala Gly Asn Ala Phe Ile Ala Arg
    210                 215                 220
Gly Ile Leu Tyr Val Thr Asp Thr Lys Asp Met Arg Val Thr Phe Ala
225                 230                 235                 240
Phe Asp Leu Leu Gly Gly Lys Gln Ile Asn Ala Asn Phe Asp Leu Arg
                245                 250                 255
Thr Ser Gln Ser Val Leu Ala Met Leu Ala Tyr Asn Met Arg Asp Gln
            260                 265                 270
His Leu Tyr Ser Trp Glu Asp Gly His Leu Met Leu Tyr Pro Val Gln
        275                 280                 285
Phe Leu Ser
    290

<210> SEQ ID NO 38
<211> LENGTH: 255
```

-continued

```
<212> TYPE: PRT
<213> ORGANISM: Unknown Organism
<220> FEATURE:
<223> OTHER INFORMATION: Description of Unknown Organism: Amino acid
      sequence of the olfactomedin-like domain

<400> SEQUENCE: 38

Gly Ile Leu Ala Gly Val Gly Ile Pro Val Leu Leu Ala Glu Ser Gln
 1               5                  10                  15

Tyr Gly Lys Ser Gly Ala Trp Met Arg Asp Pro Leu Pro Asn Ser Met
             20                  25                  30

Lys Ala Lys Arg Arg Trp Val Met Asp Gly Phe Ala Asp Val Ser Arg
         35                  40                  45

Val Leu Arg Glu Tyr Ser Ser Met Ser Asp Phe Leu Asp Gly Val Asn
     50                  55                  60

Lys Ile Lys Tyr Tyr Leu Pro His Ala Ala Ser Gly Thr Gly Asn Val
 65                  70                  75                  80

Val Tyr Asn Gly Ser Leu Tyr Phe Asn Lys Phe Gly Ser His Ser Ile
             85                  90                  95

Val Arg Tyr Glu Leu Glu Thr Gly Val Gln Val Lys Glu Glu Leu Leu
            100                 105                 110

Pro Glu Ala Gly Tyr Asn Asp Cys Phe Pro Tyr Ala Trp Gly Gly His
            115                 120                 125

Ser Asp Ile Asp Leu Ala Val Asp Glu Asn Gly Leu Trp Val Ile Tyr
    130                 135                 140

Ala Thr Glu Gln Asn Ala Gly Lys Ile Val Ile Ser Lys Leu Asn Pro
145                 150                 155                 160

Ala Thr Leu Phe Val Glu Asn Thr Trp Asn Thr Glu Tyr Asn Lys Arg
                165                 170                 175

Ser Ala Ala Asn Ala Phe Met Ile Cys Gly Val Leu Tyr Val Thr Lys
                180                 185                 190

Ser Ala Asn Ser Leu Gly Thr Lys Ile Thr Tyr Ala Tyr Asp Thr Asn
            195                 200                 205

Thr Gly Lys Thr Ile Pro Leu Asp Ile Pro Phe Tyr Asn Pro Tyr Gln
        210                 215                 220

Tyr Ile Ser Met Leu Asp Tyr Asn Pro Leu Asp Arg Lys Leu Tyr Ala
225                 230                 235                 240

Trp Asp Asn Gly His Leu Leu Ser Tyr Asp Ile Arg Leu Glu Glu
                245                 250                 255
```